US012690386B2

(12) United States Patent
Lee et al.

(10) Patent No.: US 12,690,386 B2
(45) Date of Patent: Jul. 21, 2026

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Su-Hyun Lee, Gyeonggi-do (KR); Bitnari Kim, Gyeonggi-do (KR); So-Young Jung, Gyeonggi-do (KR); Hyo-Nim Shin, Gyeonggi-do (KR); Mi-Ja Lee, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 1123 days.

(21) Appl. No.: 17/272,519

(22) PCT Filed: Aug. 28, 2019

(86) PCT No.: PCT/KR2019/010999
§ 371 (c)(1),
(2) Date: Mar. 1, 2021

(87) PCT Pub. No.: WO2020/045981
PCT Pub. Date: Mar. 5, 2020

(65) Prior Publication Data

US 2022/0384744 A1 Dec. 1, 2022

(30) Foreign Application Priority Data

Aug. 29, 2018 (KR) ........................ 10-2018-0102278
Jun. 28, 2019 (KR) ........................ 10-2019-0077904
Aug. 26, 2019 (KR) ........................ 10-2019-0104458

(51) Int. Cl.

| | |
|---|---|
| ***H10K 85/60*** | (2023.01) |
| ***C07D 405/10*** | (2006.01) |
| ***C07D 405/14*** | (2006.01) |
| ***C07D 487/04*** | (2006.01) |
| ***C07F 15/00*** | (2006.01) |
| ***C09K 11/02*** | (2006.01) |
| ***C09K 11/06*** | (2006.01) |
| *H10K 50/11* | (2023.01) |
| *H10K 101/00* | (2023.01) |
| *H10K 101/10* | (2023.01) |

(52) U.S. Cl.
CPC ....... *H10K 85/6574* (2023.02); *C07D 405/10* (2013.01); *C07D 405/14* (2013.01); *C07D 487/04* (2013.01); *C07F 15/0033* (2013.01); *C09K 11/02* (2013.01); *C09K 11/06* (2013.01); *H10K 85/615* (2023.02); *H10K 85/626* (2023.02); *H10K 85/6572* (2023.02); *H10K 85/6576* (2023.02); *C09K 2211/1007* (2013.01); *C09K 2211/1029* (2013.01); *C09K 2211/185* (2013.01); *H10K 50/11* (2023.02); *H10K 2101/10* (2023.02); *H10K 2101/90* (2023.02)

(58) Field of Classification Search
CPC .................................................. H10K 2101/90
See application file for complete search history.

(56) References Cited

U.S. PATENT DOCUMENTS

| | | | | |
|---|---|---|---|---|
| 2013/0248849 | A1* | 9/2013 | Feldman | H10K 85/346 252/500 |
| 2014/0231769 | A1 | 8/2014 | Nishimura et al. | |
| 2017/0047527 | A1* | 2/2017 | Lee | C09K 11/06 |
| 2017/0104163 | A1 | 4/2017 | Lee et al. | |
| 2017/0222160 | A1 | 8/2017 | Lee et al. | |
| 2017/0309841 | A1 | 10/2017 | Kim et al. | |
| 2018/0315930 | A1 | 11/2018 | Han et al. | |
| 2019/0252613 | A1 | 8/2019 | Song et al. | |
| 2019/0312215 | A1* | 10/2019 | Kang | H10K 85/6574 |

FOREIGN PATENT DOCUMENTS

| | | | | |
|---|---|---|---|---|
| KR | 20160107975 | A | 9/2016 | |
| KR | 20170089599 | A | 8/2017 | |
| WO | WO-2010114264 | A2 * | 10/2010 | C09K 11/06 |
| WO | WO-2016080749 | A1 * | 6/2016 | C07F 15/00 |

* cited by examiner

*Primary Examiner* — Sean M DeGuire
(74) *Attorney, Agent, or Firm* — G. Creston Campbell

(57) ABSTRACT

The present disclosure relates to a plurality of host materials comprising a first host compound represented by formula 1 and a second host compound represented by formula 2 and an organic electroluminescent device comprising the same. By comprising the specific combination of the compound as host materials, an organic electroluminescent device having low driving voltage, high luminous efficiency and/or long lifespan can be provided compared with a conventional organic electroluminescent device.

12 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

The TPD/$Alq_3$ bilayer small molecule organic electroluminescent device (OLED) with green-emission, which is constituted with a light-emitting layer and a charge transport layer, was first developed by Tang, et al., of Eastman Kodak in 1987. Thereafter, the studies on an organic electroluminescent device have been rapidly commercialized. At present, an organic electroluminescent device mainly includes phosphorescent materials having excellent luminous efficiency in panel realization. For prolonged use and high resolution of the display, an OLED having high luminous efficiency and/or long lifespan is necessary.

US 2014/0231769 A1 discloses a plurality of host materials using a dibenzofuran- or dibenzothiophene-derivative compound; however, there is still a demand for development for improving the performance of the OLED.

DISCLOSURE OF INVENTION

Technical Problem

The object of the present disclosure is to provide an organic electroluminescent device having low driving voltage, high luminous efficiency and/or long lifespan by comprising a specific combination of compounds as host materials.

Solution to Problem

The present inventors found that the aforementioned objective can be achieved by a plurality of host materials comprising a first host material comprising the compound represented by the following formula 1 and a second host material comprising the compound represented by the following formula 2, so that the present invention was completed.

(1)

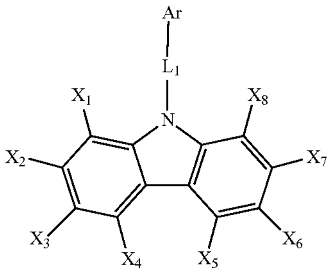

In formula 1,

Ar represents a substituted or unsubstituted (C6-C30)aryl, or a substituted or unsubstituted (3- to 30-membered) heteroaryl containing at least one of N, O and S, or $-NX_9X_{10}$;

$L_1$ represents a single bond, a substituted or unsubstituted (C6-C30)arylene, or a substituted or unsubstituted (3- to 30-membered)heteroarylene;

$X_1$ to $X_8$ each independently represent hydrogen, deuterium, halogen, cyano, carboxyl, nitro, hydroxy, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NX_{11}X_{12}$, or $-SiX_{13}X_{14}X_{15}$; or two or more adjacent substituents among $X_1$ to $X_8$ may be linked to each other to form a ring; provided that, at least one of $X_1$ and $X_2$, $X_2$ and $X_3$, $X_3$ and $X_4$, $X_4$ and $X_5$, $X_5$ and $X_8$, $X_6$ and $X_7$, and $X_7$ and $X_8$ are linked to each other to form a substituted or unsubstituted monocyclic ring or polycyclic ring having 2 to 5 rings;

$X_9$ and $X_{10}$ each independently represent a substituted or unsubstituted (C1-C30)alkyl, a substituted or unsubstituted (C3-C30)cycloalkyl, a substituted or unsubstituted (C6-C30)aryl, or a substituted or unsubstituted (3- to 30-membered)heteroaryl; and $X_{11}$ to $X_{15}$ each independently represent hydrogen, deuterium, halogen, cyano, carboxyl, nitro, hydroxy, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30)aryl, or a substituted or unsubstituted (3- to 30-membered)heteroaryl; or may be linked to adjacent substituents to form a ring.

(2)

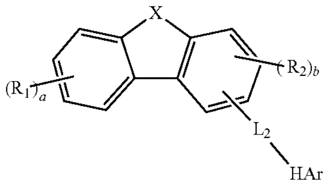

In formula 2,

X represents —O— or —S—;

HAr represents a substituted or unsubstituted (3- to 30-membered)heteroaryl containing at least one nitrogen atom;

$L_2$ represents a single bond, a substituted or unsubstituted (C6-C30)arylene, or a substituted or unsubstituted (3- to 30-membered)heteroarylene;

$R_1$ and $R_2$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to adjacent substituents to form a ring; and a represents an integer of 1 to 4, b represents an integer of 1 to 3, when a and b are 2 or more, each of $R_1$ and each of $R_2$ may be the same or different.

Advantageous Effects of Invention

By comprising a specific combination of compounds according to the present disclosure as host materials, an organic electroluminescent device having low driving voltage, high luminous efficiency and/or long lifespan can be provided as compared with a conventional organic electroluminescent device, and a display device or a lighting device using the same can be prepared.

MODE FOR THE INVENTION

Hereinafter, the present disclosure will be described in detail. However, the following description is intended to explain the invention, and is not meant in any way to restrict the scope of the invention.

Herein, "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, or an electron injection material, etc.

Herein, "a plurality of organic electroluminescent material" means an organic electroluminescent material in which two or more compounds may be comprised in any layer constituting an organic electroluminescent device. It may mean both a material before being comprised in an organic electroluminescent device (e.g., before vapor deposition) and a material after being comprised in an organic electroluminescent device (e.g., after vapor deposition). For example, a plurality of organic electroluminescent material may be a combination of two or more compounds which may be contained in at least one of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such two or more compounds may be included in the same or different layers, and may be mixture-evaporated or co-evaporated, or may be individually evaporated.

Herein, "a plurality of host materials" means an organic electroluminescent material comprising a combination of at least two compounds. It may mean both a material before being comprised in an organic electroluminescent device (e.g., before vapor deposition) and a material after being comprised in an organic electroluminescent device (e.g., after vapor deposition). A plurality of host materials of the present disclosure may be comprised in any light-emitting layer constituting an organic electroluminescent device. The at least two compounds comprised in a plurality of host materials may be comprised together in one light-emitting layer, or may each be comprised in separate light-emitting layers. When at least two compounds are comprised in one light-emitting layer, the at least two compounds may be mixture-evaporated or co-evaporated, or may be individually evaporated to form layer.

Herein, "(C1-C30)alkyl" is meant to be a linear or branched alkyl having 1 to 30 carbon atoms constituting the chain, in which the number of carbon atoms is preferably 1 to 10, and more preferably 1 to 6. The above alkyl may include methyl, ethyl, n-propyl, isopropyl, n-butyl, isobutyl, tert-butyl, etc. "(C3-C30)cycloalkyl" is a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. "(3- to 7-membered)heterocycloalkyl" is a cycloalkyl having 3 to 7 ring backbone atoms and at least one heteroatom selected from the group consisting of B, N, O, S, Si, and P, preferably O, S, and N, and includes tetrahydrofuran, pyrrolidine, thiolan, tetrahydropyran, etc. "(C6-C30)aryl" or "(C6-C30)arylene" is a monocyclic or fused ring radical derived from an aromatic hydrocarbon having 6 to 30 ring backbone carbon atoms, in which the number of the ring backbone carbon atoms is preferably 6 to 20, more preferably 6 to 15, may be partially saturated, and may comprise a spiro structure. Examples of the aryl specifically may include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluorene-fluorene]yl, spiro[fluorene-benzofluorene]yl, azulenyl, etc. More specifically, the aryl may be o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenyl, 4-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, etc. "(3- to 50-membered)heteroaryl or (3- to 30-membered)heteroarylene" is an aryl having 3 to 50 or 3 to 30 ring backbone atoms including at least one heteroatom selected from the group consisting of B, N, O, S, Si, P, and Ge. Wherein the number of ring backbone atoms is preferably 3 to 30, more preferably 5 to 20, and the number of heteroatoms is preferably 1 to 4. The above heteroaryl may be a monocyclic ring, or a fused ring condensed with at least one benzene ring; and may be partially saturated. Also, the above heteroaryl or heteroarylene may be one formed by linking at least one heteroaryl or aryl group to a heteroaryl group via a single bond(s); and may comprise a spiro structure. Examples of the heteroaryl specifically may include a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acrylidinyl, silafluorenyl, germafluorenyl, etc. More specifically, the heteroaryl may be 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazole-1-yl, azacarbazole-2-yl, azacarbazole-3-yl, azacarbazole-4-yl, azacarbazole-5-yl, azacarbazole-6-yl, azacarbazole-7-yl, azacarbazole-8-yl, azacarbazole-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acrylidinyl, 2-acrylidinyl, 3-acrylidinyl, 4-acrylidinyl, 9-acrylidinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. Herein, "Halogen" includes F, Cl, Br, and I.

In addition, "ortho (o)," "meta (m)," and "para (p)" are meant to signify the substitution position of all substituents. Ortho position is a compound with substituents, which are adjacent to each other, e.g., at the 1 and 2 positions on benzene. Meta position is the next substitution position of the immediately adjacent substitution position, e.g., a compound with substituents at the 1 and 3 positions on benzene. Para position is the next substitution position of the meta position, e.g. a compound with substituents at the 1 and 4 positions on benzene.

In addition, "substituted" in the expression "substituted or unsubstituted" means that a hydrogen atom in a certain functional group is replaced with another atom or functional group, i.e., a substituent. The substituents of the substituted alkyl, the substituted cycloalkyl, the substituted cycloalkenyl, the substituted heterocycloalkyl, the substituted aryl, the substituted arylene, the substituted heteroaryl, the substituted heteroarylene, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, or the substituted alkylarylamino, each independently are at least one selected from the group consisting of deuterium; halogen; cyano; carboxyl; nitro; hydroxy; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (C3-C30)cycloalkenyl; (3- to 7-membered) heterocycloalkyl; (C6-C30)aryloxy; (C6-C30)arylthio; at least one of (C1-C30)alkyl-, (C6-C30)aryl- and di(C6-C30)arylamino-substituted or unsubstituted (3- to 50-membered) heteroaryl; at least one of cyano-, (C1-C30)alkyl-, (3- to 50-membered)heteroaryl-, di(C6-C30)arylamino- and tri(C6-C30)arylsilyl-substituted or unsubstituted (C6-C30)aryl; tri(C1-C30)alkylsilyl; tri(C6-C30)arylsilyl; di(C1-C30)alkyl(C6-C30)arylsilyl; (C1-C30)alkyldi(C6-C30)arylsilyl; amino; mono or di(C1-C30)alkylamino; mono or di(C6-C30)arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl. Preferably, the substituents may be at least one selected from the group consisting of (C1-C20)alkyl; at least one of (C1-C20)alkyl-, (3- to 30-membered)heteroaryl- and di(C6-C25)arylamino-substituted or unsubstituted (C6-C25)aryl; at least one of (C1-C20)alkyl- and (C6-C25)aryl-substituted or unsubstituted (3- to 30-membered)heteroaryl; and di(C6-C20)arylamino. More preferably, the substituents may be at least one selected from the group consisting of (C1-C10)alkyl; at least one of (C1-C10)alkyl-, (5- to 20-membered) heteroaryl- and di(C6-C18)arylamino-substituted or unsubstituted (C6-C20)aryl; at least one (C6-C18)aryl-substituted or unsubstituted (5- to 25-membered)heteroaryl; and di(C6-C18)arylamino. For example, the substituents may be at least one of methyl; tert-buthyl; at least one of pyridinyl-, diphenyltriazinyl-, phenylquinoxalinyl-, phenylquinazolinyl-, biphenylquinazolinyl-, dibenzofuranyl-, dibenzothiophenyl-, carbazolyl-, and diphenylamino-substituted or unsubstituted phenyl; at least one diphenyltriazinyl-substituted or unsubstituted naphthyl; biphenyl; naphthylphenyl; phenylnaphthyl; terphenyl; dimethylfluorenyl; phenylfluorenyl; diphenylfluorenyl; dimethylbenzofluorenyl; phenanthrenyl; triphenylenyl; pyridinyl; at least one of phenyl- and naphthyl-substituted triazinyl; at least one phenyl-substituted indolyl; at least one phenyl-substituted benzoimidazolyl; quinolyl; at least one of phenyl- and biphenyl-substituted quinazolinyl; at least one phenyl-substituted quinoxalinyl; at least one phenyl-substituted or unsubstituted carbazolyl; dibenzofuranyl; dibenzothiophenyl; benzonaphthothiophenyl; at least one phenyl-substituted or unsubstituted benzocarbazolyl; dibenzocarbazolyl; benzophenanthrothiophenyl; diphenylamino; dimethylfluorenylphenylamino; and a substituted or unsubstituted (16- to 33-membered)heteroaryl containing at least one of N, O and S.

Herein, "a ring formed by linking to an adjacent substituent" means a substituted or unsubstituted (3- to 30-membered) mono- or polycyclic, alicyclic, aromatic ring, or a combination thereof, formed by linking or fusing two or more adjacent substituents; preferably, may be a substituted or unsubstituted (3- to 26-membered), more preferably a substituted or unsubstituted (5- to 20-membered) mono- or polycyclic, alicyclic, aromatic ring, or a combination thereof. In addition, the formed ring may contain at least one heteroatom selected from the group consisting of B, N, O, S, Si, and P, preferably, N, O, and S.

Herein, heteroaryl, heteroarylene, and heterocycloalkyl each independently may contain at least one heteroatom selected from the group consisting of B, N, O, S, Si and P. In addition, the heteroatom may be linked with at least one substituent selected from the group consisting of hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl (C6-C30)arylamino.

In formula 1, Ar represents a substituted or unsubstituted (C6-C30)aryl, or a substituted or unsubstituted (3- to 30-membered)heteroaryl containing at least one of N, O and S, or —$NX_9X_{10}$. According to one embodiment of the present disclosure, Ar represents a substituted or unsubstituted (C6-C25)aryl, or a substituted or unsubstituted (5- to 25-membered)heteroaryl containing at least one of N, O and S, or —$NX_9X_{10}$. According to another embodiment of the present disclosure, Ar represents at least one (C1-C10)alkyl-substituted or unsubstituted (C6-C25)aryl; at least one (C6-C18)aryl-substituted or unsubstituted, (5- to 25-membered) heteroaryl containing at least one of N, O and S; or —$NX_9X_{10}$. Specifically, Ar may be a substituted or unsubstituted phenyl, a substituted or unsubstituted naphthyl, a substituted or unsubstituted biphenyl, a substituted or unsubstituted terphenyl, a substituted or unsubstituted spirobifluorenyl, a substituted or unsubstituted pyridyl, a substituted or unsubstituted triazinyl, a substituted or unsubstituted pyrimidinyl, a substituted or unsubstituted quinolyl, a substituted or unsubstituted quinazolinyl, a substituted or unsubstituted quinoxalinyl, a substituted or unsubstituted benzoquinazolinyl, a substituted or unsubstituted benzoquinoxalinyl, a substituted or unsubstituted benzofuropyrimidinyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted fluorenyl, a substituted or unsubstituted benzofluorenyl, a substituted or unsubstituted triphenylenyl, a substituted or unsubstituted benzonaphthofuranyl, or a substituted or unsubstituted benzonaphthothiophenyl, or —$NX_9X_{10}$. For example, Ar may be phenyl, naphthyl, biphenyl, terphenyl, dimethylfluorenyl, dimethylbenzofluorenyl, spirobifluorenyl, pyridyl substituted with phenyl, triazinyl substituted with at least one phenyl, pyrimidinyl substituted with at least one phenyl, quinolyl substituted with phenyl, quinazolinyl substituted with at least one of phenyl and naphthyl, quinoxalinyl substituted with at least one of phenyl and naphthyl, naphthyridinyl substituted with at least one phenyl, dibenzofuranyl, dibenzothiophenyl, benzofuropyrimidinyl substituted with at least one phenyl, at least one phenyl-substituted or unsubstituted carbazolyl, benzoquinoxalinyl substituted with at least one phenyl, benzoquinazolinyl substituted with at least one phenyl, or —$NX_9X_{10}$.

$X_9$ and $X_{10}$ each independently represent a substituted or unsubstituted (C1-C30)alkyl, a substituted or unsubstituted (C3-C30)cycloalkyl, a substituted or unsubstituted (C6-C30)aryl, or a substituted or unsubstituted (3- to 30-membered)heteroaryl. According to one embodiment of the present disclosure, $X_9$ and $X_{10}$ each independently represent a substituted or unsubstituted (C6-C25)aryl, or a substituted or unsubstituted (5- to 25-membered)heteroaryl. According to another embodiment of the present disclosure, $X_9$ and $X_{10}$ each independently represent (C6-C18)aryl-substituted or unsubstituted (C6-C18)aryl, or (C6-C18)aryl-substituted or unsubstituted (5- to 20-membered)heteroaryl. For example, X and $X_{10}$ each independently may be phenyl, naphthyl, biphenyl, naphthylphenyl, or phenyl-substituted or unsubstituted carbazolyl.

In formula 1, $L_1$ represents a single bond, a substituted or unsubstituted (C6-C30)arylene, or a substituted or unsubstituted (3- to 30-membered)heteroarylene. According to one embodiment of the present disclosure, $L_1$ represents a single bond, a substituted or unsubstituted (C6-C25)arylene, or a substituted or unsubstituted (5- to 25-membered)heteroarylene. According to another embodiment of the present disclosure, $L_1$ represents a single bond, an unsubstituted (C6-C18)arylene, or an unsubstituted (5- to 20-membered) heteroarylene. For example, $L_1$ may be a single bond, phenylene, naphthylene, biphenylene, carbazolylene, quinazolylene, quinoxalinylene, benzofuropyrimidinylene, naphthyridinylene, benzoquinoxalinylene, quinolylene, or benzoquinazolinylene.

In formula 1, $X_1$ to $X_8$ each independently represent hydrogen, deuterium, halogen, cyano, carboxyl, nitro, hydroxy, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$NX_{11}X_{12}$ or —$SiX_{13}X_{14}X_{15}$; or two or more adjacent substituents among $X_1$ to $X_8$ may be linked to each other to form a ring; provided that, at least one of $X_1$ and $X_2$, $X_2$ and $X_3$, $X_3$ and $X_4$, $X_4$ and $X_5$, $X_5$ and $X_8$, $X_6$ and $X_7$, and $X_7$ and $X_8$ are linked to each other to form a substituted or unsubstituted monocyclic ring or polycyclic ring having 2 to 5 rings. According to one embodiment of the present disclosure, $X_1$ to $X_8$ each independently represent hydrogen; or two or more adjacent substituents among $X_1$ to $X_8$ may be linked to each other to form a ring; provided that, at least one of $X_1$ and $X_2$, $X_2$ and $X_3$, $X_3$ and $X_4$, $X_4$ and $X_5$, $X_5$ and $X_6$, $X_6$ and $X_7$, and $X_7$ and $X_8$ are linked to each other to form a substituted or unsubstituted monocyclic ring or polycyclic ring having 2 to 5 rings. For example, $X_1$ to $X_8$ each independently may be hydrogen; or two or more adjacent substituents among $X_1$ to $X_8$ may be linked to each other to form a benzene ring, indole ring substituted with phenyl, naphthyl, biphenyl, or terphenyl, or benzoindole ring substituted with phenyl.

$X_{11}$ to $X_{15}$ each independently represent hydrogen, deuterium, halogen, cyano, carboxyl, nitro, hydroxy, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; or may be linked to adjacent substituents to form a ring.

According to one embodiment of the present disclosure, the compound represented by formula 1 may be represented by any one of the following formulae 1-1 to 1-5.

(1-1)

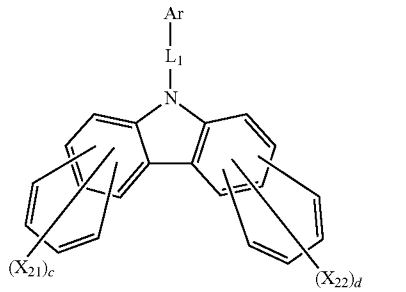

(1-2)

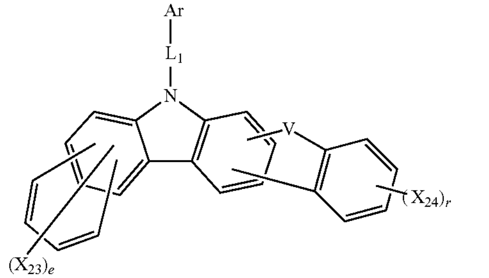

(1-3)

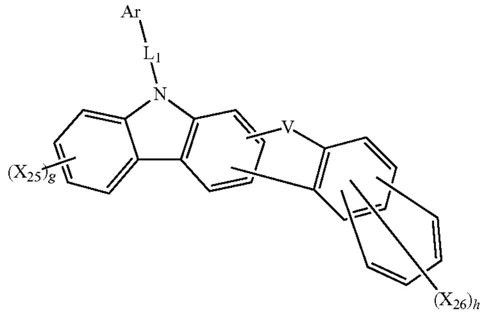

(1-4)

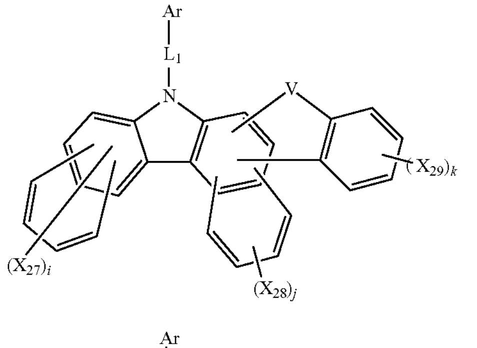

(1-5)

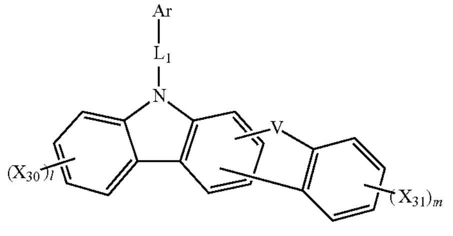

In formulae 1-1 to 1-5, Ar and $L_1$ are as defined in formula 1, V each independently represents $CX_{18}X_{19}$, $NX_{20}$, O, or S. According to one embodiment of the present disclosure, V represents $NX_{20}$.

$X_{18}$ to $X_{31}$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C3)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino. According to one embodiment of the present disclosure, $X_{18}$ to $X_{20}$ each independently represent a substituted or unsubstituted (C1-C20)alkyl, a substituted or unsubstituted (C6-C25)aryl, a substituted or unsubstituted (5- to 25-membered)heteroaryl, and $X_{21}$ to $X_{31}$ each independently represent hydrogen or deuterium. According to another embodiment of the present disclosure, $X_1$a to $X_{20}$ each independently represent an unsubstituted (C6-C18) aryl, and $X_{21}$ to $X_{31}$ each independently represent hydrogen or deuterium. For example, $X_{18}$ to $X_{20}$ each independently may be phenyl, naphthyl, biphenyl, or terphenyl, and $X_{21}$ to $X_{31}$ each independently may be hydrogen.

f, g, j, k, l, and m each independently represent an integer of 1 to 4; c to e, h, and i each independently represent an integer of 1 to 6, when c to m are 2 or more, and each of $X_{21}$ to $X_{31}$ may be the same or different.

According to one embodiment of the present disclosure, the formula 1-5 may be excluded from the case of formula 1-6.

(1-6)

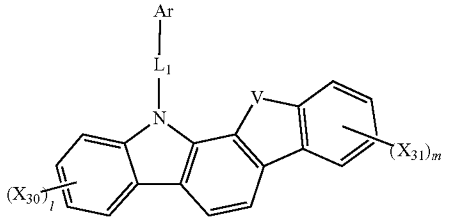

In formula 1-6, Ar, $L_1$, V, $X_{30}$, $X_{31}$, l and m are as defined in formula 1-5.

In formula 2, X represents —O— or —S—.

In formula 2, HAr represents a substituted or unsubstituted (3- to 30-membered)heteroaryl containing at least one nitrogen atom. According to one embodiment of the present disclosure, HAr represents a substituted or unsubstituted (5- to 25-membered)heteroaryl containing at least one nitrogen atom. According to another embodiment of the present disclosure, HAr represents at least one of (C6-C18)aryl- and (3- to 20-membered)heteroaryl-substituted (5- to 25-membered)heteroaryl containing at least one nitrogen atom. Specifically, HAr may be a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzothienopyrimidinyl, a substituted or unsubstituted carbazolyl, or a substituted or unsubstituted pyridopyrazinyl. For example, HAr may be a substituted quinoxalinyl, a substituted quinazolinyl, a substituted naphthyridinyl, a substituted carbazolyl, a substituted pyridopyrazinyl, a substituted benzoquinoxalinyl, a substituted benzoquinazolinyl, or a substituted triazinyl; and wherein the substituents of the substituted quinoxalinyl, the substituted quinazolinyl, the substituted naphthyridinyl, the substituted carbazolyl, the substituted pyridopyrazinyl, the substituted benzoquinoxalinyl, the substituted benzoquinazolinyl, and the substituted triazinyl may be at least one of phenyl, phenyl substituted with carbazolyl, phenyl substituted with diphenylamino, phenyl substituted with phenquinoxalinyl, phenyl substituted with dibenzofuranyl, phenyl substituted with dibenzothiophenyl, naphthyl, phenylnaphthyl, naphthylphenyl, biphenyl, terphenyl, dimethylfluorenyl, dimethylbenzofluorenyl, phenanthrenyl, triphenylenyl, carbazolyl substituted with phenyl, dibenzofuranyl, and dibenzothiophenyl.

In formula 2, $L_2$ represents a single bond, a substituted or unsubstituted (C6-C30)arylene, or a substituted or unsubstituted (3- to 30-membered)heteroarylene. According to one embodiment of the present disclosure, $L_2$ represents a single bond, a substituted or unsubstituted (C6-C25)arylene, or a substituted or unsubstituted (5- to 25-membered)heteroarylene. According to another embodiment of the present disclosure, $L_2$ represents a single bond, (C6-C11)aryl-substituted or unsubstituted (C6-C20)arylene, or an unsubstituted (5- to 20-membered)heteroarylene. For example, $L_2$ may be a single bond, phenylene, naphthylene, biphenylene, phenylnaphthylene, naphthylphenylene, or naphthyridinylene.

In formula 2, $R_1$ and $R_2$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino; or may be linked to adjacent substituents to form a ring. For example, two $R_1$s, two $R_2$s, and/or $R_1$ and $R_2$ may be linked to each other to form a ring. According to one embodiment of the present disclosure, $R_1$ and $R_2$ each independently may be hydrogen or deuterium.

In formula 2, a represents an integer of 1 to 4, b represents an integer of 1 to 3, when a and b are 2 or more, each of $R_1$ and each of $R_2$ may be the same or different.

According to one embodiment of the present disclosure, the compound represented by formula 2 may be represented by at least one of the following formula 2-1 or 2-2.

(2-1)

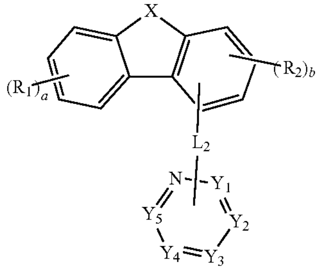

(2-2)

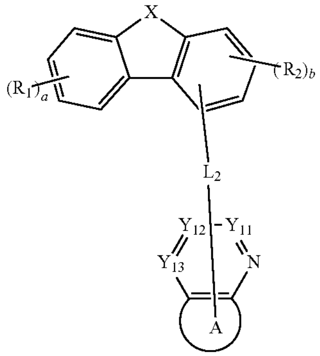

In formulae 2-1 and 2-2, X, $R_1$, $R_2$, $L_2$, a, and b are as defined in formula 2.

In formula 2-2, A ring is a substituted or unsubstituted (6- to 10-membered) ring. According to one embodiment of the present disclosure, A ring may be (C6-C18)aryl or (5- to 20-membered)heteroaryl-substituted or unsubstituted (6- to 10-membered) mono- or polycyclic ring. For example, A ring may be benzene ring; naphthalene ring; phenyl-, biphenyl-, naphthyl-, dimethylfluorenyl-, dimethylbenzofluorenyl-, or phenylcarbazolyl-substituted or unsubstituted pyridine ring; or phenyl-substituted pyrazine ring, etc.

In formulae 2-1 and 2-2, $Y_1$ to $Y_5$, and $Y_{11}$ to $Y_{13}$ each independently represent N or $CR_3$.

$R_3$ each independently represent hydrogen, deuterium, halogen, cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or adjacent $R_3$s may be linked to each other to form a ring. According to one embodiment of the present disclosure, $R_3$ each independently represent hydrogen, deuterium, a substituted or unsubstituted (C1-C20)alkyl, a substituted or unsubstituted (C6-C25)aryl, or a substituted or unsubstituted (5- to 25-membered)heteroaryl. According to another embodiment of the present disclosure, $R_3$ each independently represent hydrogen, deuterium, at least one of (C1-C10)alkyl- and (3- to 20-membered)heteroaryl-substituted or unsubstituted (C6-C20)aryl, or (C6-C18)aryl-substituted or unsubstituted (5- to 20-membered)heteroaryl. For example, $R_3$ each independently may be hydrogen, a substituted or unsubstituted phenyl, naphthyl, biphenyl, dimethylfluorenyl, phenanthrenyl, naphthylphenyl, phenylnaphthyl, dimethylbenzofluorenyl, terphenyl, triphenylenyl, carbazolyl substituted with phenyl, dibenzofuranyl or dibenzothiophenyl, wherein the substituents of the substituted phenyl may be at least one of carbazolyl, diphenylamino, phenylquinoxalinyl, dibenzofuranyl and dibenzothiophenyl.

The compound represented by formula 1 may be illustrated by the following compounds, but is not limited thereto.

C1-1

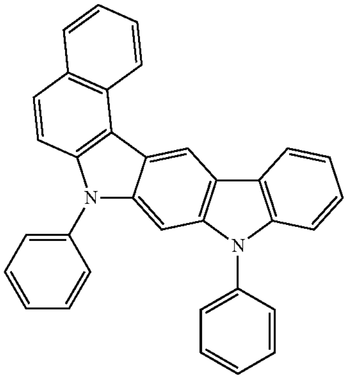

C1-2

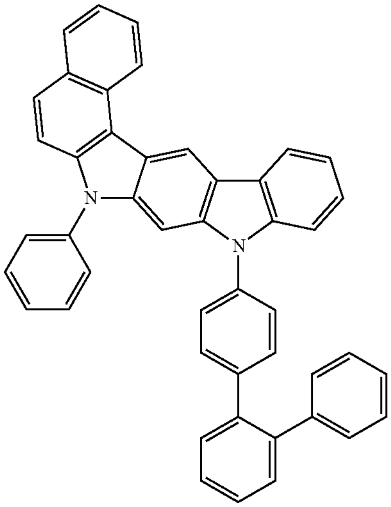

C1-3

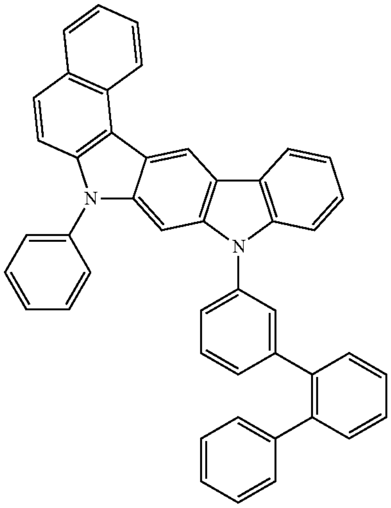

-continued

C1-4

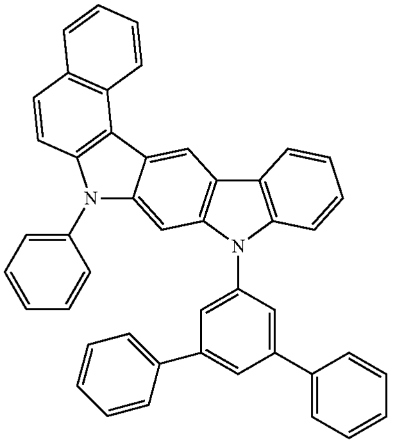

C1-5

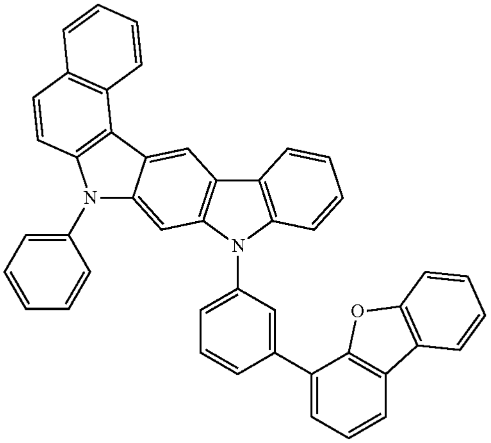

C1-6

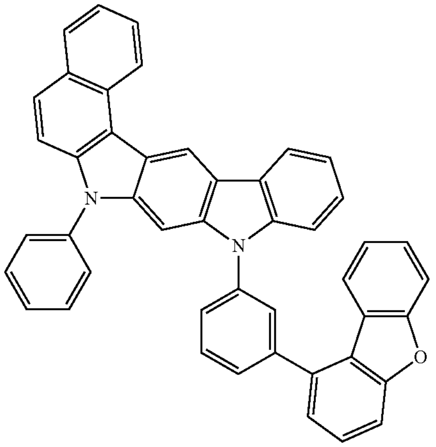

-continued
C1-7
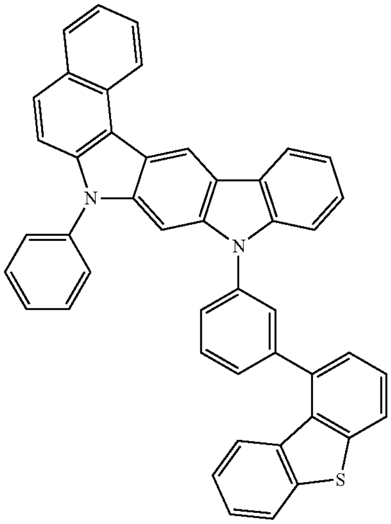
C1-8
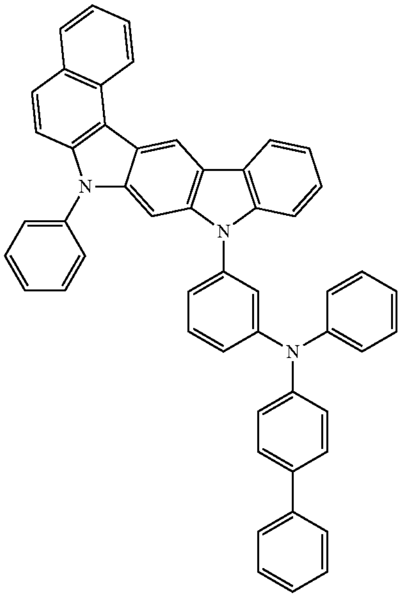
-continued
C1-9
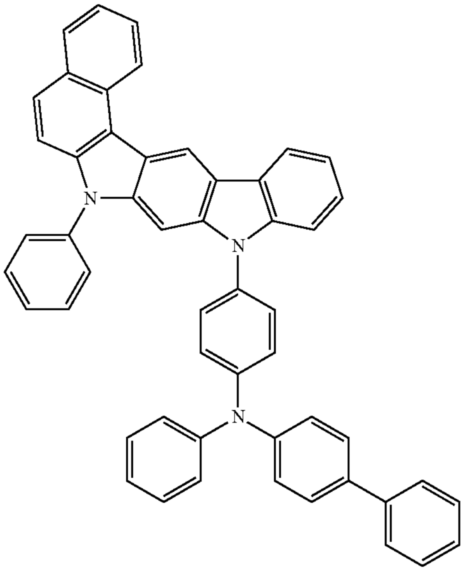
C1-10
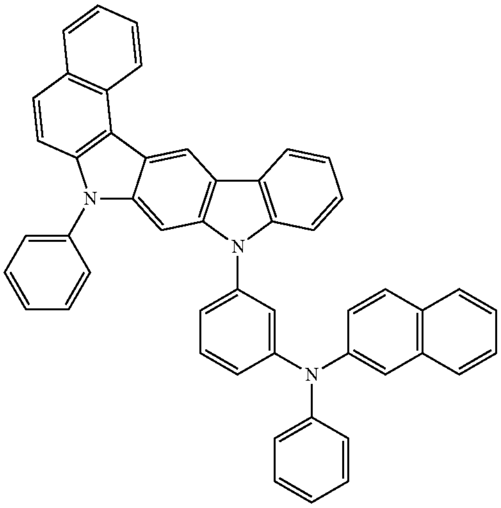
C1-11
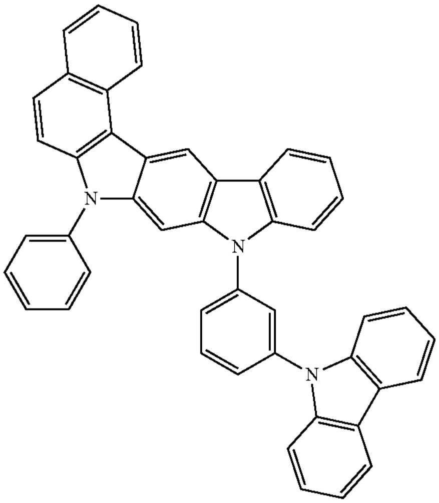

-continued
C1-12
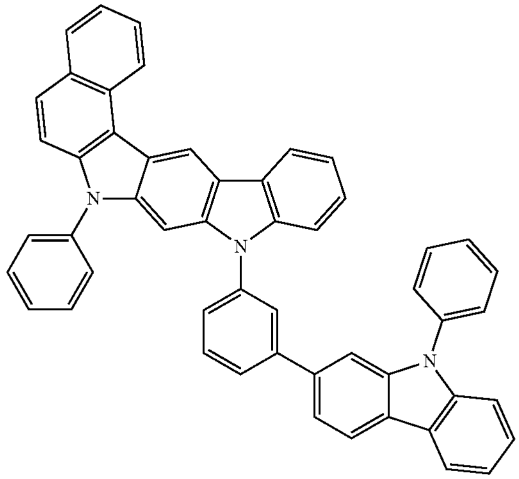
C1-13
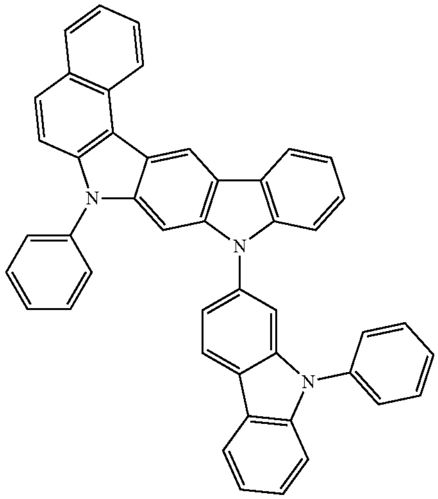
C1-14
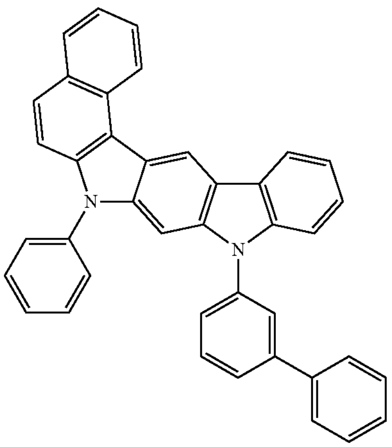
-continued
C1-15
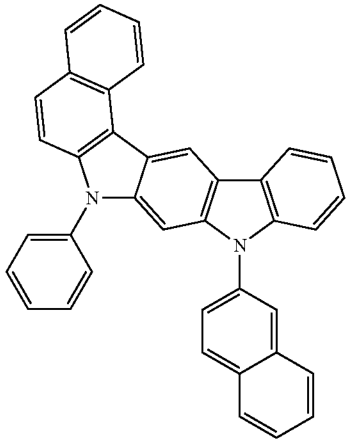
C1-16
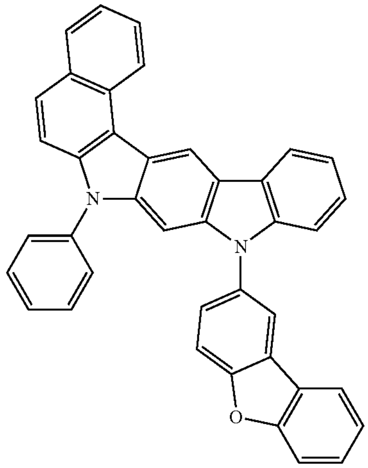
C1-17
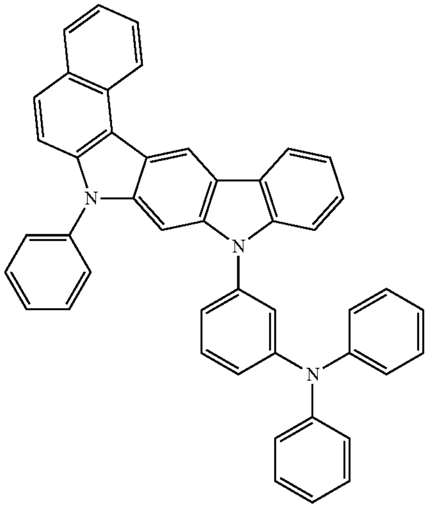

-continued
C1-18
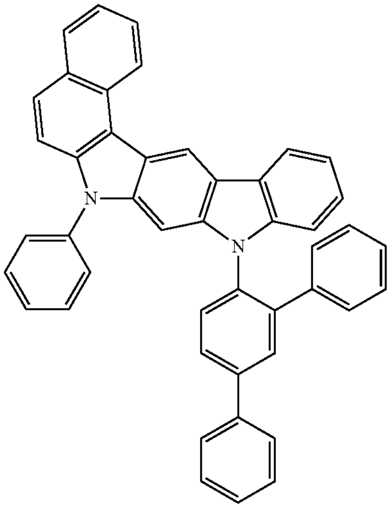
C1-19
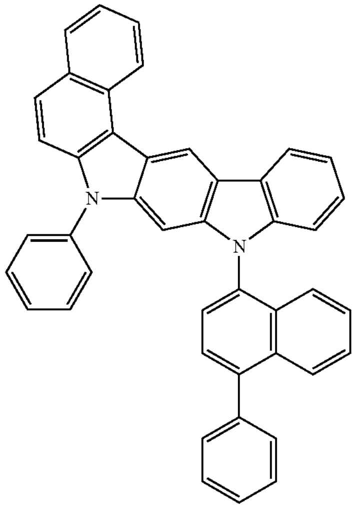
C1-20
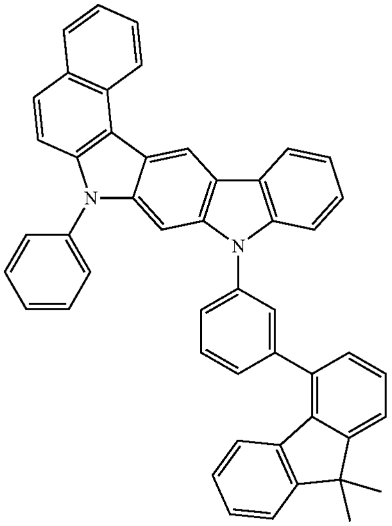
-continued
C1-21
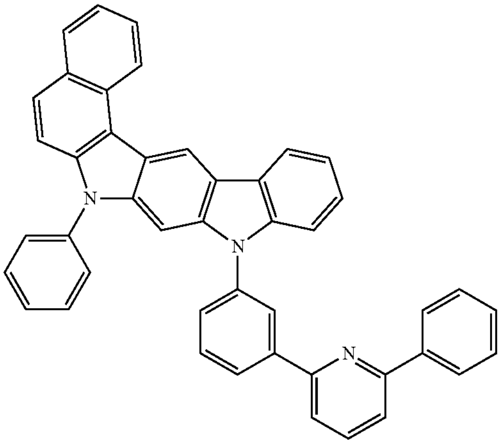
C1-22
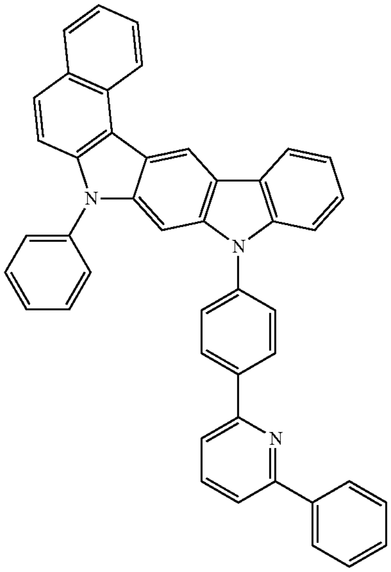
C1-23
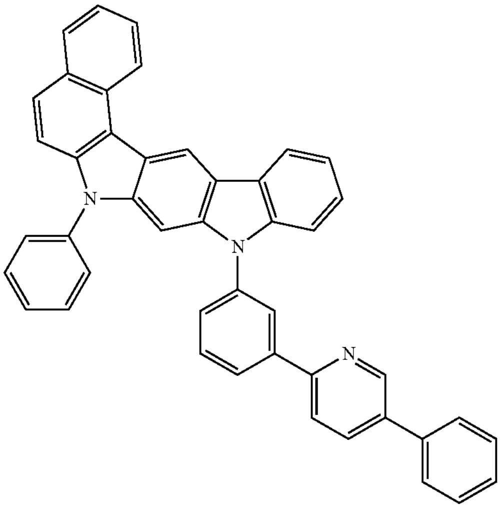

-continued
C1-24
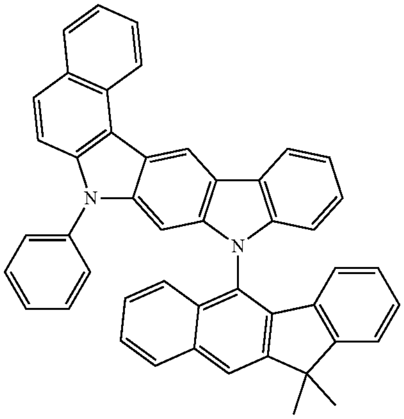
C1-25
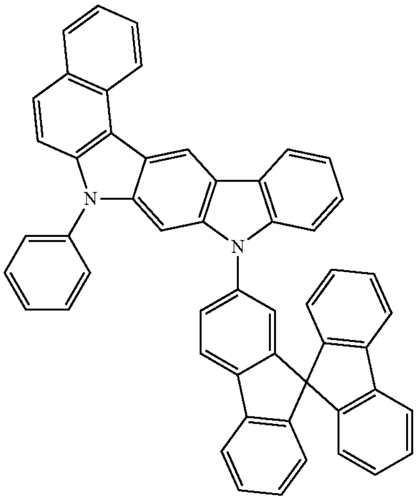
C1-26
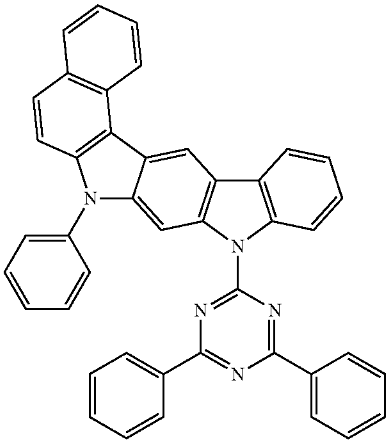
-continued
C1-27
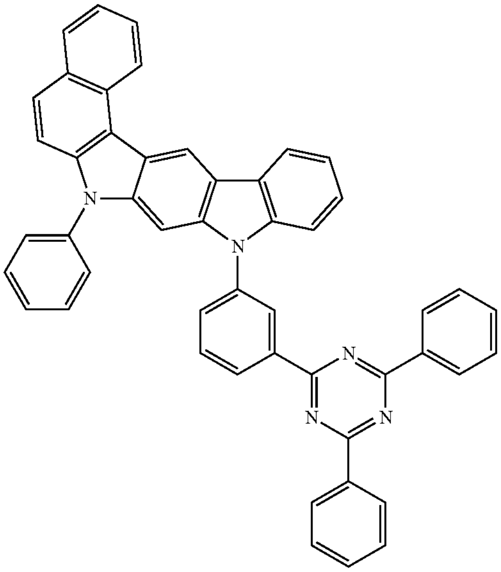
C1-28
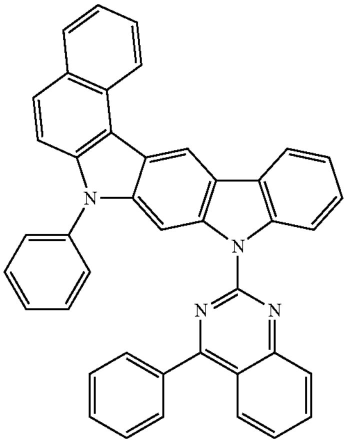
C1-29
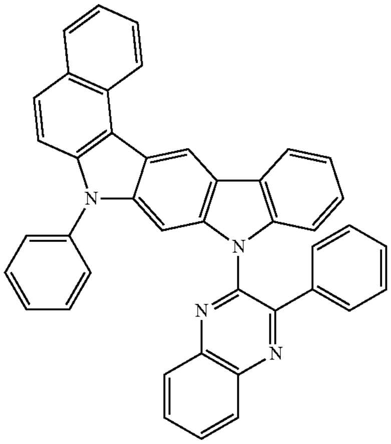

-continued
C1-30
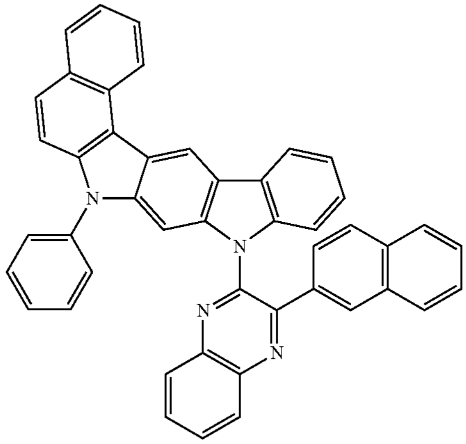
C1-31
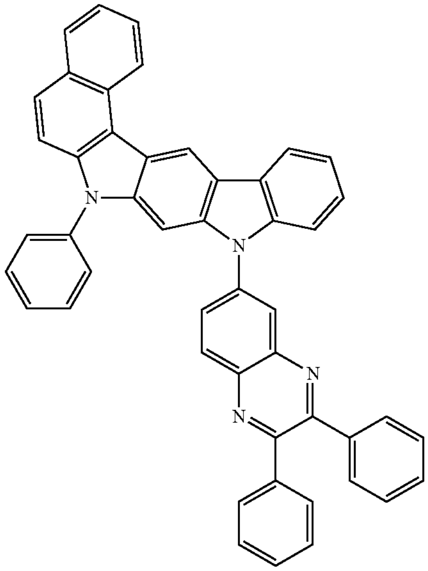
C1-32
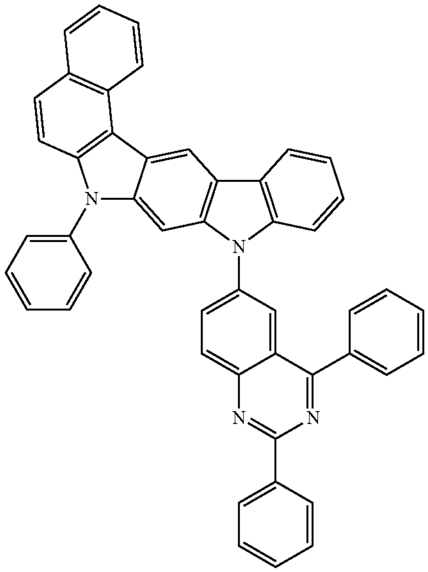
-continued
C1-33
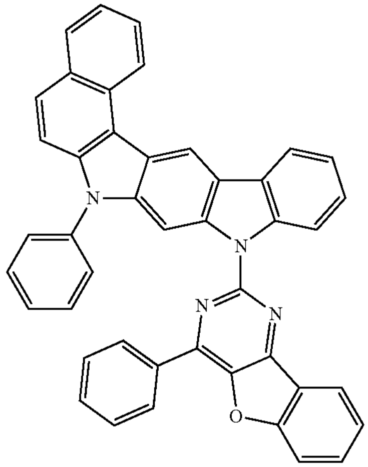
C1-34
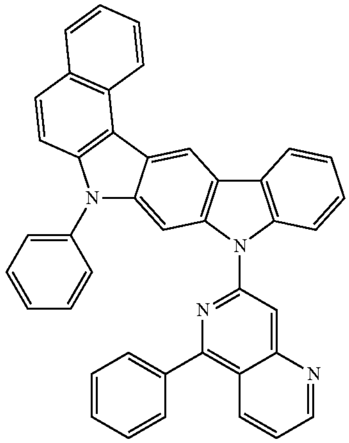
C1-35
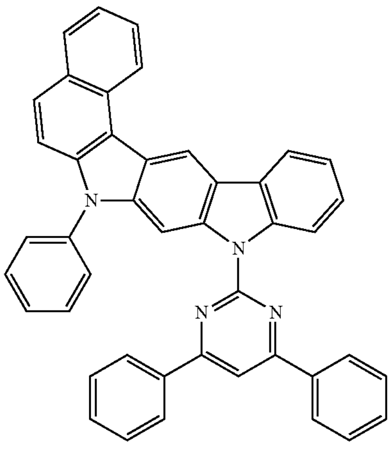

-continued
C1-36
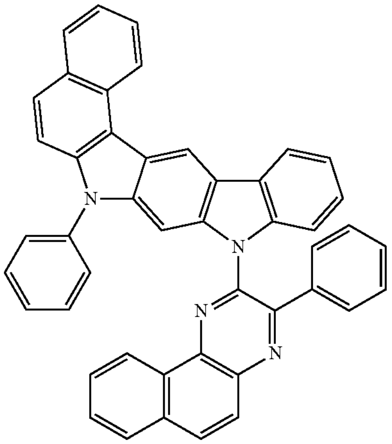
C1-37
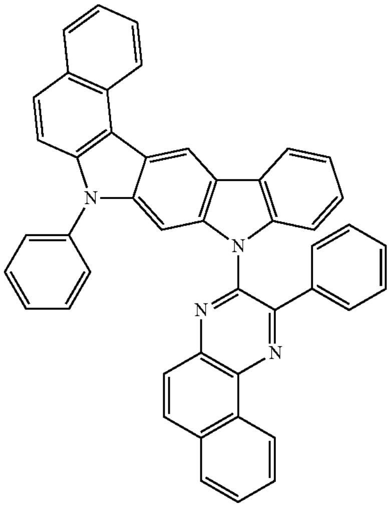
C1-38
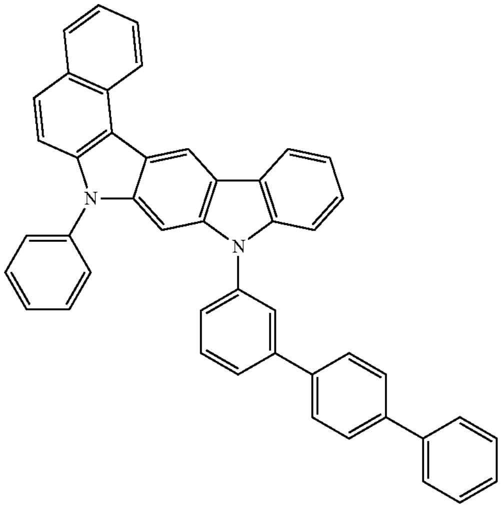
-continued
C1-39
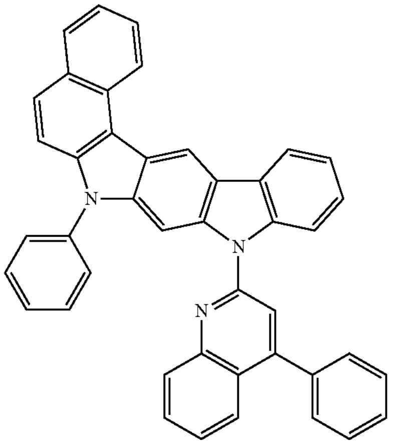
C1-40
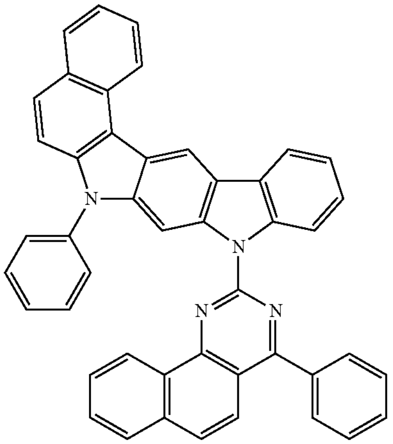
C1-41
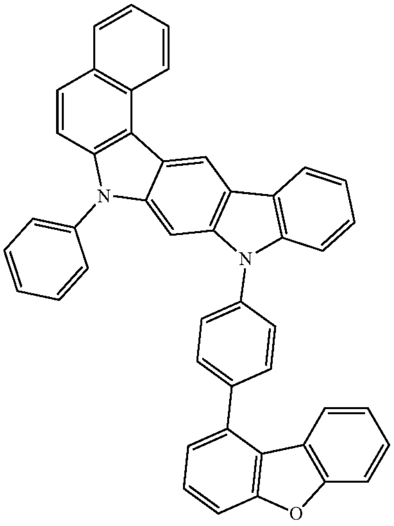

-continued
C1-42
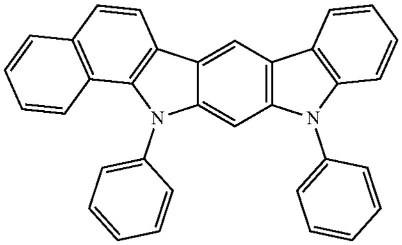
C1-43
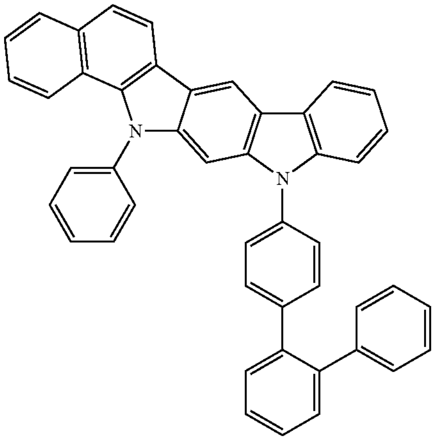
C1-44
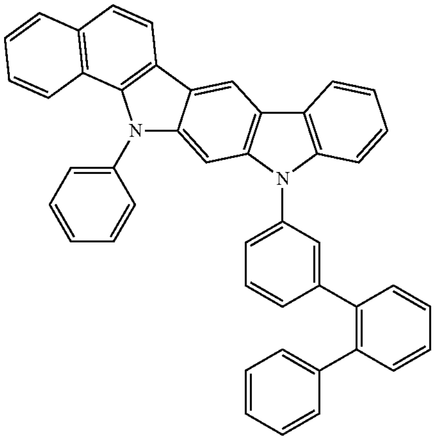
C1-45
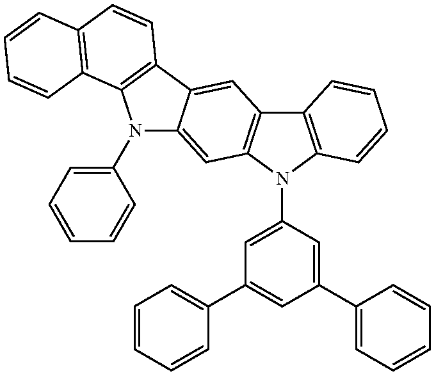
-continued
C1-46
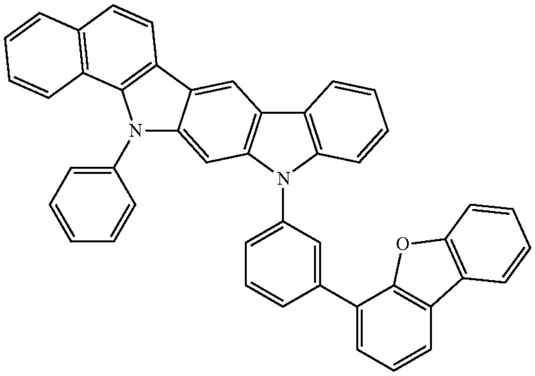
C1-47
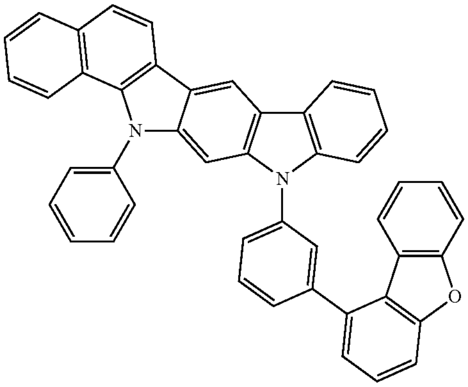
C1-48
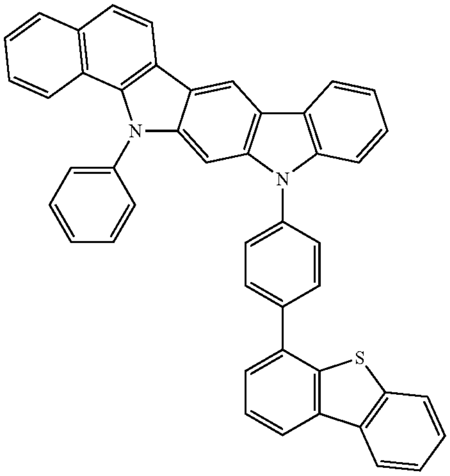

-continued
C1-49
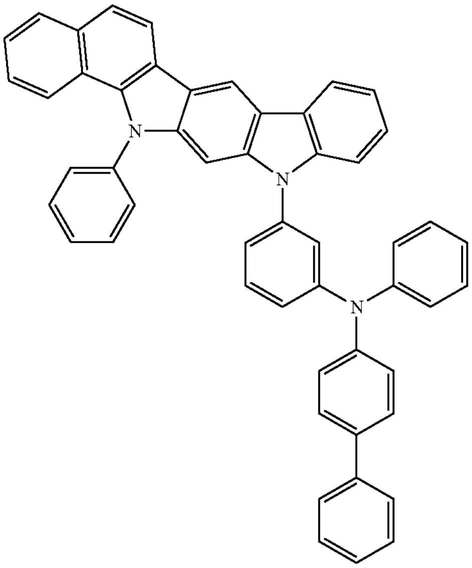
C1-50
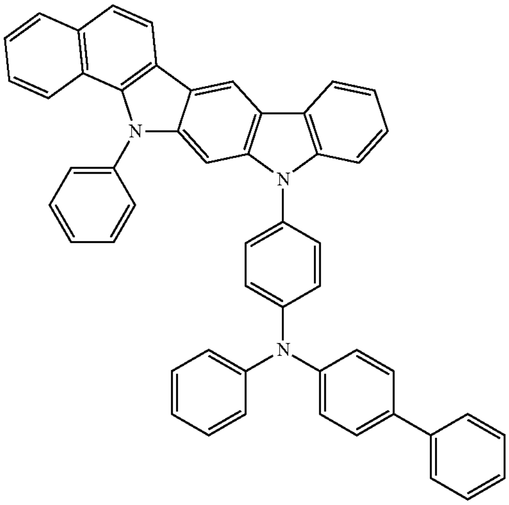
C1-51
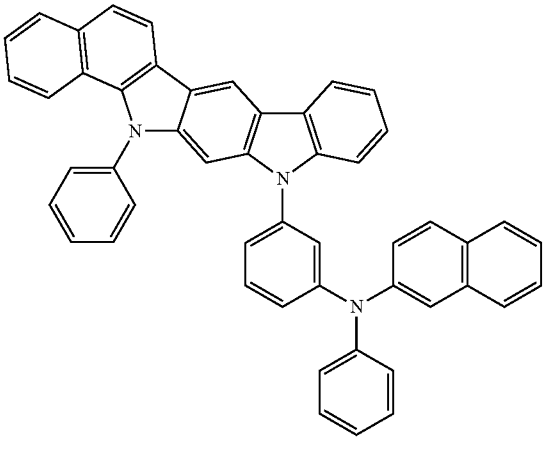
-continued
C1-52
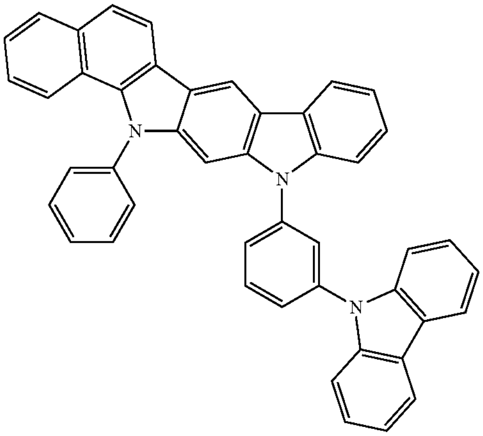
C1-53
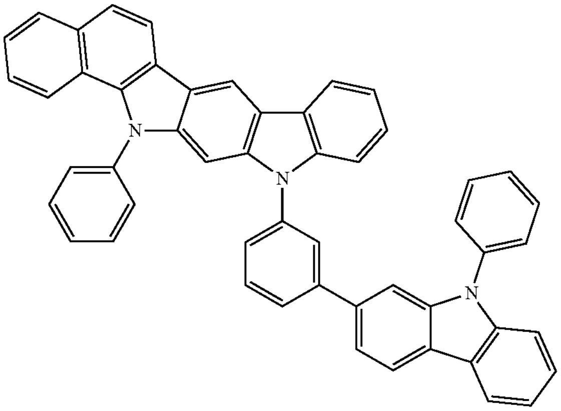
C1-54
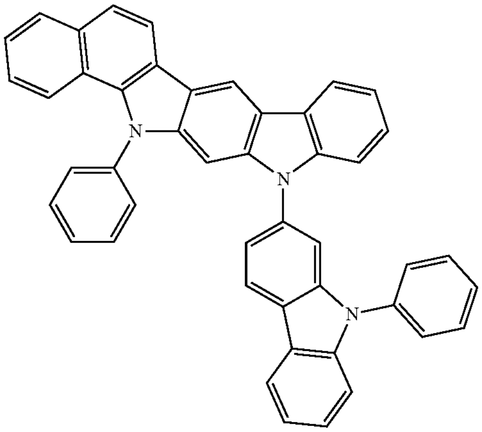

-continued
C1-55
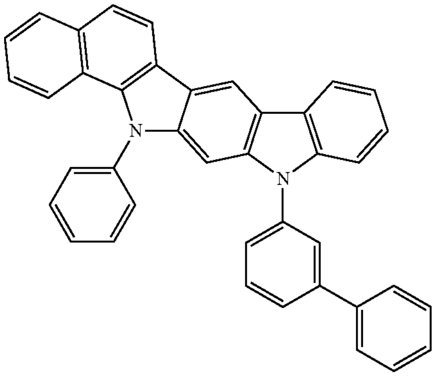
C1-56
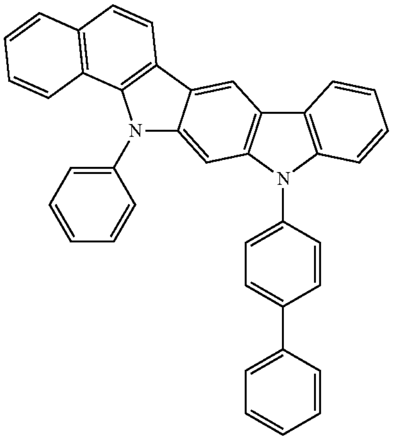
C1-57
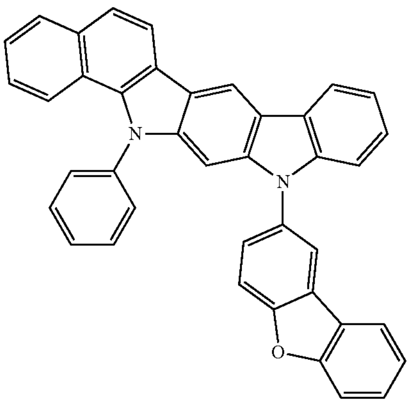
-continued
C1-58
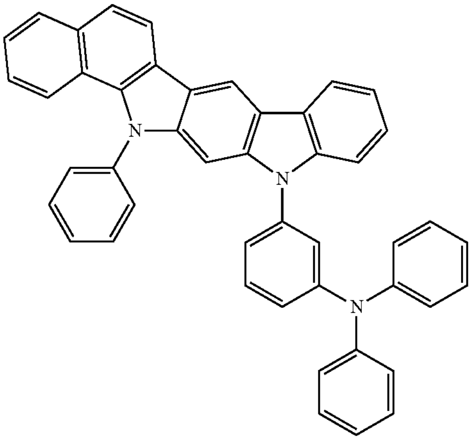
C1-59
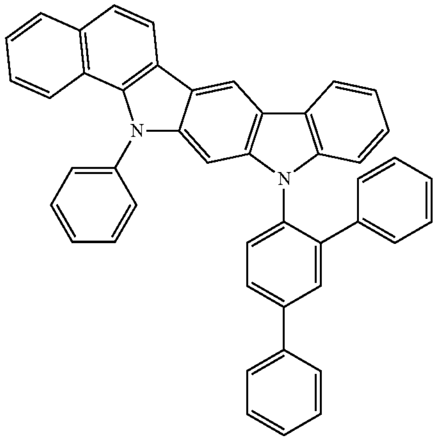
C1-60
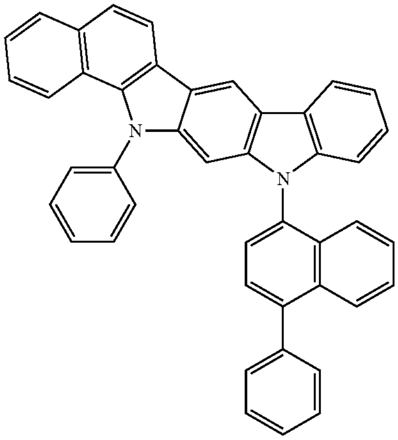

-continued
C1-61
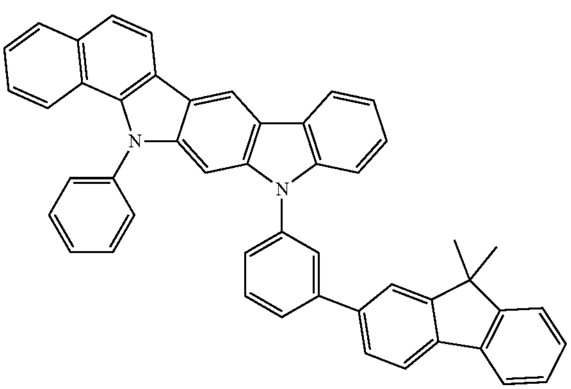
C1-62
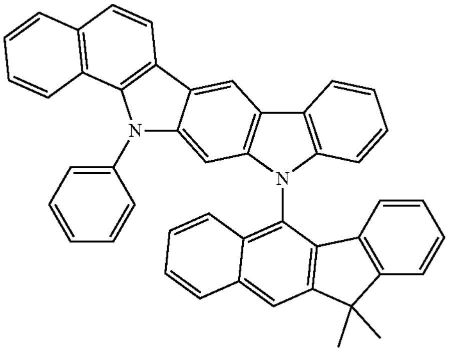
C1-63
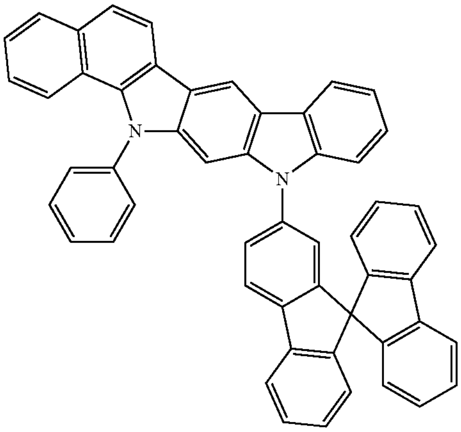
C1-64
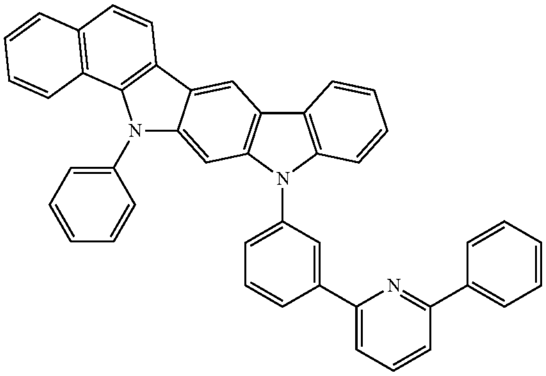
-continued
C1-65
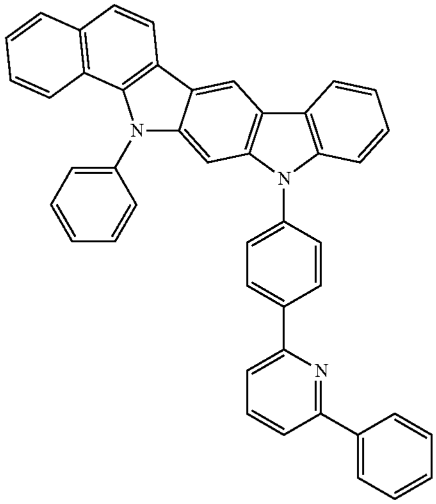
C1-66
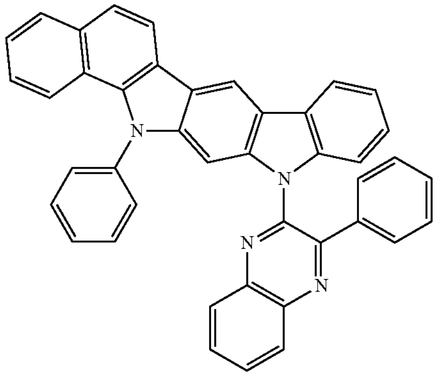
C1-67
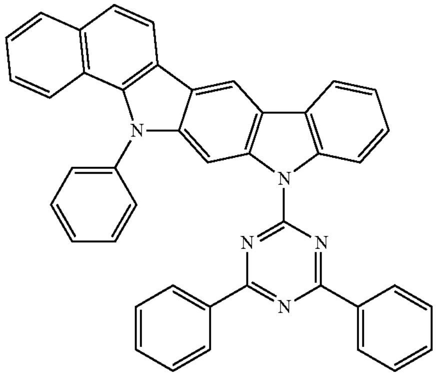

C1-68
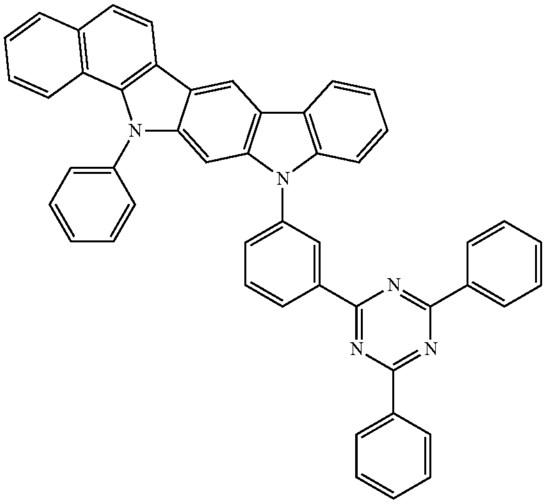
C1-69
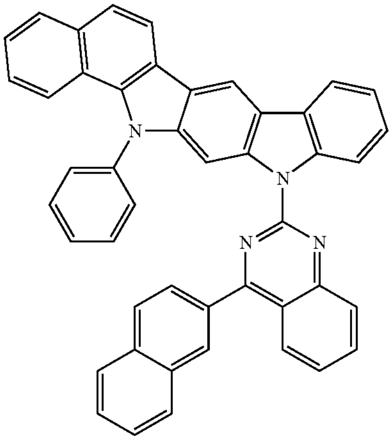
C1-70
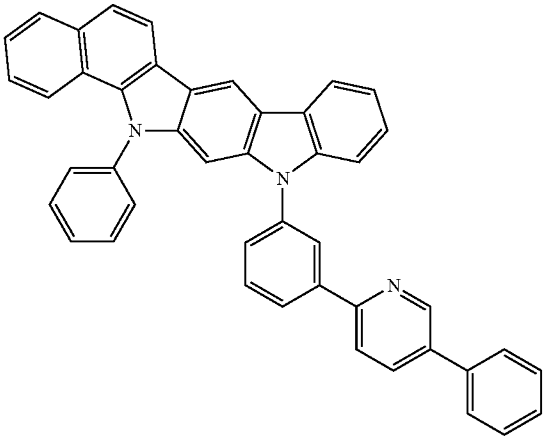
C1-71
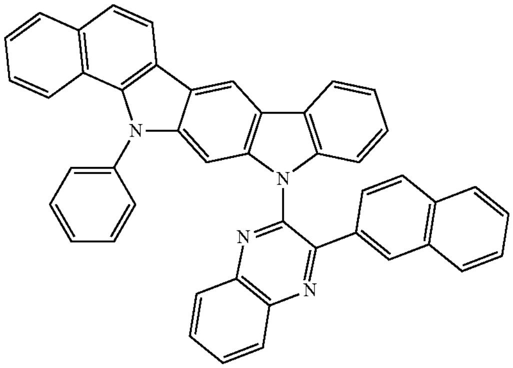
C1-72
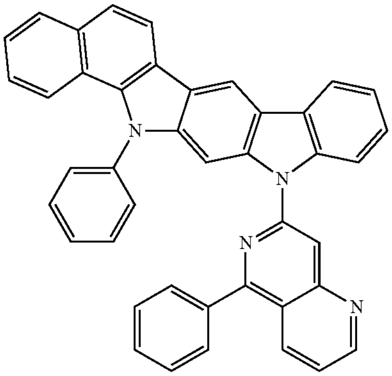
C1-73
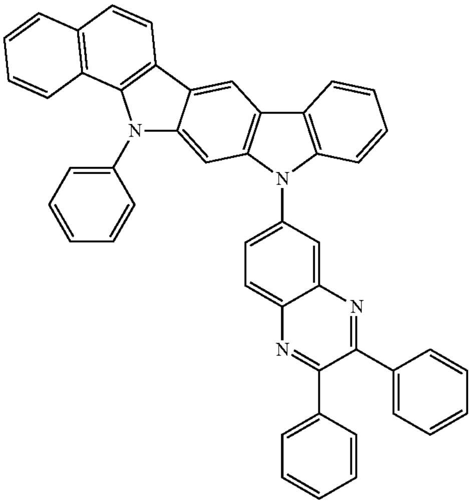

-continued
C1-74
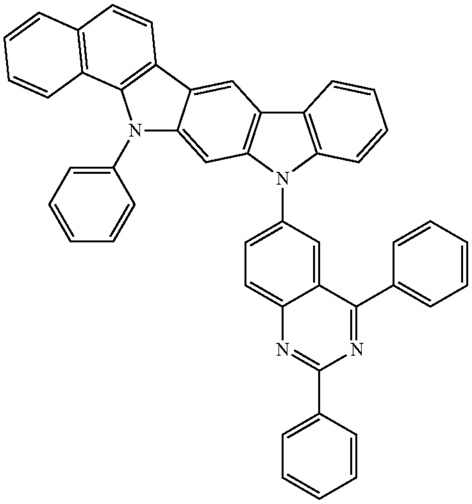
C1-75
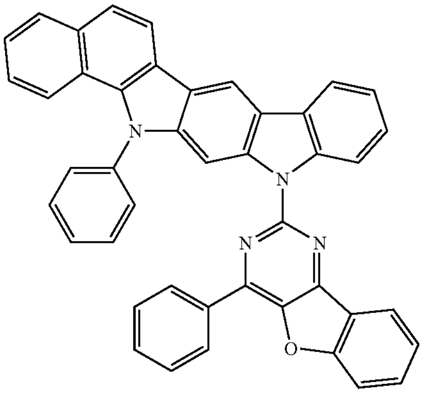
C1-76
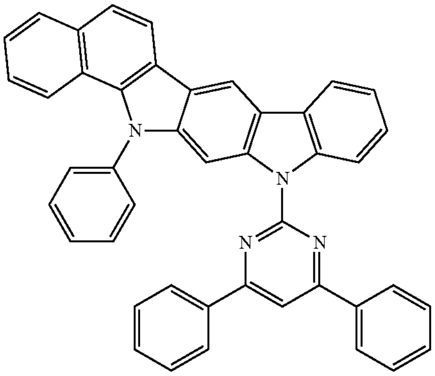
C1-77
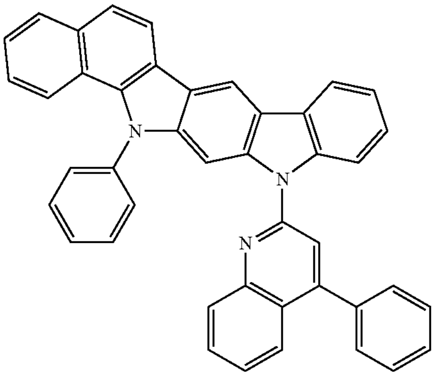
-continued
C1-78
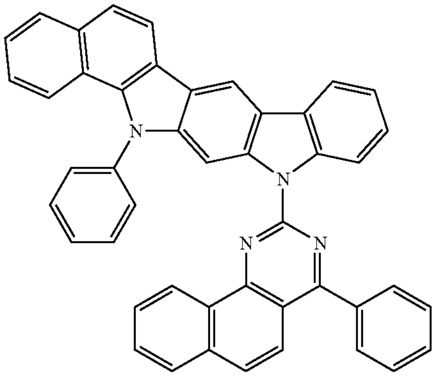
C1-79
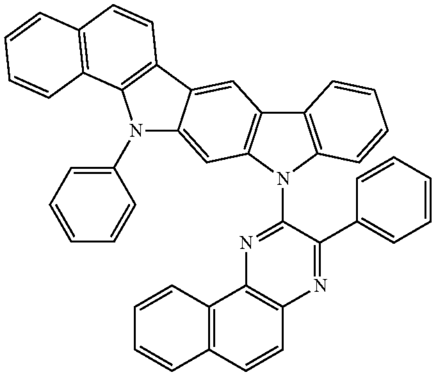
C1-80
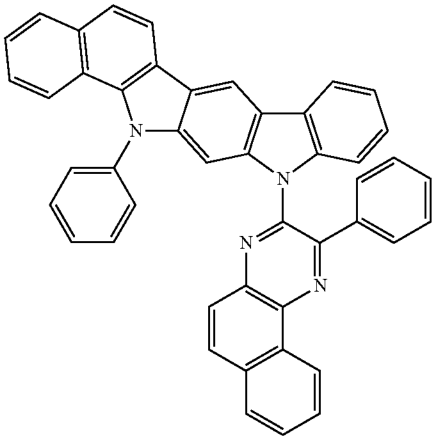

-continued
C1-81
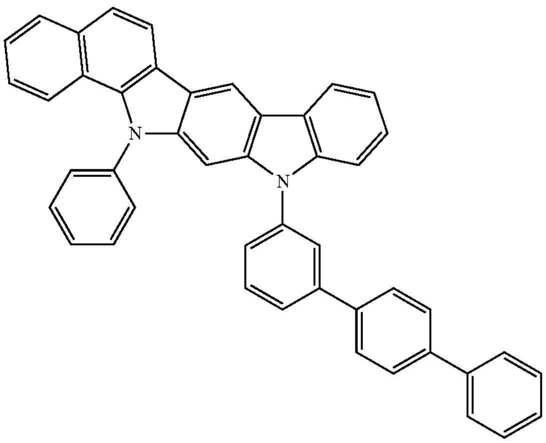
C1-82
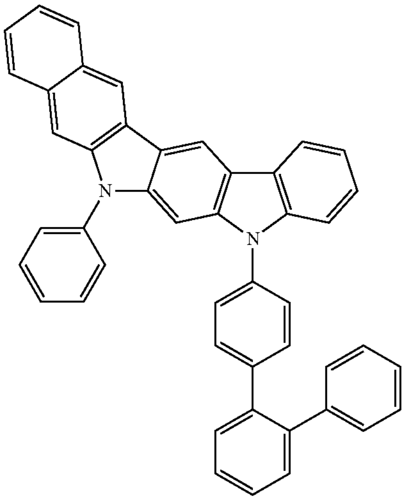
C1-83
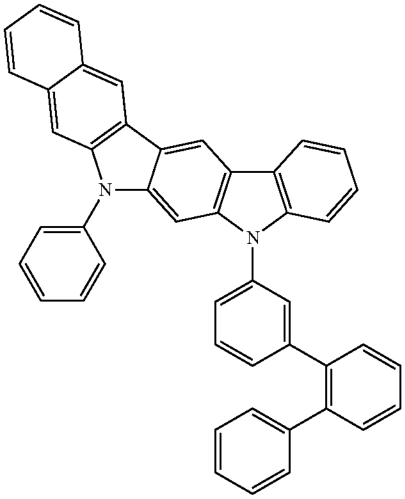
-continued
C1-84
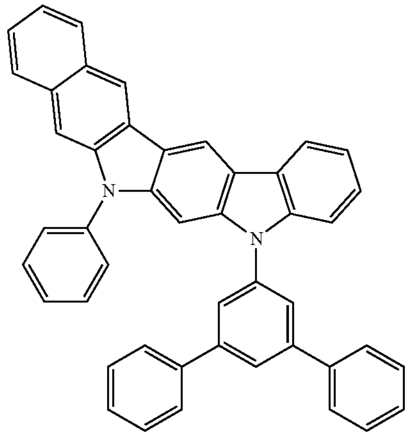
C1-85
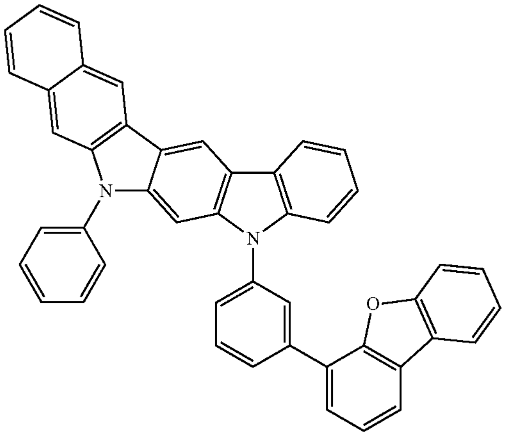
C1-86
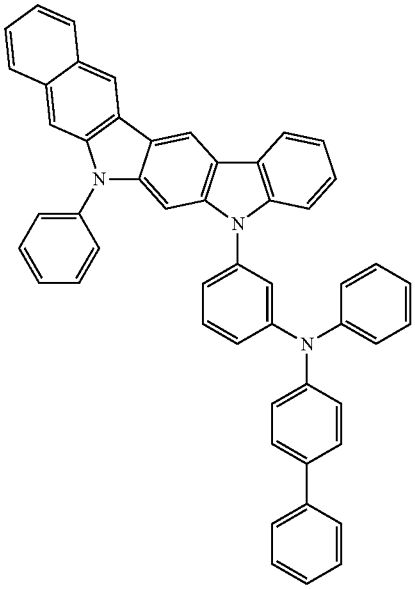

-continued
C1-87
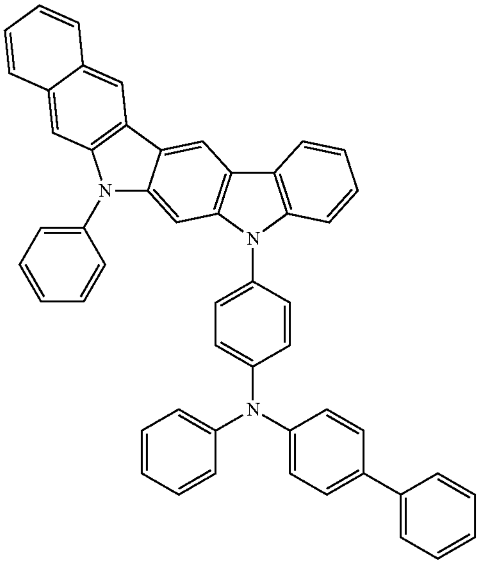
C1-88
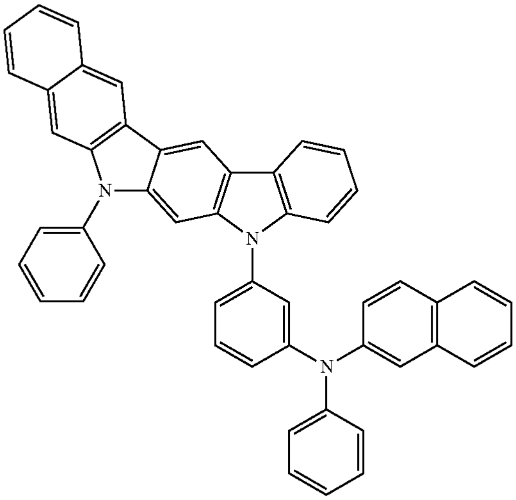
C1-89
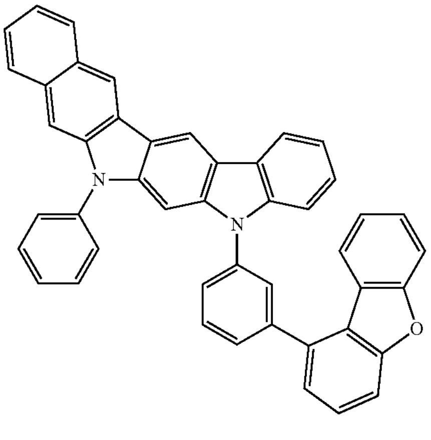
-continued
C1-90
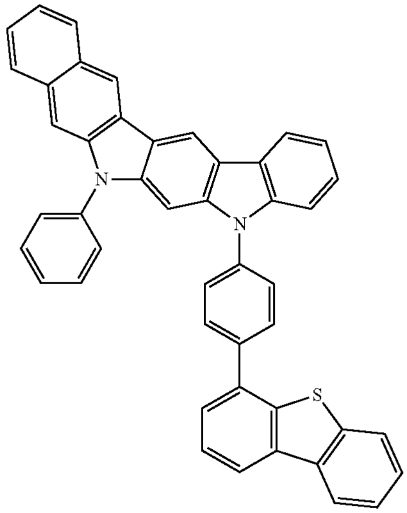
C1-91
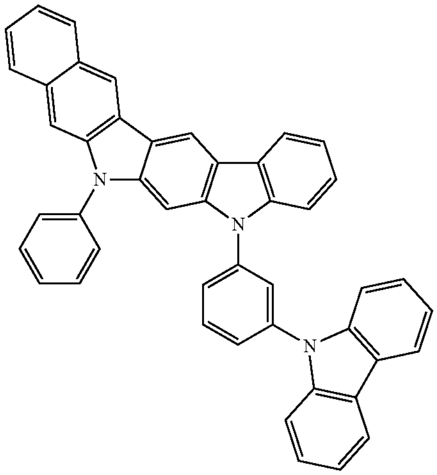
C1-92
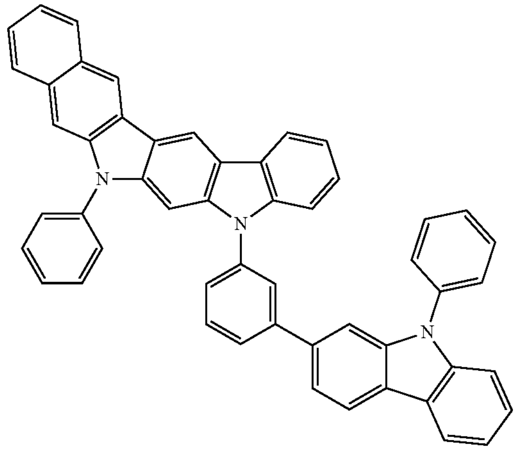

-continued
C1-93
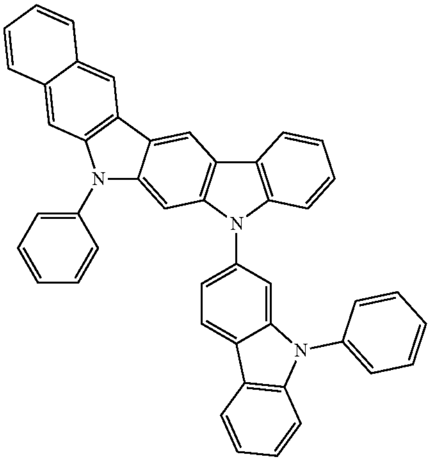
C1-94
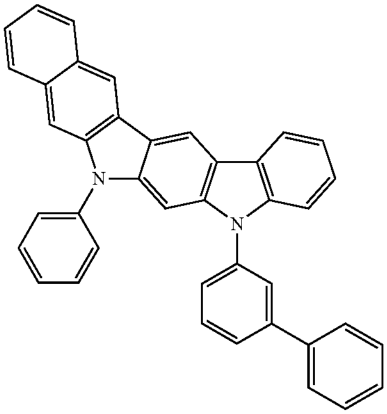
C1-95
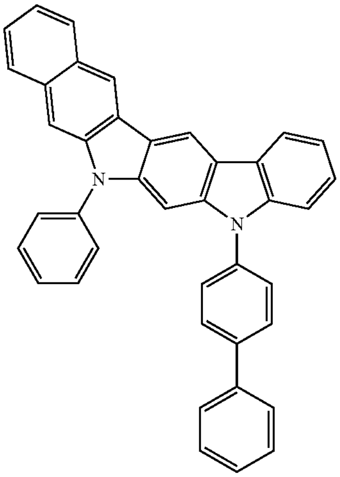
-continued
C1-96
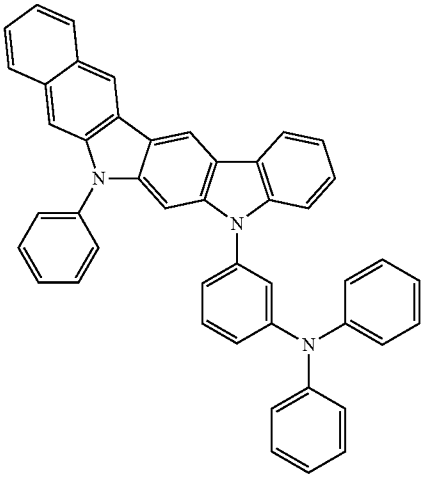
C1-97
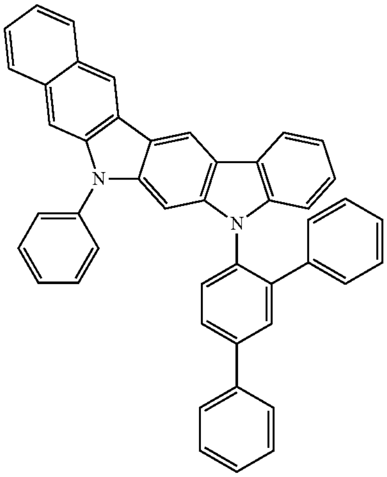
C1-98
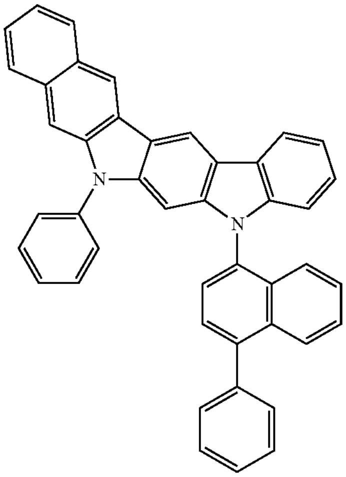

-continued
C1-99
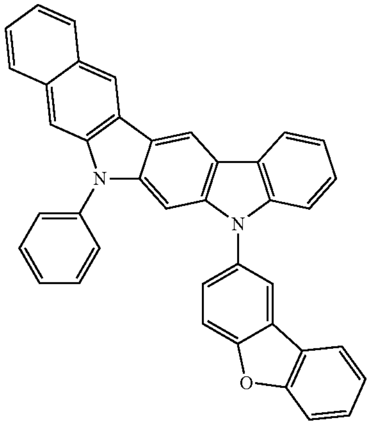
C1-100
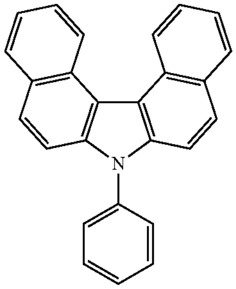
C1-101
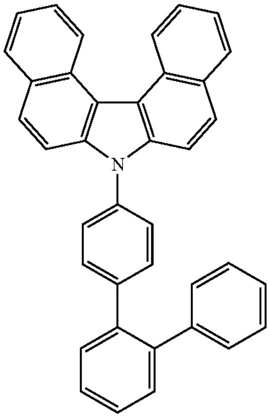
C1-102
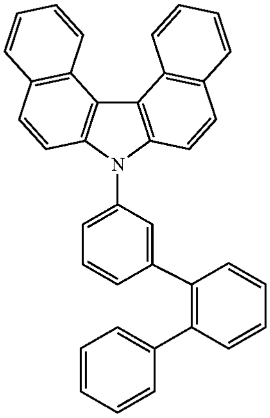
-continued
C1-103
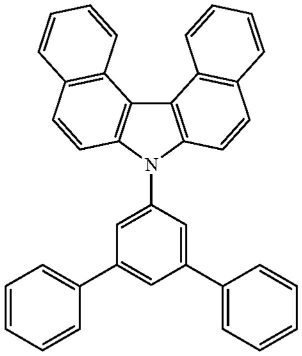
C1-104
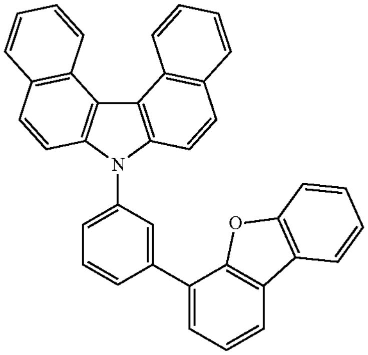
C1-105
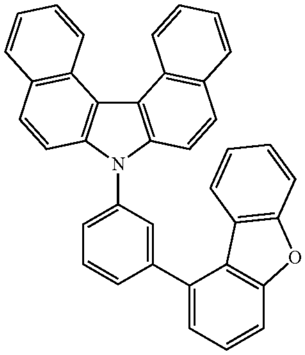
C1-106
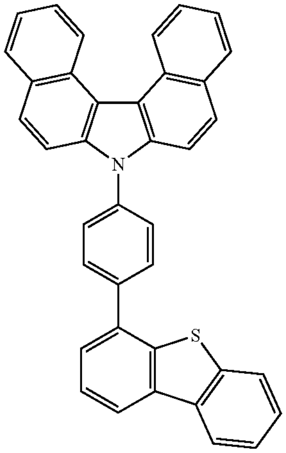

-continued
C1-107
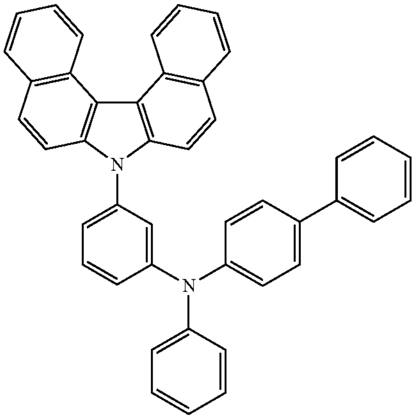
C1-108
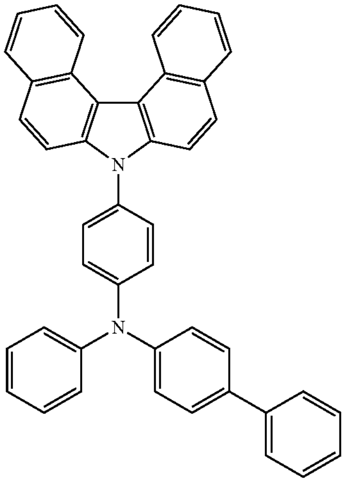
C1-109
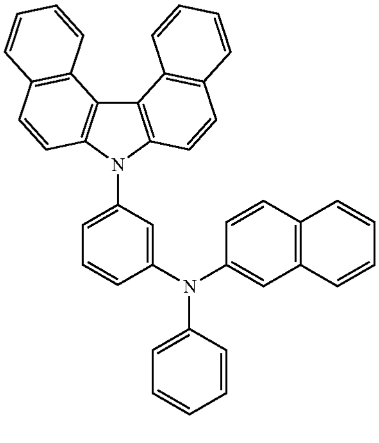
-continued
C1-110
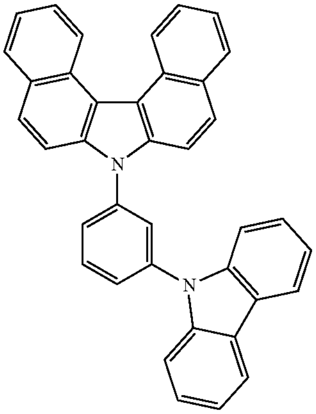
C1-111
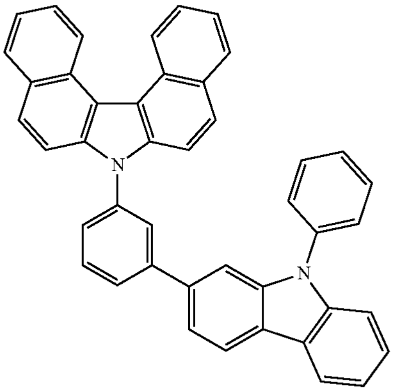
C1-112
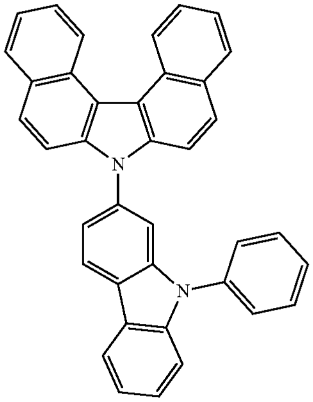

-continued
C1-113
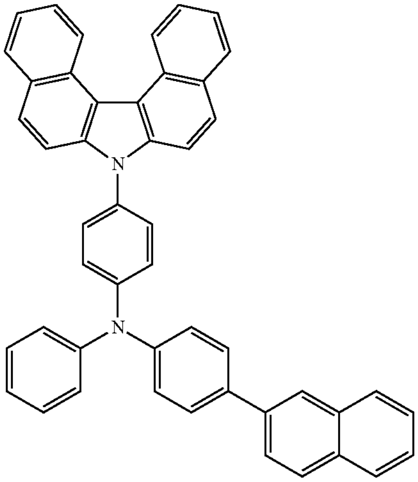
C1-114
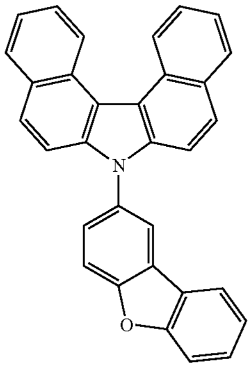
C1-115
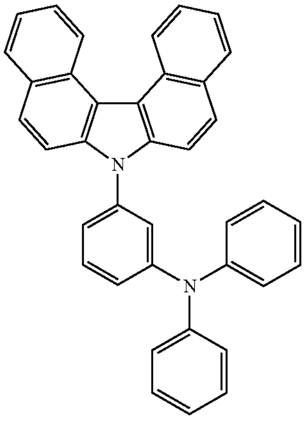
-continued
C1-116
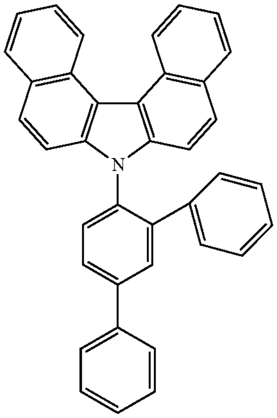
C1-117
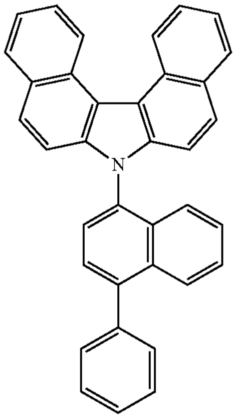
C1-118
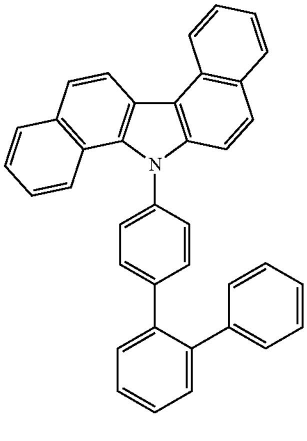
C1-119
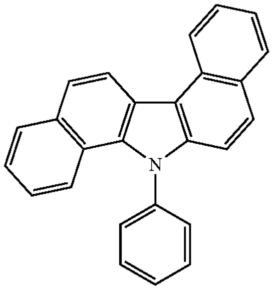

-continued
C1-120
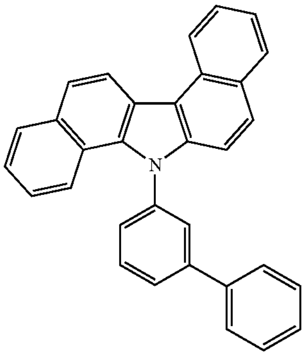
C1-121
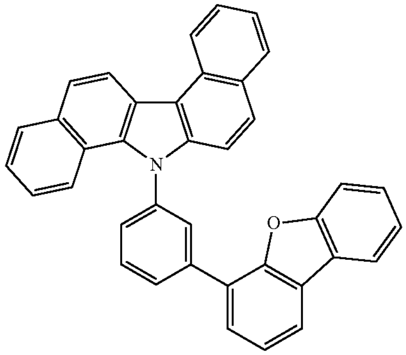
C1-122
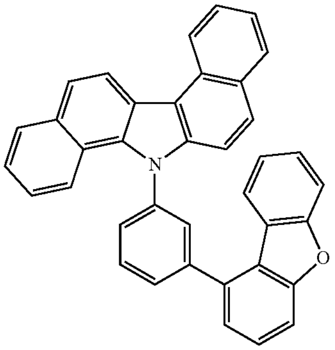
C1-123
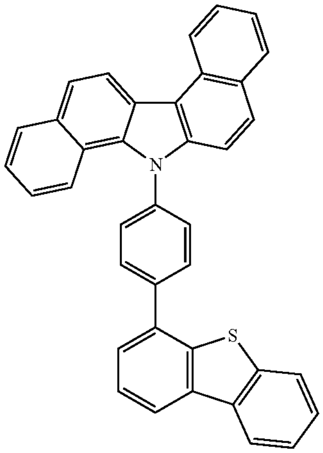
-continued
C1-124
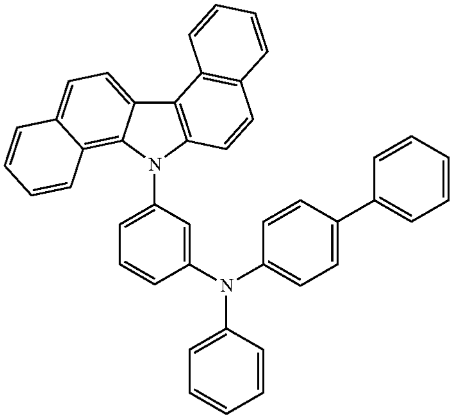
C1-125
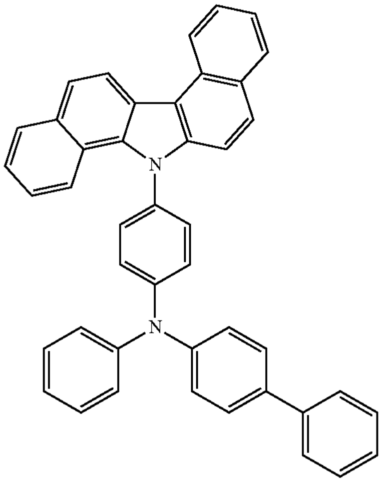
C1-126
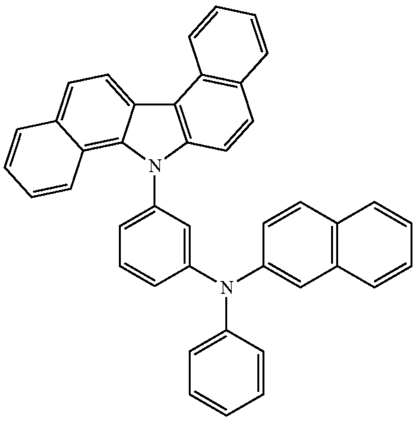

-continued
C1-127
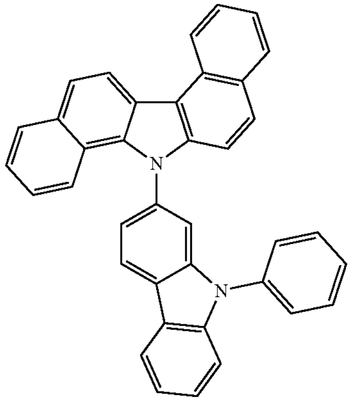
C1-128
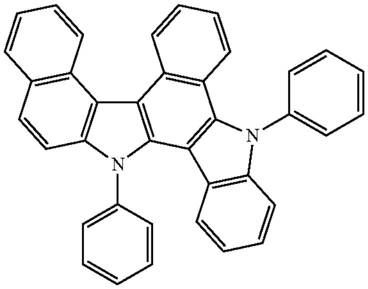
C1-129
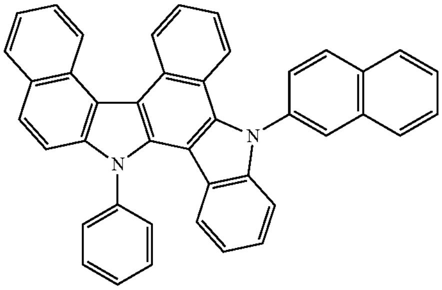
C1-130
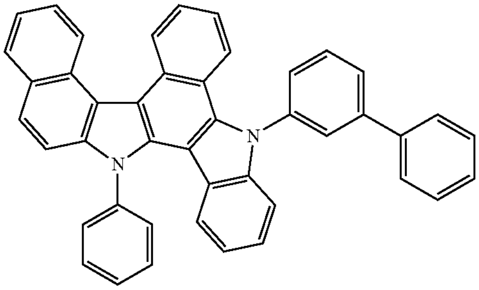
-continued
C1-131
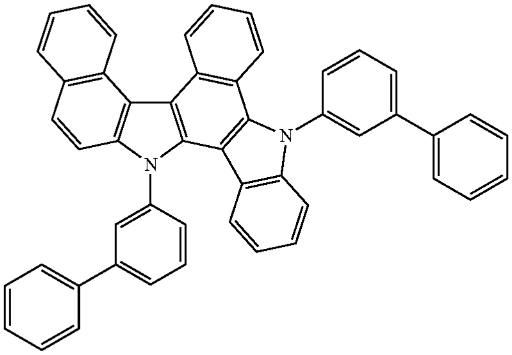
C1-132
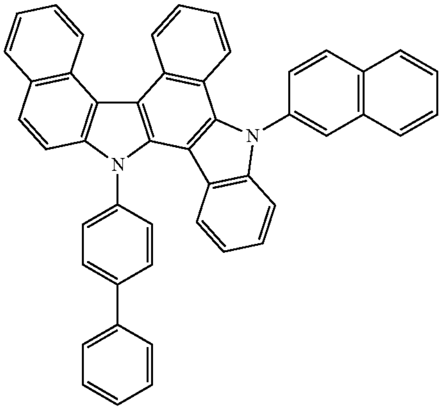
C1-133
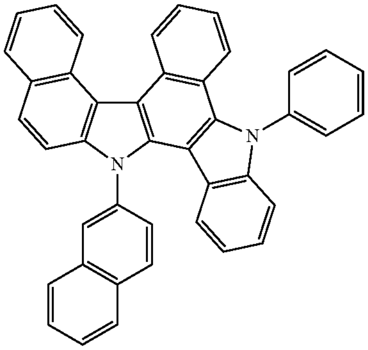
C1-134
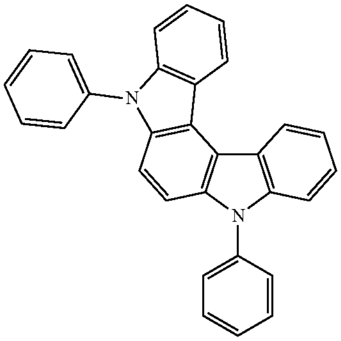

-continued
C1-135
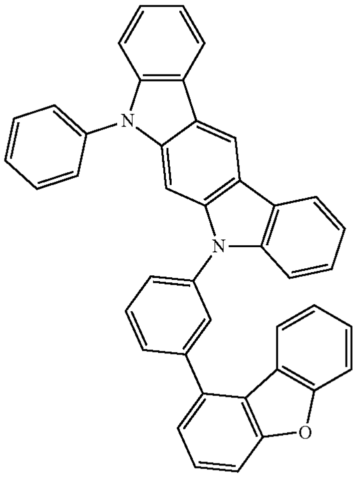
C1-136
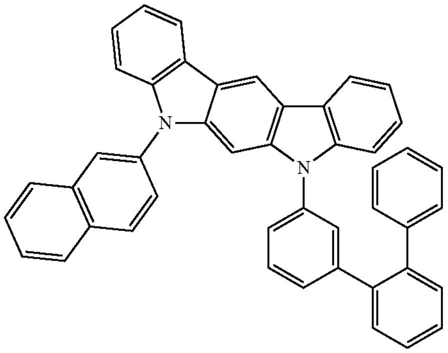
C1-137
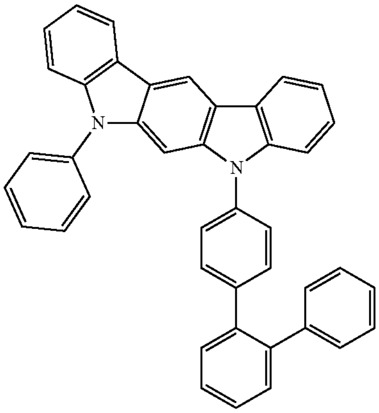
C1-138
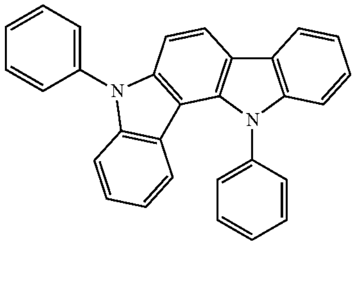
-continued
C1-139
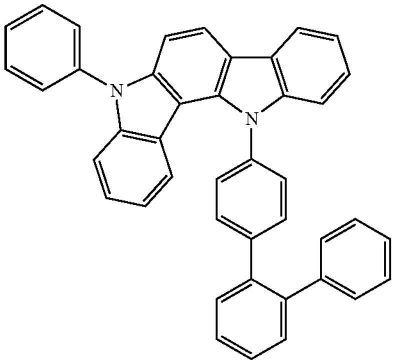
C1-140
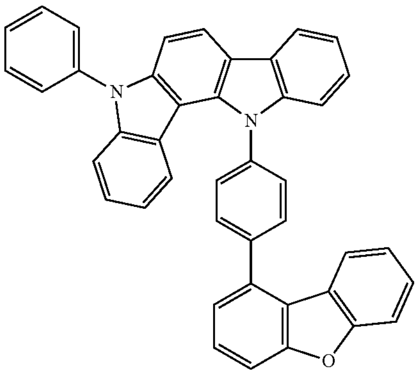
C1-141
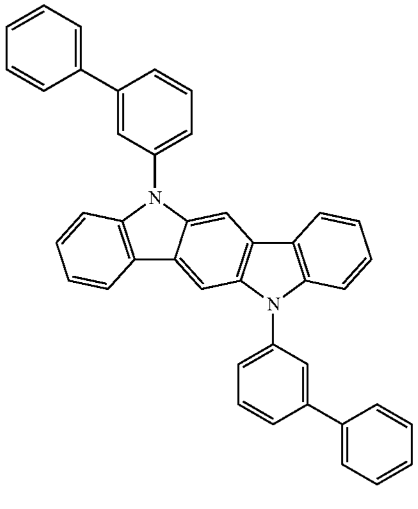

-continued
C1-142
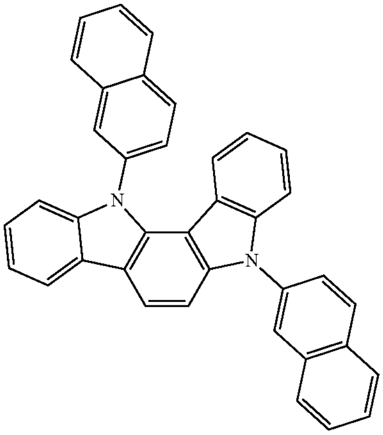
C1-143
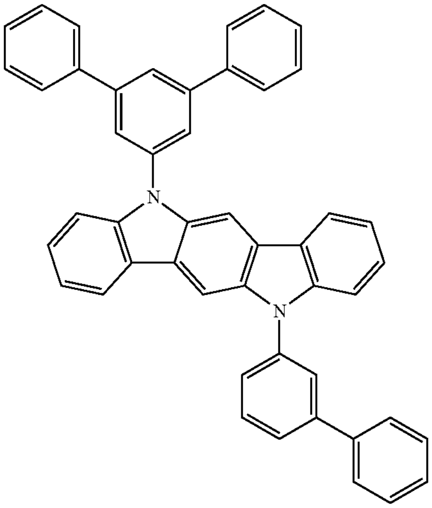
C1-144
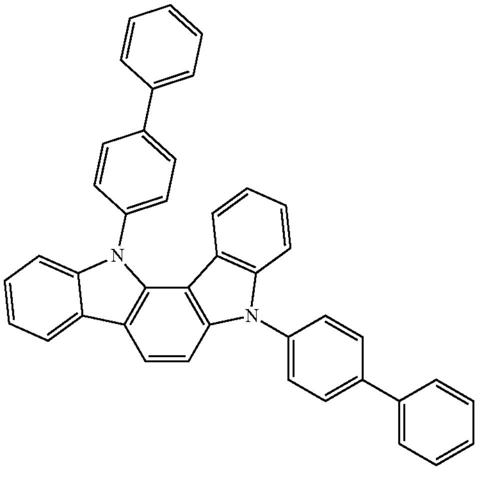
-continued
C1-145
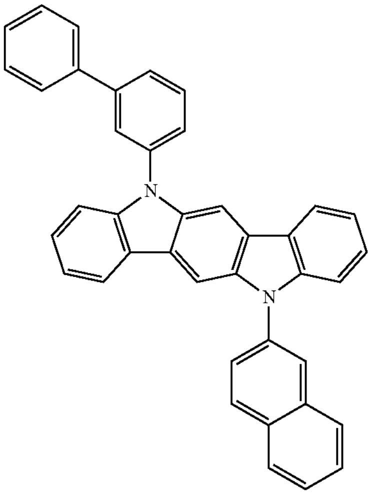
The compound represented by formula 2 may be illustrated by the following compounds, but is not limited thereto.
C2-1
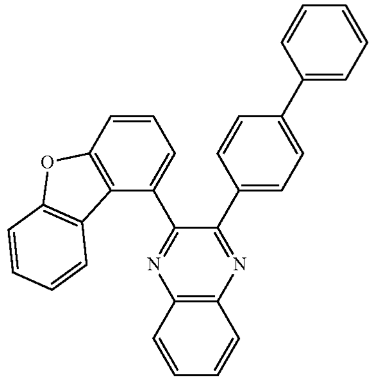
C2-2
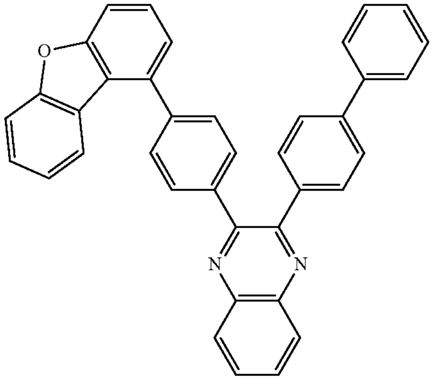

-continued
C2-3
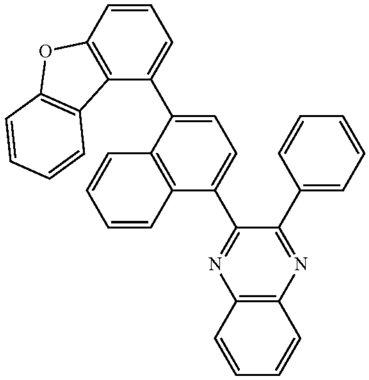
C2-4
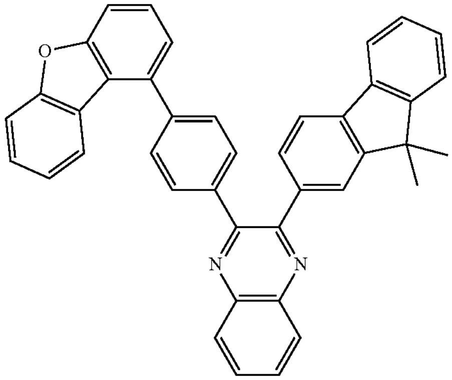
C2-5
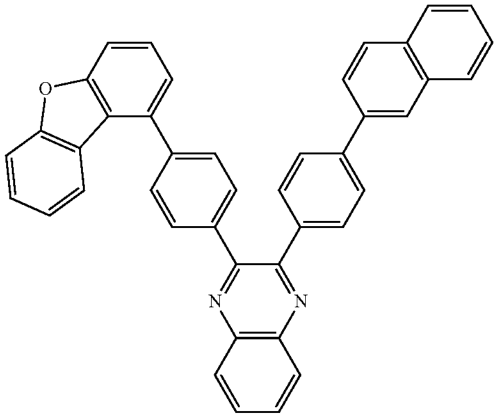
C2-6
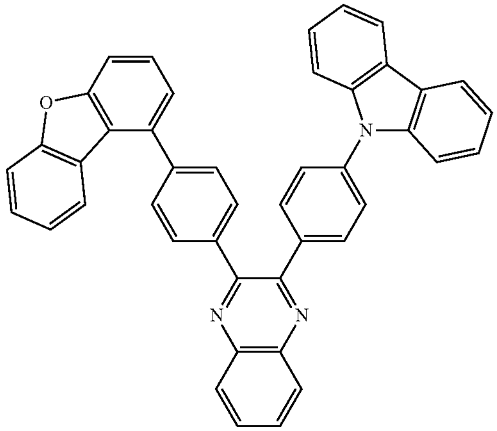
-continued
C2-7
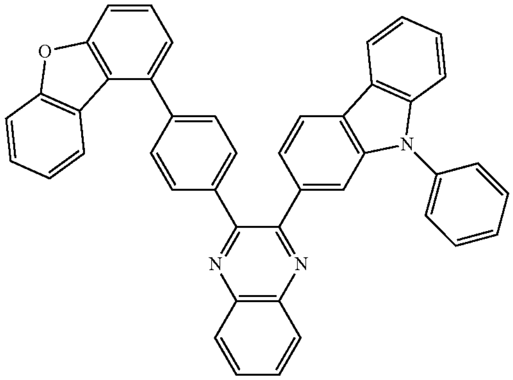
C2-8
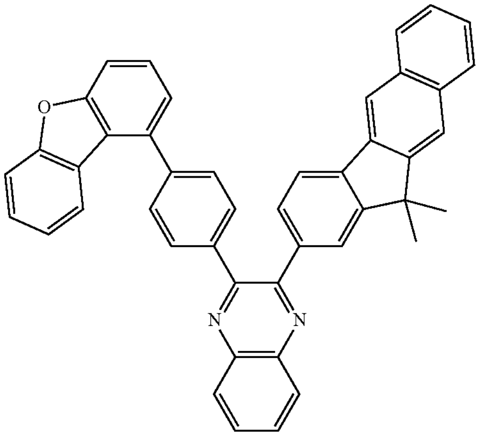
C2-9
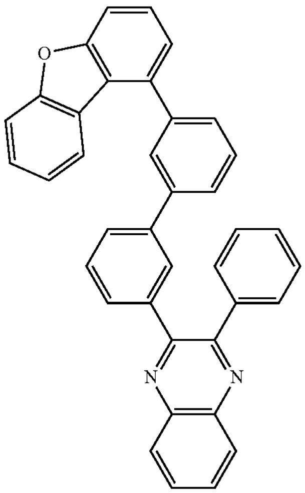

-continued
C2-10
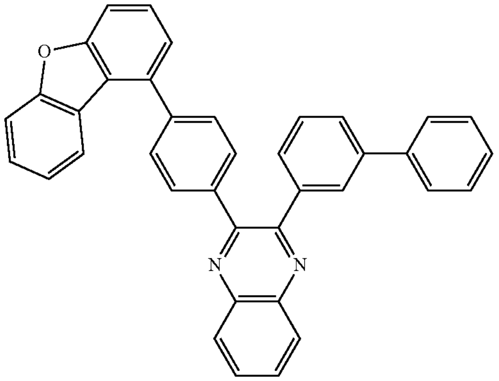
C2-11
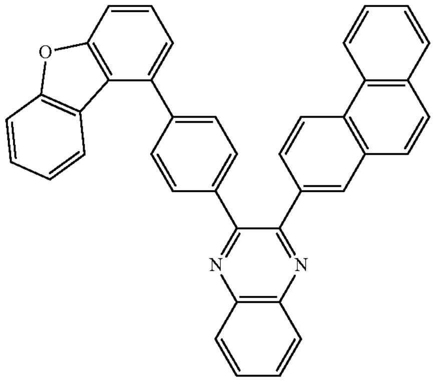
C2-12
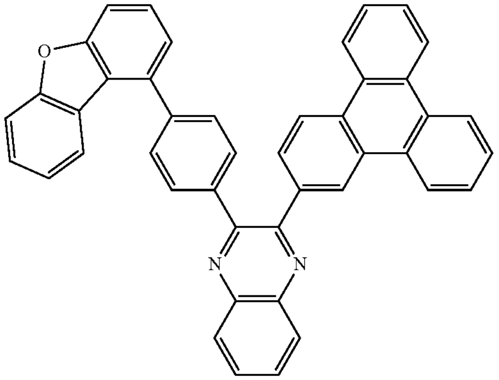
C2-13
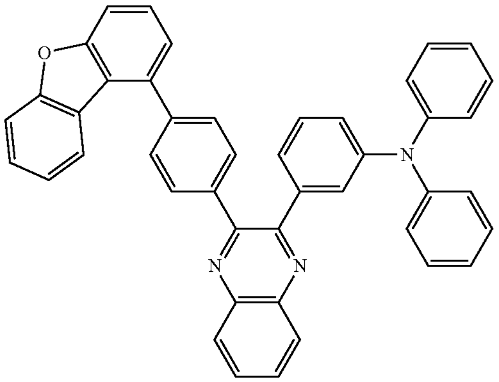
-continued
C2-14
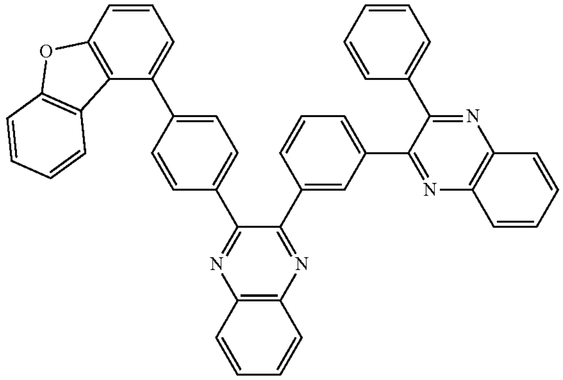
C2-15
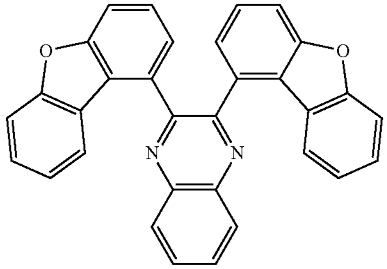
C2-16
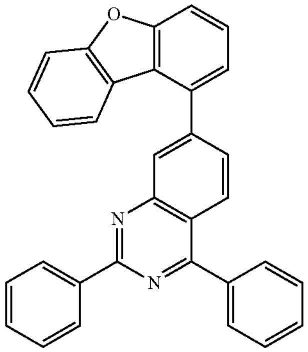
C2-17
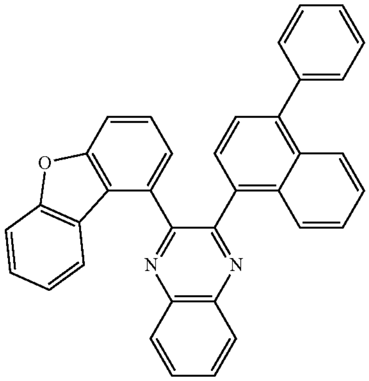

-continued
C2-18
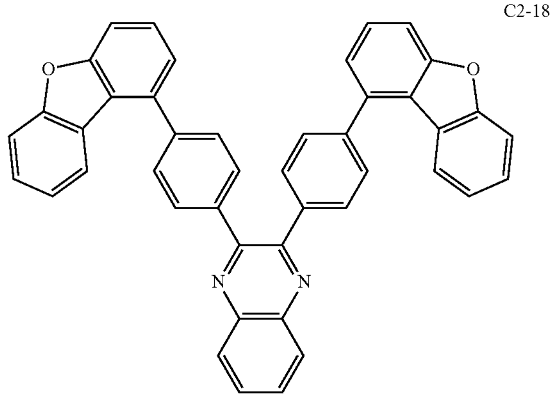
C2-19
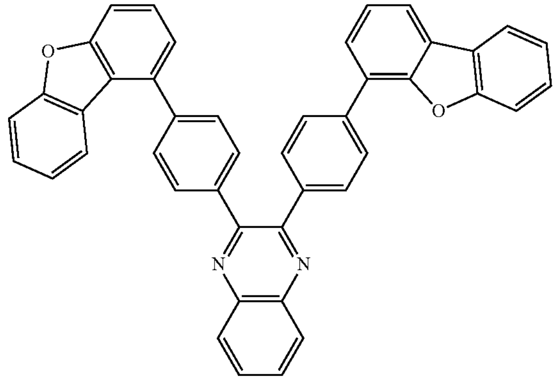
C2-20
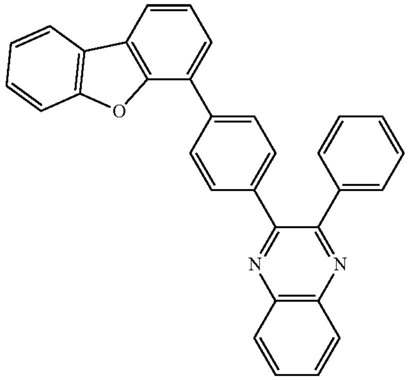
C2-21
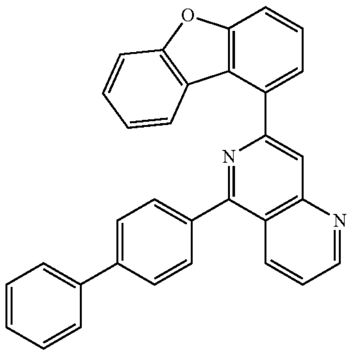
-continued
C2-22
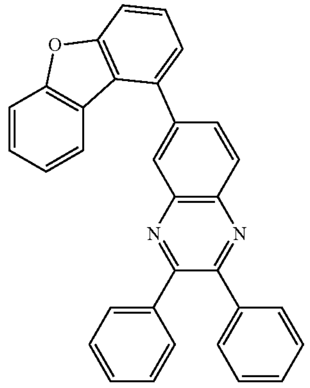
C2-23
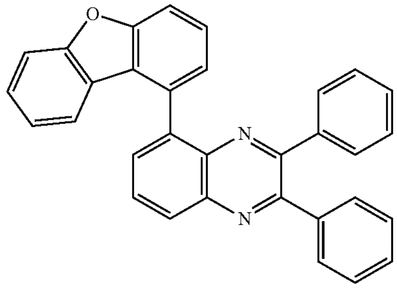
C2-24
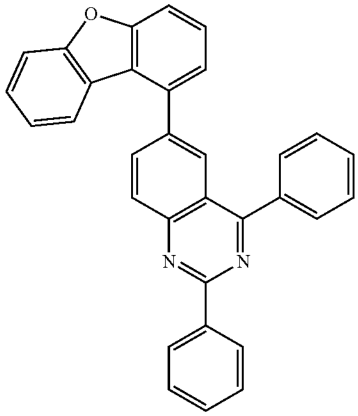
C2-25
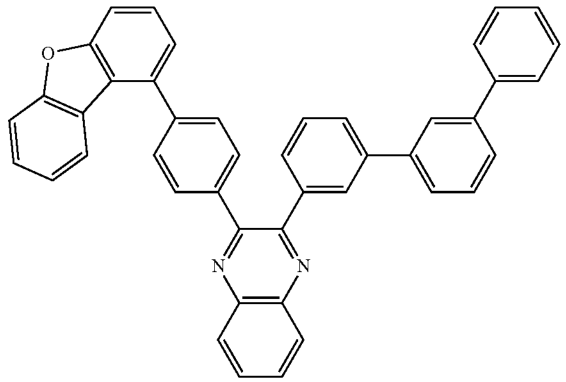

-continued
C2-26
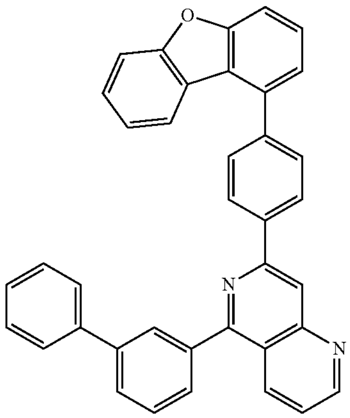
C2-27
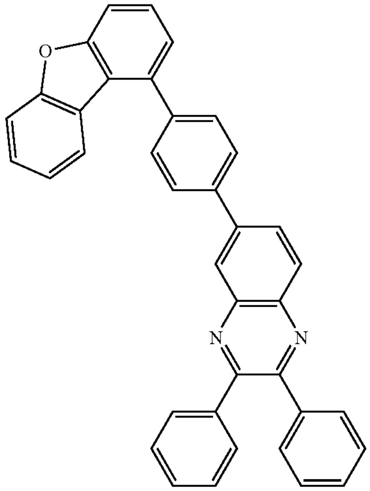
C2-28
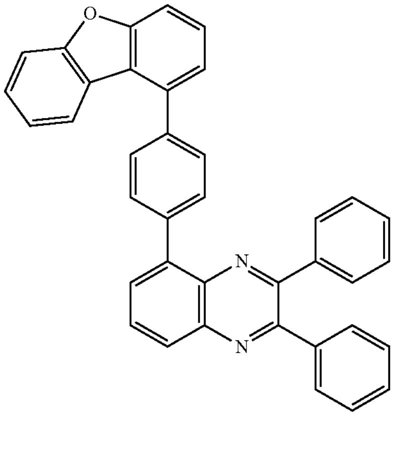
-continued
C2-29
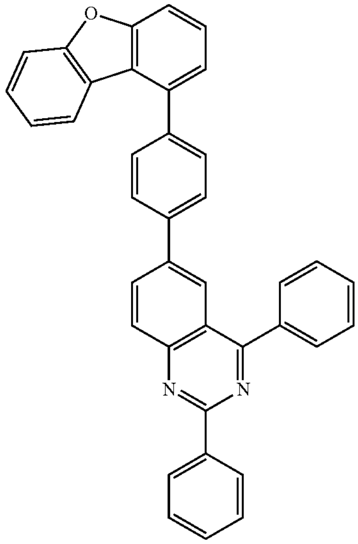
C2-30
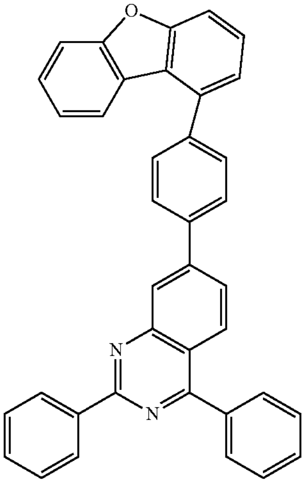
C2-31
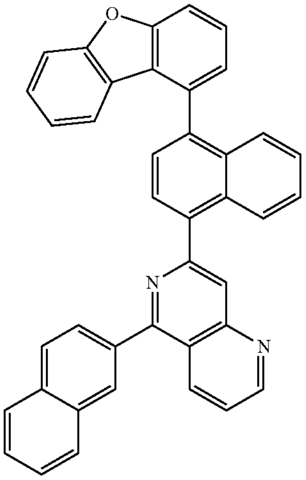

-continued
C2-32
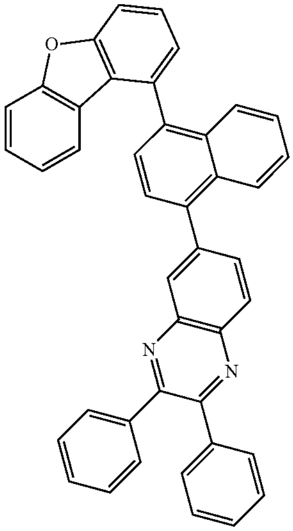
C2-33
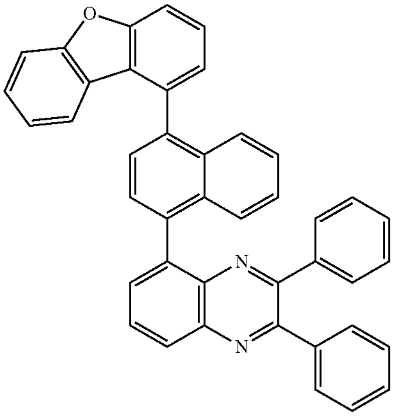
C2-34
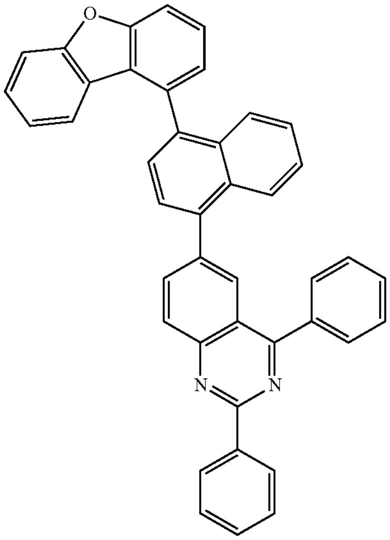
-continued
C2-35
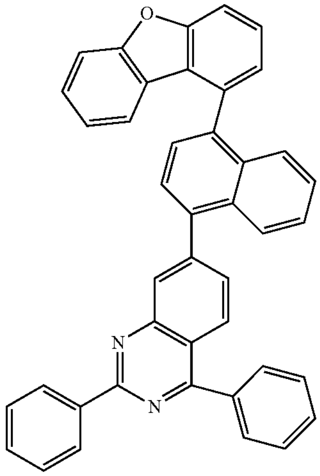
C2-36
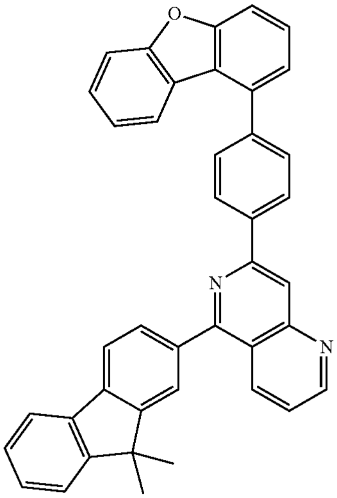
C2-37
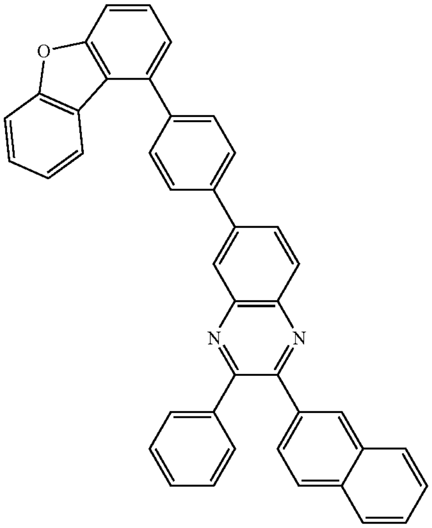

-continued
C2-38
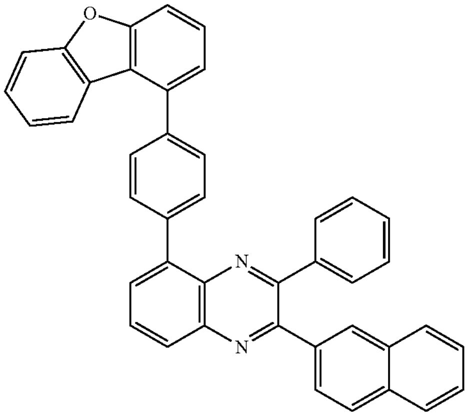
C2-39
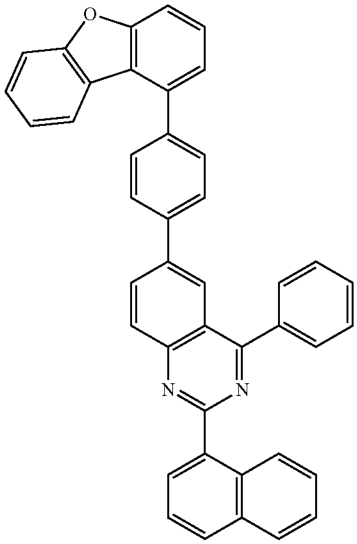
C2-40
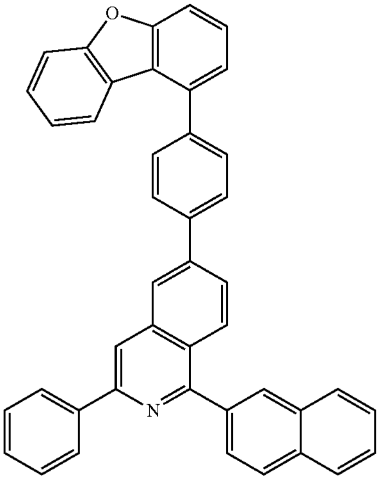
-continued
C2-41
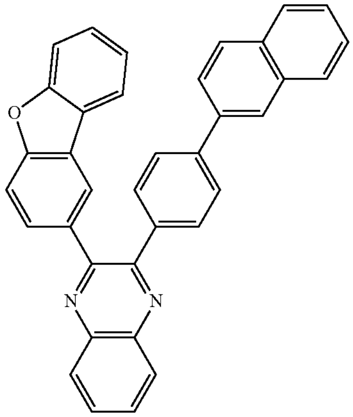
C2-42
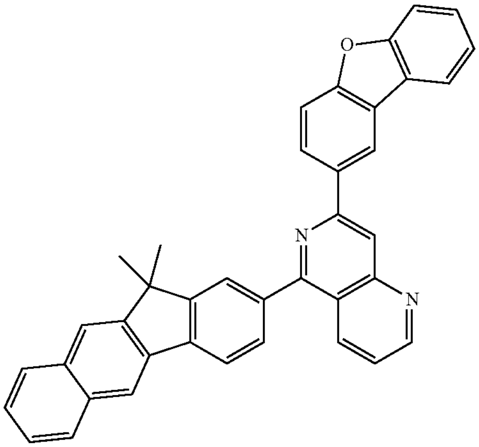
C2-43
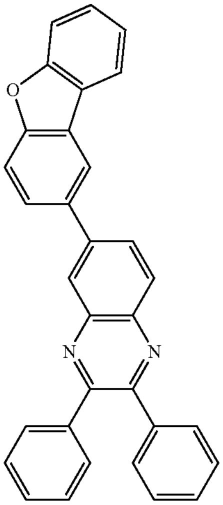

-continued
C2-44
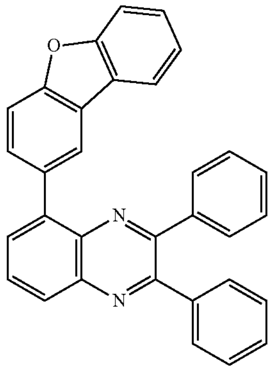
C2-45
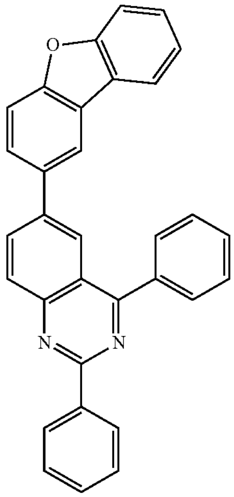
C2-46
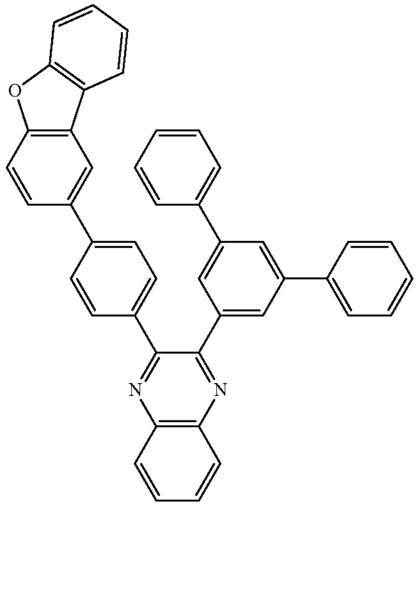
-continued
C2-47
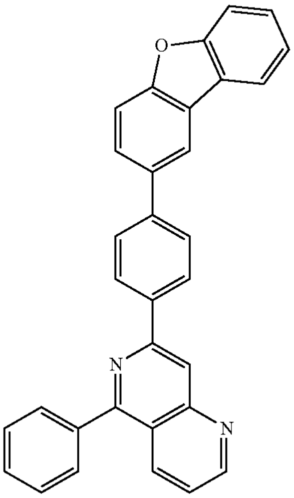
C2-48
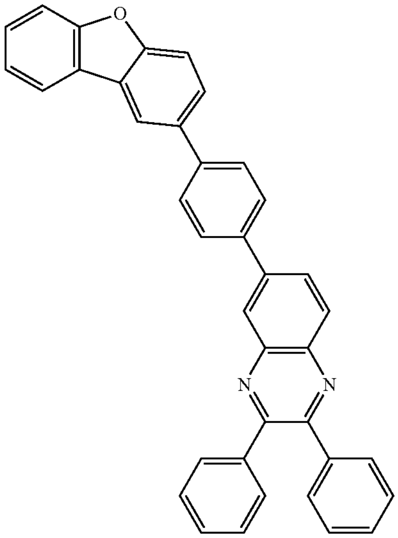
C2-49
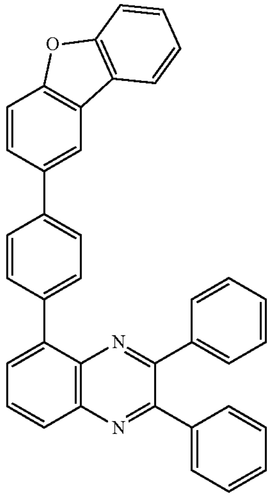

-continued
C2-50
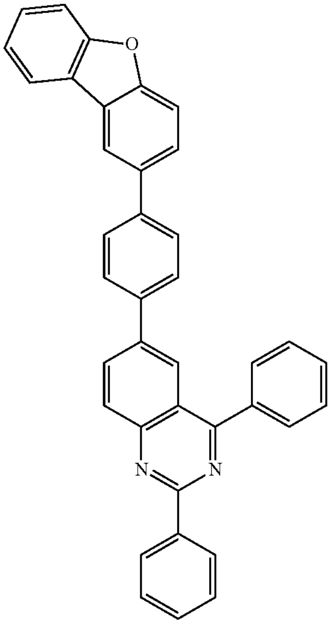
C2-51
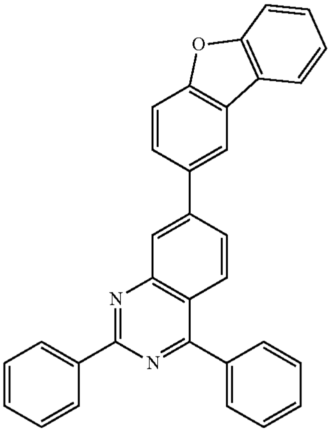
C2-52
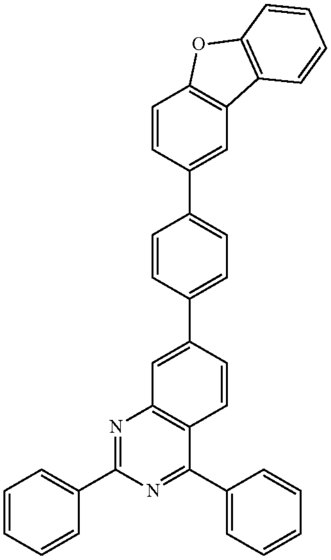
-continued
C2-53
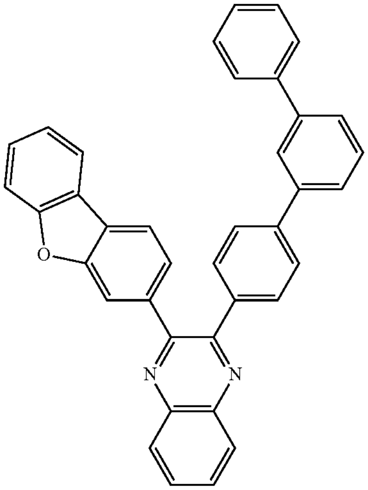
C2-54
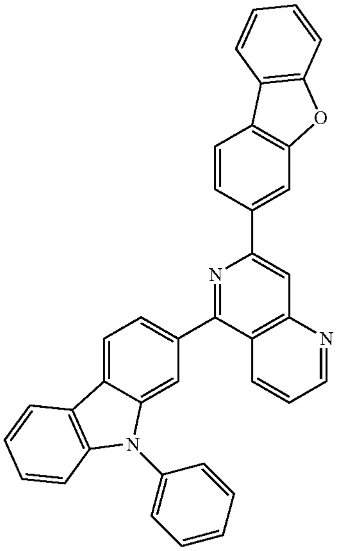
C2-55
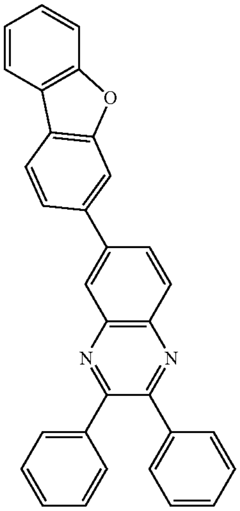

-continued
C2-56
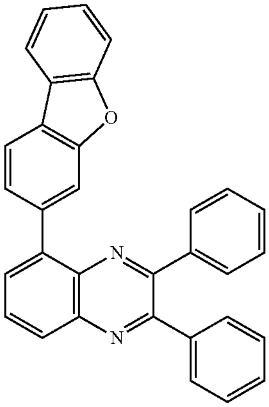
C2-57
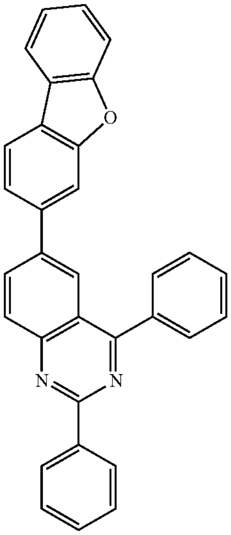
C2-58
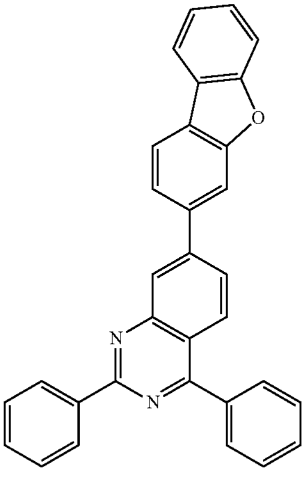
-continued
C2-59
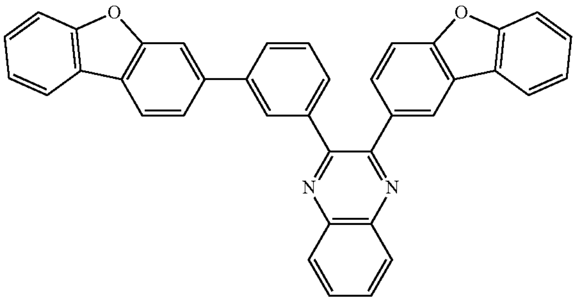
C2-60
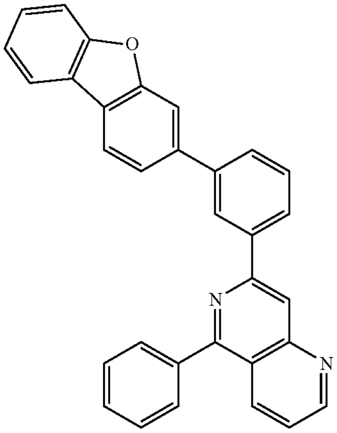
C2-61
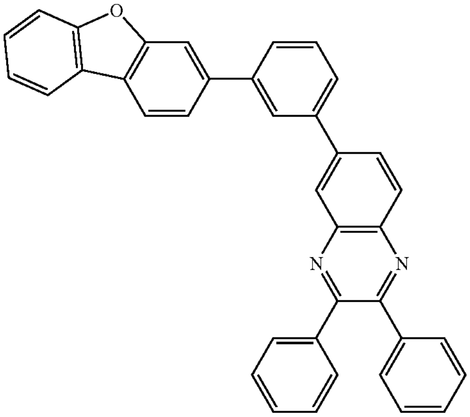
C2-62
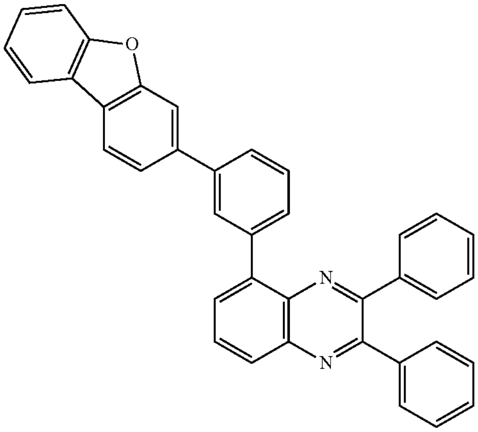

-continued
C2-63
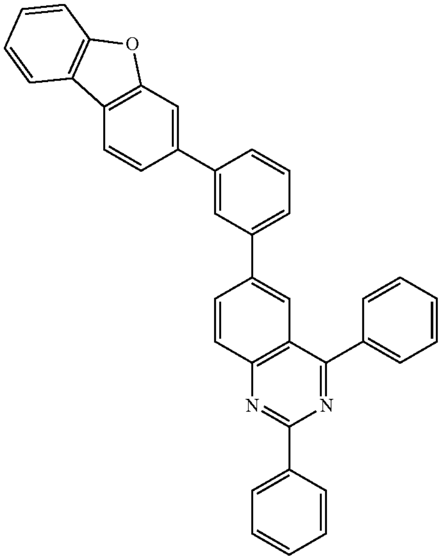
C2-64
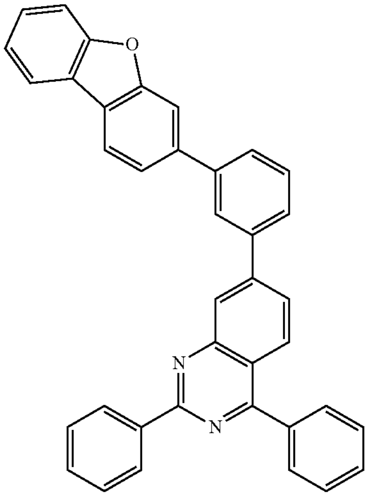
C2-65
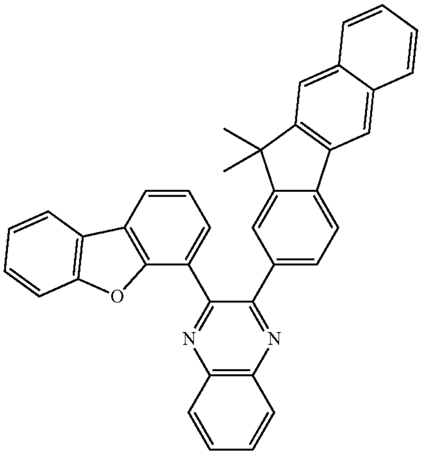
-continued
C2-66
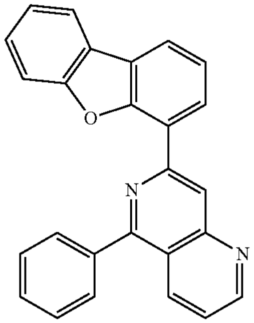
C2-67
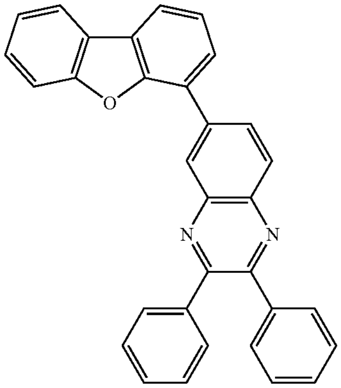
C2-68
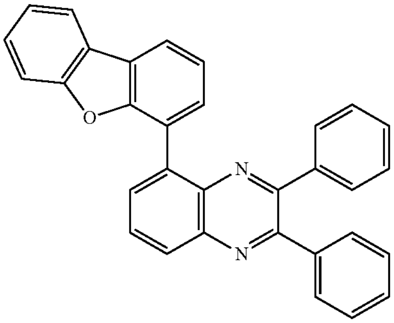
C2-69
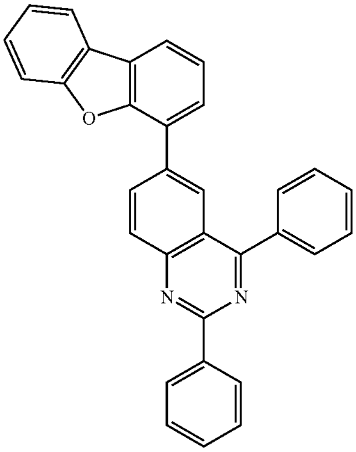

-continued
C2-70
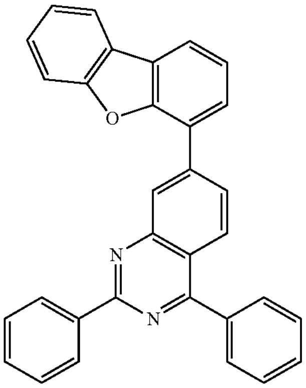
C2-71
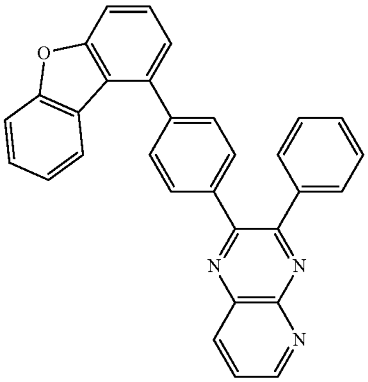
C2-72
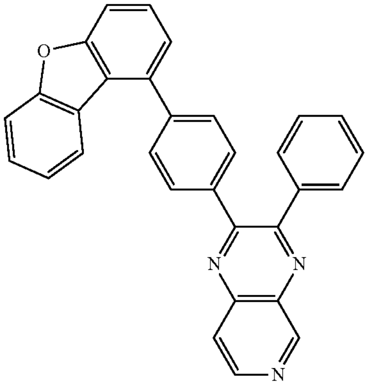
C2-73
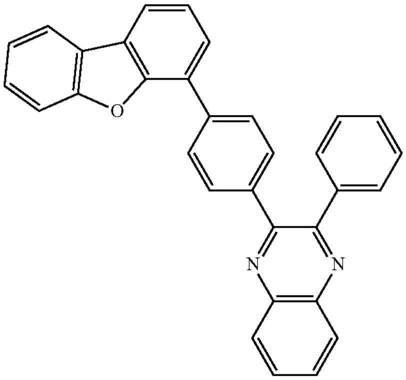
-continued
C2-74
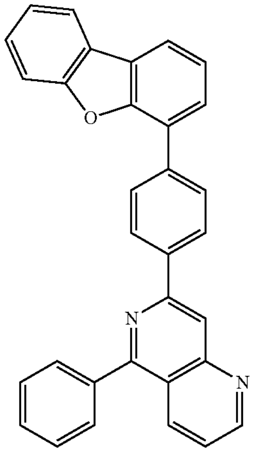
C2-75
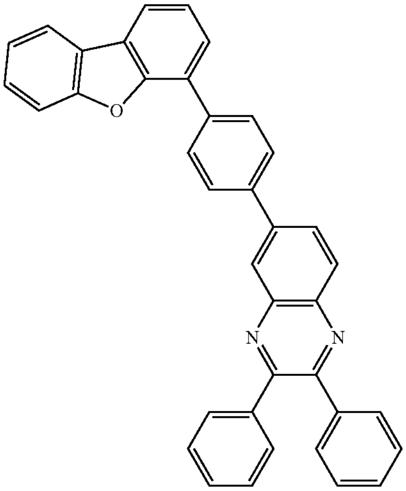
C2-76
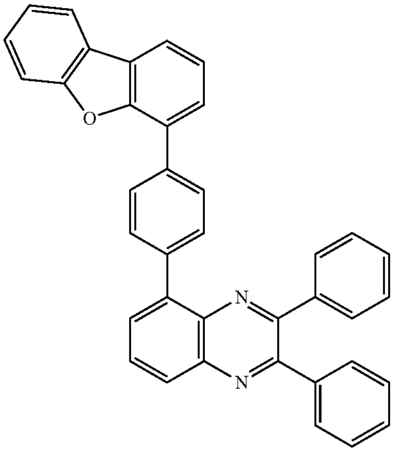

-continued
C2-77
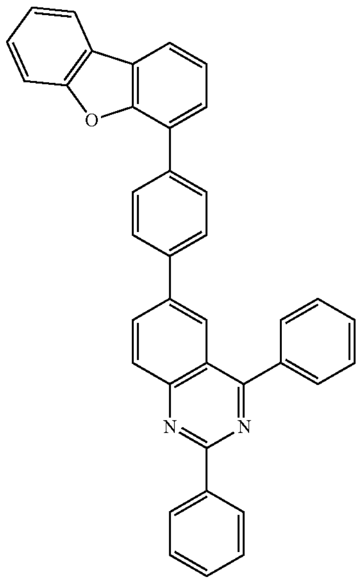
C2-78
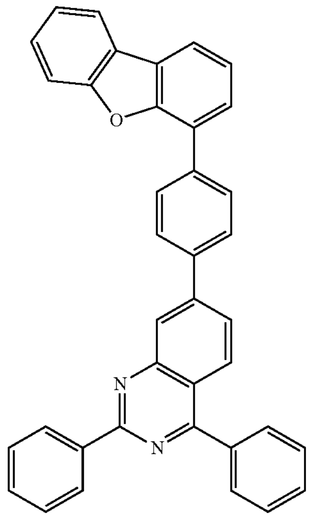
C2-79
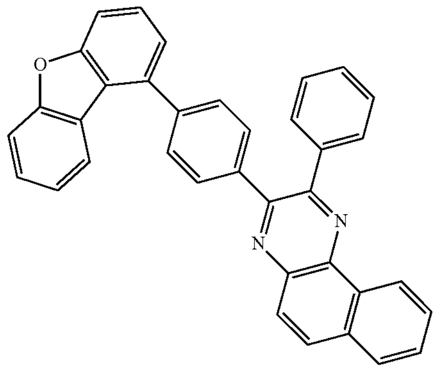
-continued
C2-80
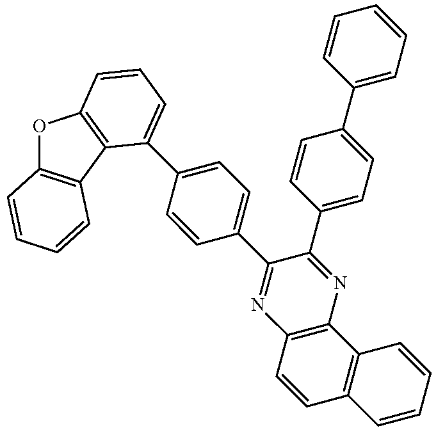
C2-81
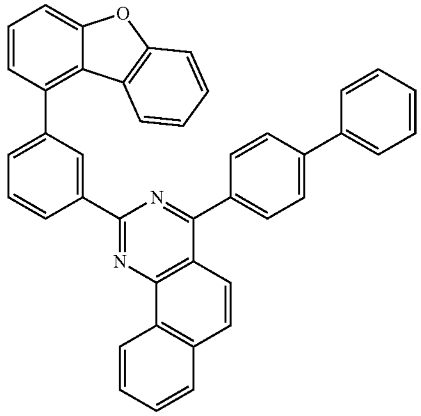
C2-82
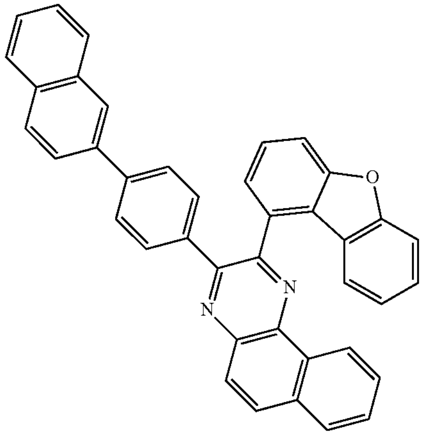

-continued
C2-83
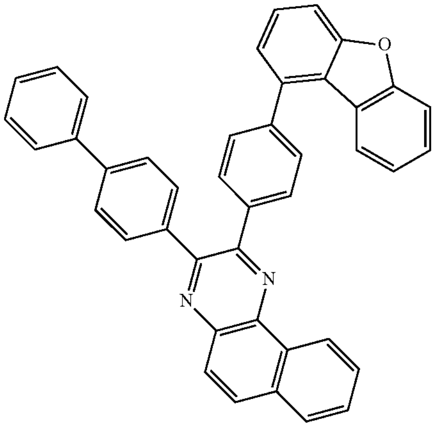
C2-84
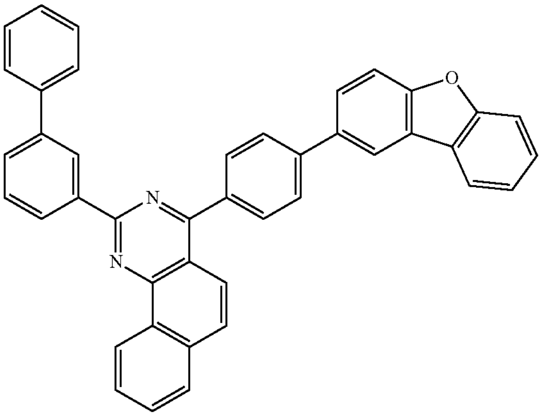
C2-85
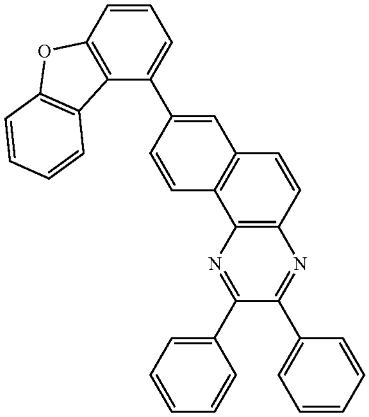
-continued
C2-86
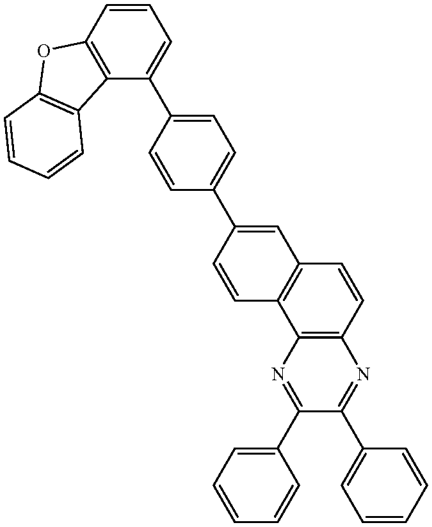
C2-87
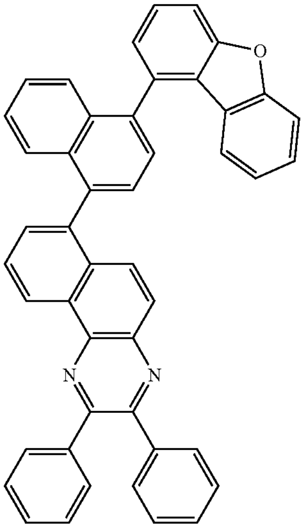
C2-88
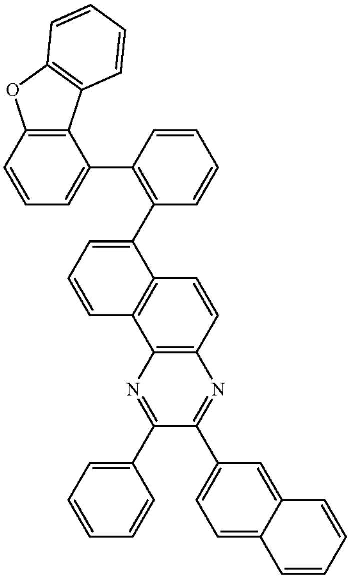

-continued
C2-89
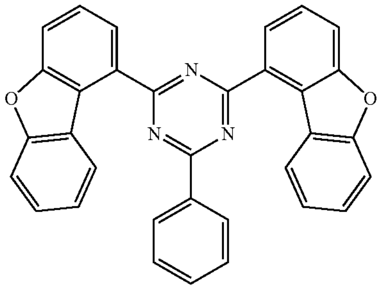
C2-90
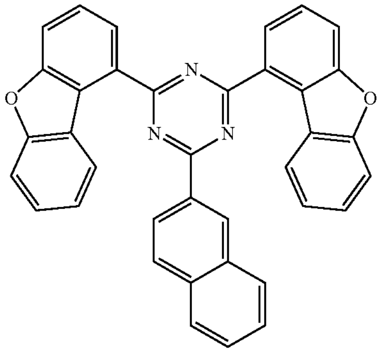
C2-91
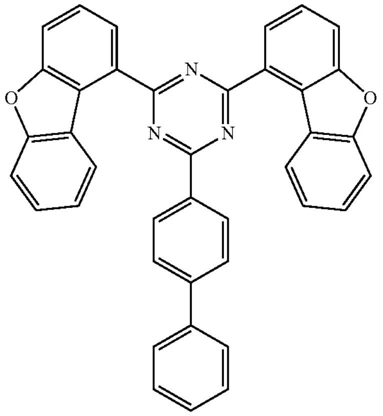
C2-92
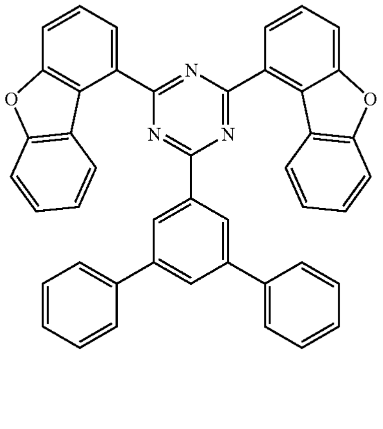
-continued
C2-93
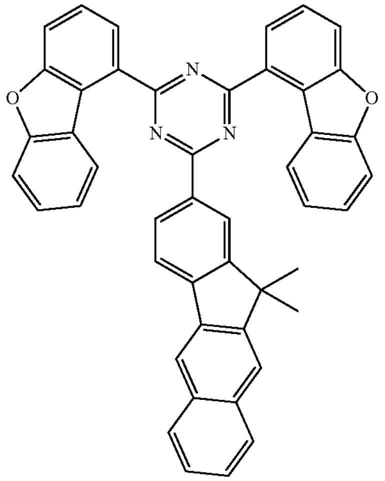
C2-94
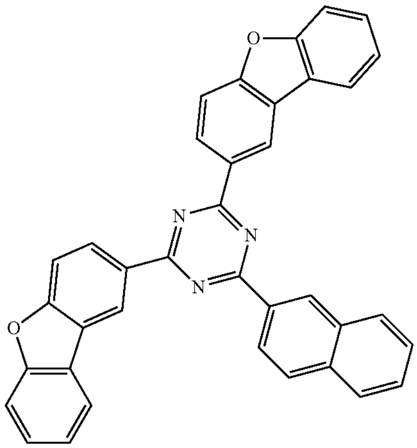
C2-95
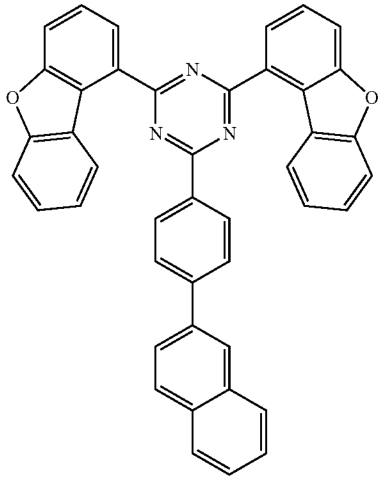

C2-96
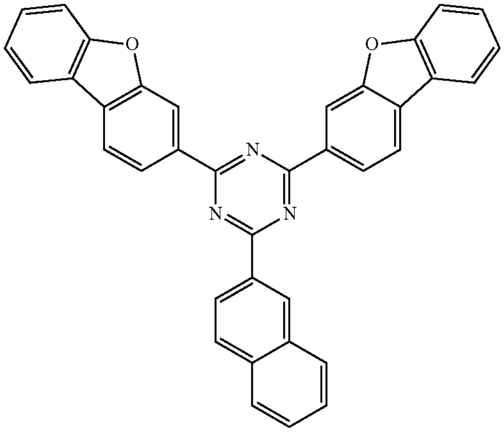
C2-97
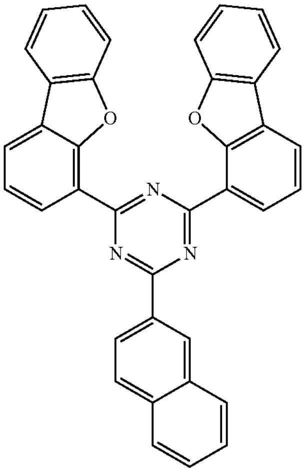
C2-98
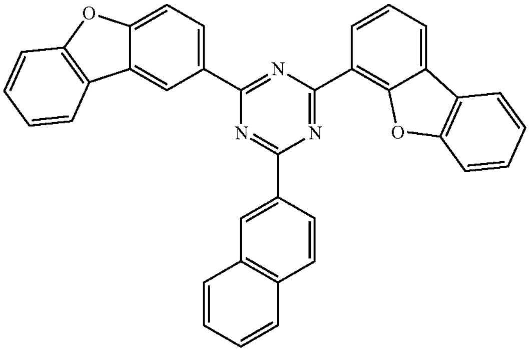
C2-99
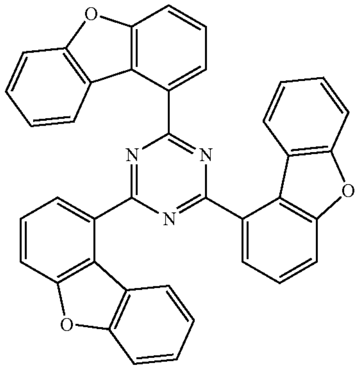
C2-100
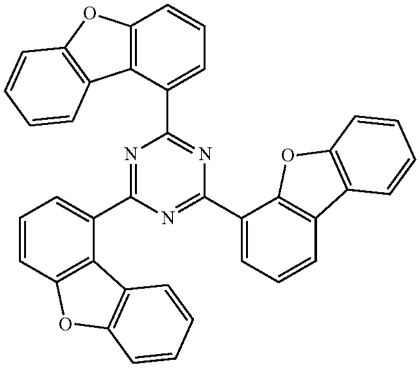
C2-101
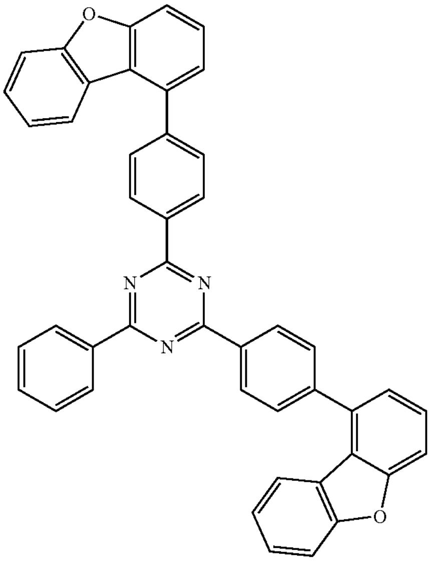

-continued
C2-102
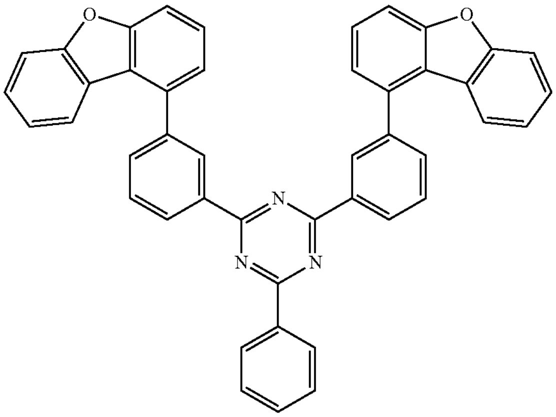
C2-103
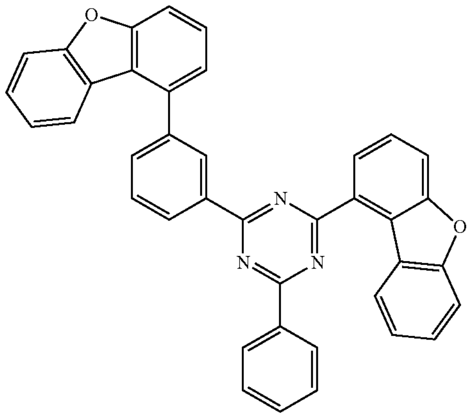
C2-104
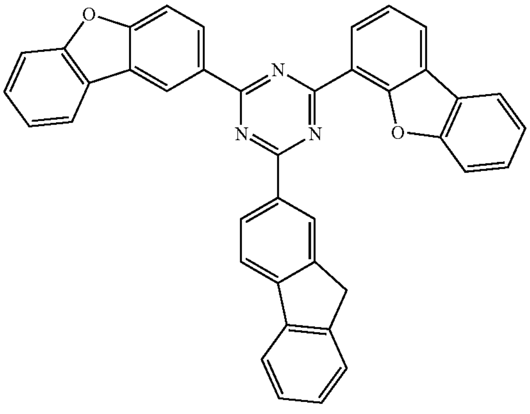
-continued
C2-105
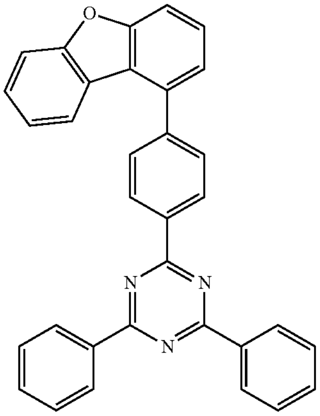
C2-106
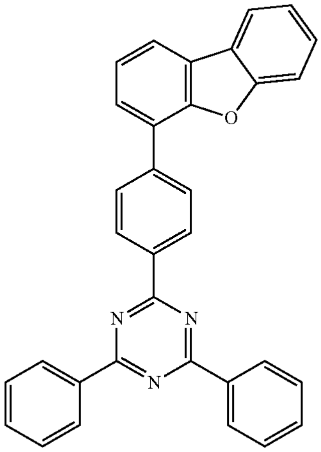
C2-107
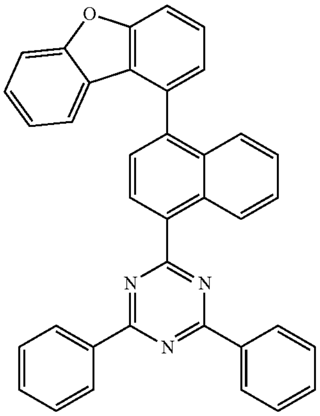

-continued
C2-108
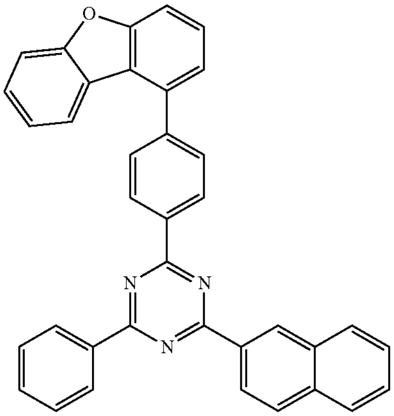
C2-109
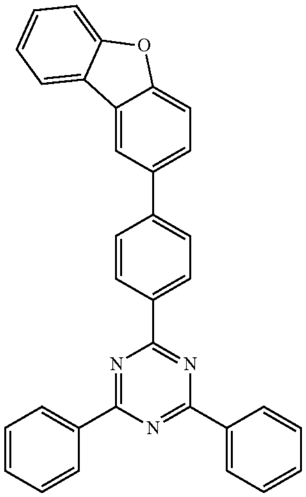
C2-110
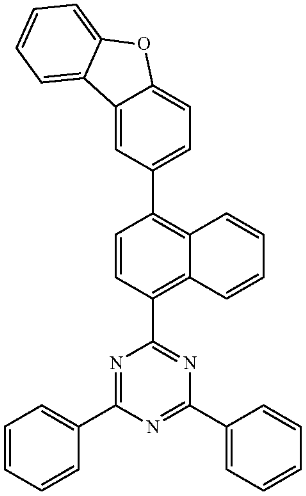
-continued
C2-111
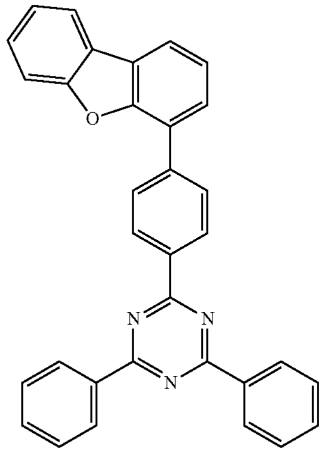
C2-112
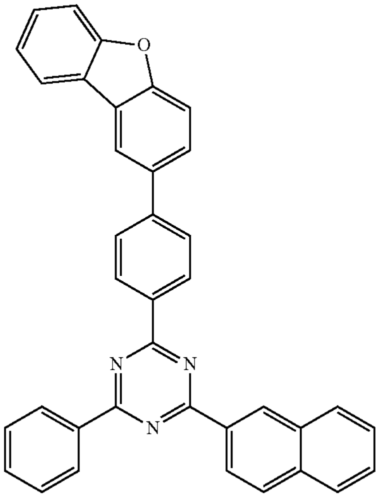
C2-113
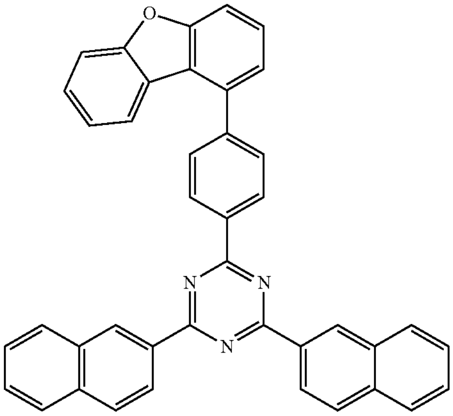

-continued
C2-114
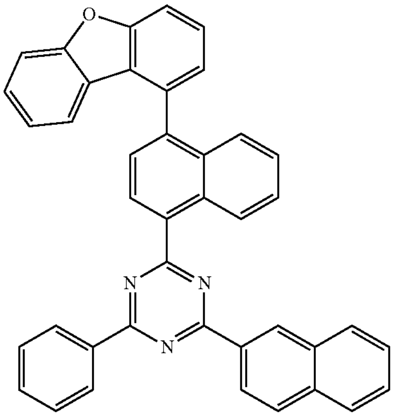
C2-115
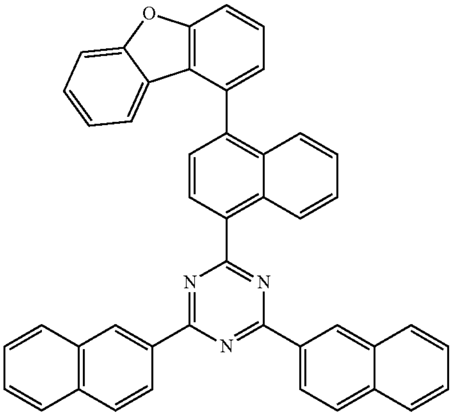
C2-116
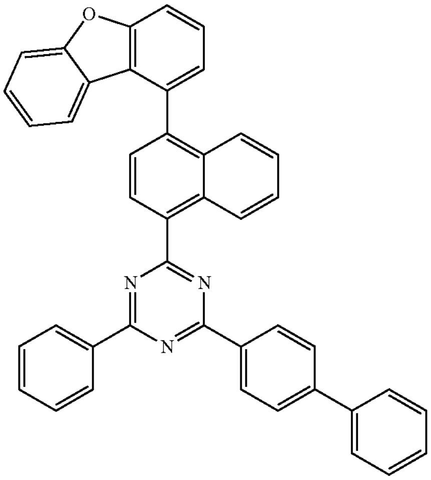
-continued
C2-117
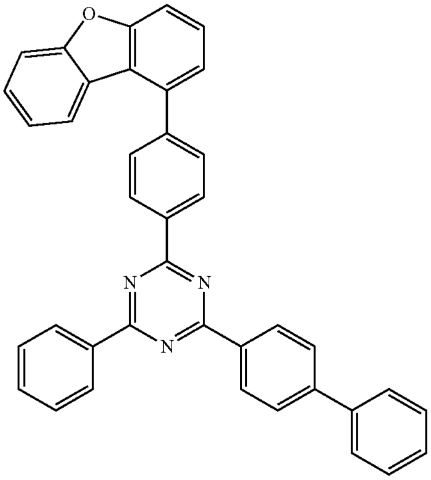
C2-118
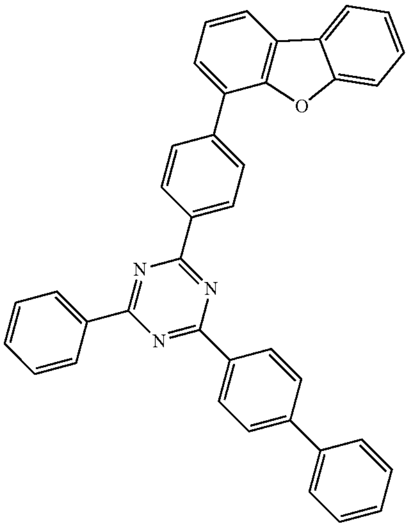
C2-119
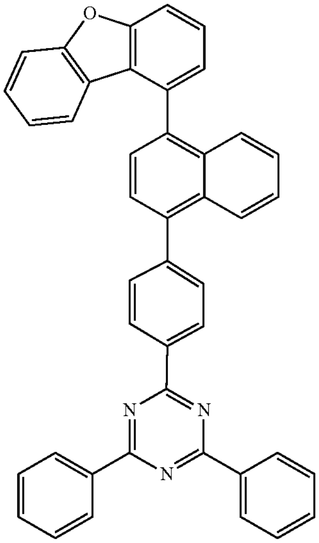

-continued
C2-120
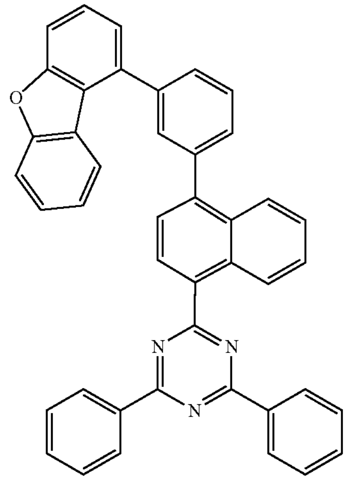
C2-121
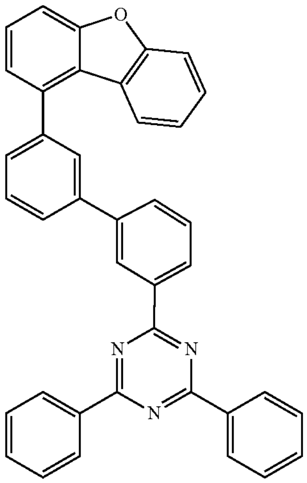
C2-122
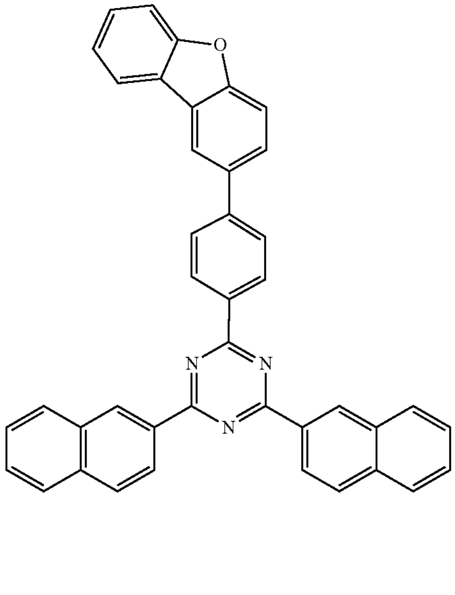
-continued
C2-123
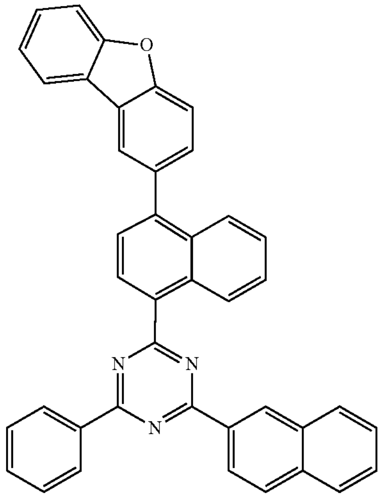
C2-124
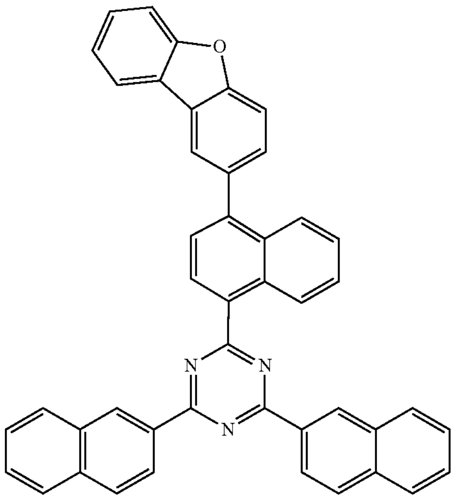
C2-125
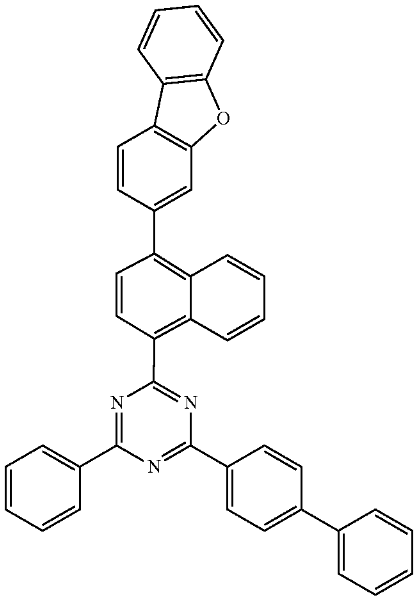

-continued
C2-126
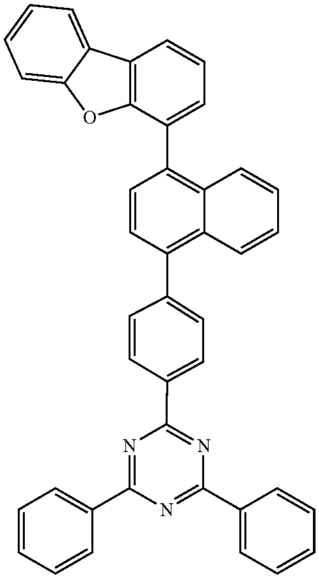
C2-127
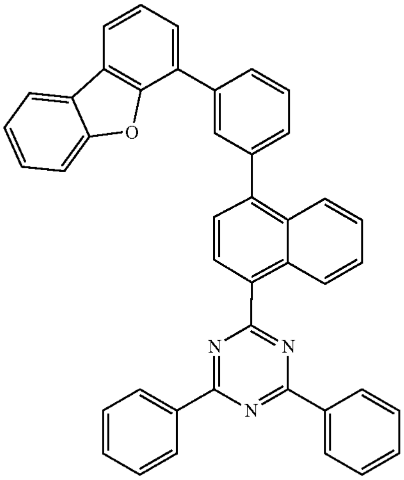
C2-128
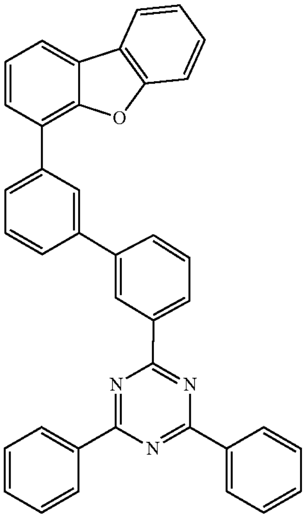
-continued
C2-129
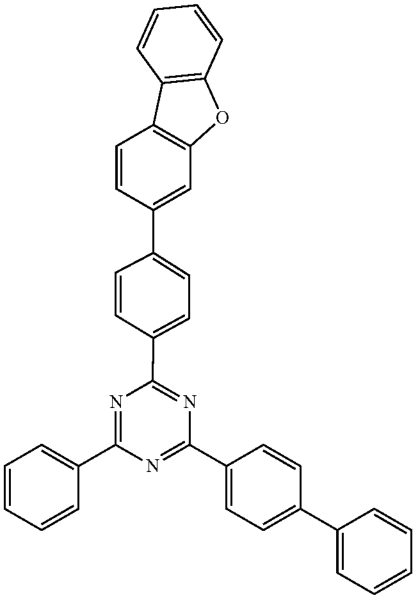
C2-130
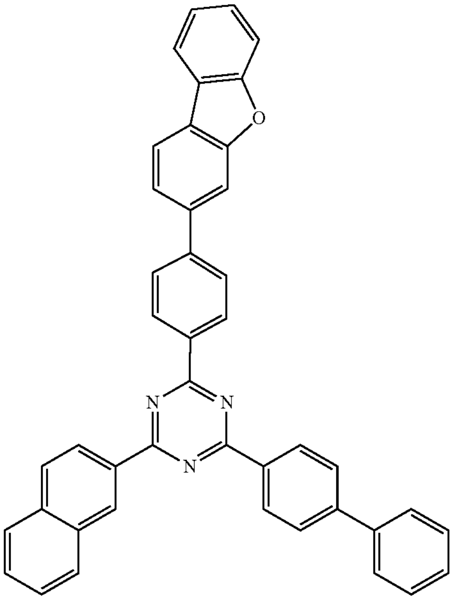
C2-131
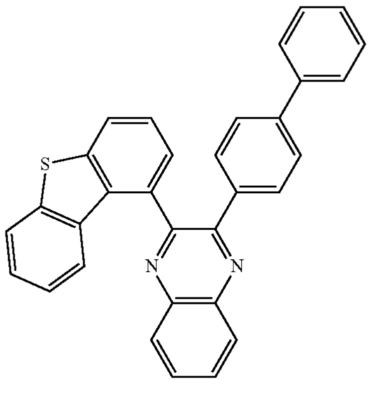

-continued
C2-132
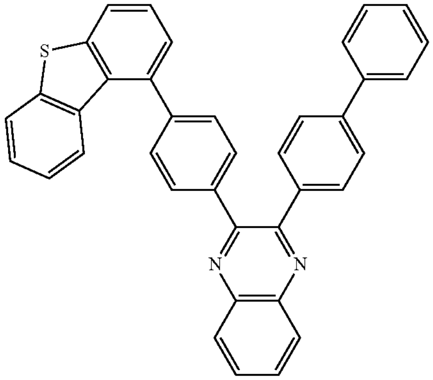
C2-133
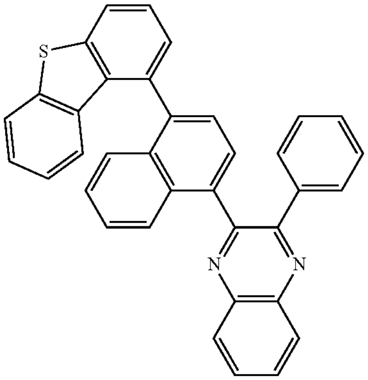
C2-134
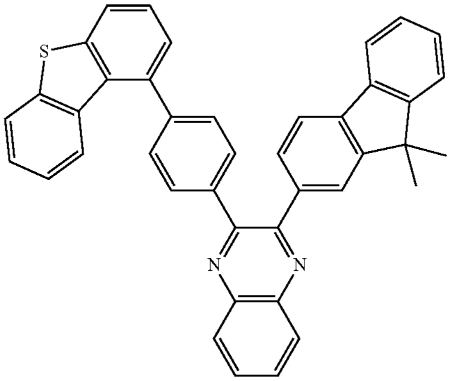
C2-135
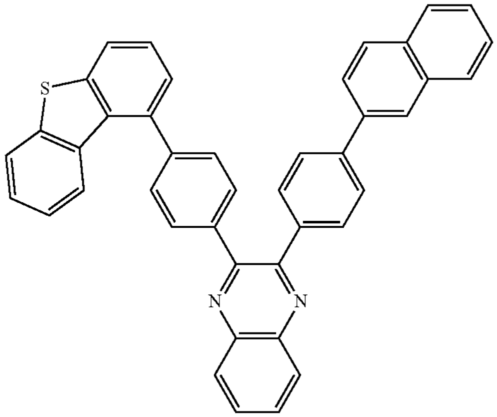
-continued
C2-136
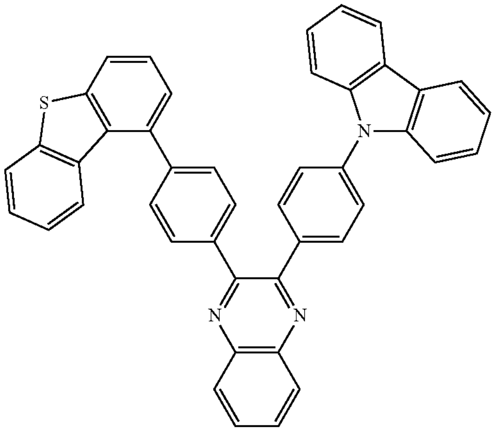
C2-137
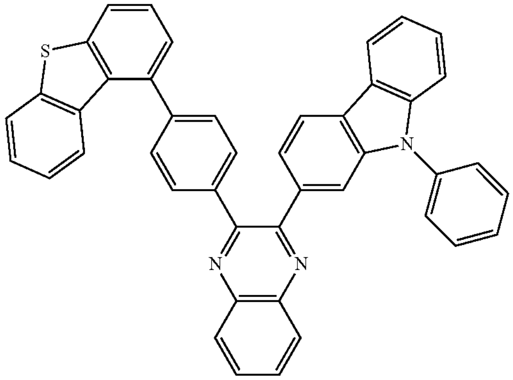
C2-138
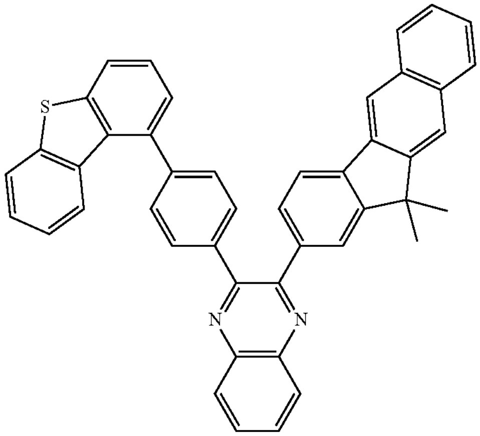

-continued
C2-139
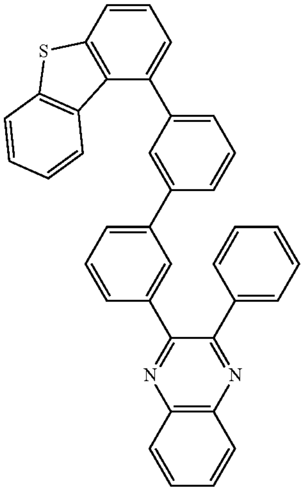
C2-140
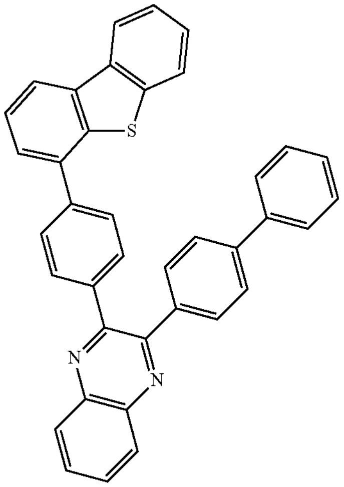
C2-141
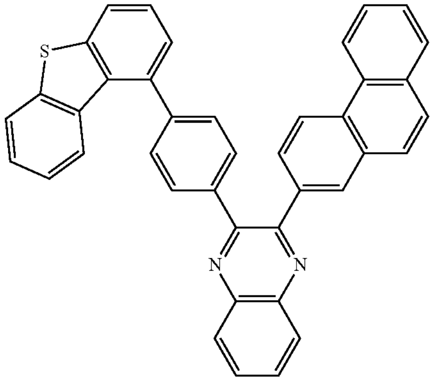
-continued
C2-142
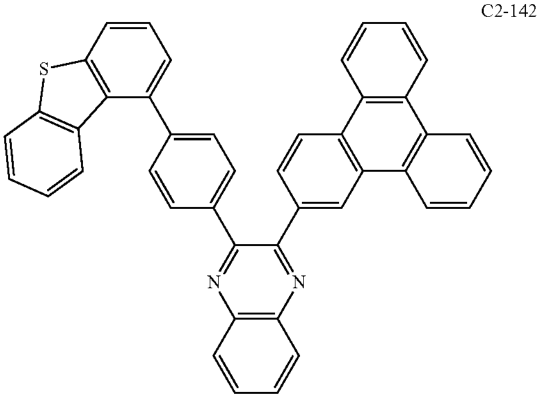
C2-143
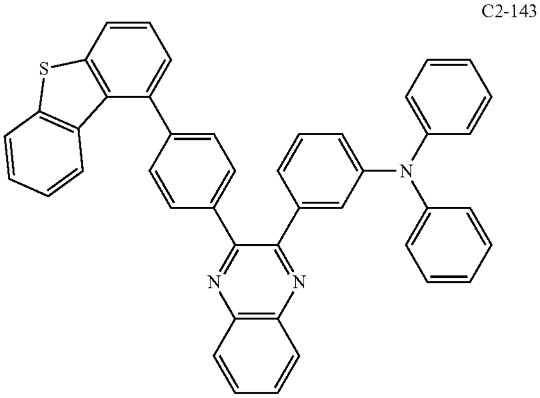
C2-144
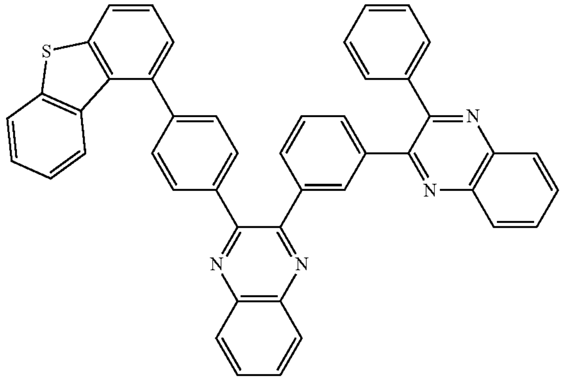
C2-145
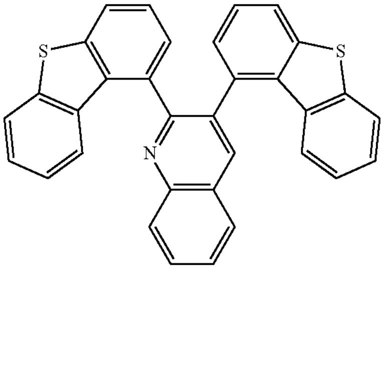

-continued
C2-146
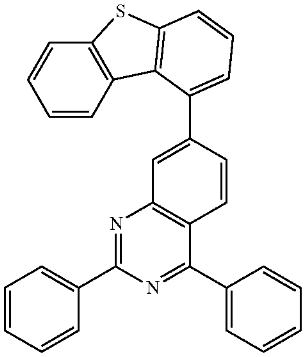
C2-147
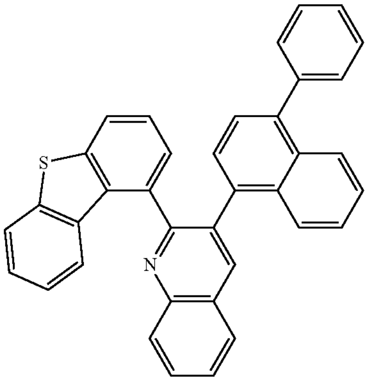
C2-148
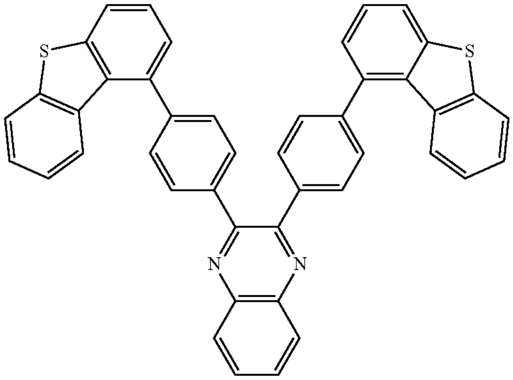
C2-149
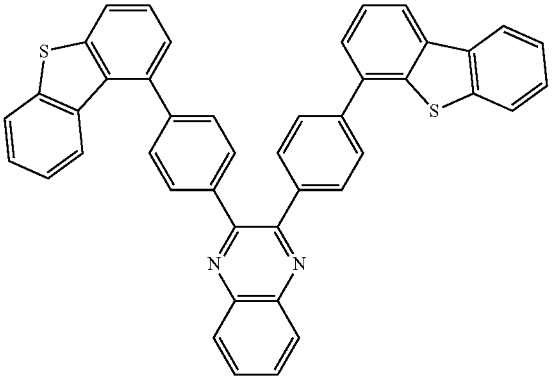
-continued
C2-150
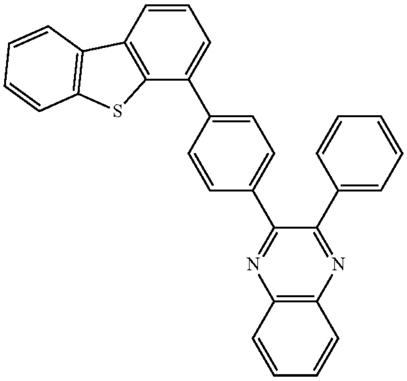
C2-151
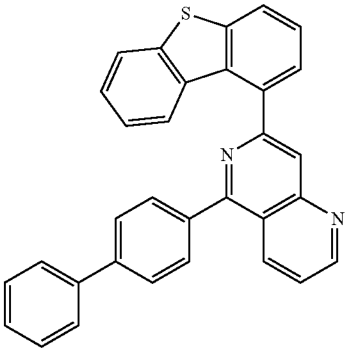
C2-152
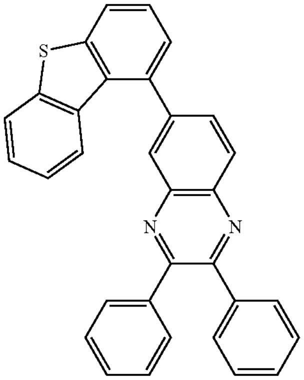
C2-153
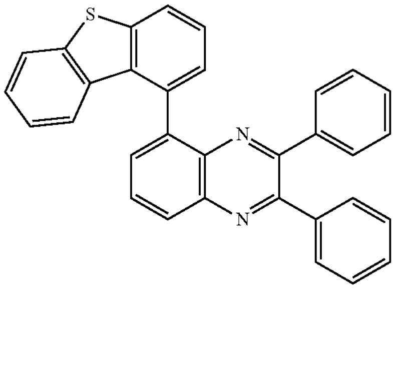

-continued
C2-154
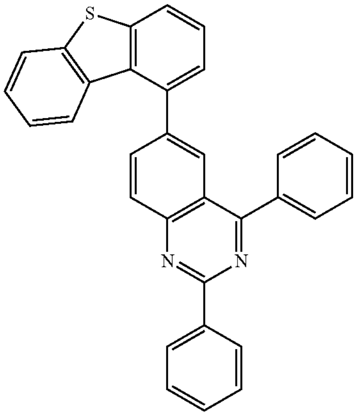
C2-155
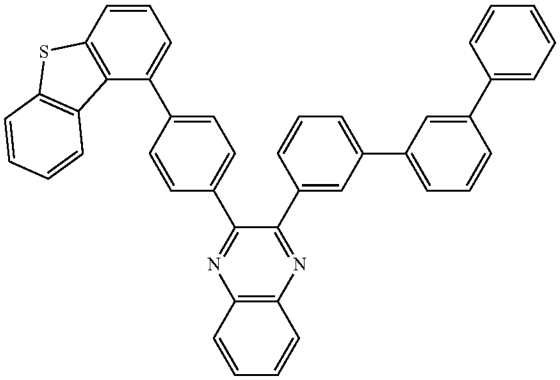
C2-156
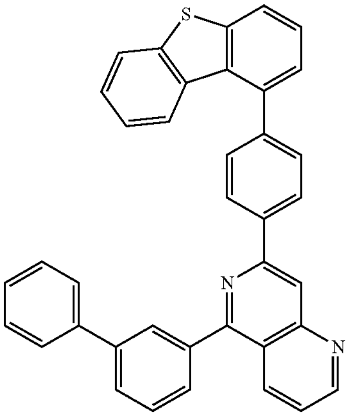
-continued
C2-157
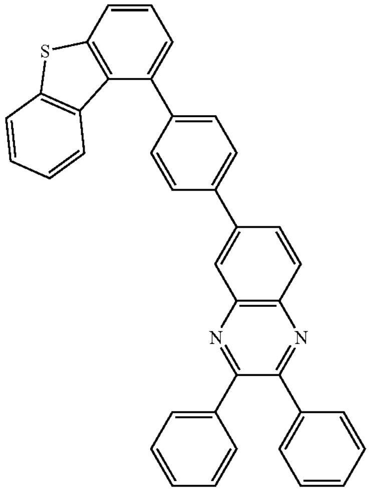
C2-158
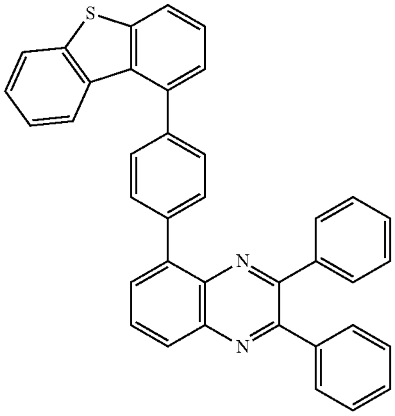
C2-159
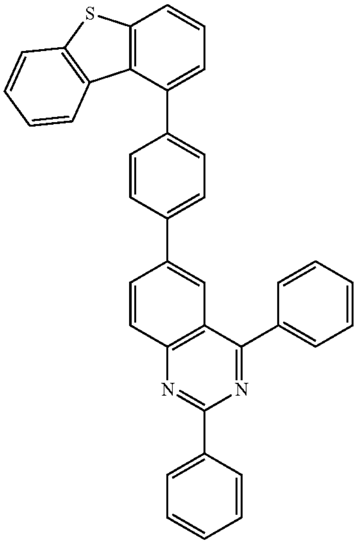

-continued
C2-160
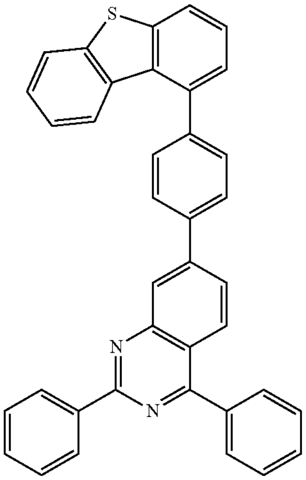
C2-161
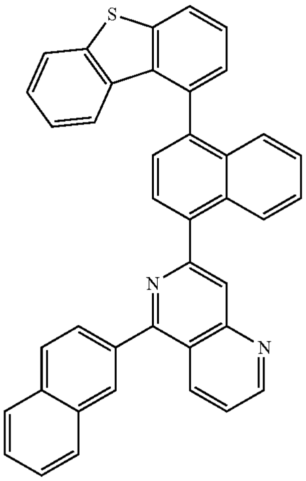
C2-162
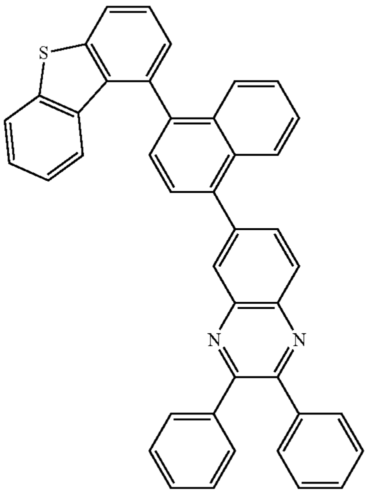
-continued
C2-163
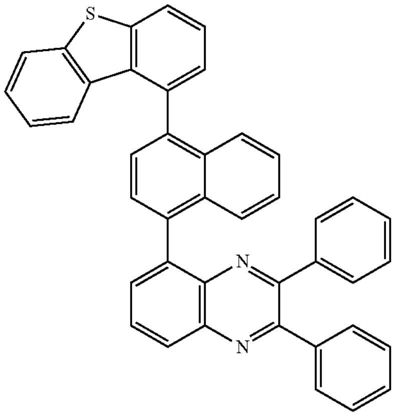
C2-164
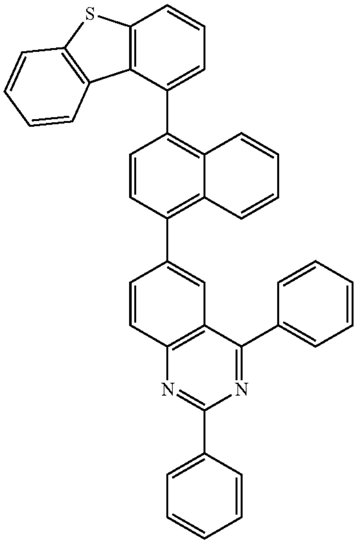
C2-165
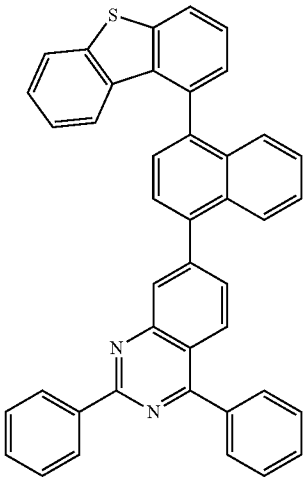

-continued
C2-166
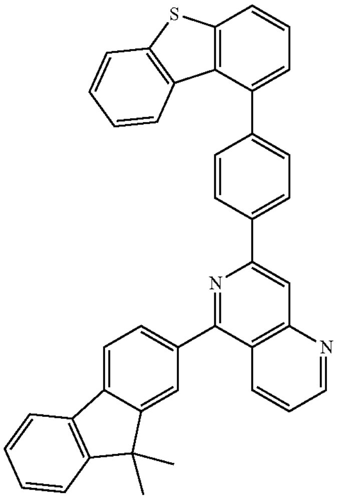
C2-167
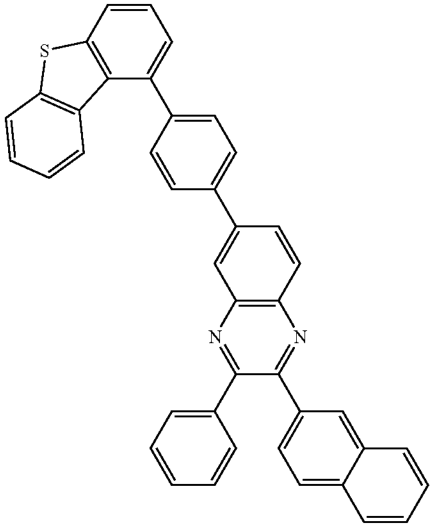
C2-168
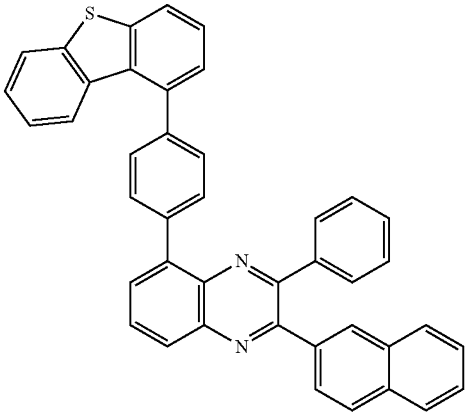
-continued
C2-169
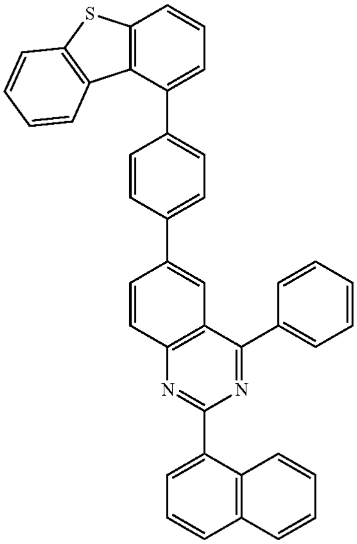
C2-170
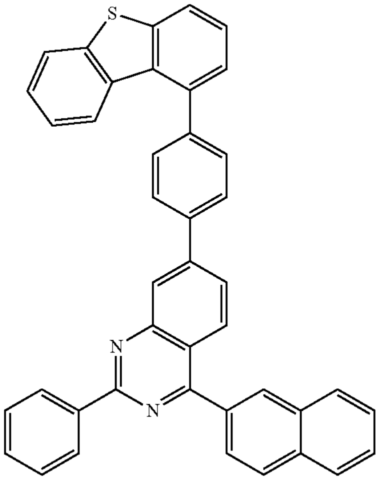
C2-171
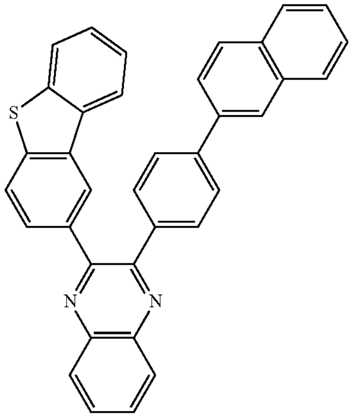

-continued
C2-172
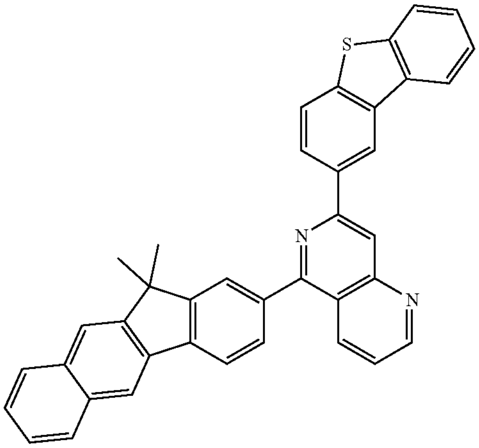
C2-173
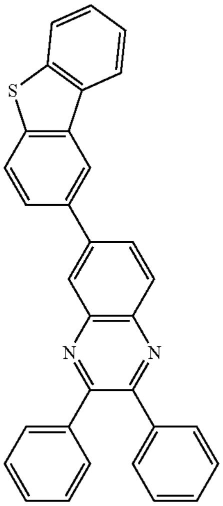
C2-174
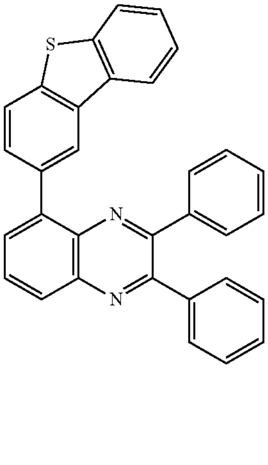
-continued
C2-175
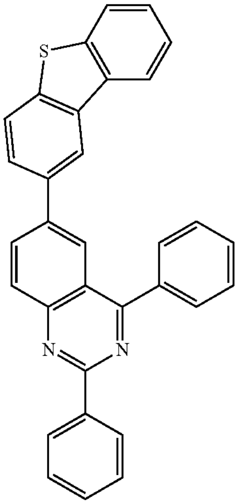
C2-176
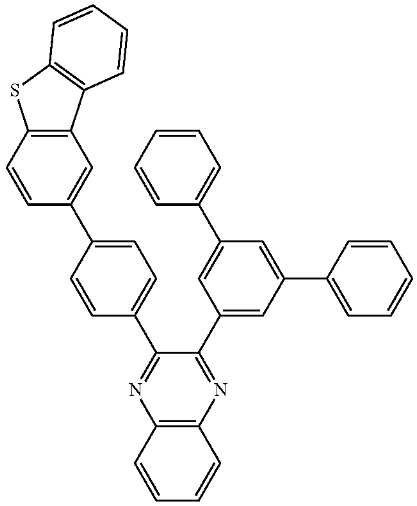
C2-177
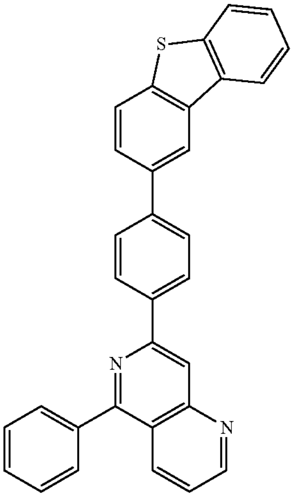

C2-178
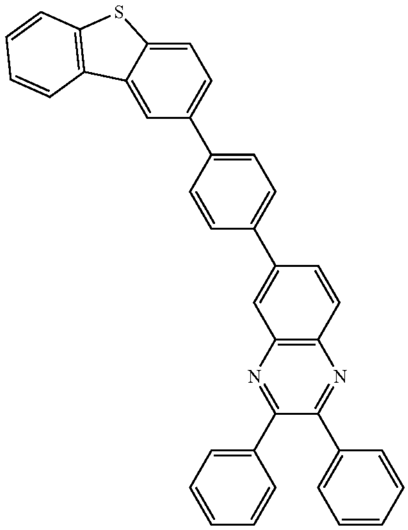
C2-179
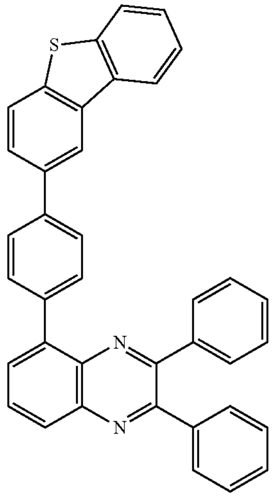
C2-180
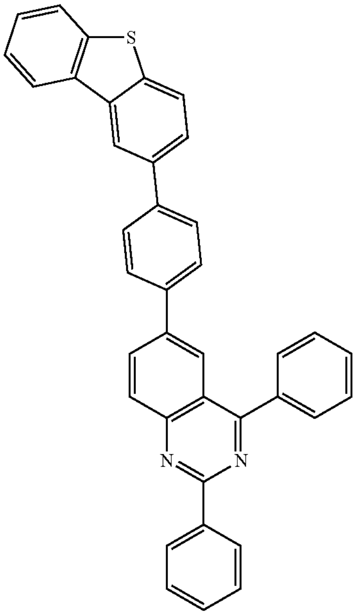
C2-181
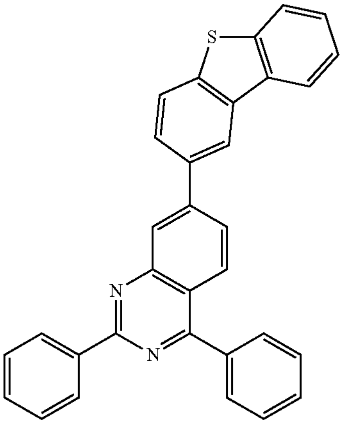
C2-182
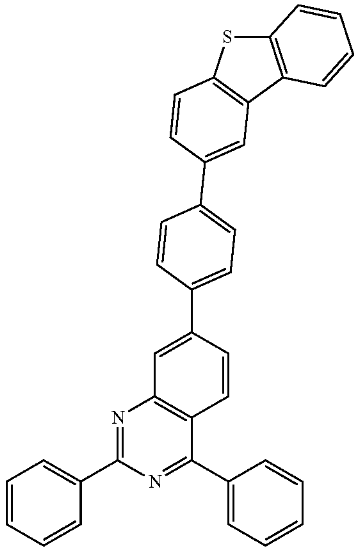
C1-183
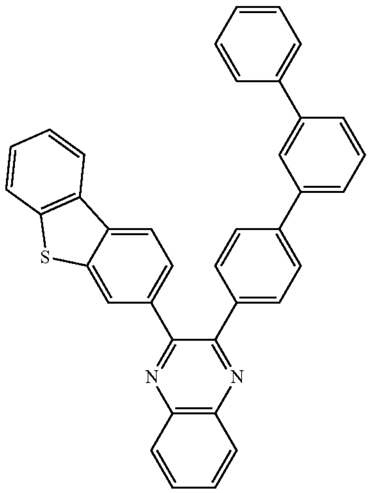

-continued
C1-184
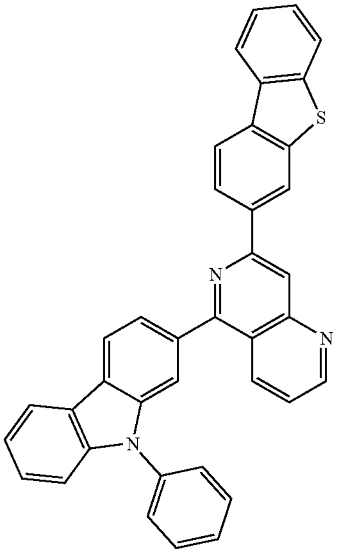
C1-185
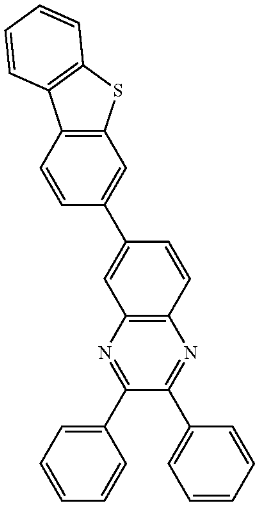
C2-186
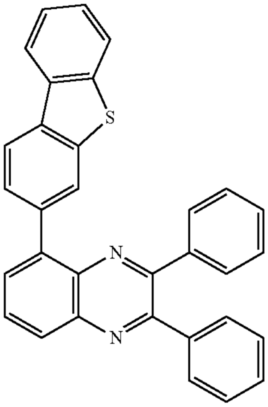
-continued
C2-187
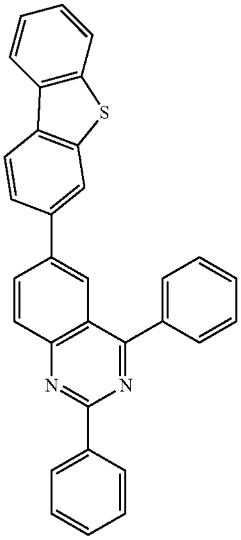
C2-188
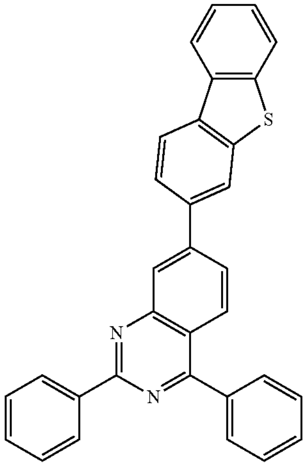
C2-189
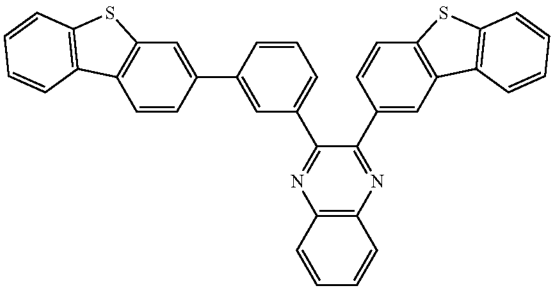

-continued
C2-190
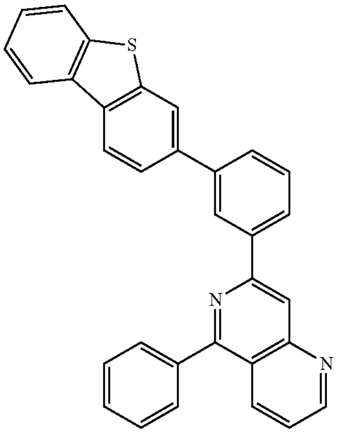
C2-191
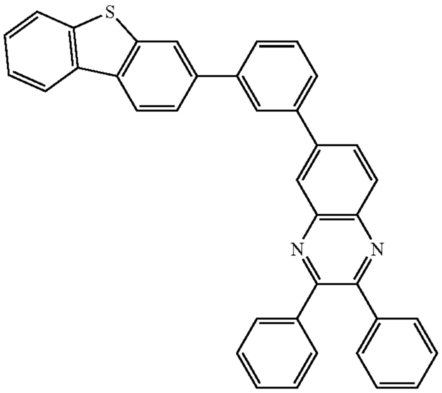
C2-192
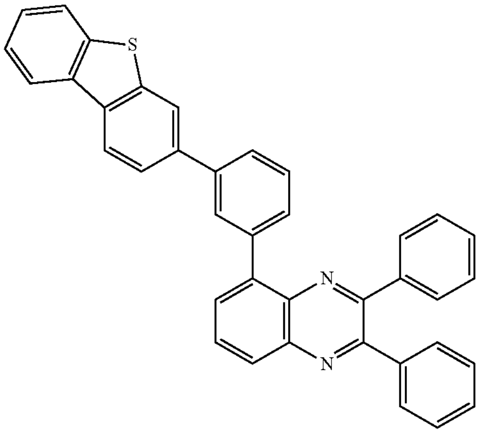
-continued
C2-193
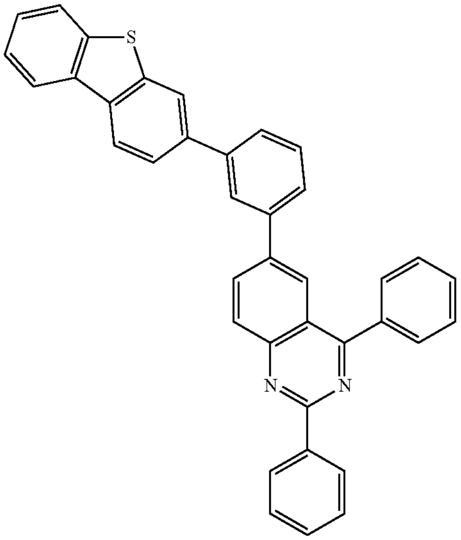
C2-194
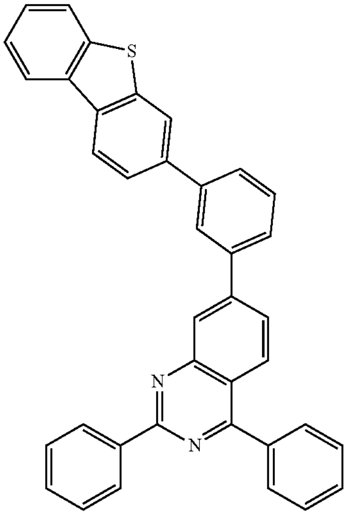
C2-195
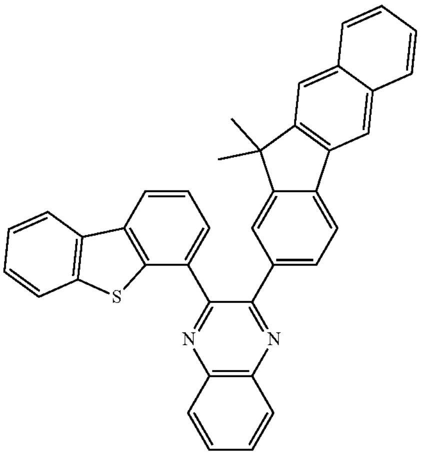

C2-196
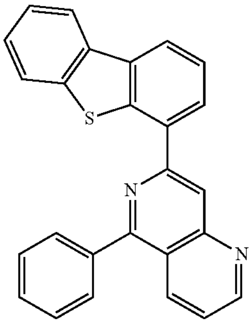
C2-197
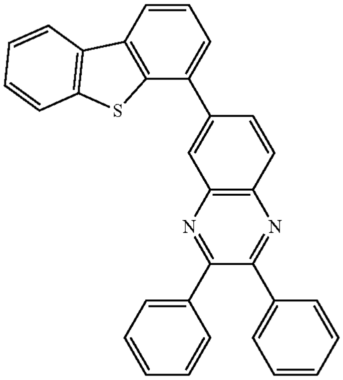
C2-198
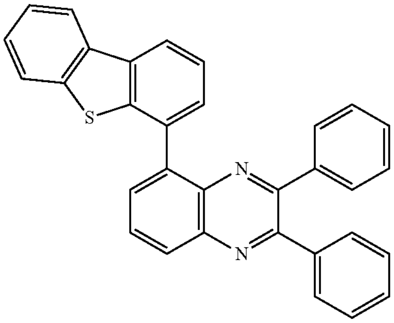
C2-199
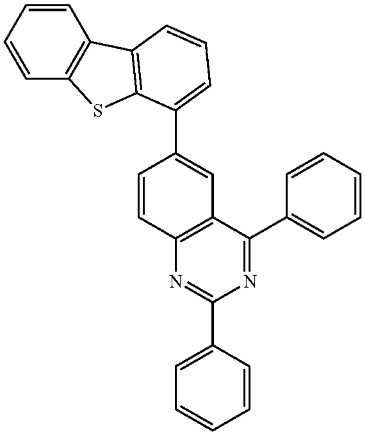
C2-200
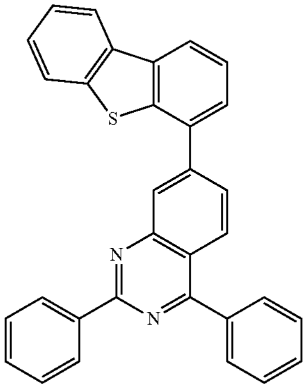
C2-201
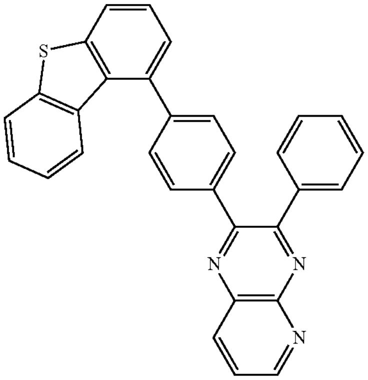
C2-202
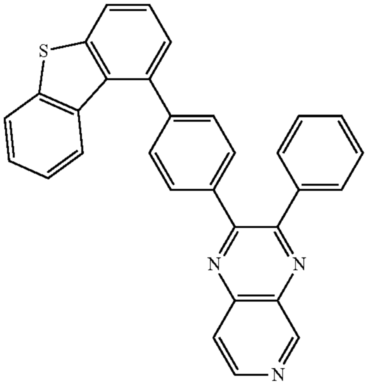
C2-203
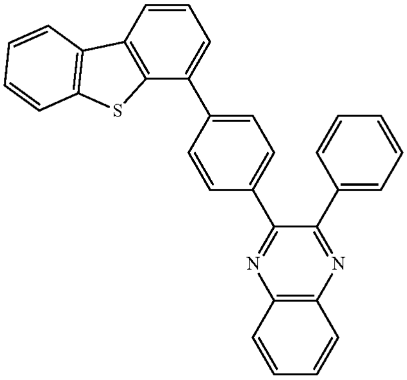

-continued
C2-204
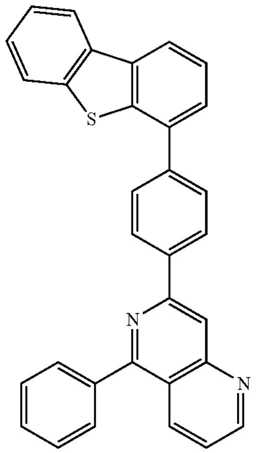
C2-205
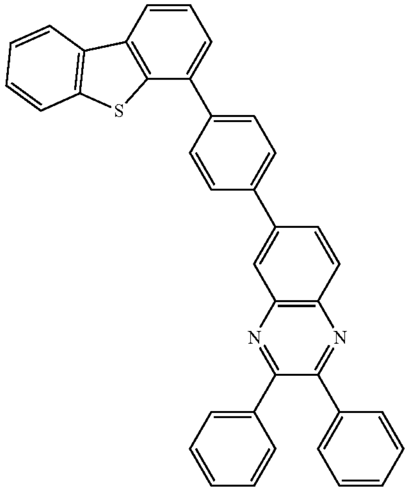
C2-206
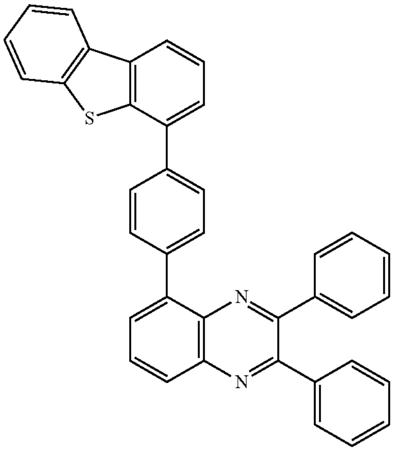
-continued
C2-207
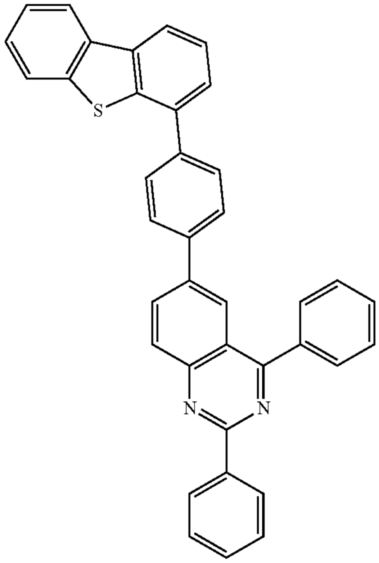
C2-208
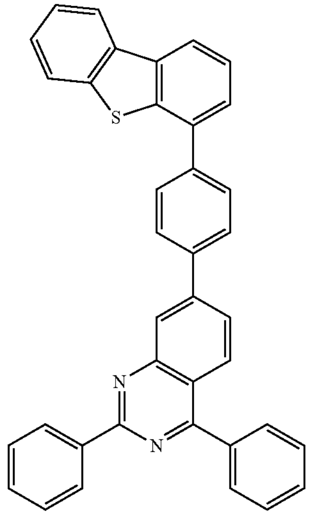
C2-209
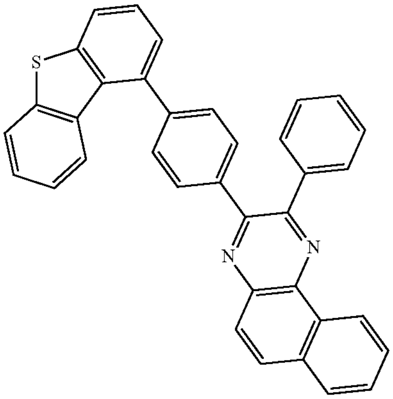

-continued
C2-210
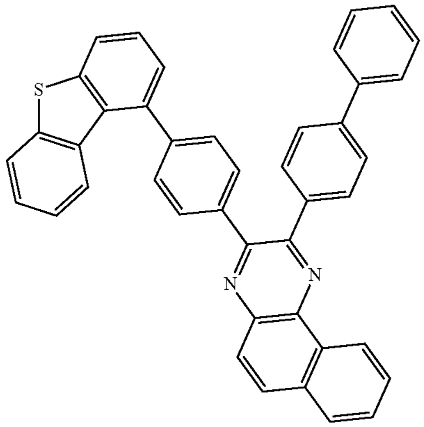
C2-211
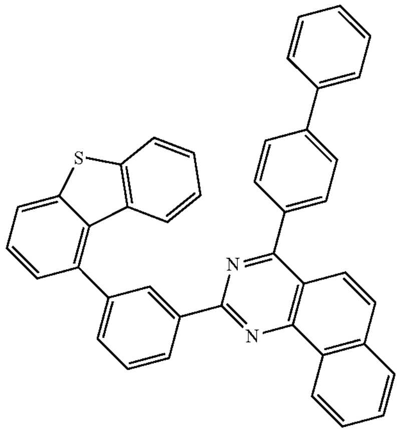
C2-212
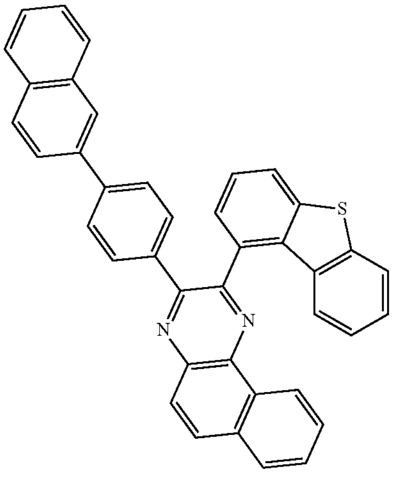
-continued
C2-213
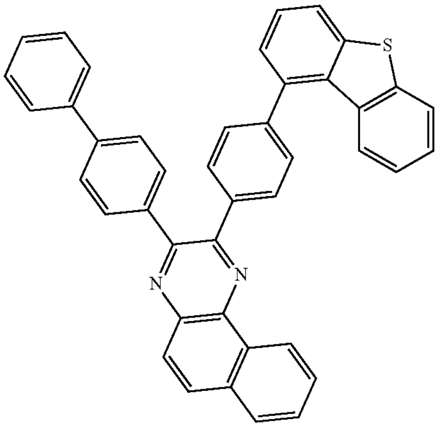
C2-214
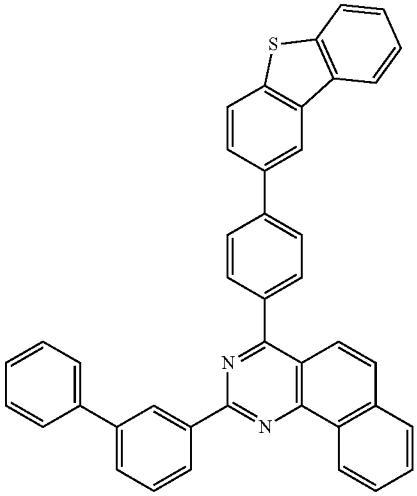
C2-215
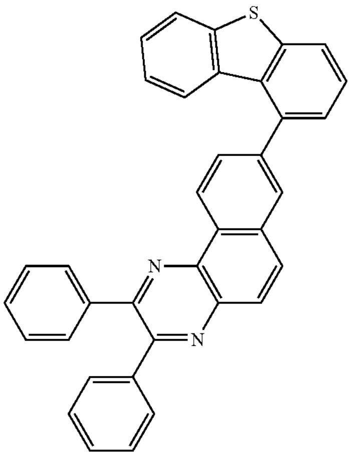

-continued
C2-216
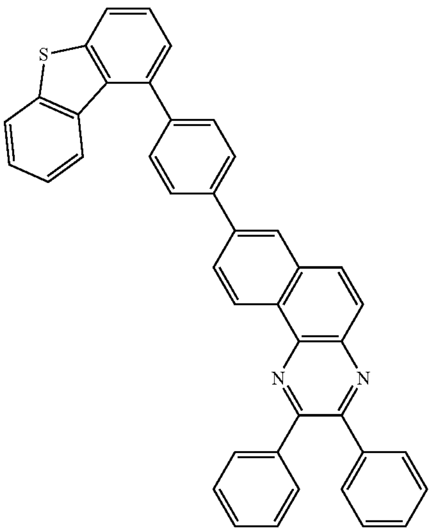
C2-217
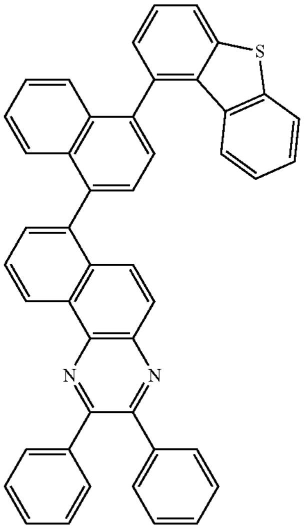
C2-218
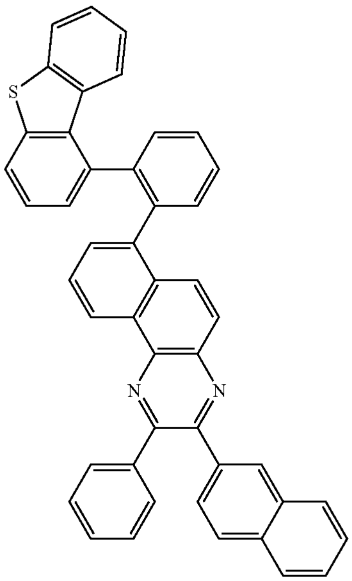
-continued
C2-219
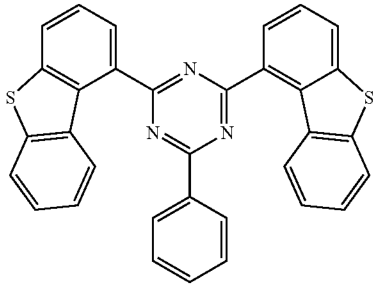
C2-220
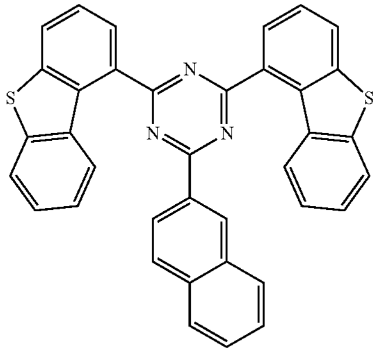
C2-221
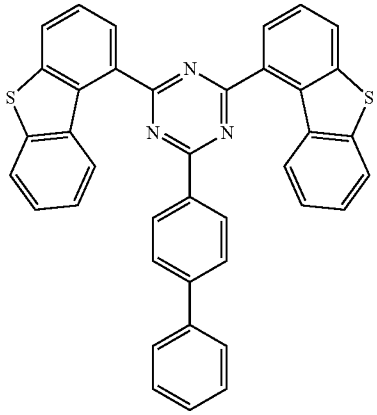
C2-222
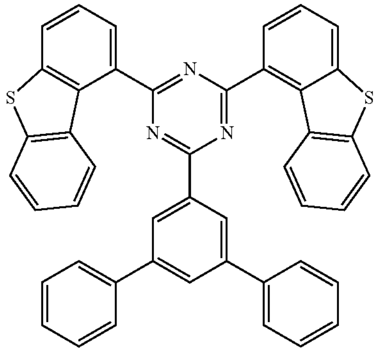

-continued
C2-223
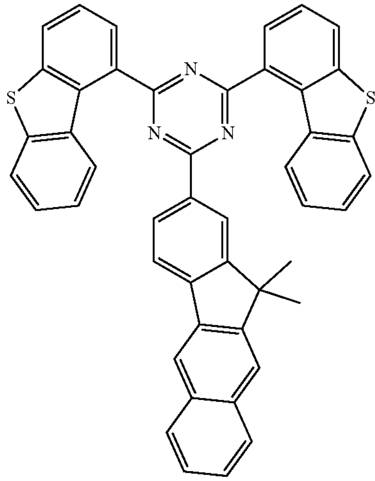
C2-224
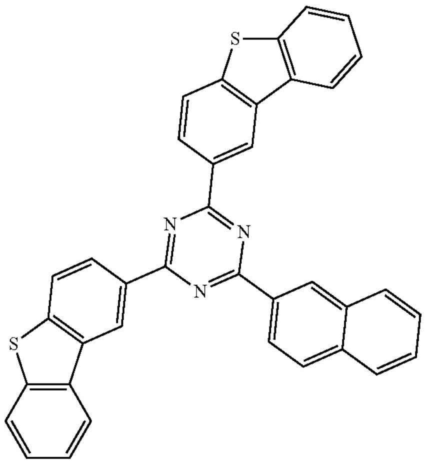
C2-225
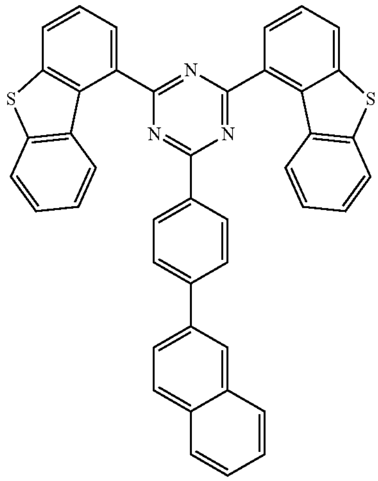
-continued
C2-226
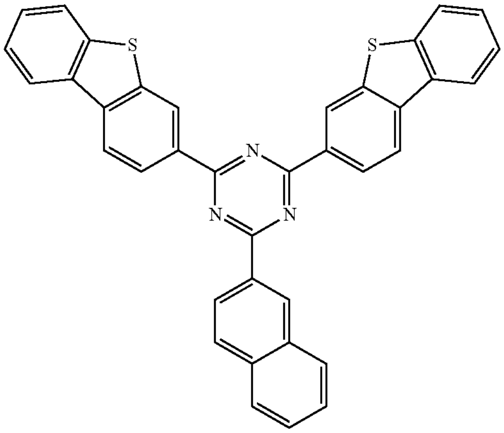
C2-227
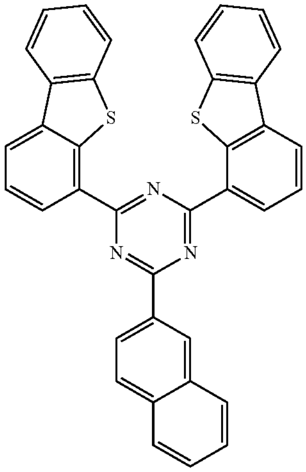
C2-229
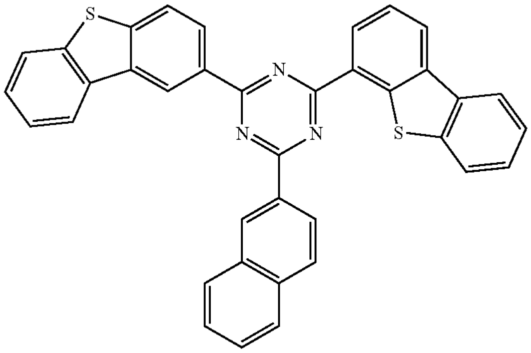

-continued
C2-229
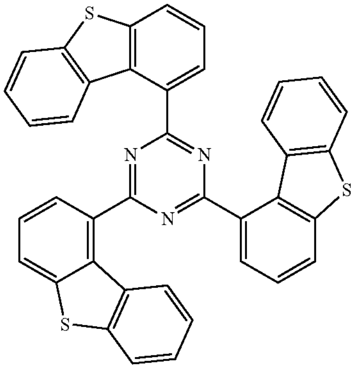
C2-230
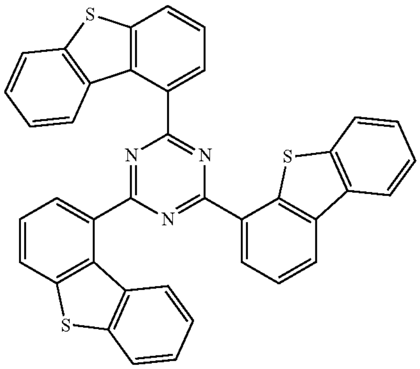
C2-231
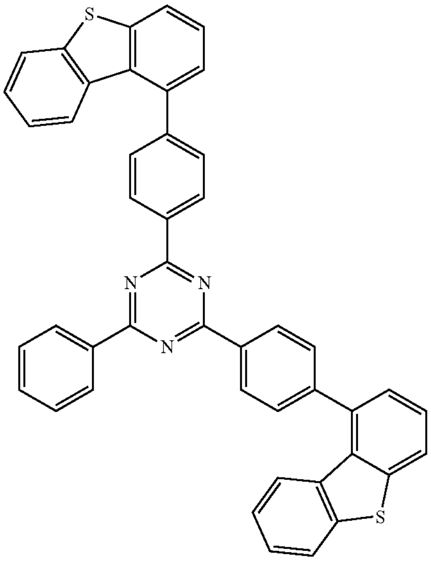
-continued
C2-232
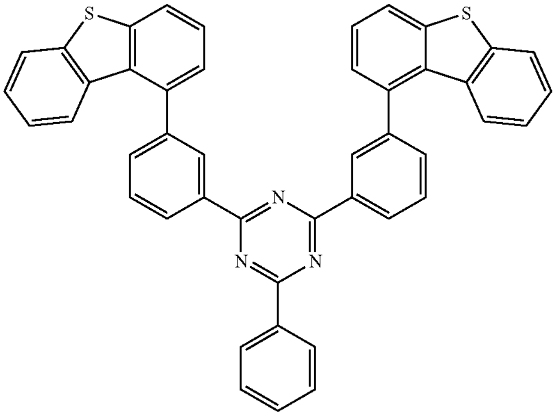
C2-233
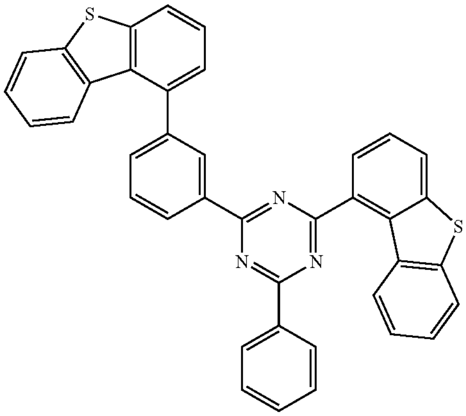
C2-234
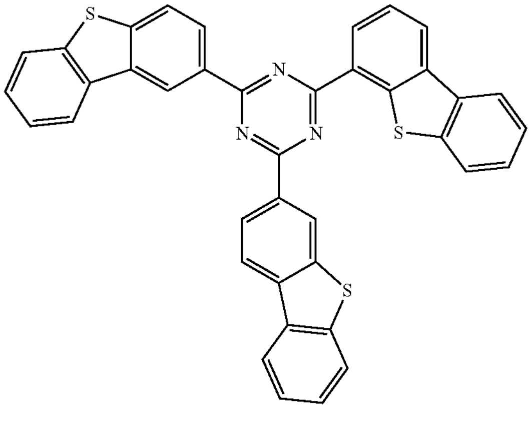

-continued
C2-235
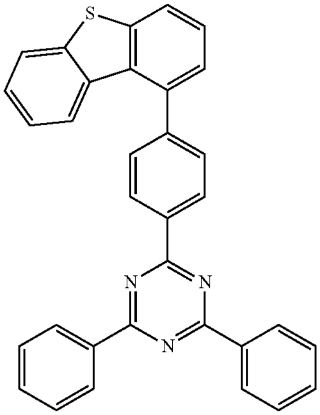
C2-236
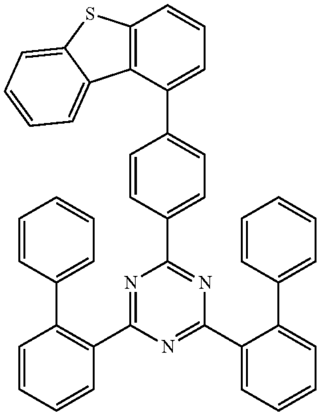
C2-237
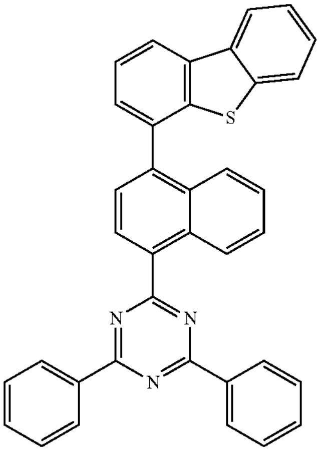
-continued
C2-238
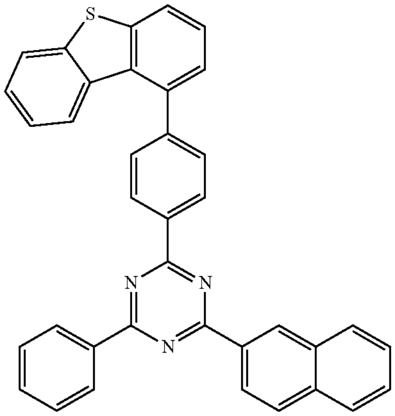
C2-239
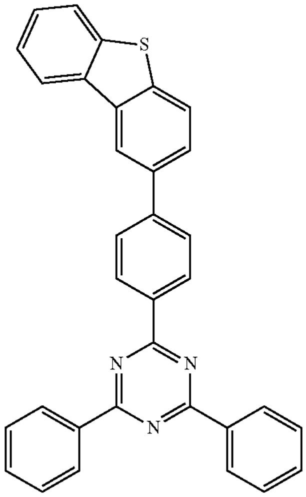
C2-240
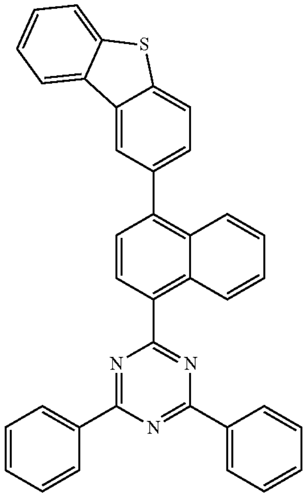

-continued
C2-241
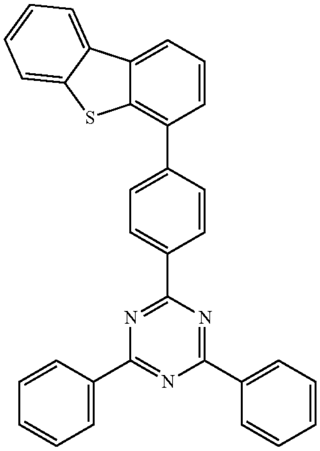
C2-242
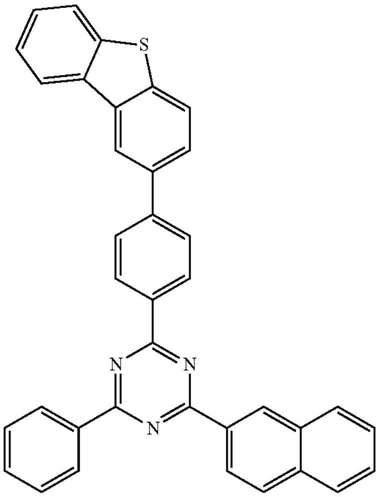
C2-243
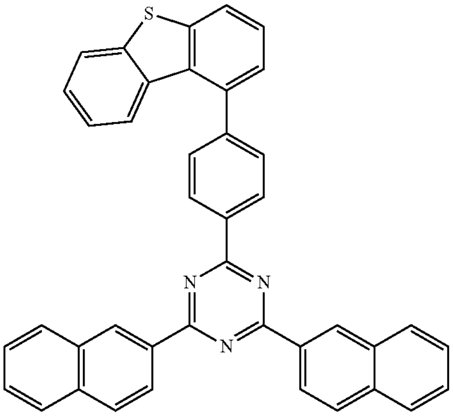
-continued
C2-244
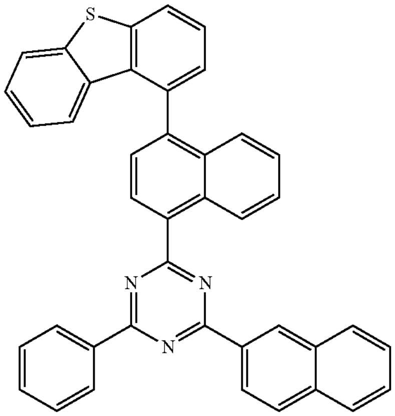
C2-245
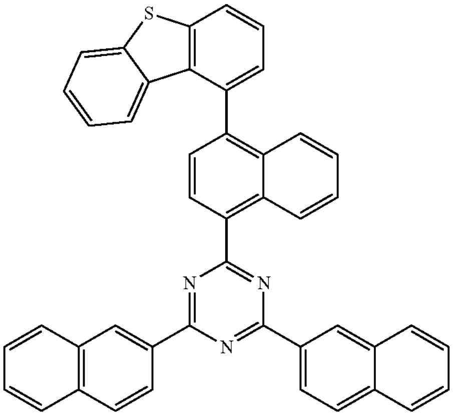
C2-246
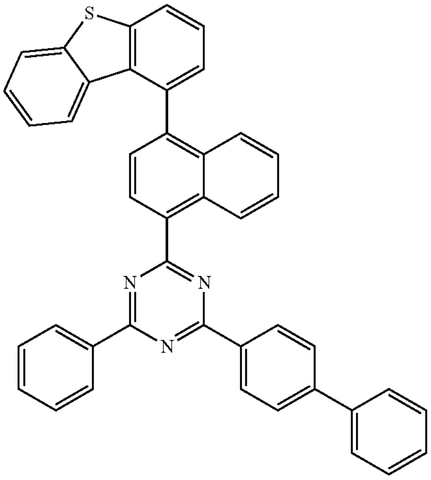

-continued
C2-247
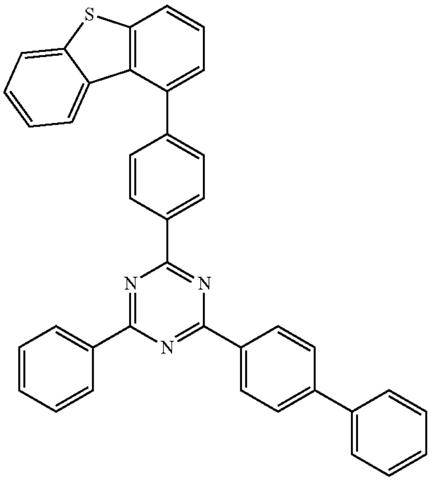
C2-248
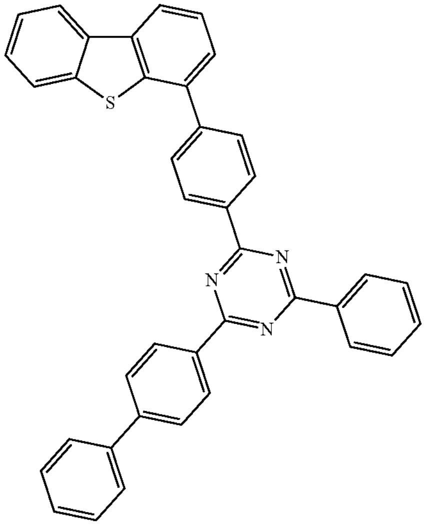
C2-249
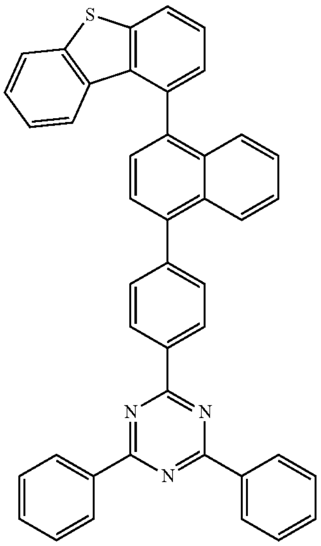
-continued
C2-250
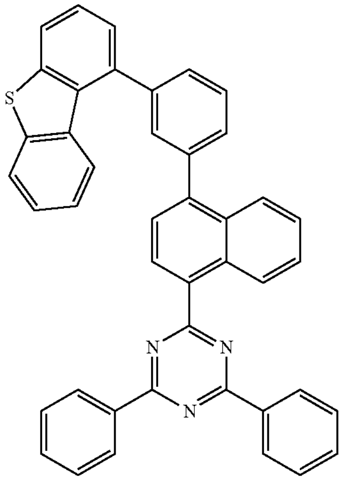
C2-251
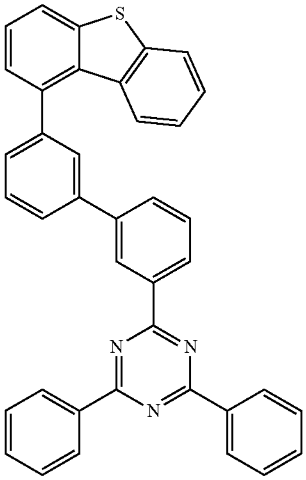
C2-252
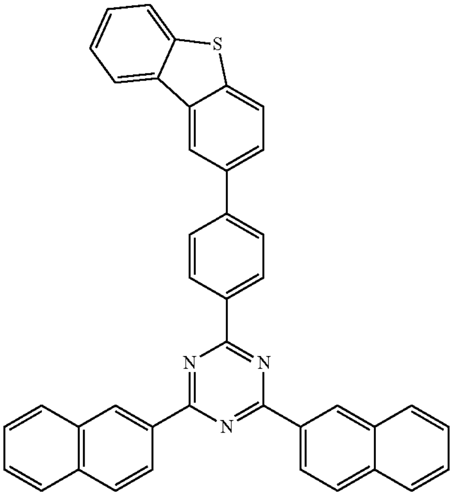

-continued
C2-253
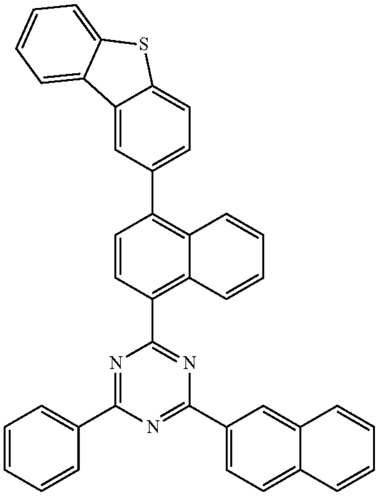
C2-254
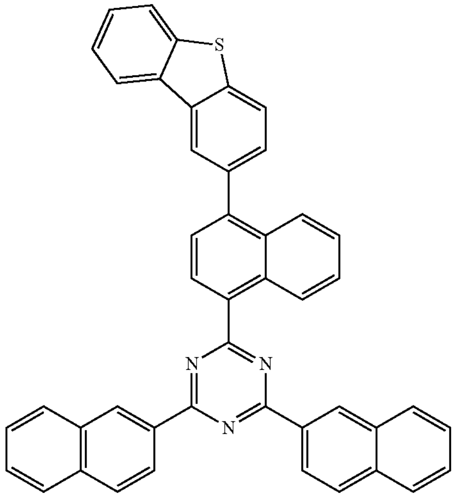
C2-255
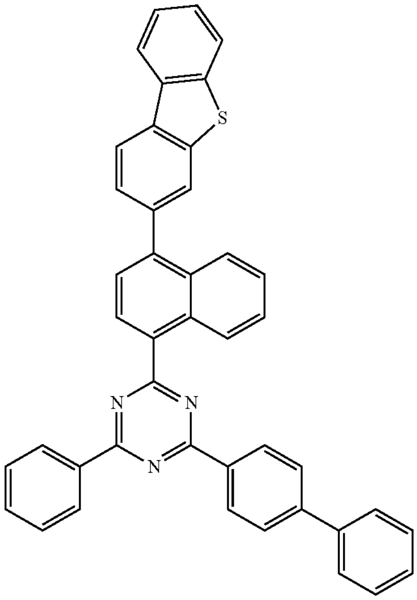
-continued
C2-256
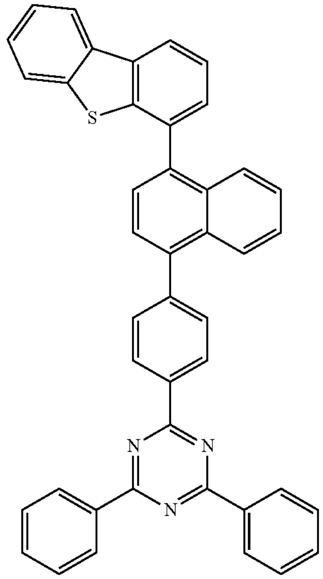
C2-257
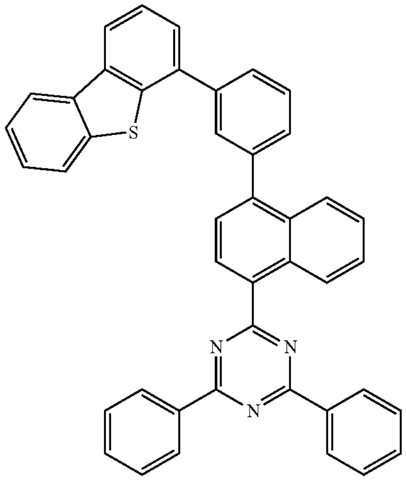
C2-258
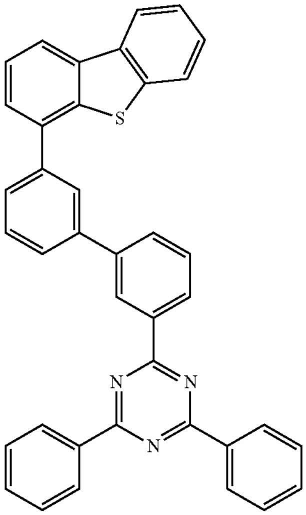

-continued
C2-259
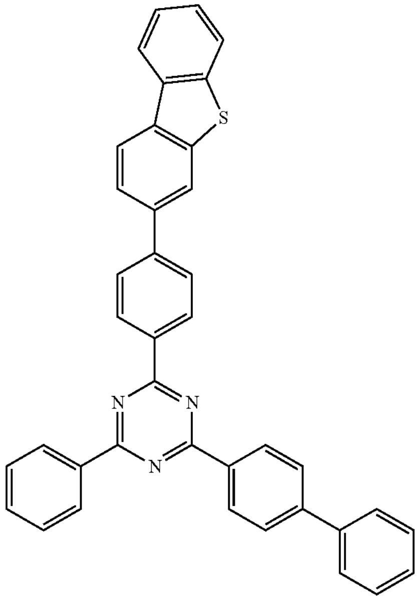
C2-260
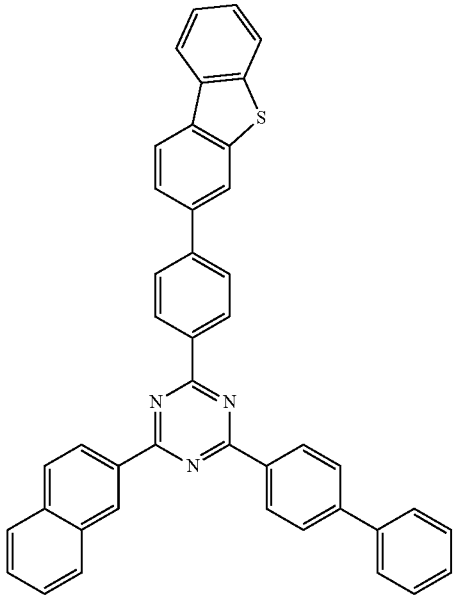
C2-261
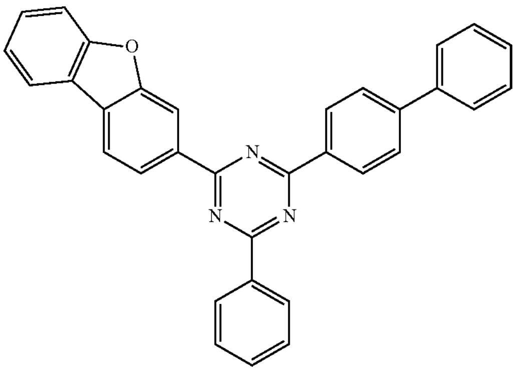
-continued
C2-262
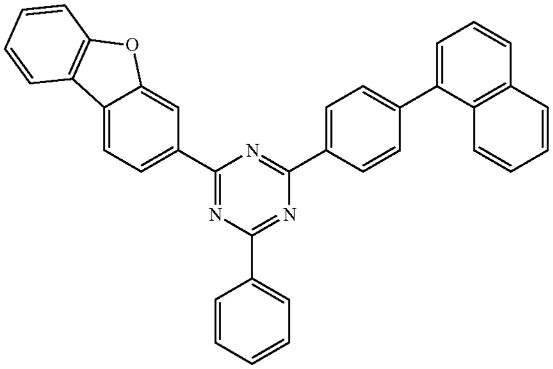
C2-263
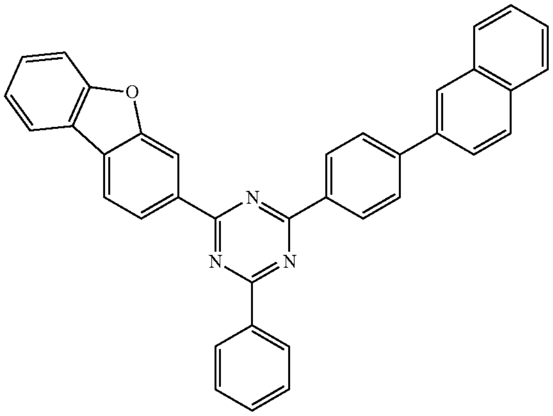
C2-264
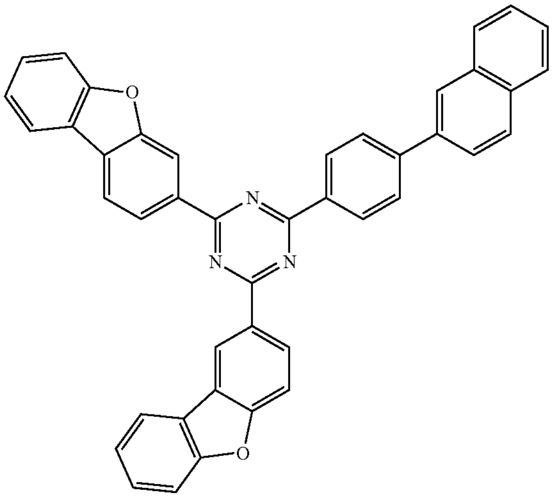

-continued
C2-265
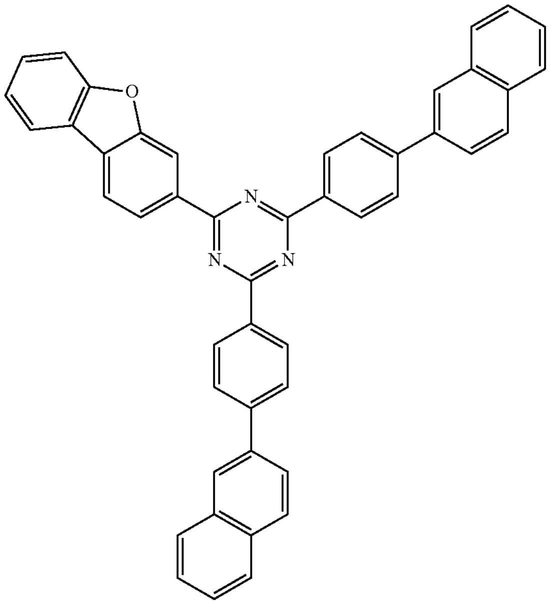
C2-266
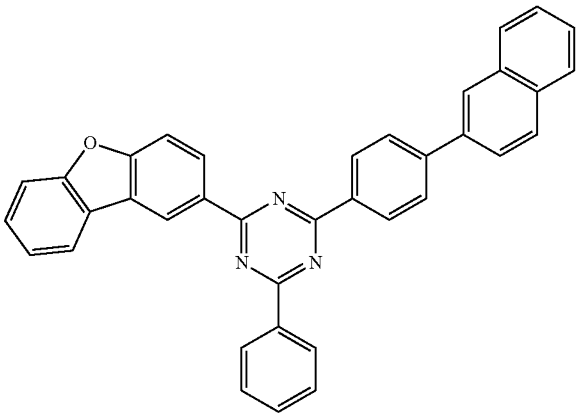
C2-267
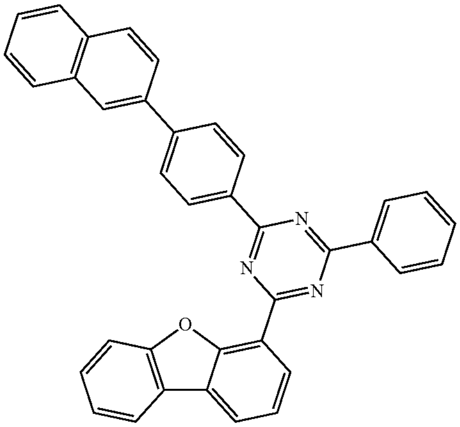
-continued
C2-268
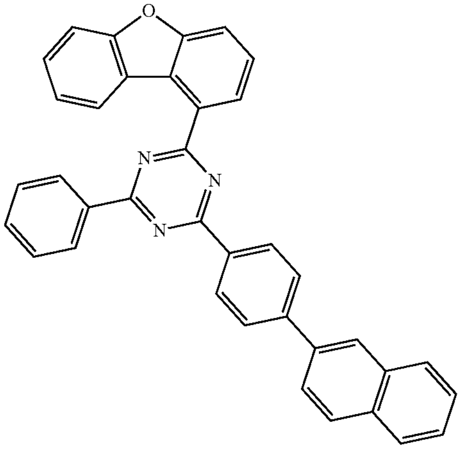
C2-269
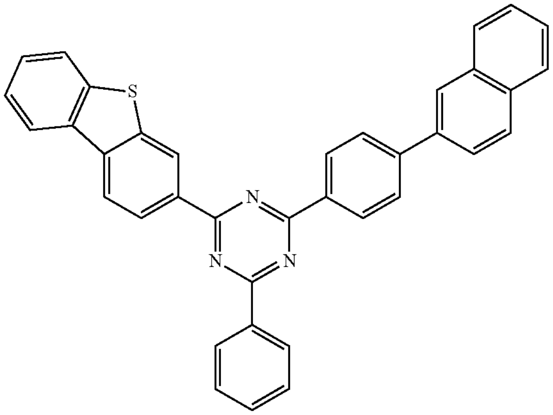
C2-270
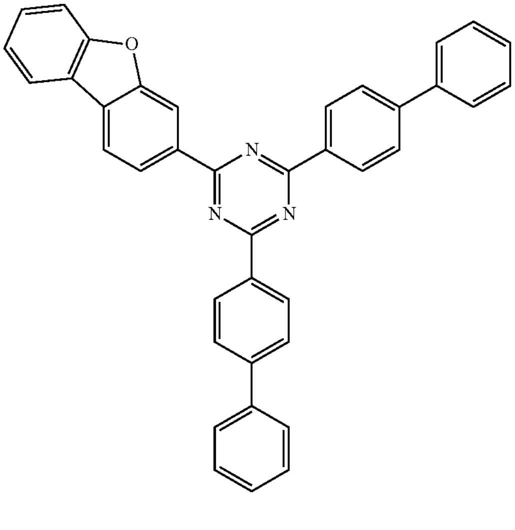

-continued

C2-271

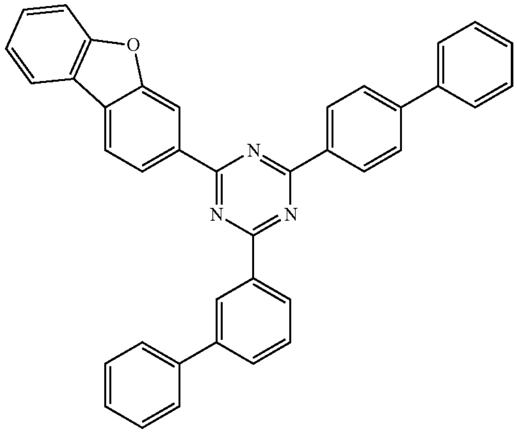

C2-272

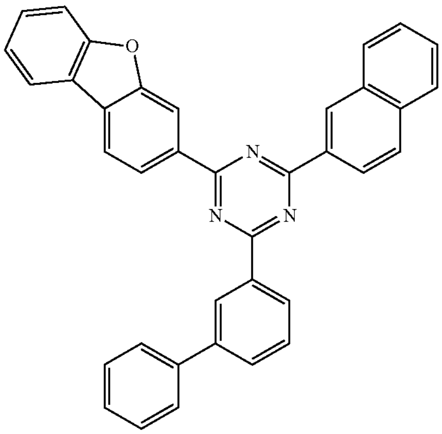

C2-273

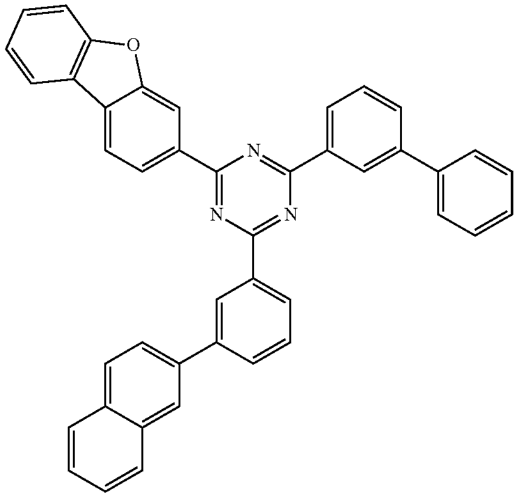

-continued

C2-274

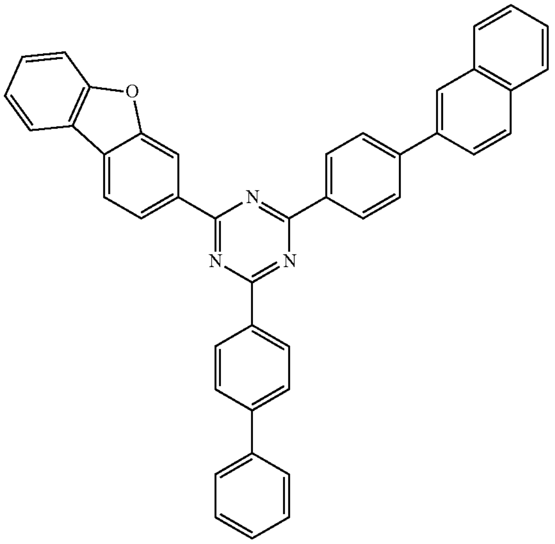

C2-275

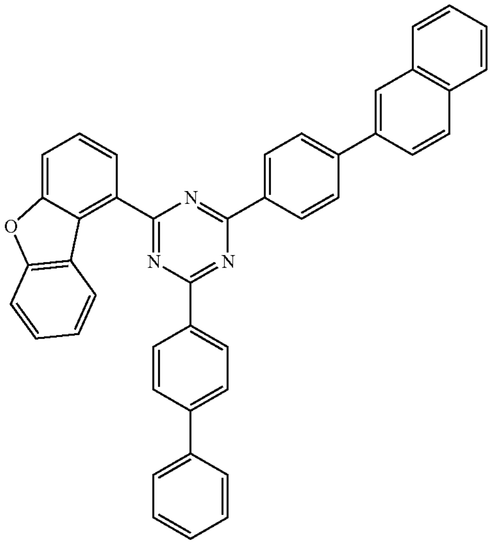

At least one C1-1 to C1-145 and at least one C2-1 to C2-275 may be combined and used in the organic electroluminescent device. According to one embodiment of the present disclosure, at least one compound represented by the formula 1-3 and at least one compound represented by formula 2-1 may be combined and used in the organic electroluminescent device.

The organic electroluminescent compound according to another embodiment of the present disclosure may be represented by the following formula 2-1-1.

(2-1-1)

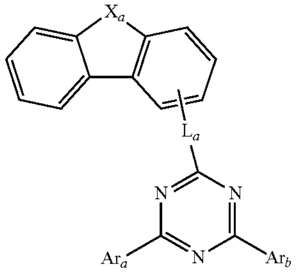

In formula 2-1-1.

$X_a$ represents O or S;

$L_a$ represents an unsubstituted naphthylene except 1,2-naphthylene structure; and $Ar_a$ and $Ar_b$ each independently represent an unsubstituted phenyl, an unsubstituted naphthyl, an unsubstituted biphenyl, an unsubstituted terphenyl, or the combination thereof.

According to one embodiment of the present disclosure, $L_a$ represents an unsubstituted naphthylene except 1,2-naphthylene structure, e.g., $L_a$ may be represented by any one of the listed substituents in the following Group 1.

[Group 1]

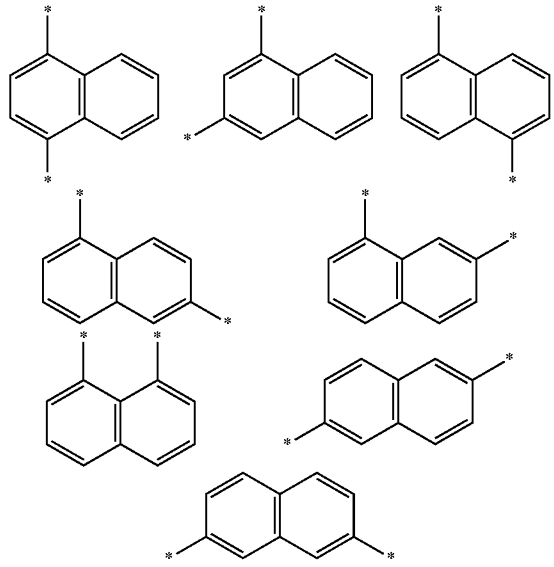

Wherein, * represents linking position with an adjacent ring in formula 2-1-1.

According to one embodiment of the present disclosure, $Ar_a$ and $Ar_b$ each independently represent an unsubstituted phenyl, an unsubstituted naphthyl, an unsubstituted biphenyl, an unsubstituted terphenyl, or the combination thereof, preferably, each independently represent an unsubstituted phenyl, an unsubstituted o-biphenyl, an unsubstituted m-biphenyl, an unsubstituted p-biphenyl, an unsubstituted naphthyl, an unsubstituted m-terphenyl, or an unsubstituted p-terphenyl.

The compound represented by formula 2-1-1 may be illustrated by the following compounds, but is not limited thereto.

C2-107

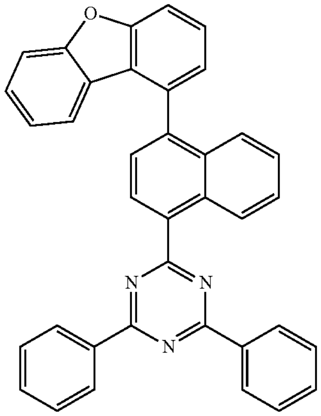

C2-114

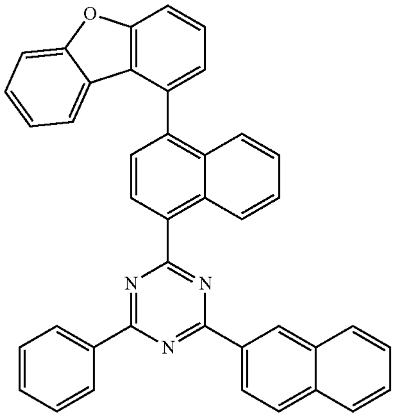

C2-115

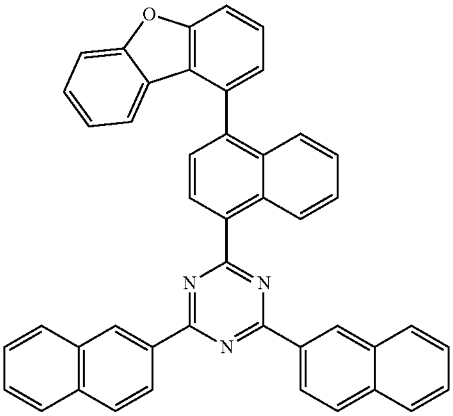

-continued
C2-116
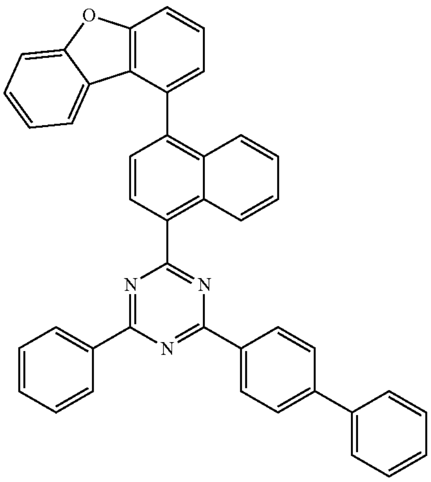
C2-123
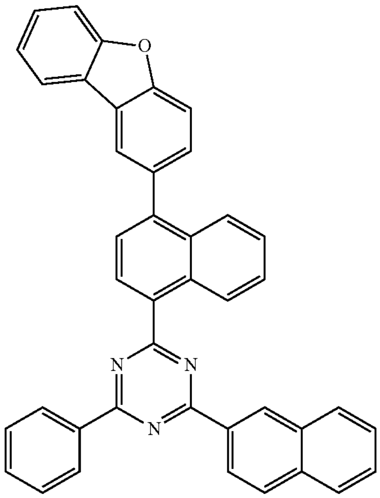
C2-124
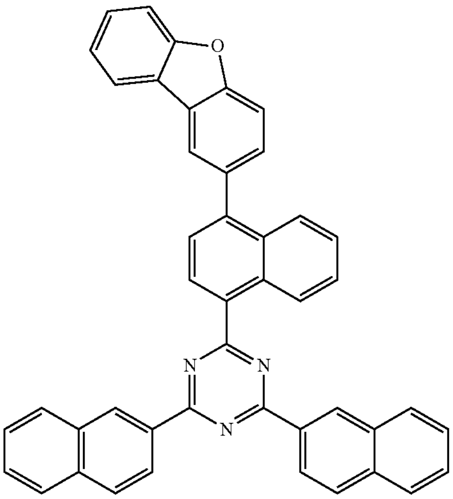
-continued
C2-125
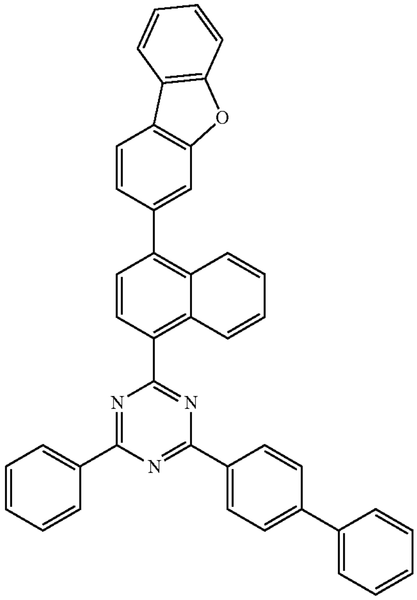
C2-237
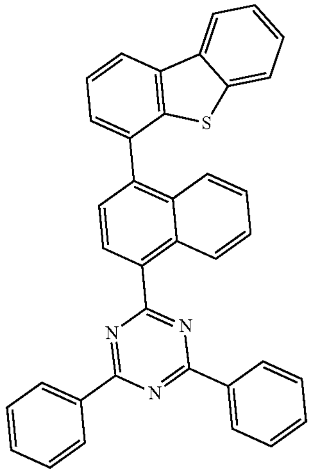
C2-240
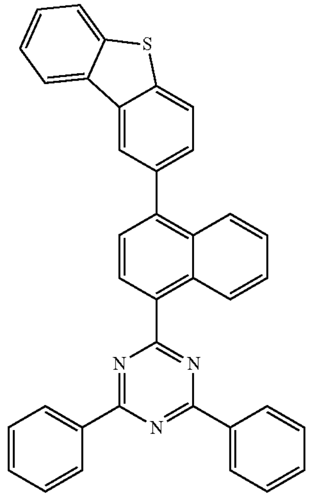

-continued
C2-244
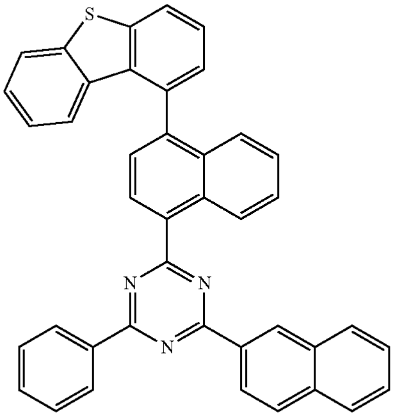
C2-245
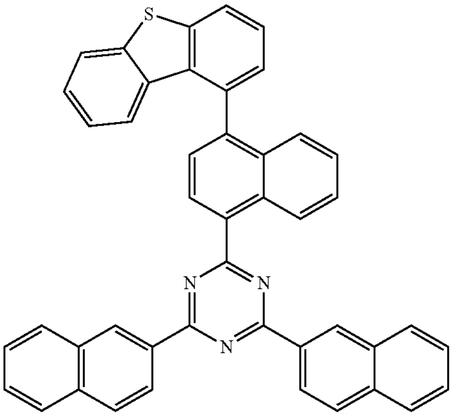
C2-246
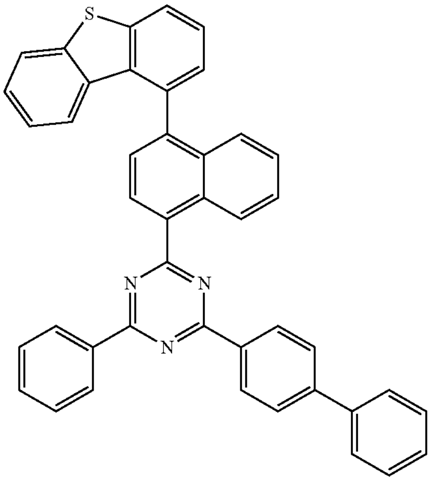
-continued
C2-253
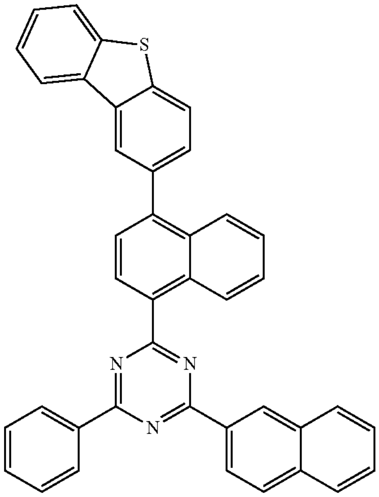
C2-254
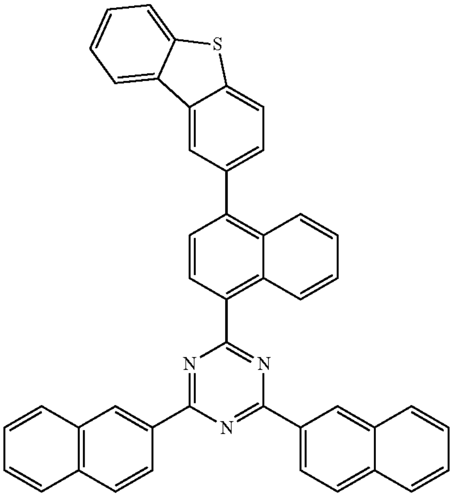
C2-255
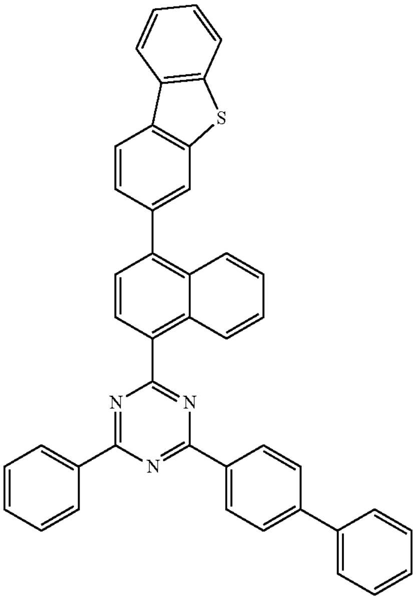

-continued
C2-110
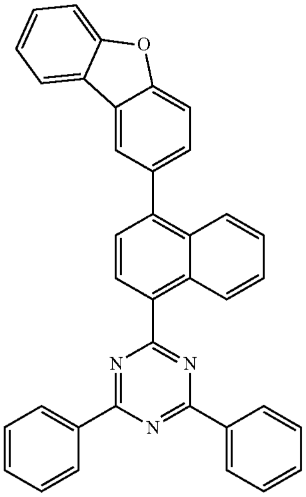
C-2
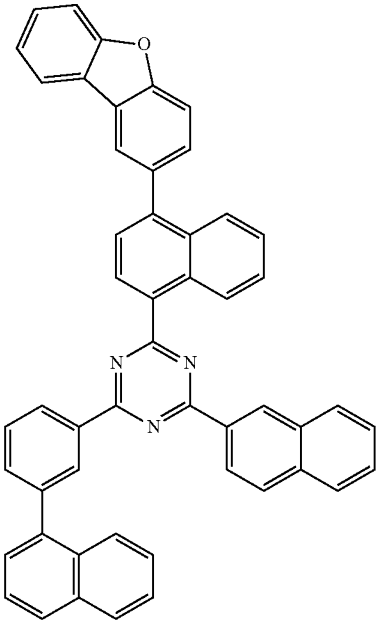
C-3
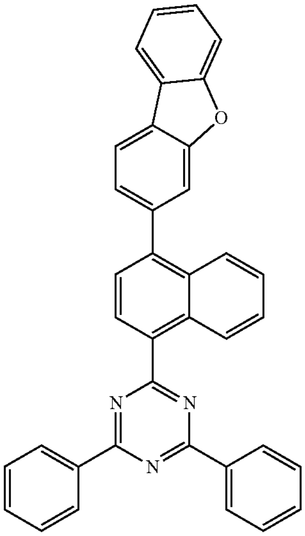
-continued
C-4
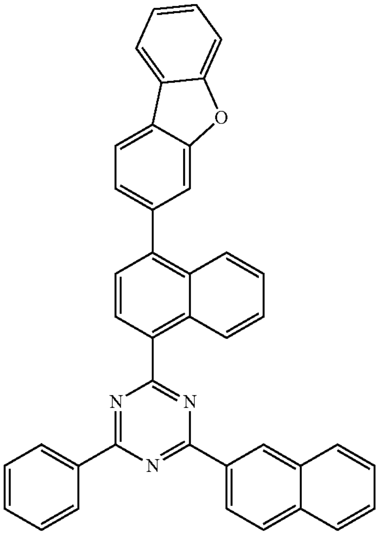
C-5
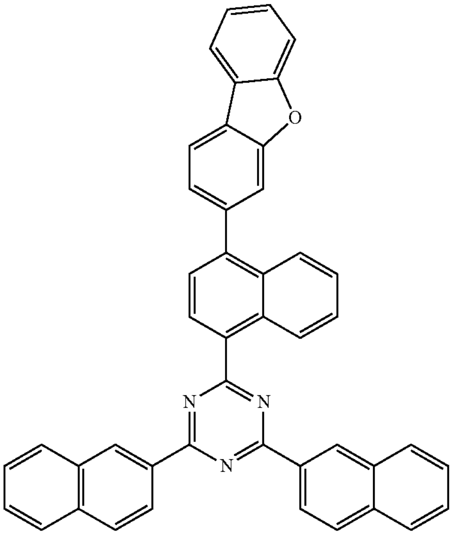
C-6
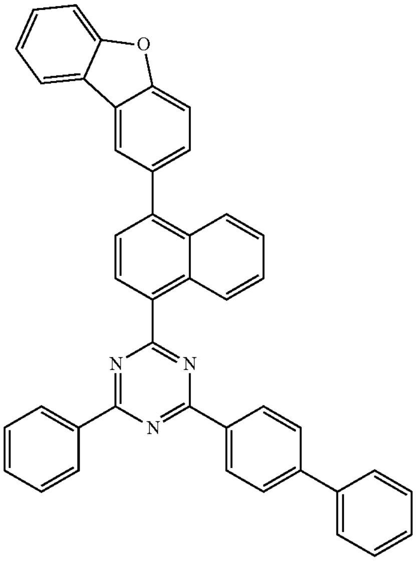

-continued
C-7
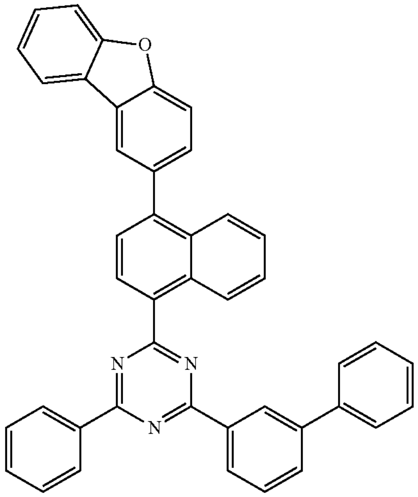
C-8
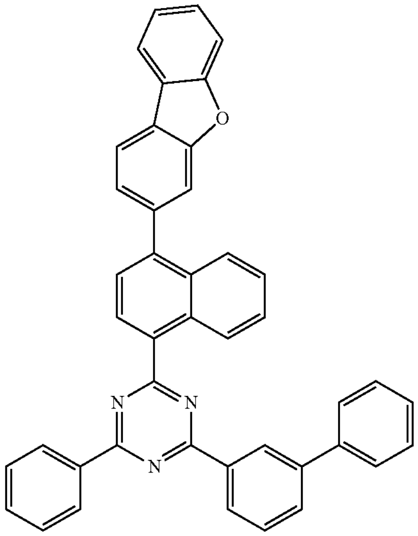
C-9
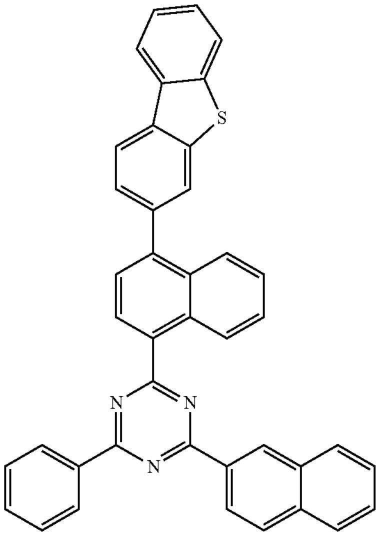
-continued
C-10
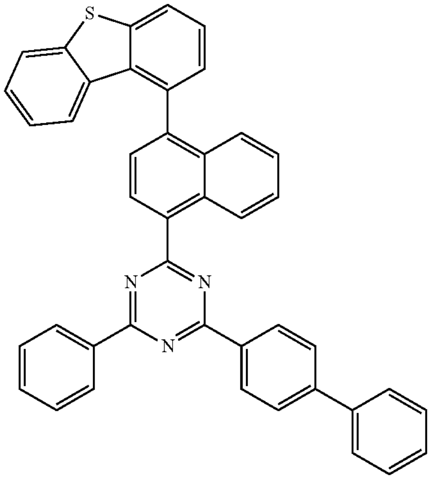
C-11
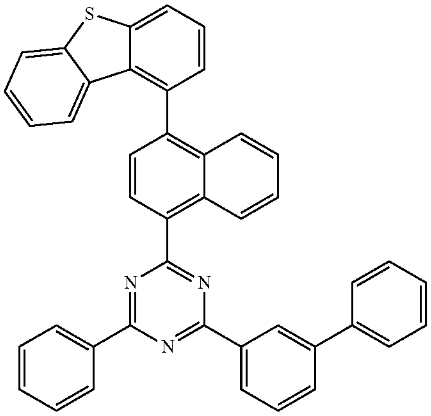
C-12
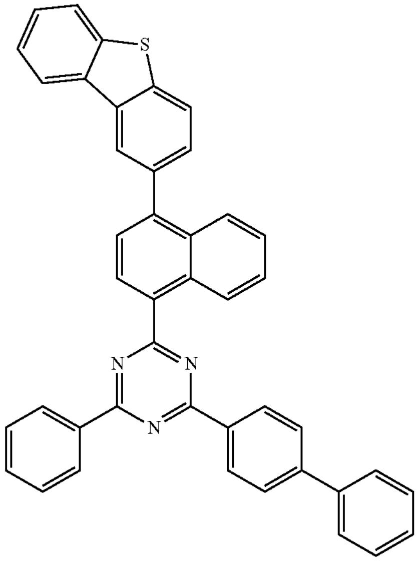

-continued
C-13
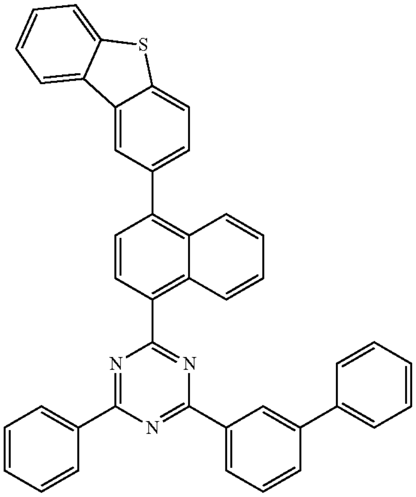
C-14
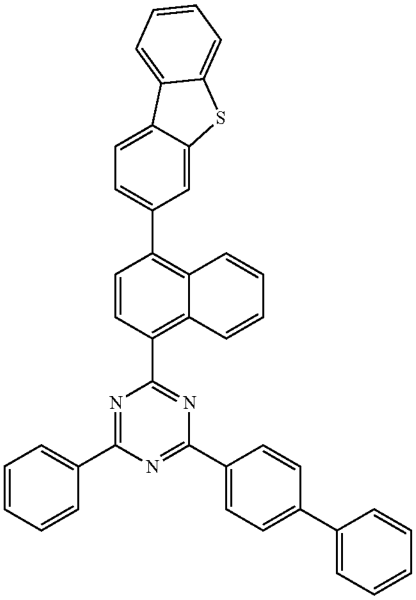
C-15
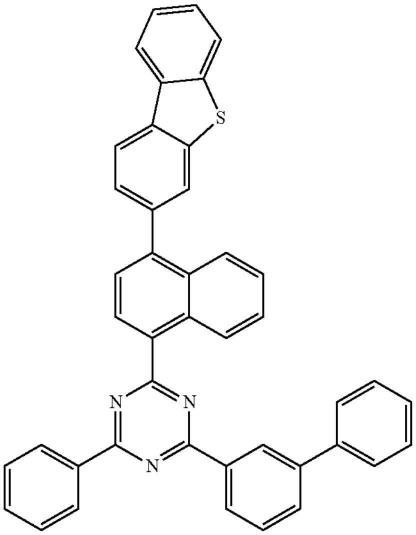
-continued
C-16
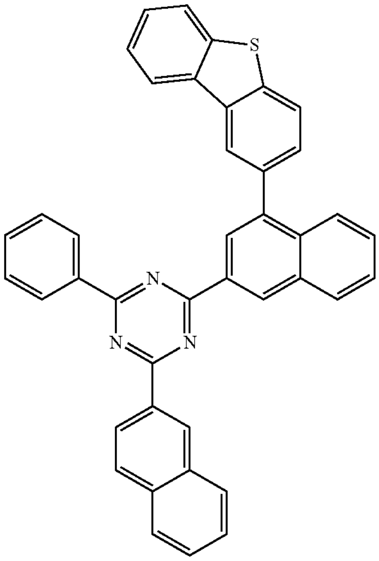
C-17
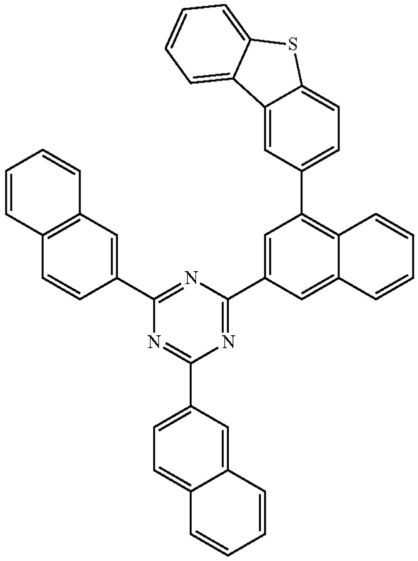

-continued
C-18
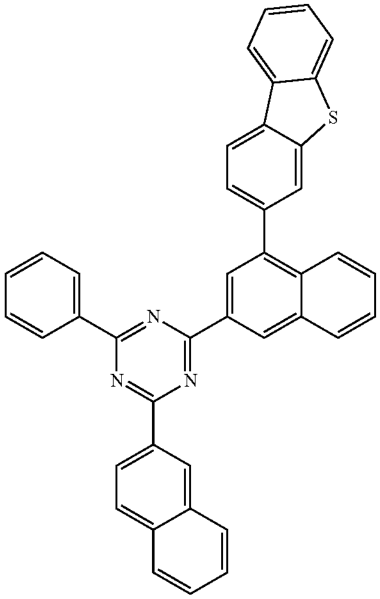
C-19
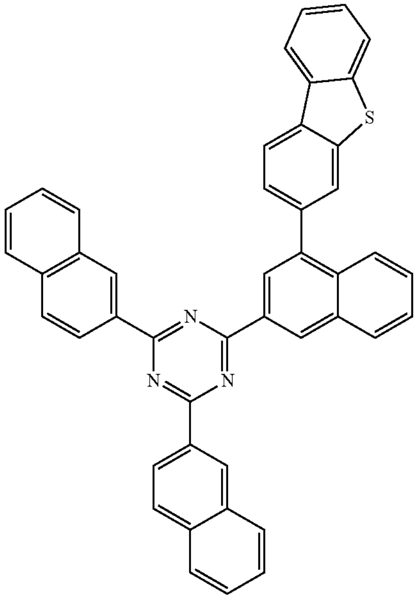
-continued
C-20
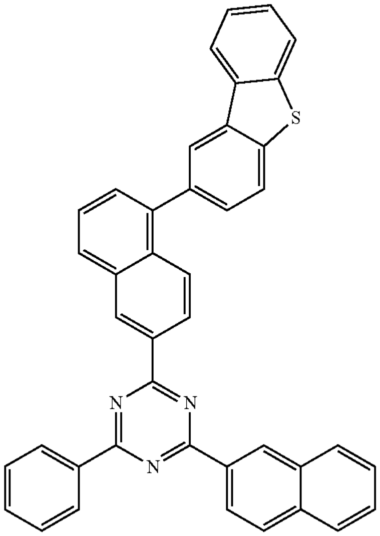
C-21
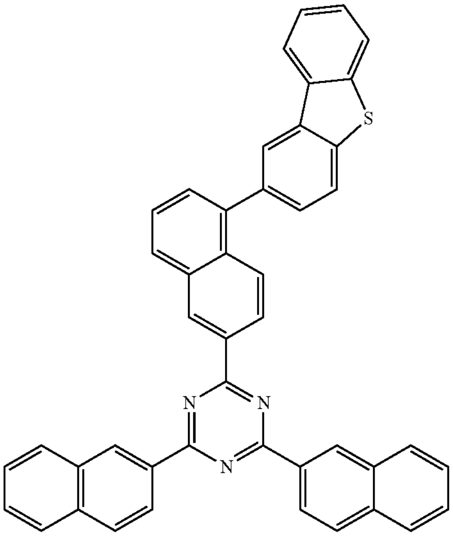
C-22
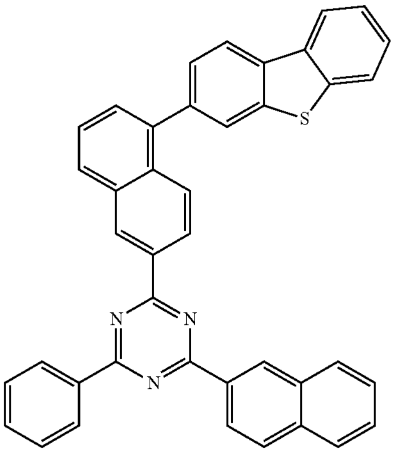

-continued
C-23
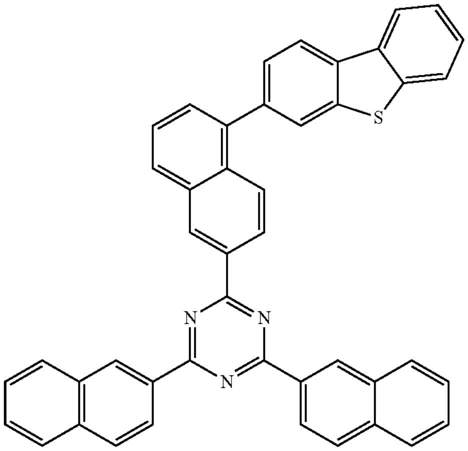
C-24
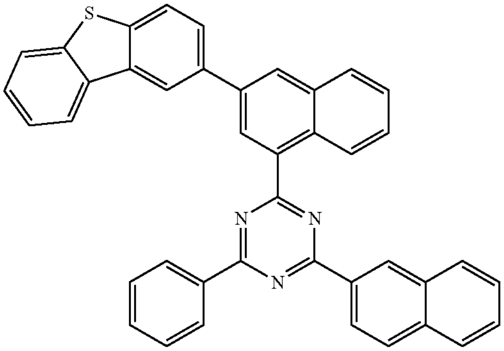
C-25
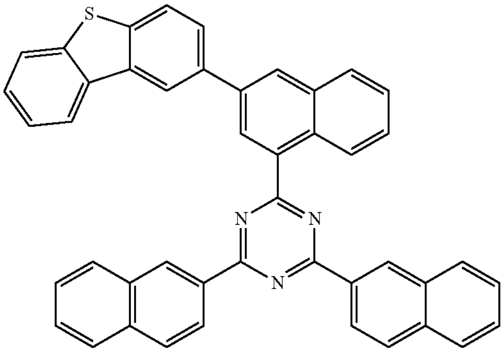
C-26
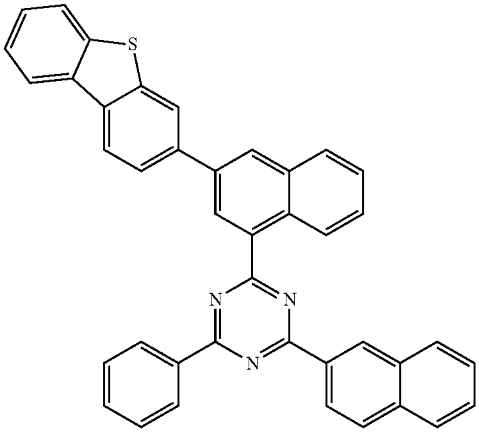
-continued
C-27
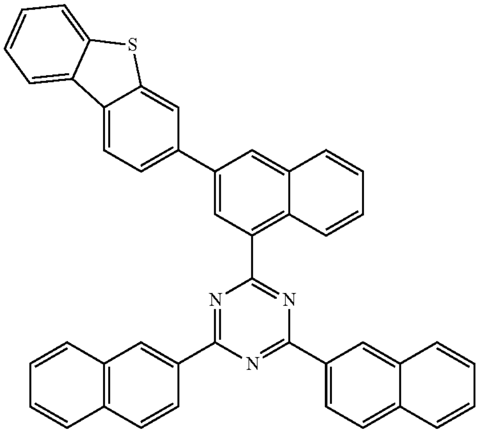
C-28
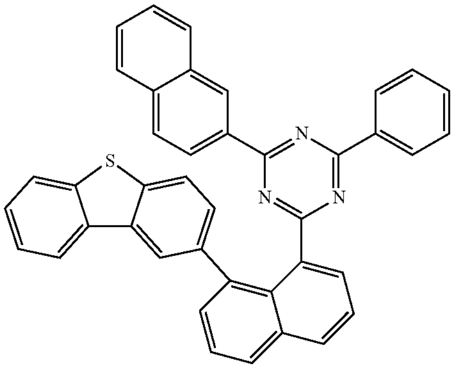
C-29
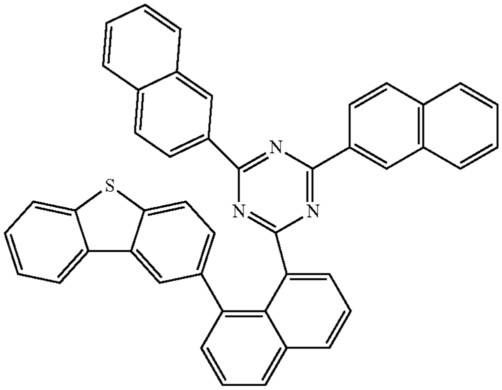
C-30
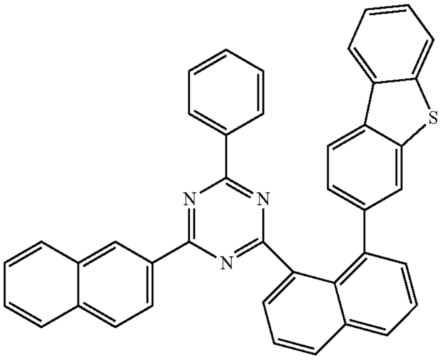

-continued
C-31
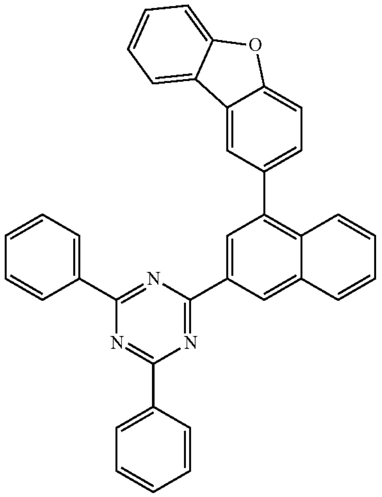
C-32
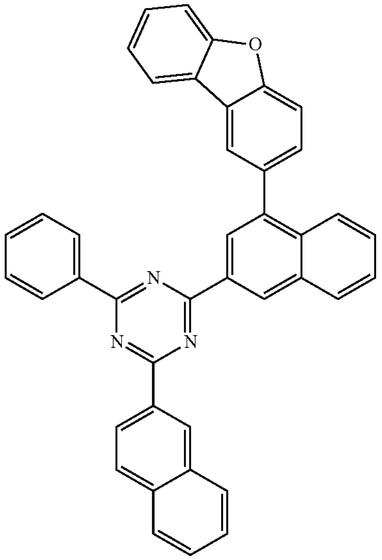
C-33
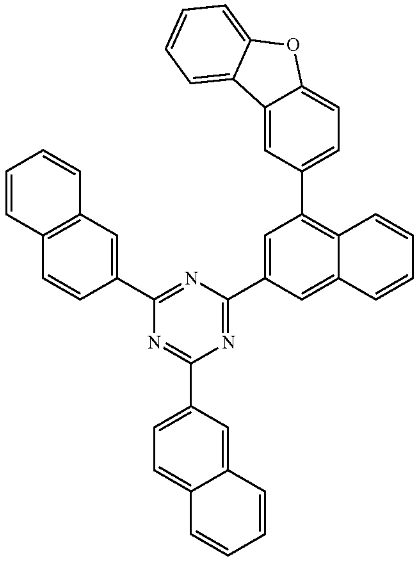
-continued
C-34
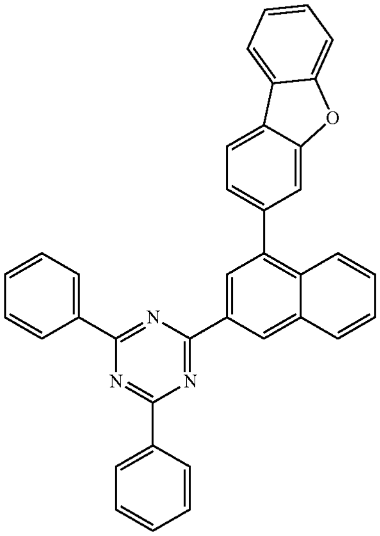
C-35
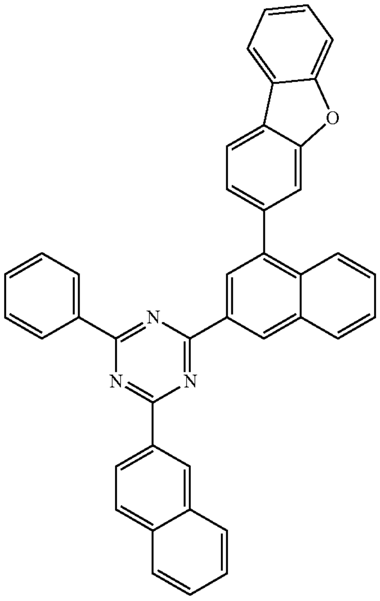

-continued
C-36
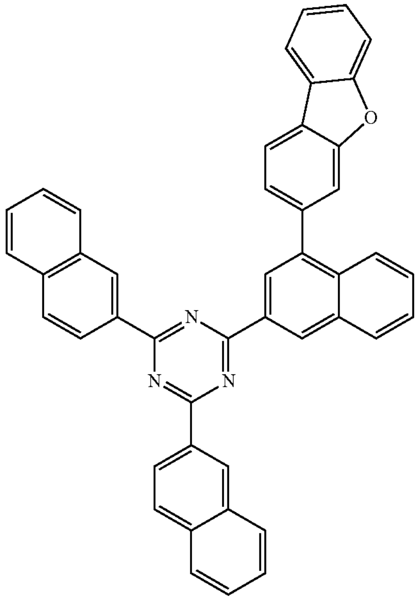
C-37
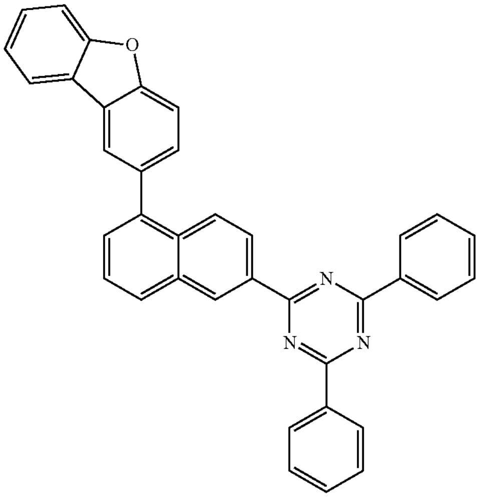
C-38
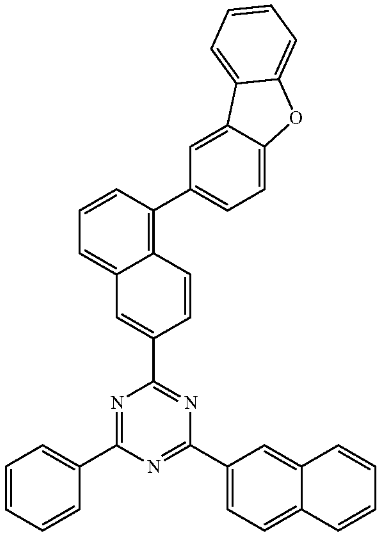
-continued
C-39
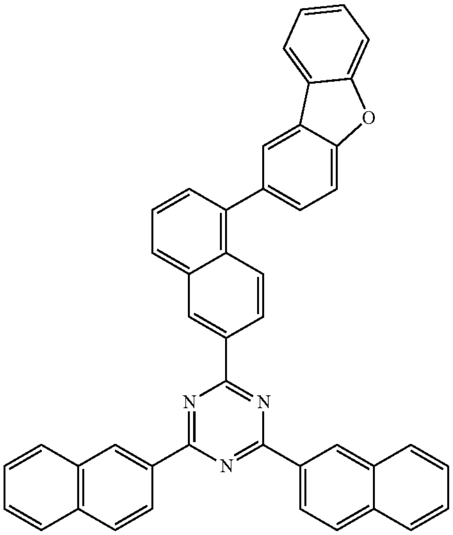
C-40
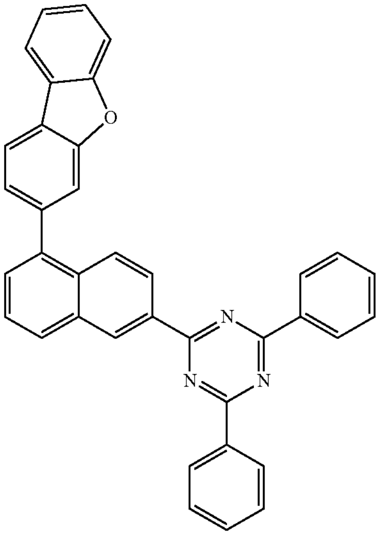
C-41
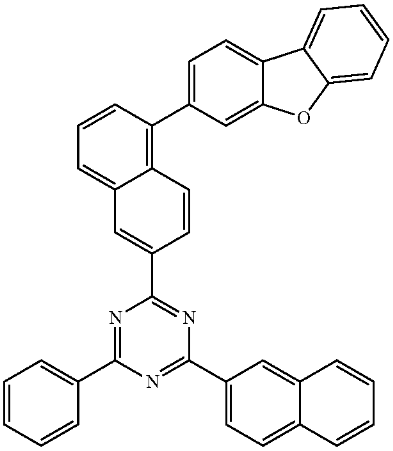

-continued
C-42
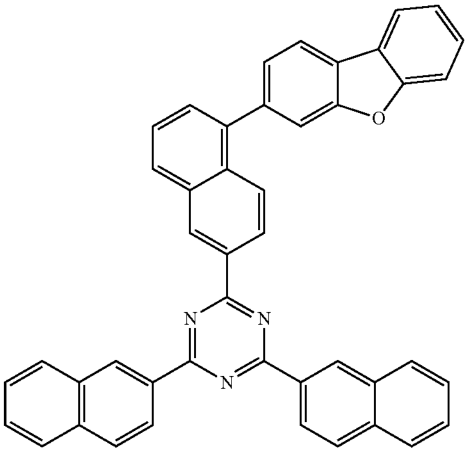
C-43
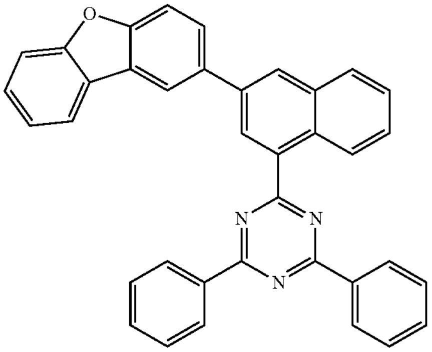
C-44
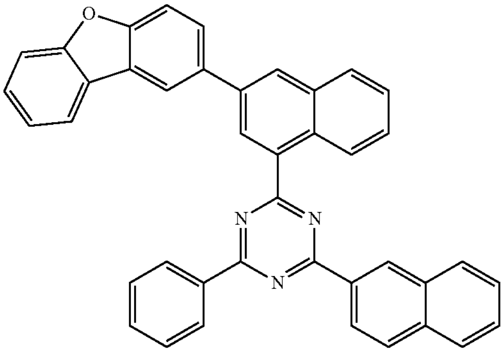
C-45
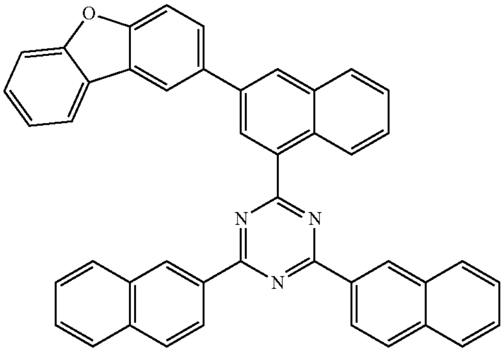
-continued
C-46
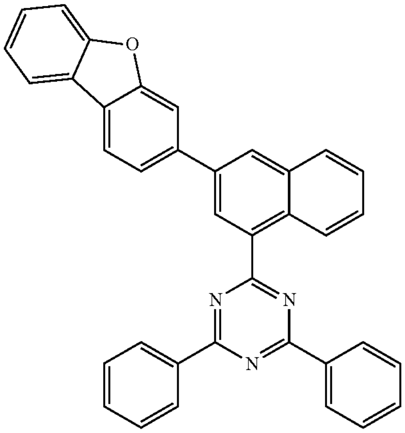
C-47
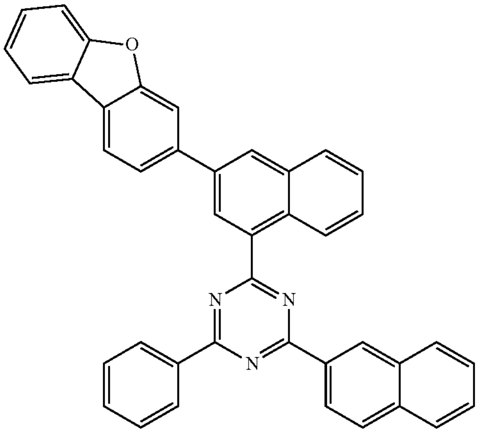
C-48
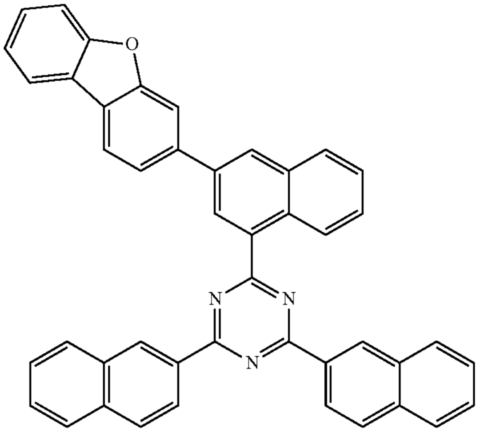

-continued
C-49
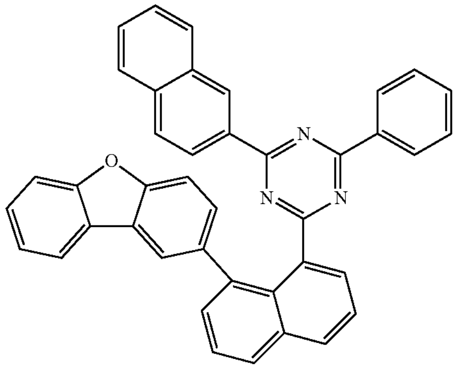
C-50
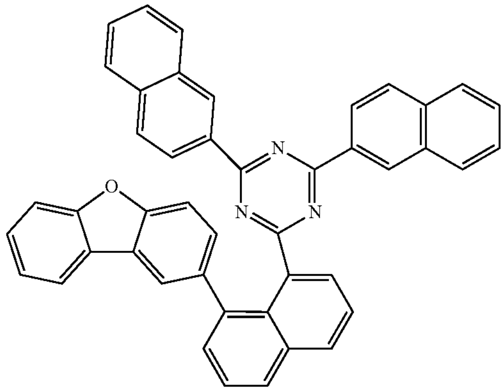
C-51
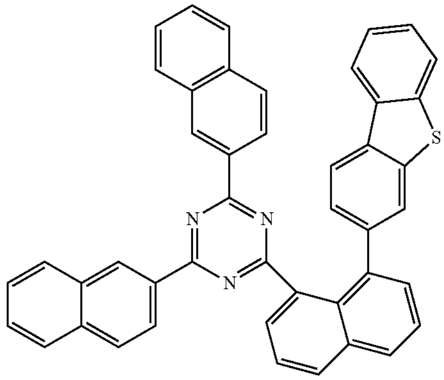
C-52
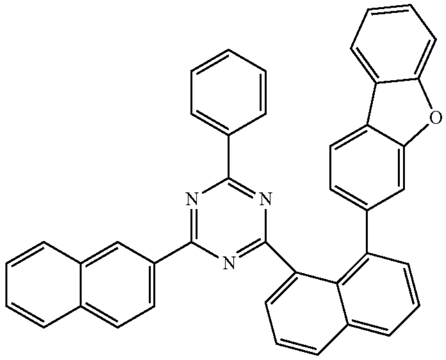
-continued
C-53
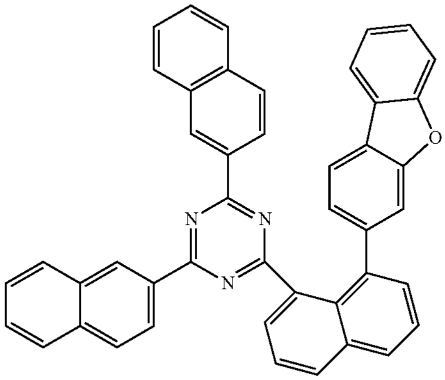
C-54
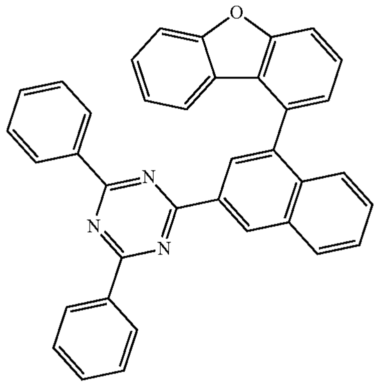
C-55
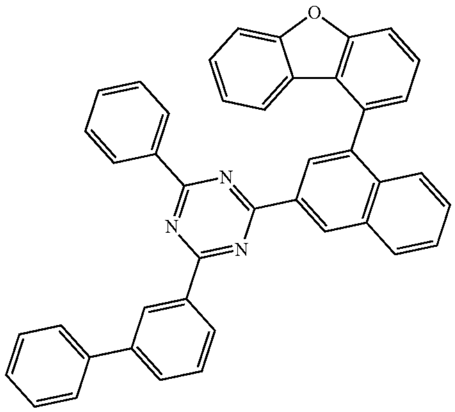

-continued
C-56
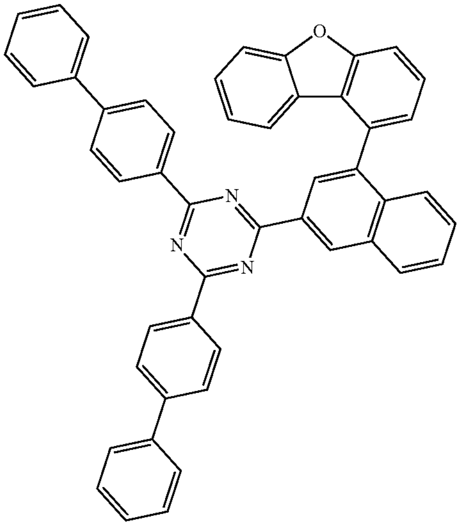
C-57
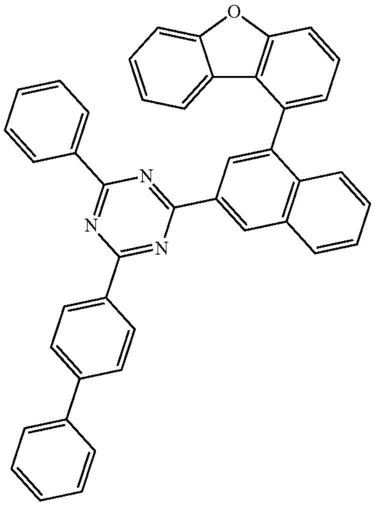
C-58
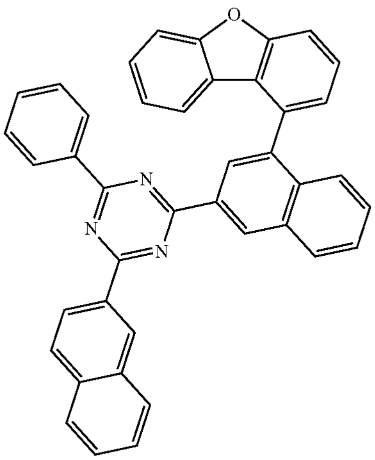
-continued
C-59
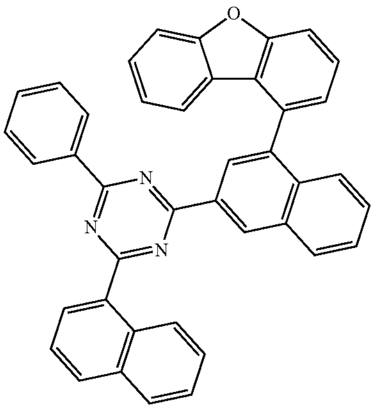
C-60
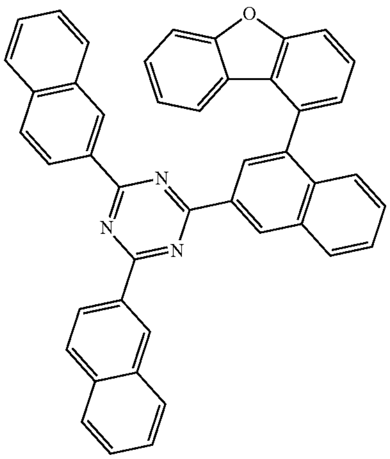
C-61
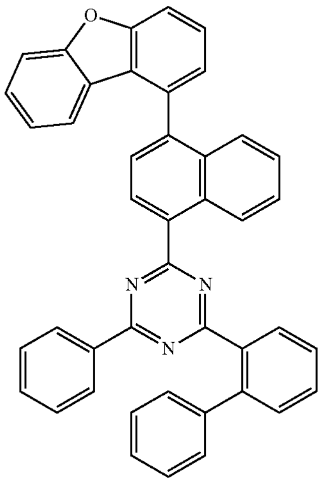

-continued
C-62
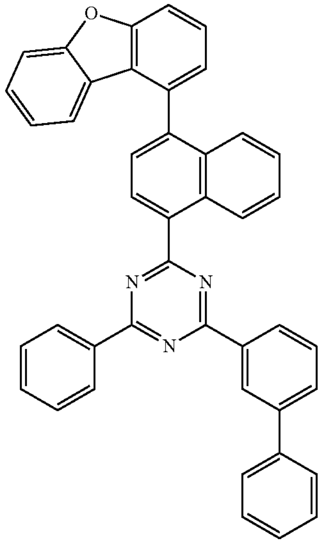
C-63
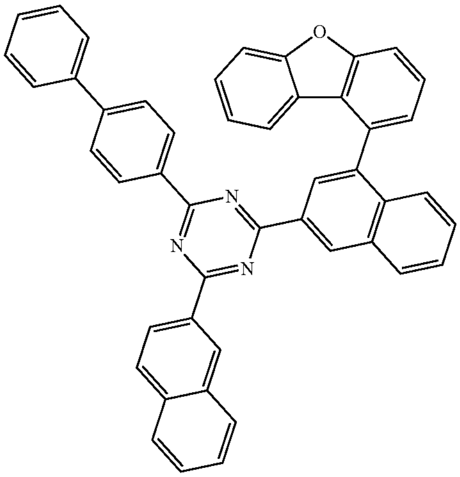
C-64
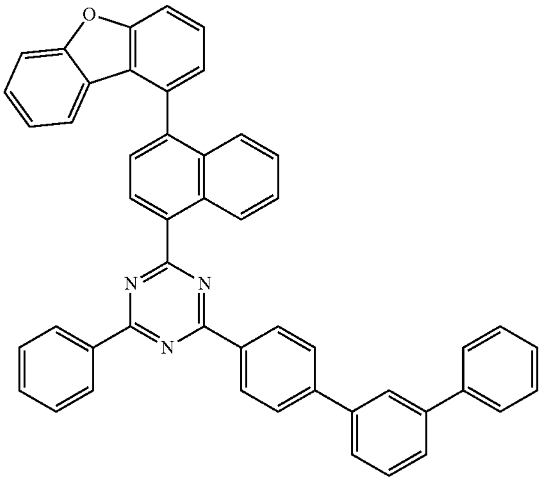
-continued
C-65
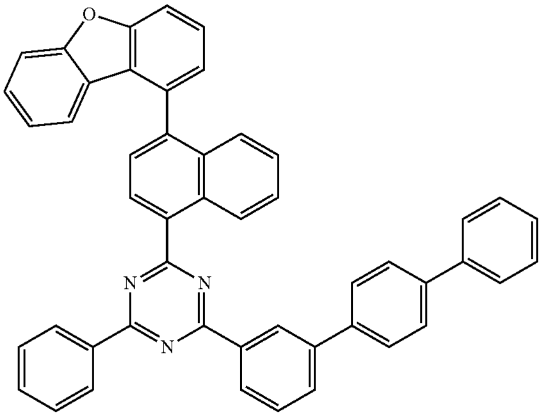
C-66
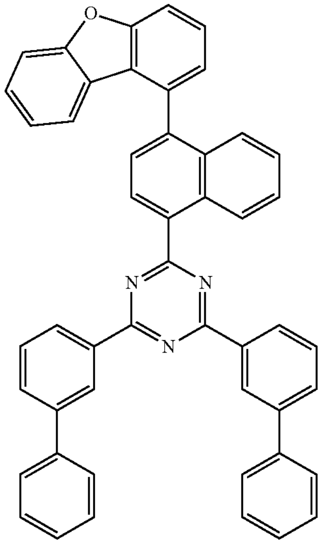
C-67
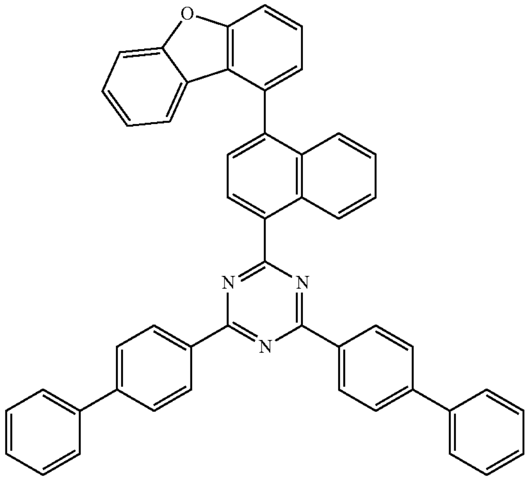

-continued
C-68
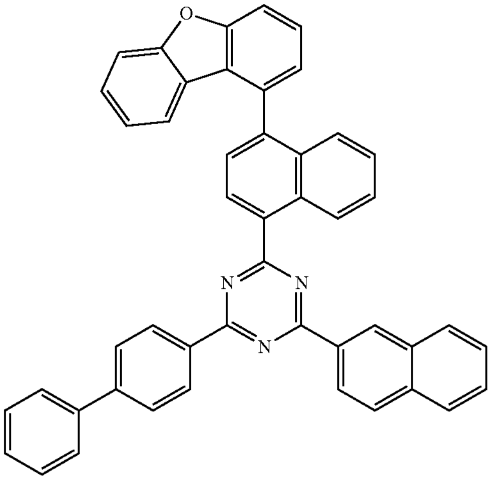
C-69
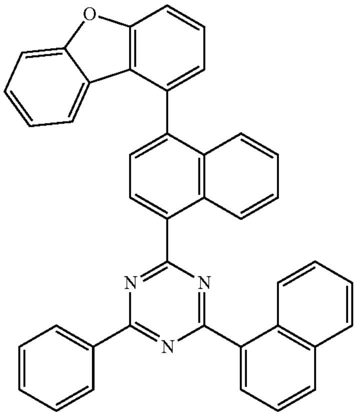
C-70
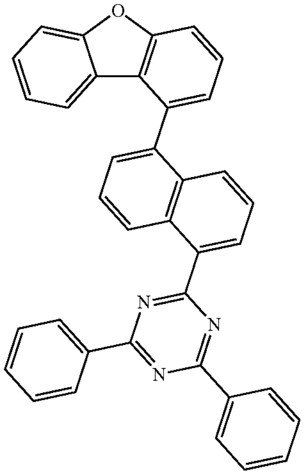
-continued
C-71
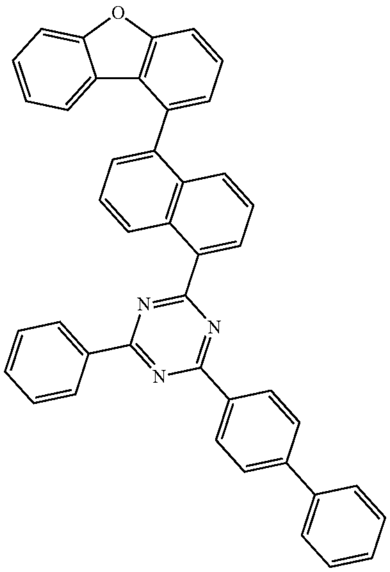
C-72
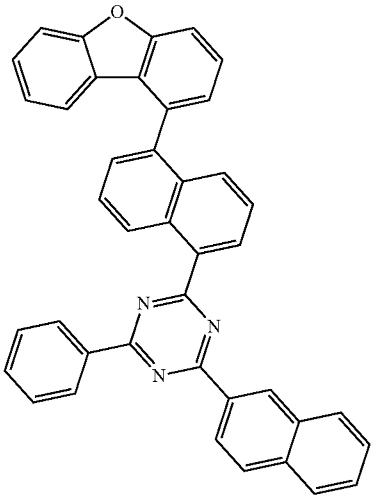
C-73
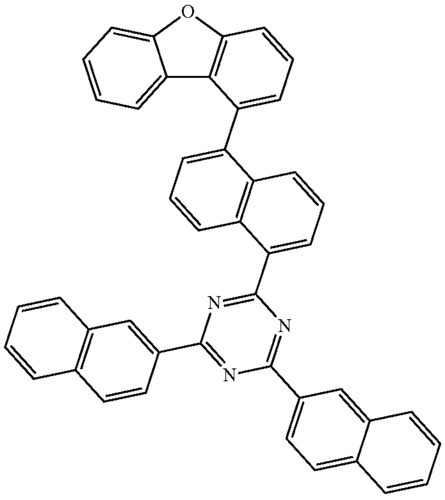

C-74
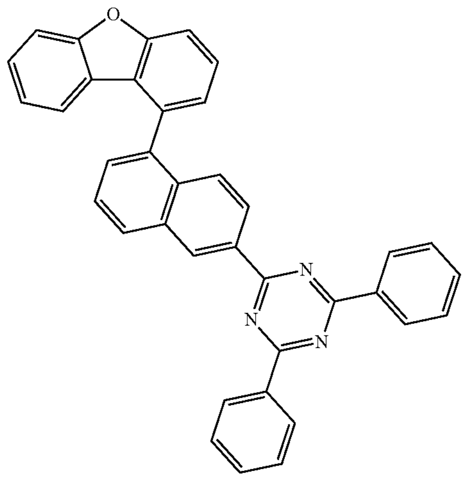
C-75
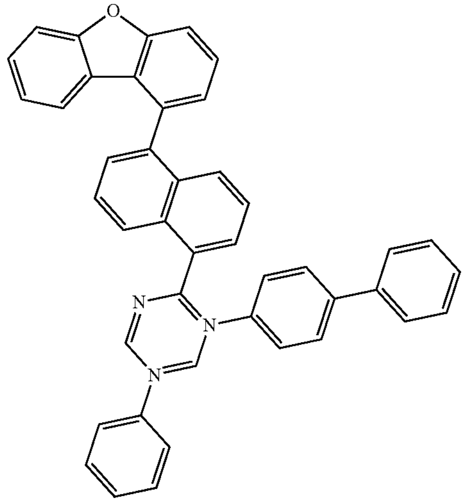
C-76
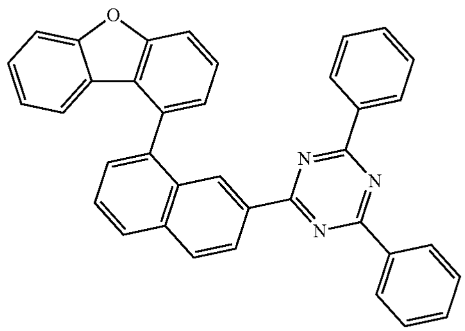
C-77
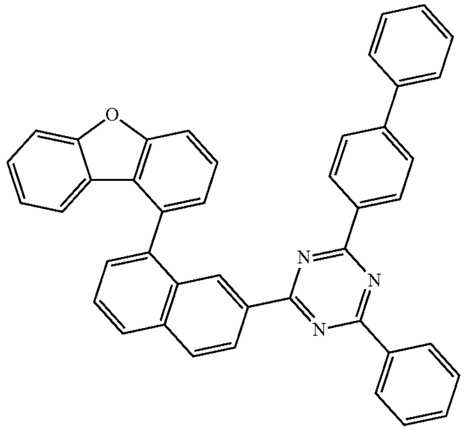
C-78
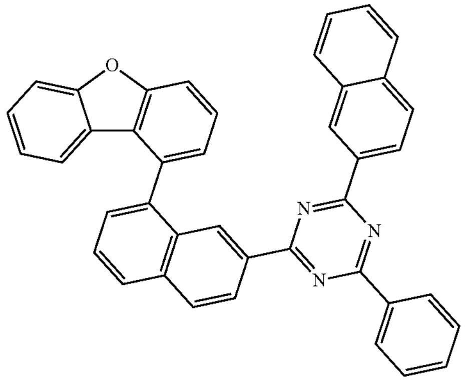
C-79
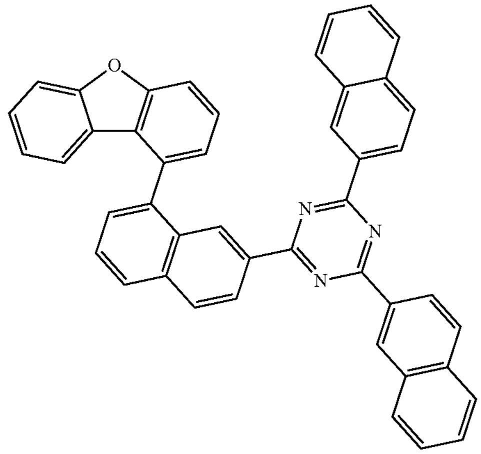

-continued
C-80
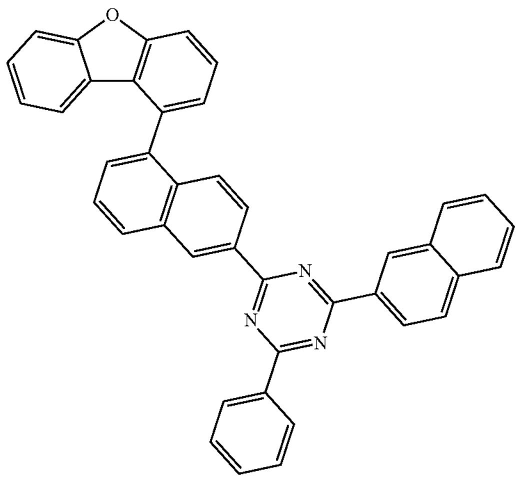
C-81
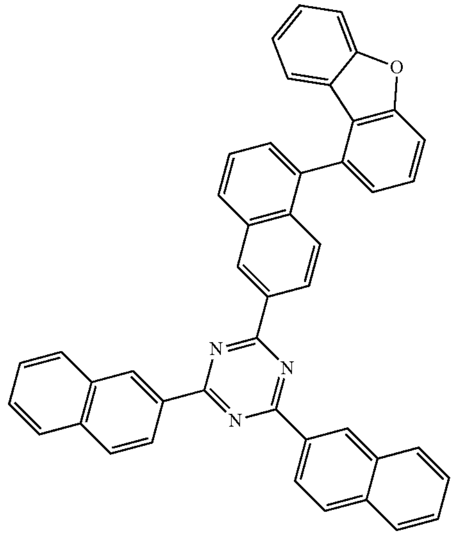
C-82
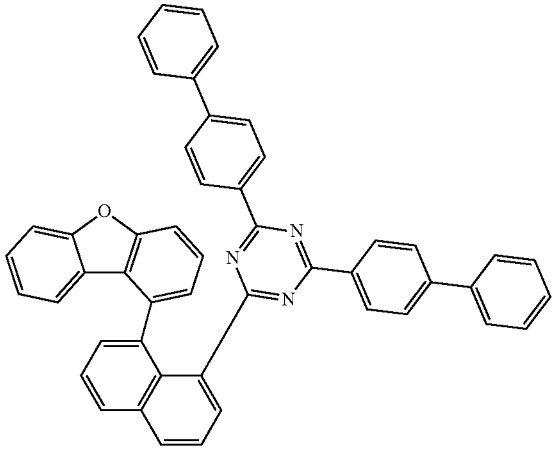
-continued
C-83
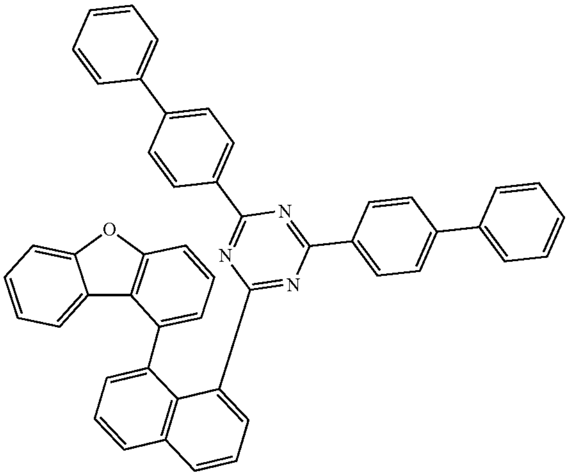
C-84
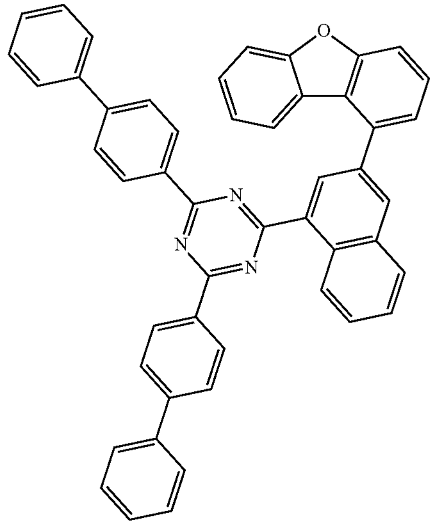
C-85
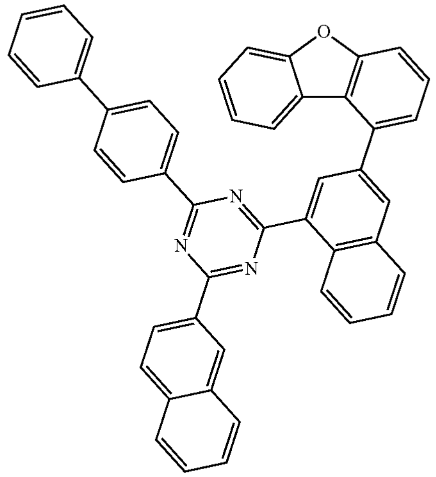

-continued
C-86
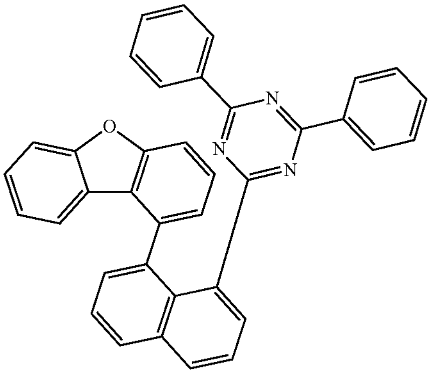
C-87
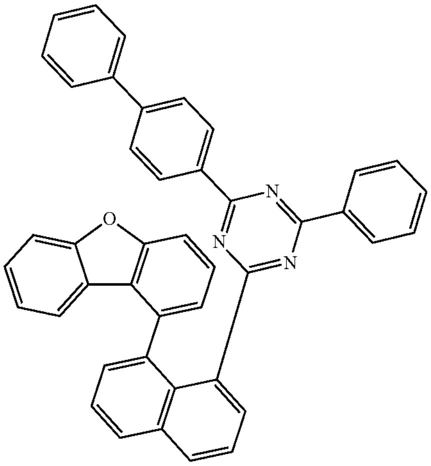
C-88
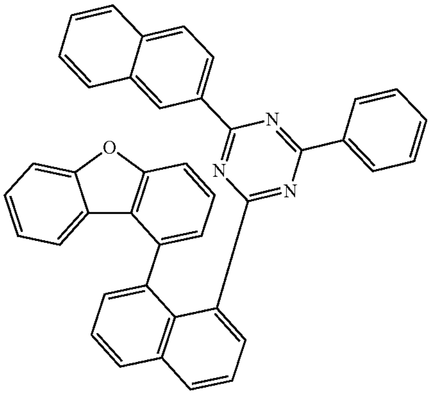
C-89
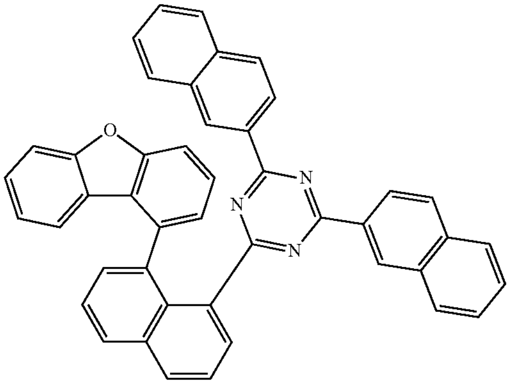
-continued
C-90
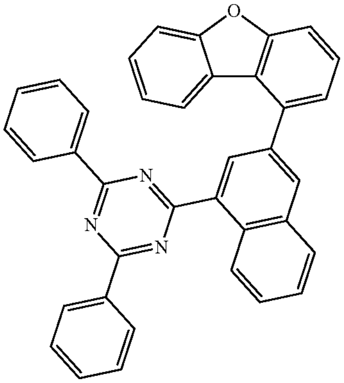
C-91
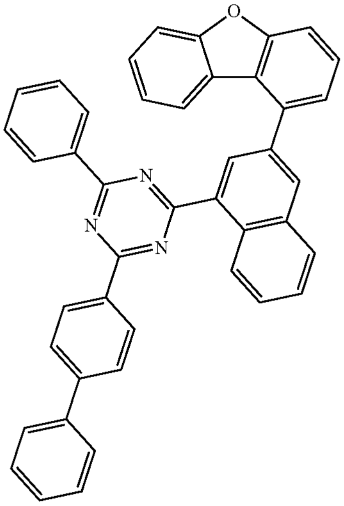
C-92
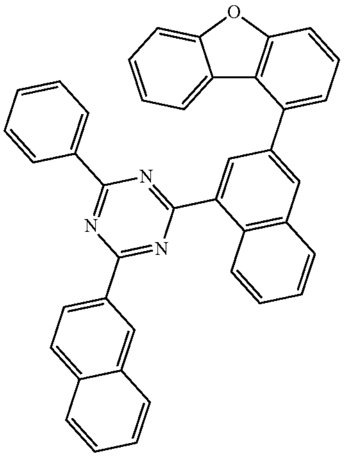

-continued
C-93
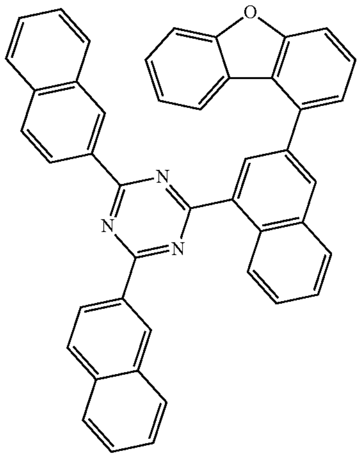
C-94
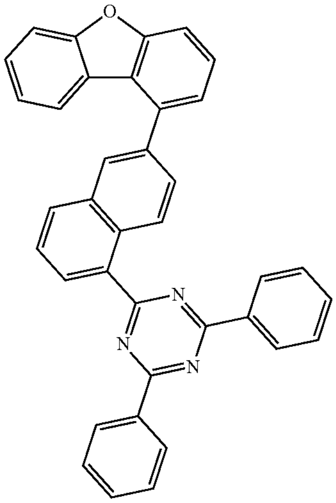
C-95
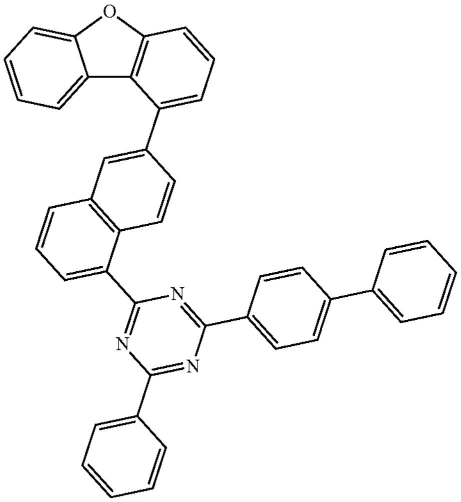
-continued
C-96
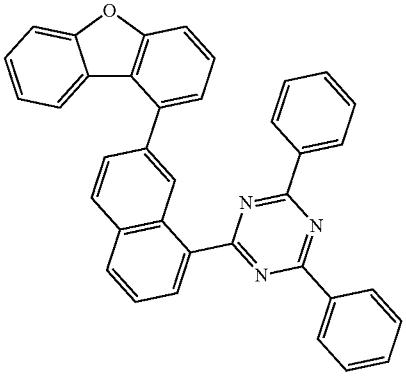
C-97
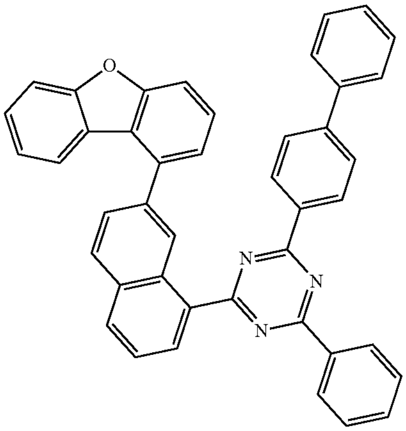
C-98
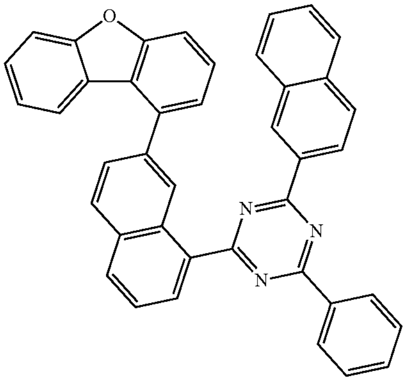
C-99
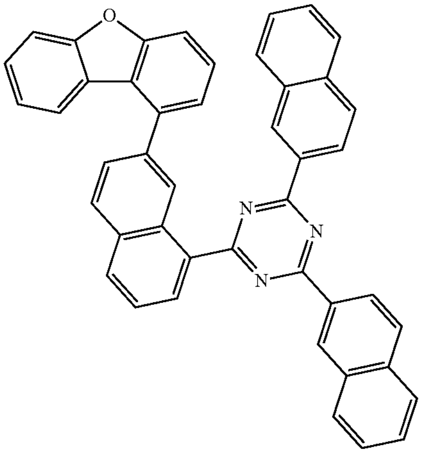

-continued
C-100
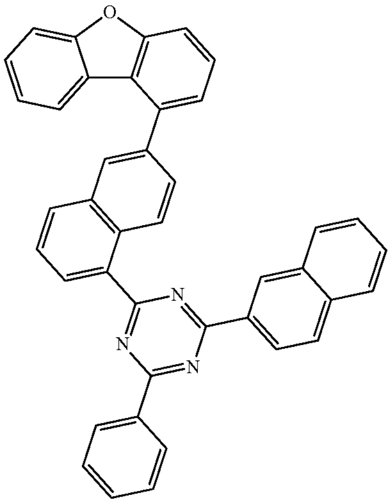
C-101
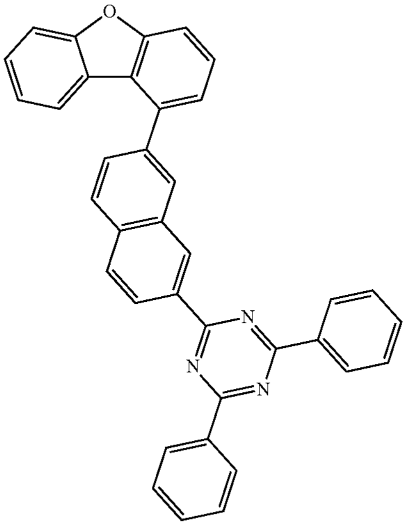
C-102
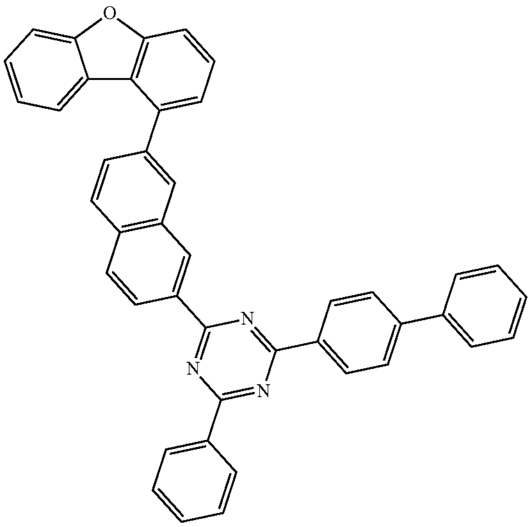
-continued
C-103
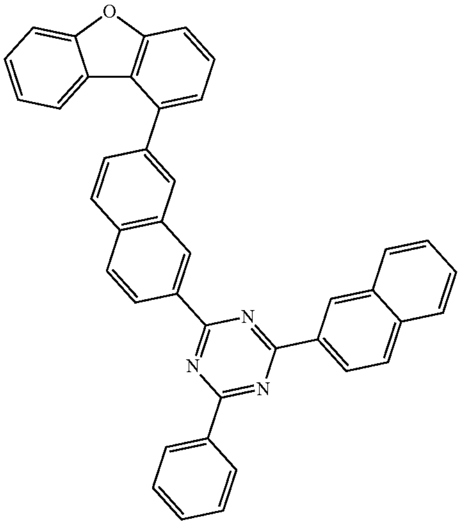
C-104
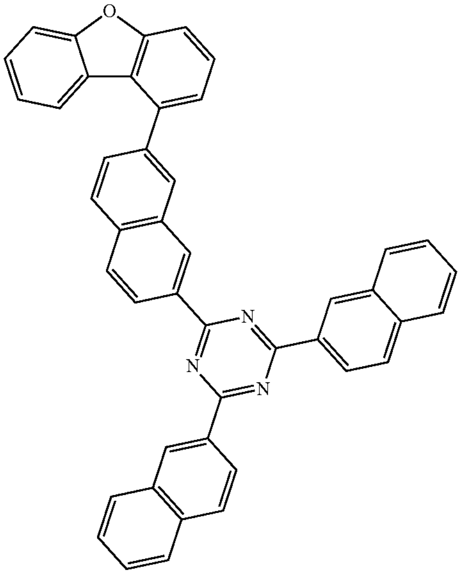
C-105
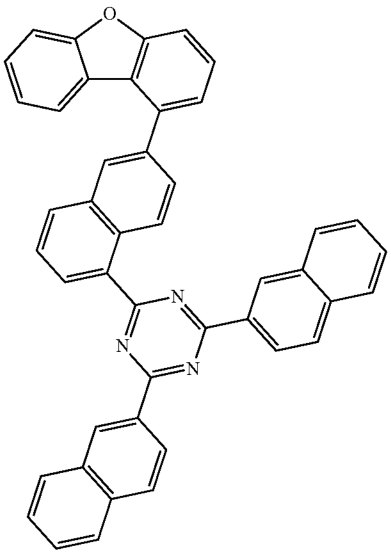

-continued

C-106

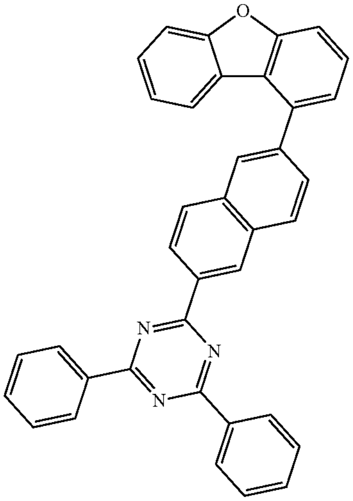

C-107

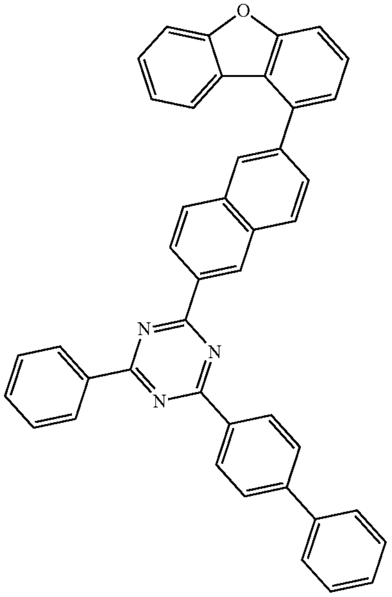

C-108

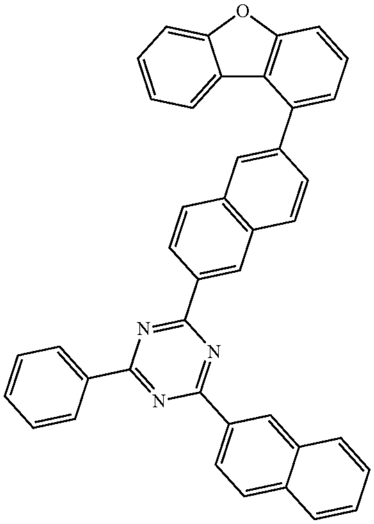

-continued

C-109

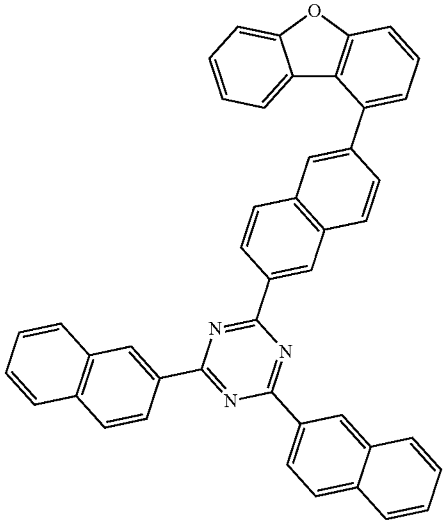

According to one embodiment of the present disclosure, the compound represented by formula 2-1-1 may be used as a sole compound or in a combination of two or more compounds in the organic electroluminescent device.

The Compound represented by formula 1 according to the present disclosure may be produced by the following reaction scheme 1 and may be produced by a synthetic method known to a person skilled in the art, e.g., may be produced by referring to the disclosed methods in KR 2015-0135109 A (2015 Dec. 2), KR 2016-0099471 A (2016 Aug. 22), KR 2015-0077513 A (2015 Jul. 8), and KR 2017-0129599 A (2017 Nov. 27), but are not limited thereto.

[Reaction Scheme 1]

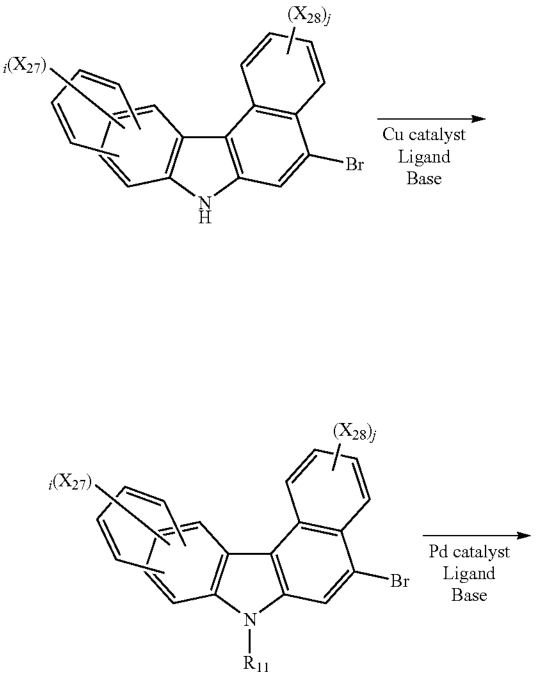

-continued

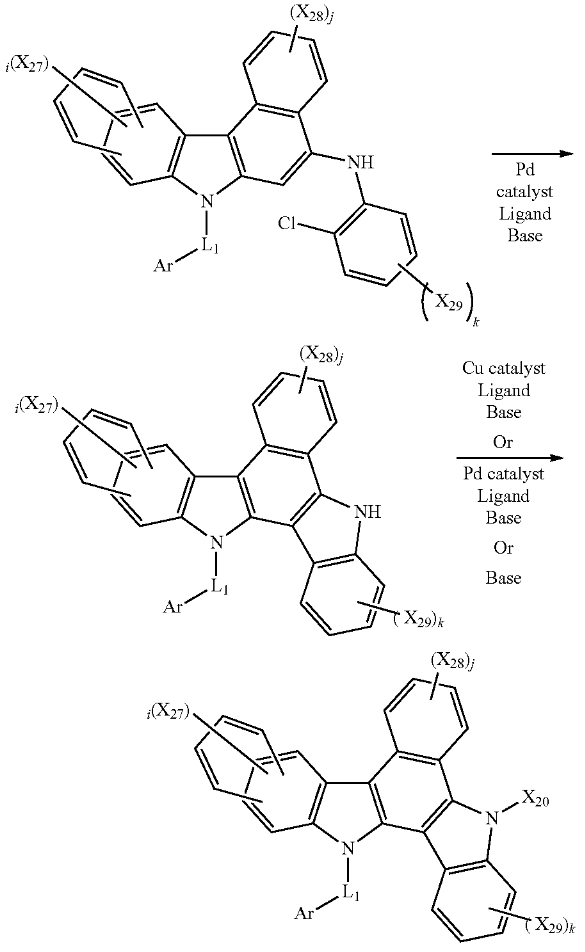

In reaction scheme 1, Ar, $L_1$, $X_{20}$, $X_{27}$ to $X_{29}$, i, j and k are as defined in formula 1-4.

The compound represented by formula 2 of the present disclosure may be produced by the following reaction scheme 2 and a synthetic method known to a person skilled in the art, but is not limited thereto.

[Reaction Scheme 2]

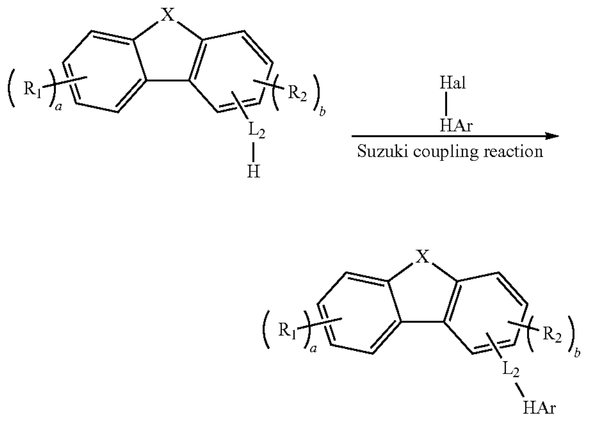

-continued

Z: $B(OH)_2$,

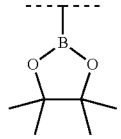

Hal: halogen

In reaction scheme 2, X, HAr, $L_2$, $R_1$, $R_2$, a, and b are as defined in formula 2.

The organic electroluminescent device according to the present disclosure includes an anode; a cathode; and at least one organic layer interposed between the andoe and cathode. The organic layer may comprise a plurality of host materials comprising the compound represented by the formula 1 as a first organic electroluminescent light-emitting material and the compound represented by the formula 2 as a second organic electroluminescent light-emitting material. According to one embodiment of the present disclosure, the organic electroluminescent device according to the present disclosure includes an anode, a cathode, and at least one light-emitting layer interposed between the anode and cathode. The at least one light-emitting layer may comprise the compound represented by the formula 1 and the compound represented by the formula 2. According to another embodiment of the present disclosure, the organic electroluminescent device according to the present disclosure includes an anode, a cathode, and at least one light-emitting layer interposed between the anode and cathode. The at least one light-emitting layer may comprise the compound represented by formula 2-1-1.

The light-emitting layer includes host and dopant materials, and the host includes a plurality of host materials. The compound represented by the formula 1 is comprised as a first host compound and the compound represented by the formula 2 is comprised as a second host compound among a plurality of host materials. Herein, the weight ratio of the first host compound to the second host compound may be about 1:99 to about 99:1, preferably about 10:90 to about 90:10, more preferably about 30:70 to about 70:30, more preferably about 40:60 to 60:40, much more preferably about 50:50.

Herein, the light-emitting layer is a layer from which light is emitted, and can be a single layer or a multi-layer of which two or more layers are stacked. In a plurality of host materials of the present disclosure, the first and the second host materials may be comprised together in one light-emitting layer, or may each be comprised in separate light-emitting layers. According to one embodiment of the present disclosure, it may be that the doping concentration of the dopant compound based on the host compound may be less than 20 wt %. According to another embodiment of the present disclosure, the light-emitting layer may comprise solely of the compound represented by formula 2-1-1.

The organic electroluminescent device of the present disclosure may further comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. According to one embodiment of the present disclosure, the organic electroluminescent device of the present disclosure may contain the amine-based compound as at least one of a hole injection material, a hole transport material, a hole auxiliary material, a light-emitting material, a light-emitting auxiliary material, and an electron blocking material other than a plurality of host materials of the present disclosure. In addition, according to one embodiment of the present disclosure, the organic electroluminescent device of the present disclosure may contain the azine-based compound as at least one of an electron transport material, an electron injection material, an electron buffer material, and a hole blocking material other than a plurality of host materials of the present disclosure.

The dopant comprised in the organic electroluminescent material of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compound(s) of a metal atom(s) selected from iridium (Ir), osmium (Os), copper (Cu), and platinum (Pt), more preferably an ortho-metallated complex compound(s) of a metal atom(s) selected from iridium (Ir), osmium (Os), copper (Cu), and platinum (Pt), and even more preferably ortho-metallated iridium complex compound(s).

The dopant comprised in the organic electroluminescent device may use the compound represented by the following formula 101, but is not limited thereto:

(101)

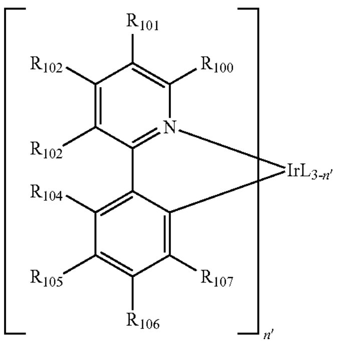

In formula 101, wherein, L is selected from the following structure 1 or 2:

structure (1)

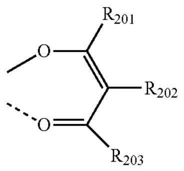

structure (2)

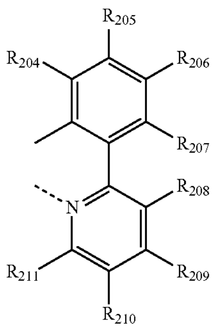

$R_{100}$ to $R_{107}$ each independently represent hydrogen, deuterium, halogen, halogen-substituted or unsubstituted (C1-C30)alkyl, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or may be linked to an adjacent substituent(s) to form a ring, e.g., $R_{100}$ to $R_{103}$ may be linked to an adjacent substituent(s) to form a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, $R_{104}$ to $R_{107}$ may be linked to an adjacent substituent(s) to form a substituted or unsubstituted naphthyl, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{211}$ each independently represent hydrogen, deuterium, halogen, halogen-substituted or unsubstituted (C1-C30)alkyl, a substituted or unsubstituted (C3-C30) cycloalkyl, or a substituted or unsubstituted (C6-C30) aryl; or may be linked to an adjacent substituent(s) to form a ring; and n' represents an integer of 1 to 3.

Specifically, the specific examples of the dopant compound include the following, but are not limited thereto.

D-1

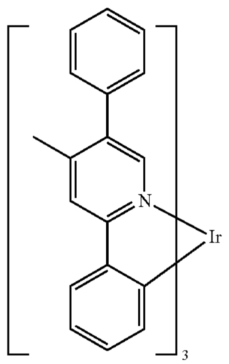

D-2

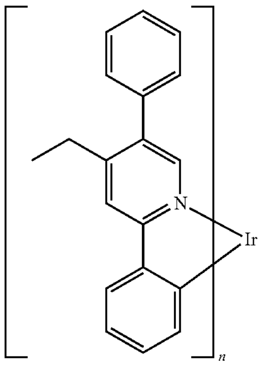

-continued
D-3
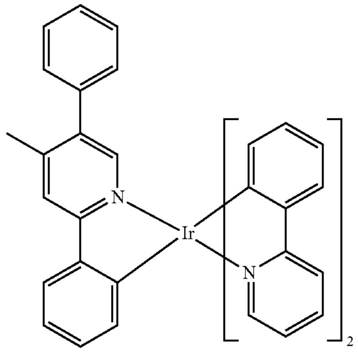
D-4
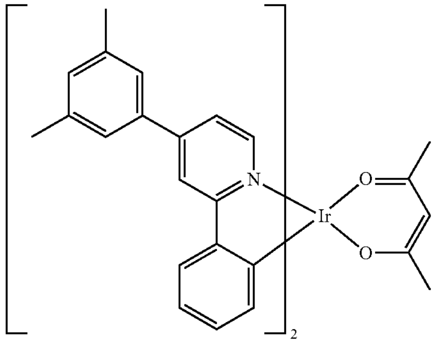
D-5
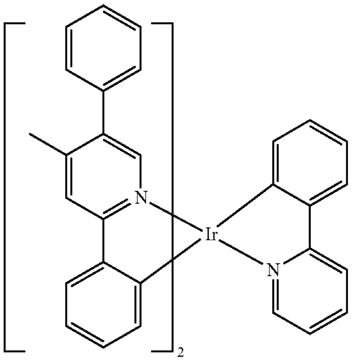
D-6
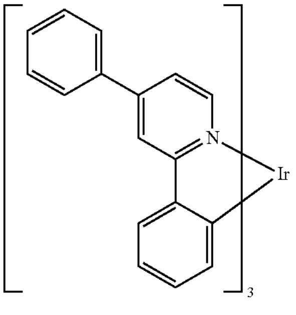
-continued
D-7
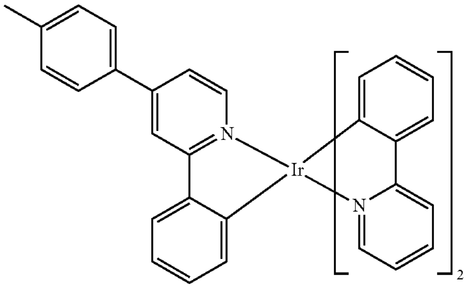
D-8
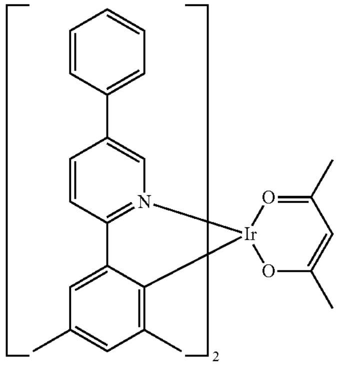
D-9
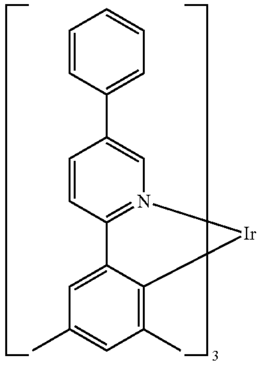
D-10
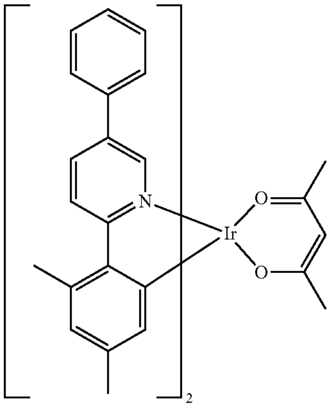

-continued
D-11
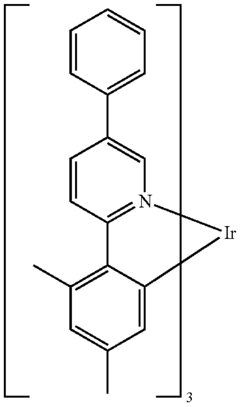
D-12
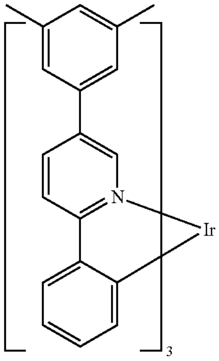
D-13
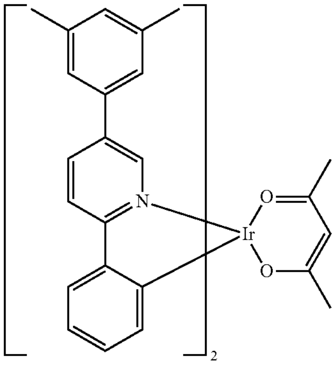
D-14
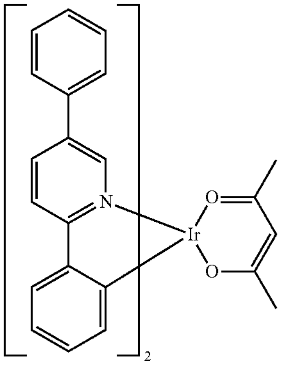
-continued
D-15
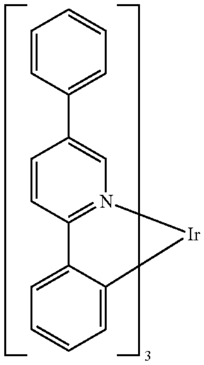
D-16
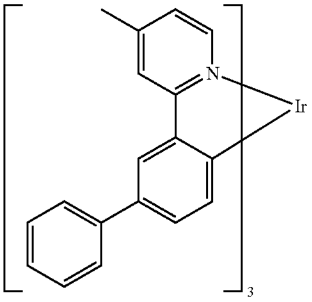
D-17
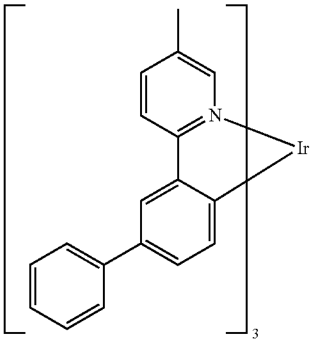
D-18
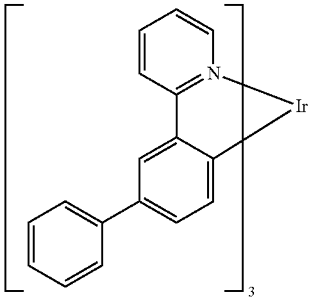

-continued
D-19
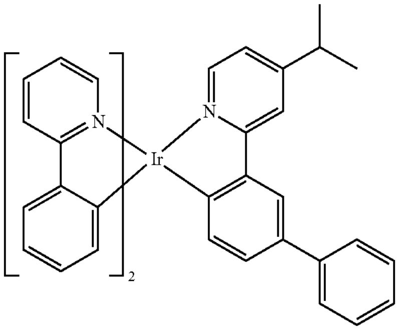
D-20
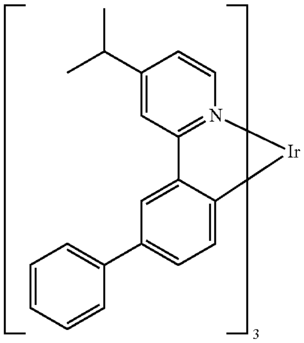
D-21
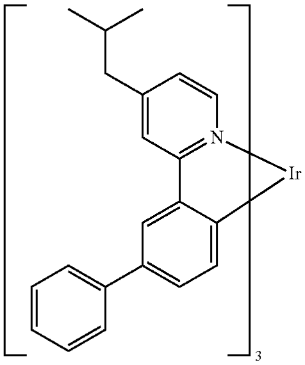
D-22
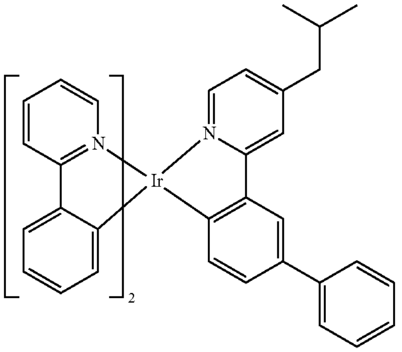
-continued
D-23
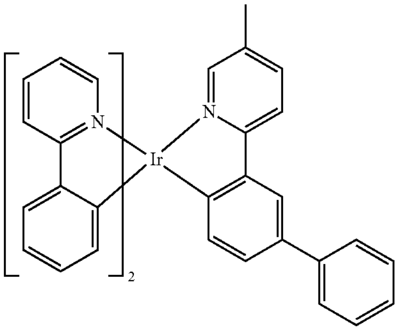
D-24
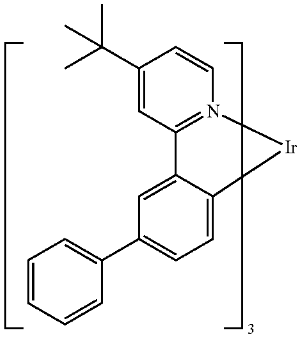
D-25
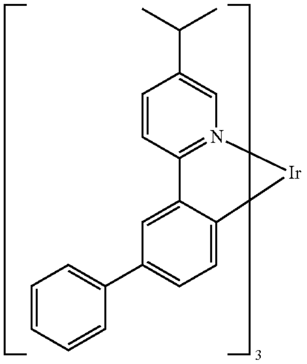
D-26
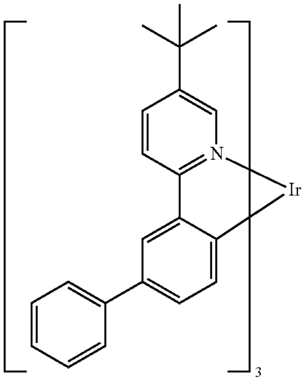

D-27
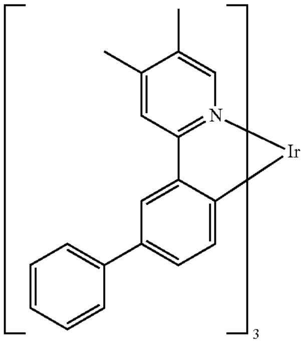
D-28
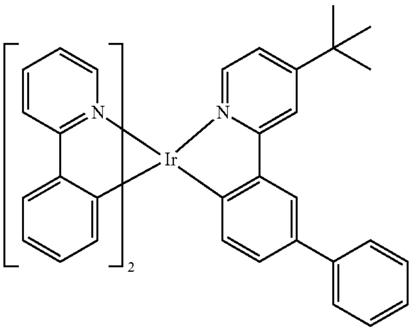
D-29
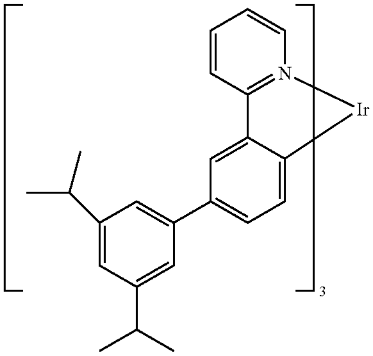
D-30
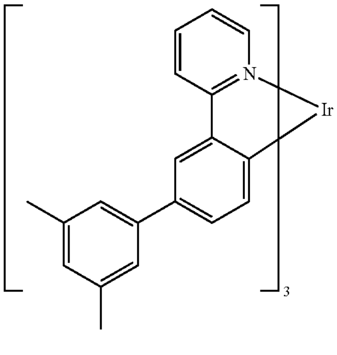
D-31
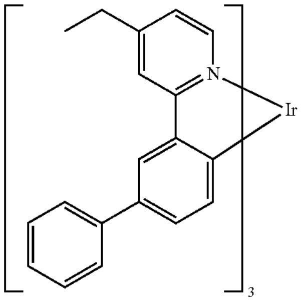
D-32
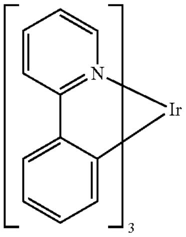
D-33
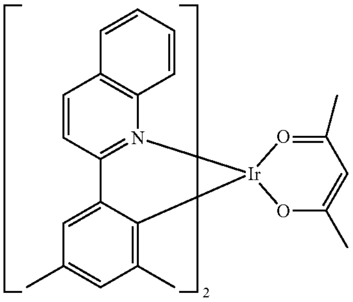
D-34
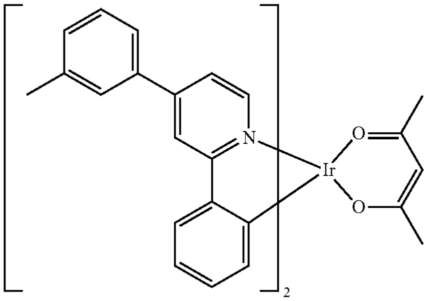
D-35
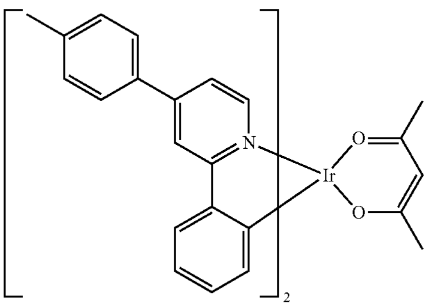

-continued
D-36
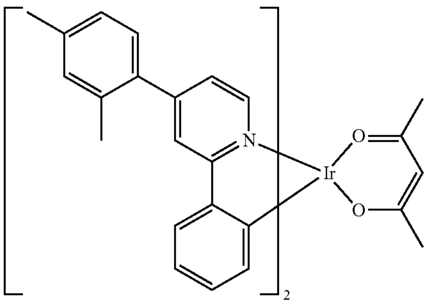
D-37
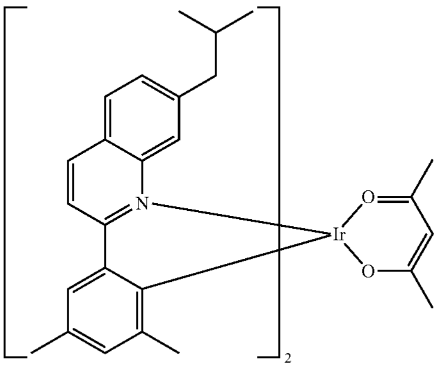
D-38
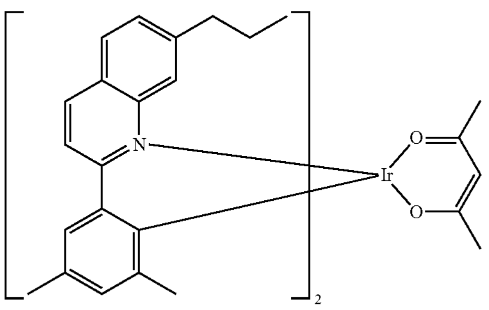
D-39
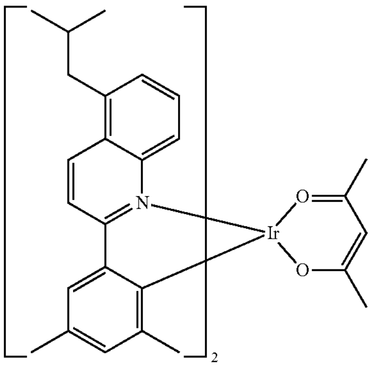
-continued
D-40
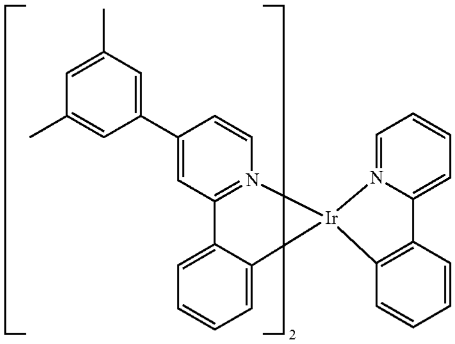
D-41
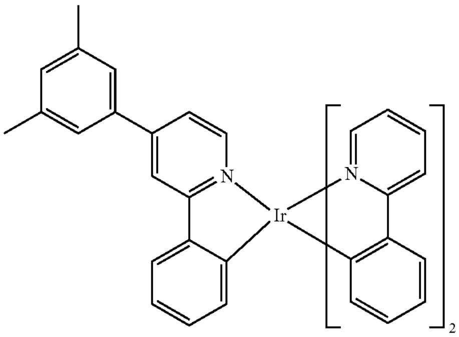
D-42
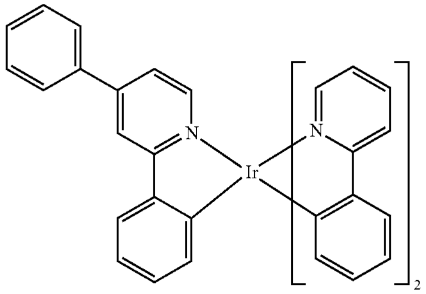
D-43
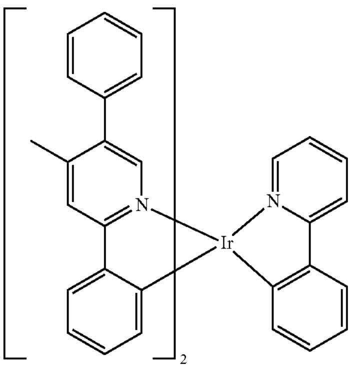

-continued
D-44
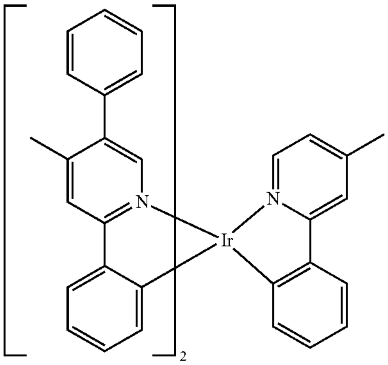
D-45
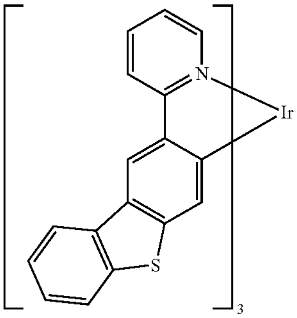
D-46
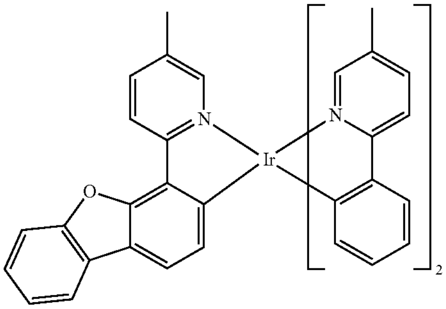
D-47
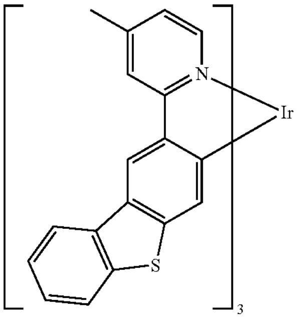
D-48
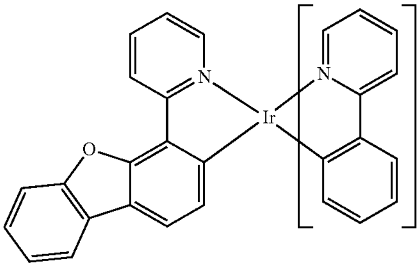
-continued
D-49
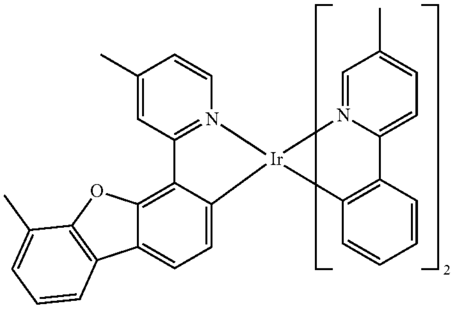
D-50
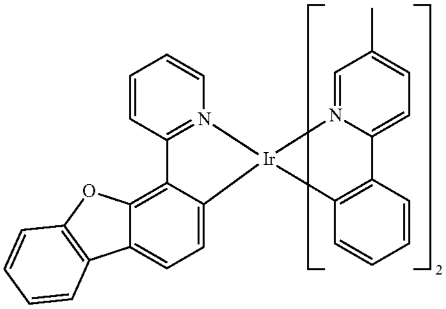
D-51
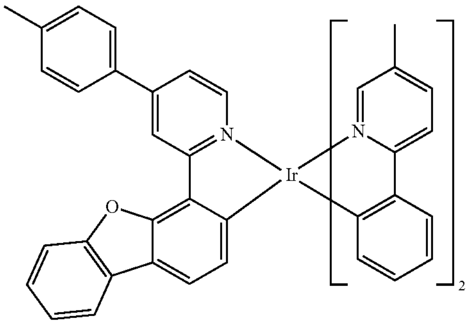
D-52
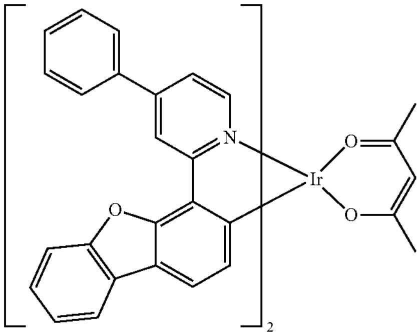
D-53
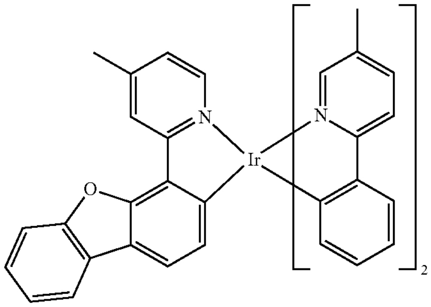

-continued
D-54
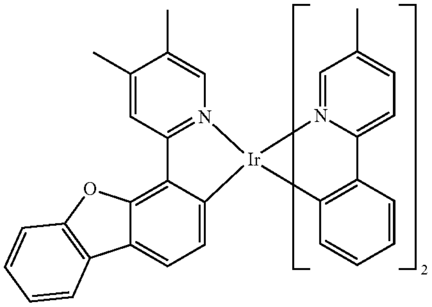
D-55
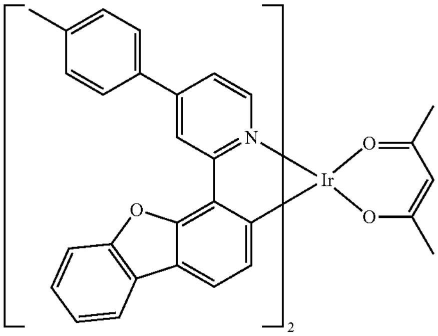
D-56
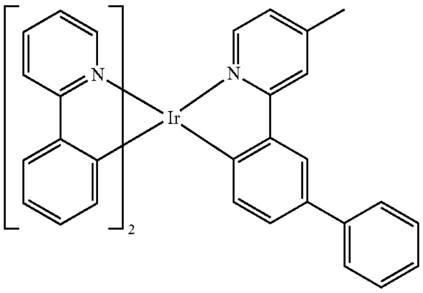
D-57
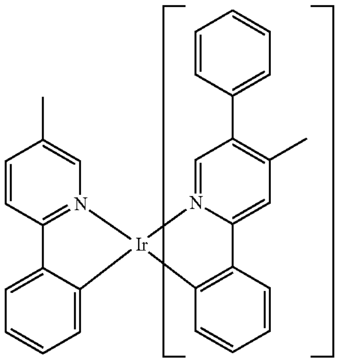
-continued
D-58
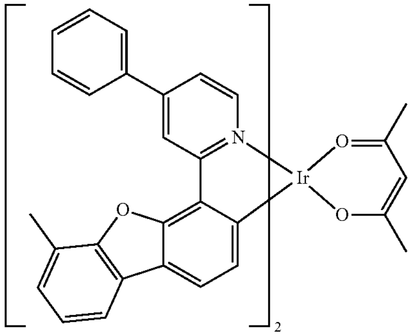
D-59
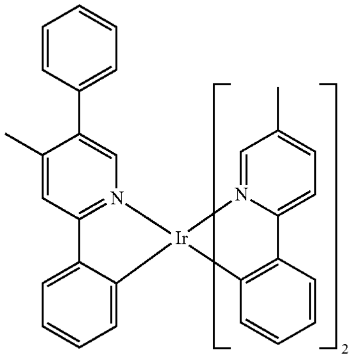
D-60
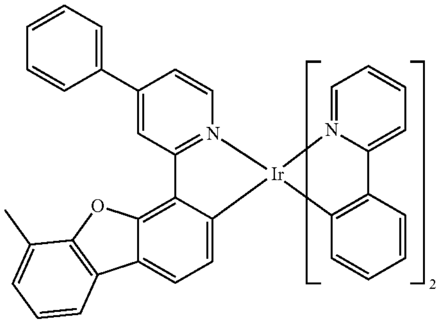
D-61
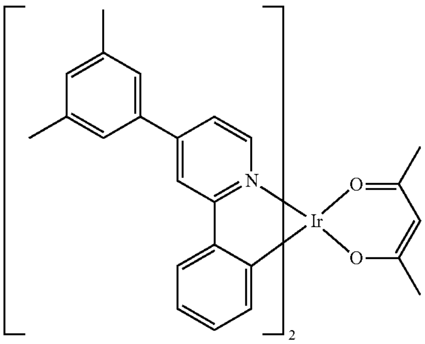

-continued
D-62
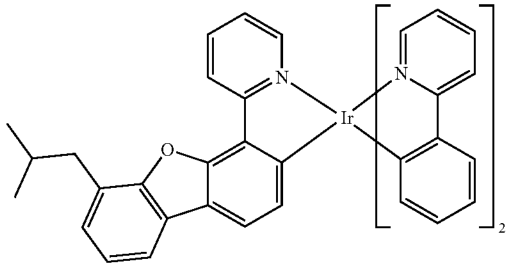
D-63
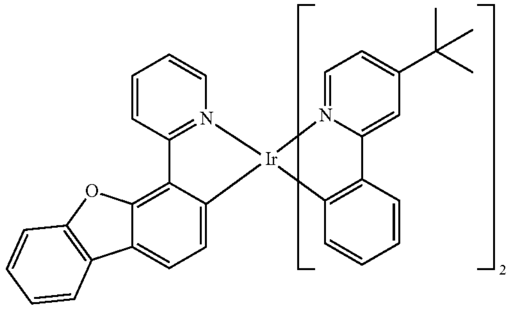
D-64
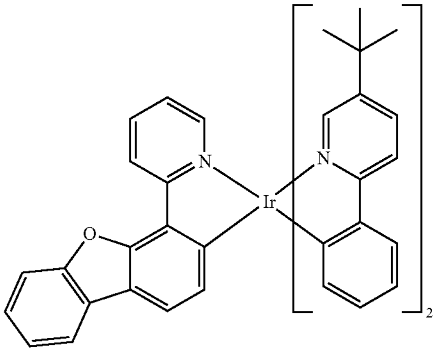
D-65
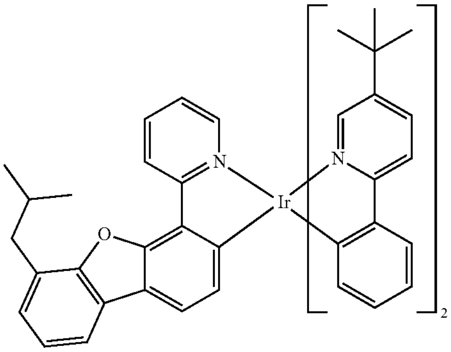
-continued
D-66
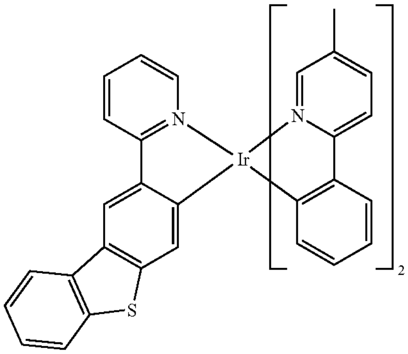
D-67
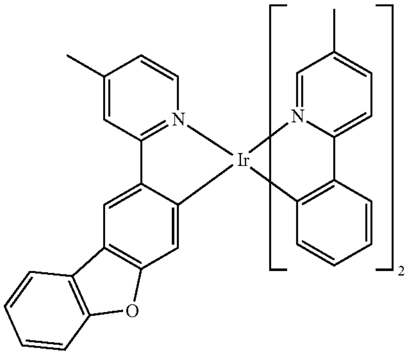
D-68
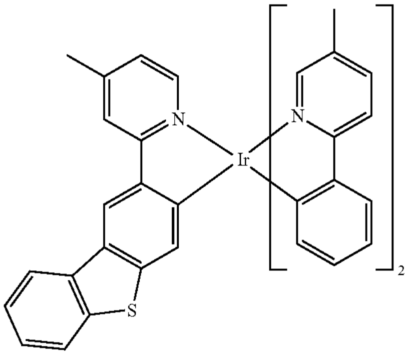
D-69
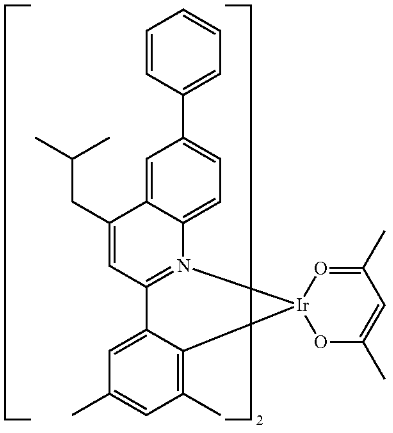

-continued
D-70
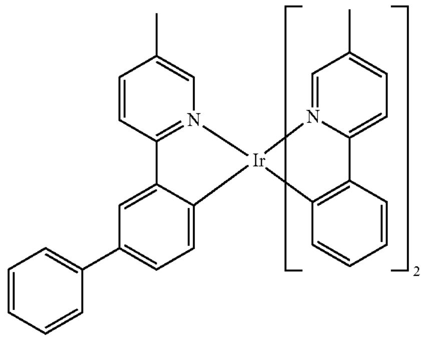
D-71
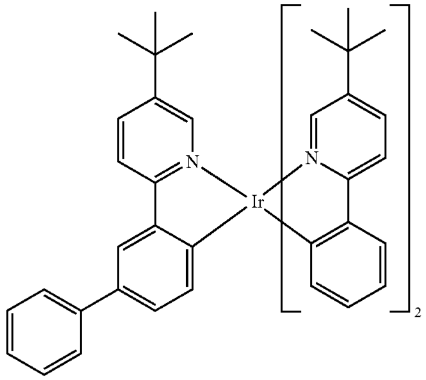
D-72
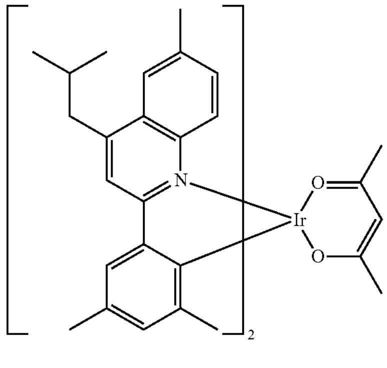
D-73
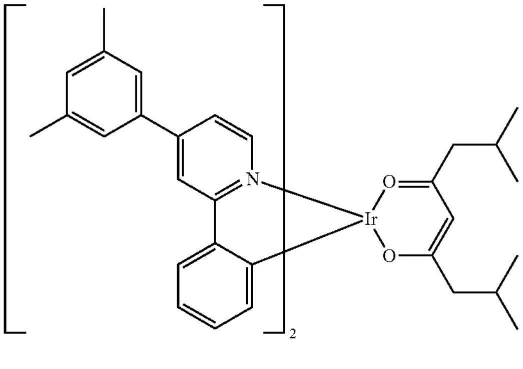
-continued
D-74
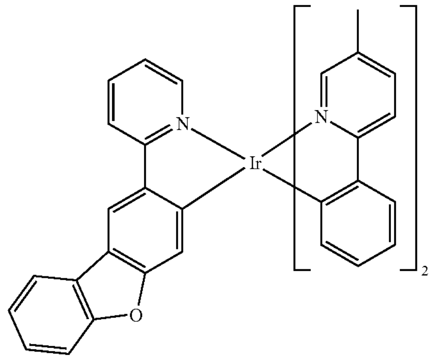
D-75
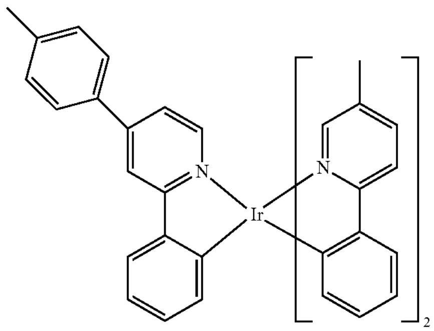
D-76
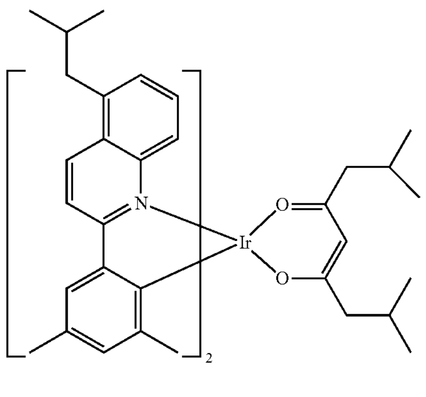
D-77
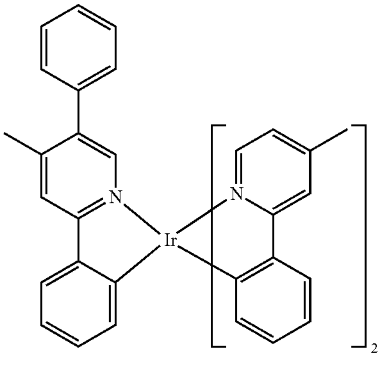

-continued
D-78
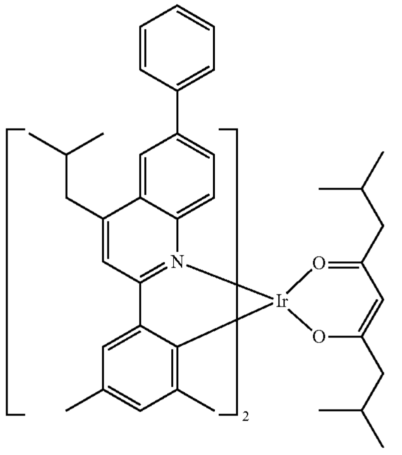
D-79
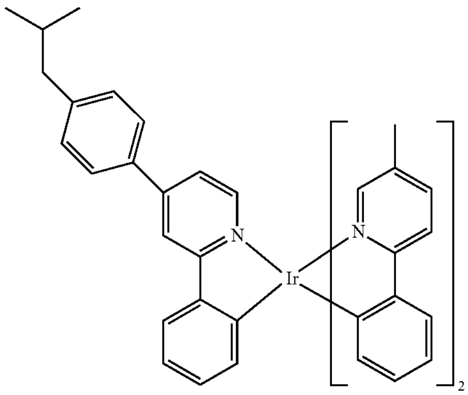
D-80
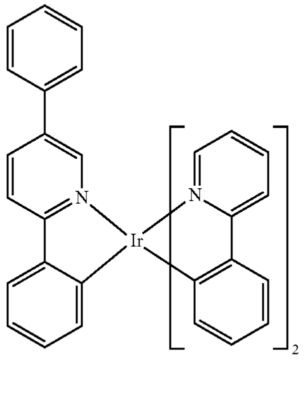
-continued
D-81
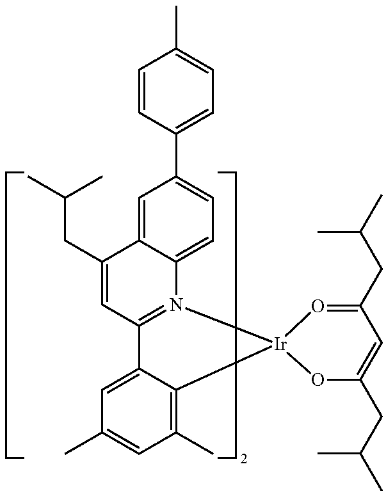
D-82
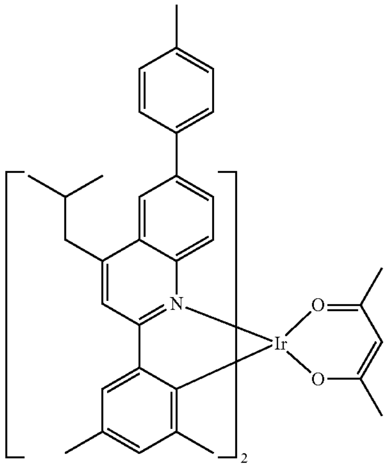
D-83
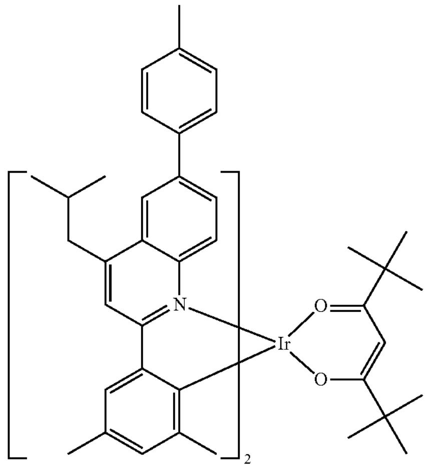

-continued
D-84
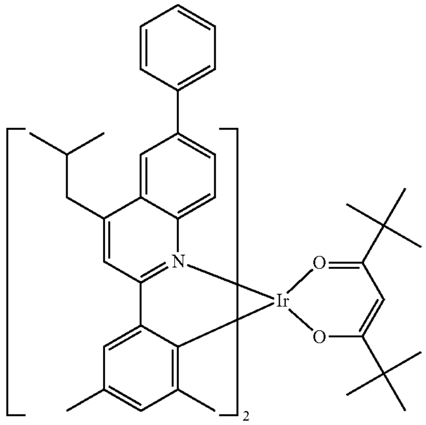
D-85
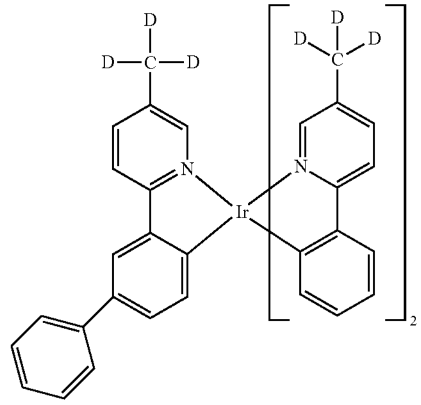
D-86
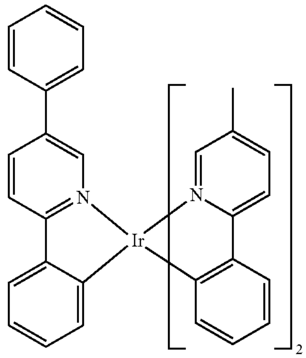
D-87
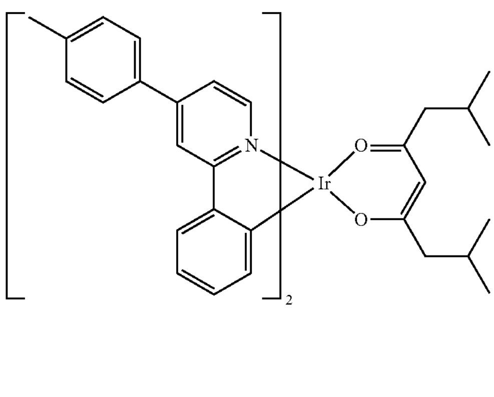
-continued
D-88
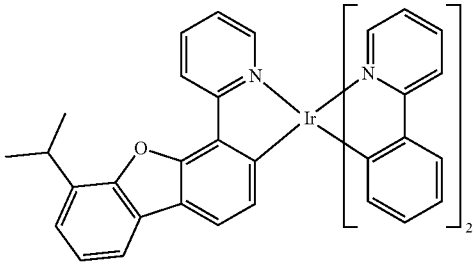
D-89
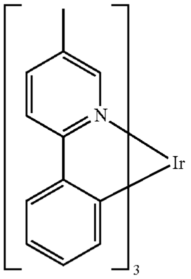
D-90
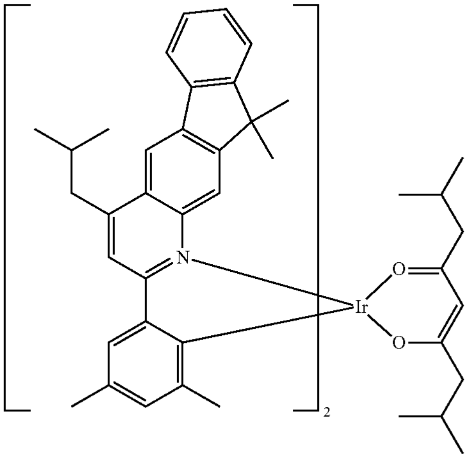
D-91
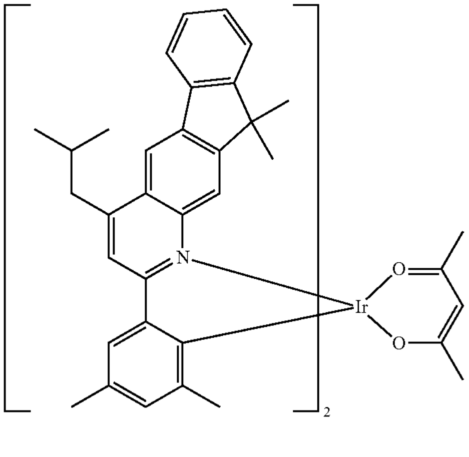

-continued
D-92
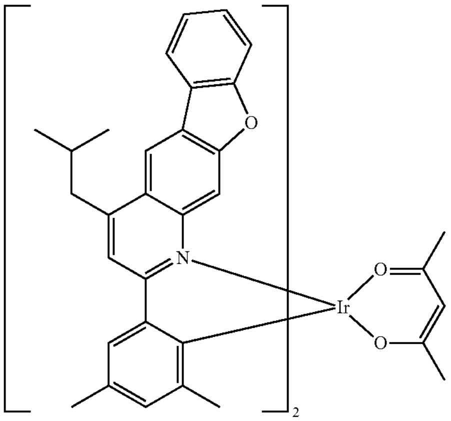
D-93
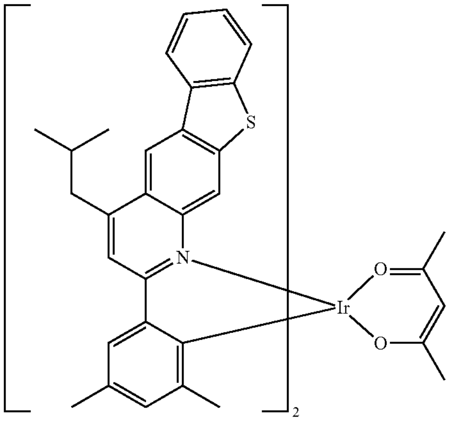
D-94
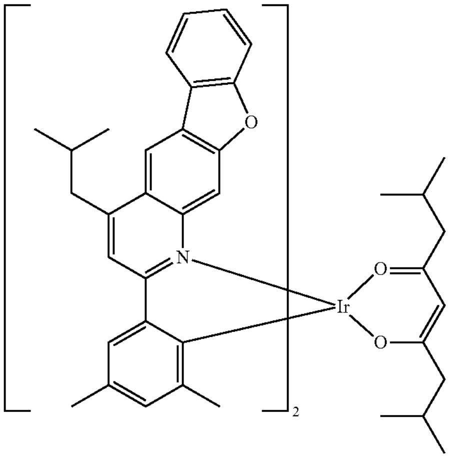
-continued
D-95
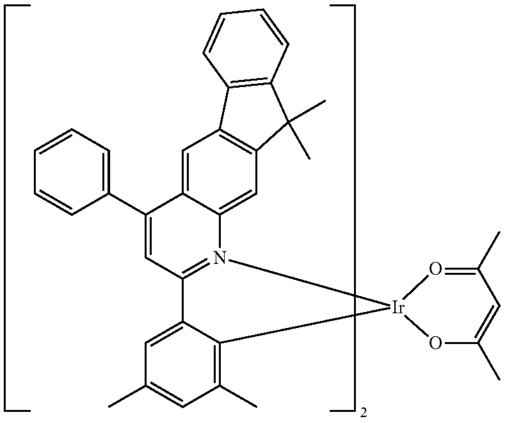
D-96
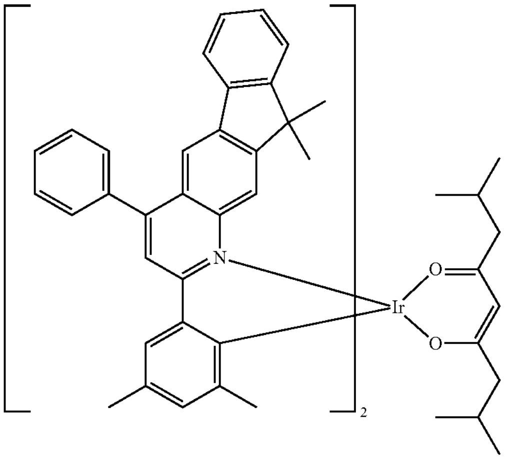
D-97
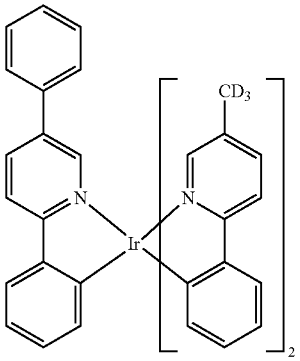
D-98
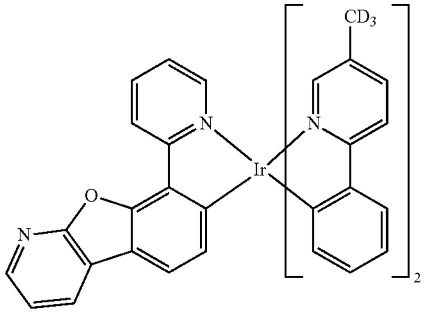

-continued
D-99
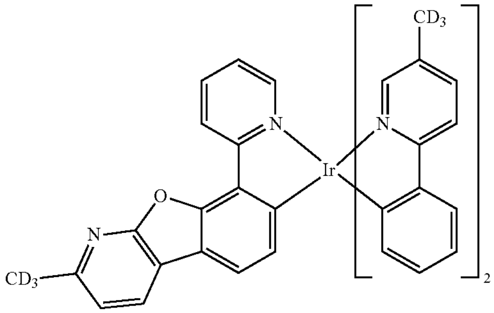
D-100
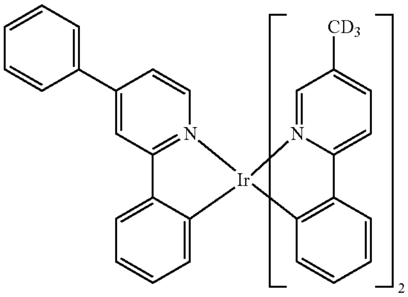
D-101
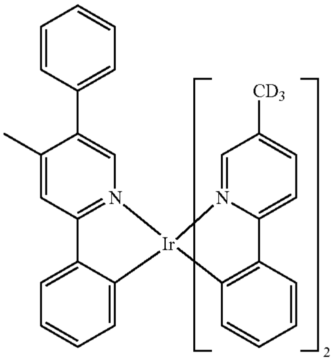
D-102
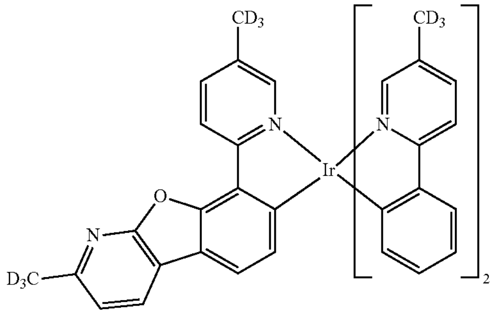
D-103
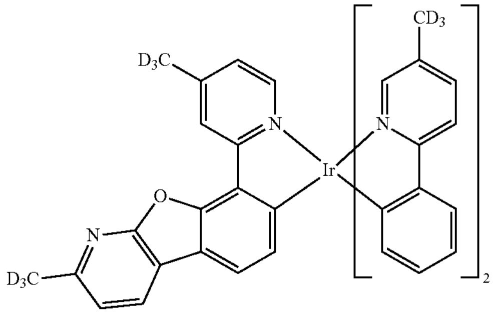
-continued
D-104
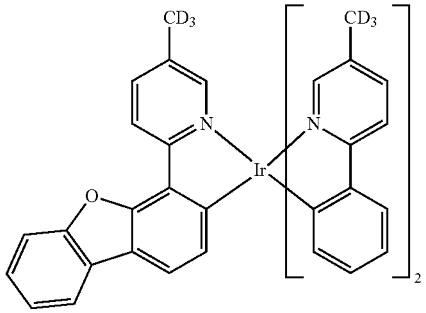
D-105
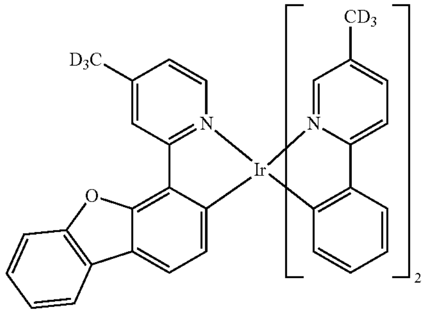
D-106
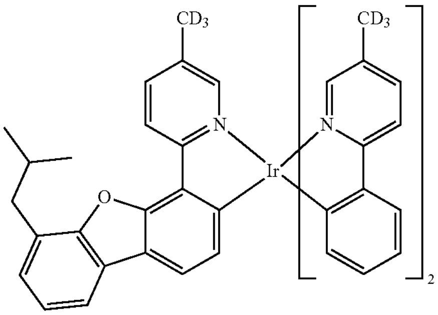
D-107
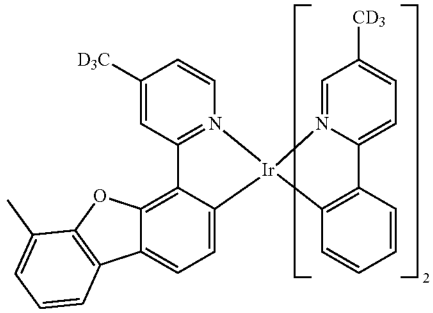
D-108
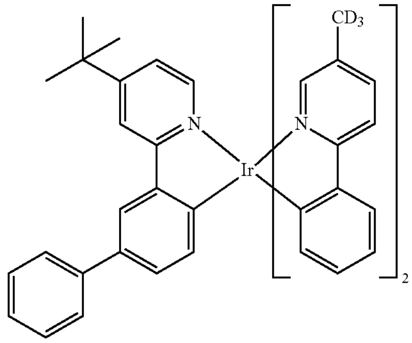

-continued
D-109
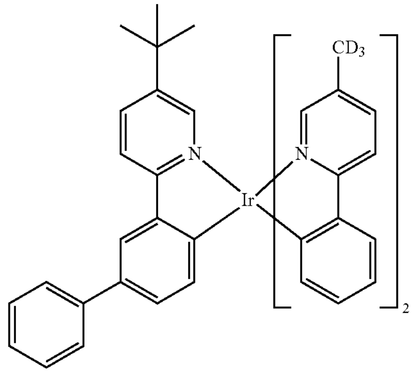
D-110
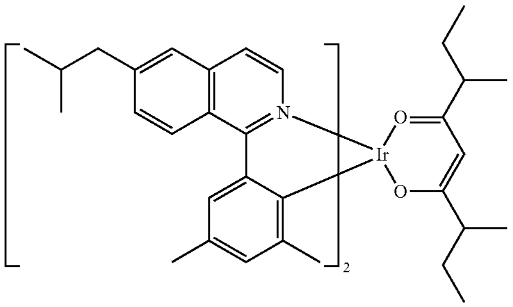
D-111
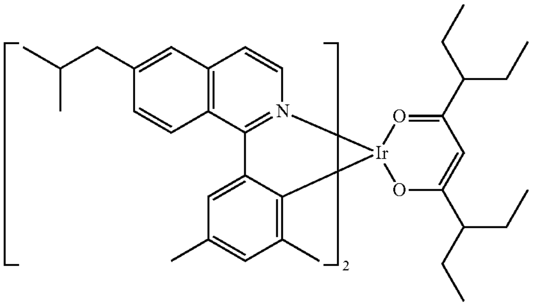
D-112
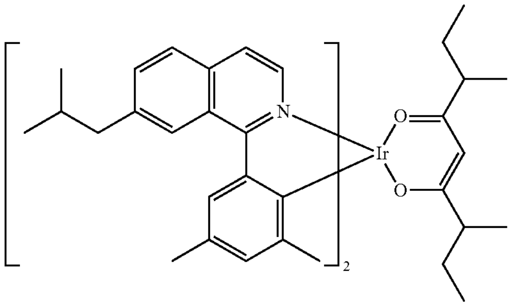
-continued
D-113
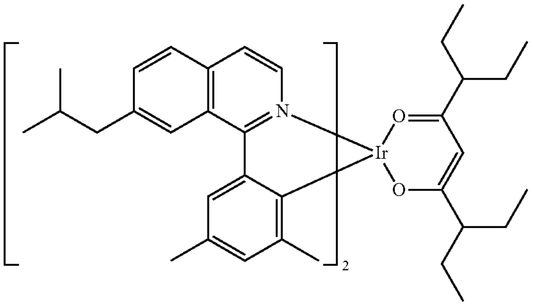
D-114
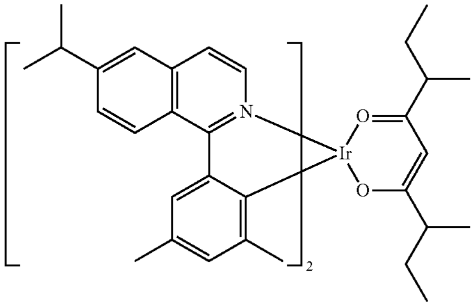
D-115
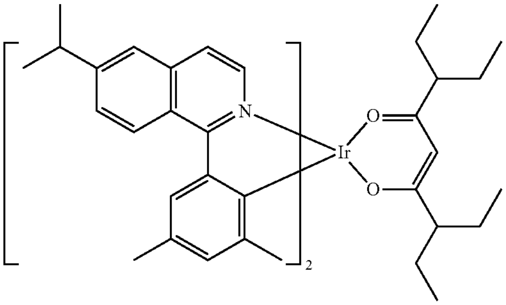
D-116
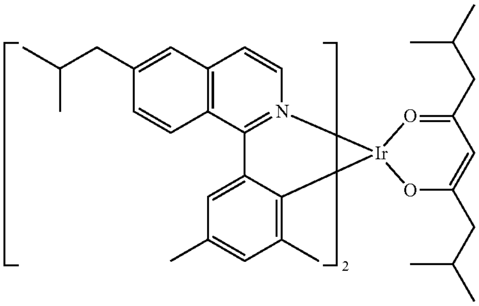
D-117
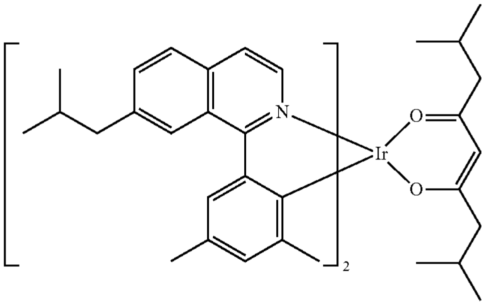

-continued

D-118

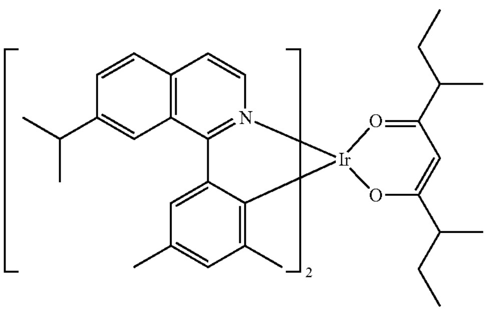

D-119

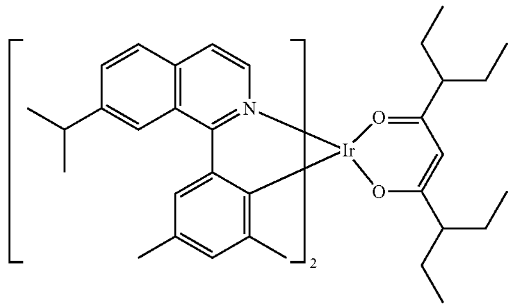

According to one embodiment of the present disclosure, the organic electroluminescent device according to the present disclosure includes an anode, a cathode, and at least one light-emitting layer interposed between the anode and the cathode, wherein the at least one light-emitting layer may comprise a plurality of host materials of the present disclosure and the compound represented by the following formula 3.

(3)

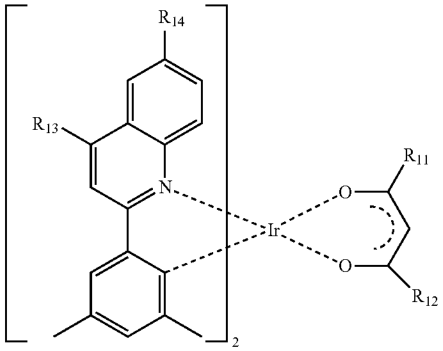

In formula 3, $R_{11}$ to $R_{13}$ each independently represent a substituted or unsubstituted (C1-C5)alkyl, and $R_{11}$ represents a substituted or unsubstituted (C1-C5)alkyl, or (C1-C5)alkyl-substituted or unsubstituted phenyl.

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used.

When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

Further, the compound represented by formula 1 and the compound represented by formula 2 may be formed by the methods listed above. Normally, when forming a layer, co-evaporation or mixture-evaporation may be used. The co-deposition is a mixed deposition method in which two or more isomer materials are put into respective individual crucible sources and a current is applied to both cells simultaneously to evaporate the materials and to perform mixed deposition; and the mixed deposition is a mixed deposition method in which two or more isomer materials are mixed in one crucible source before deposition, and then a current is applied to one cell to evaporate the materials.

A display device by comprising a plurality of host materials of the present disclosure can be provided. In addition, it is possible to manufacture a display device or a lighting device using the organic electroluminescent device of the present disclosure. Specifically, the organic electroluminescent device of the present disclosure can be used for the manufacture of display devices such as smartphones, tablets, notebooks, PCs, TVs, or display devices for vehicles, or lighting devices such as outdoor or indoor lighting.

Hereinafter, the luminous efficiency and the lifespan properties of OLED according to the present disclosure will be explained; however, the following examples are intended to explain the invention in order to understand the present disclosure in detail, and are not limited thereto.

[Example 1] Preparation of Compound C1-128

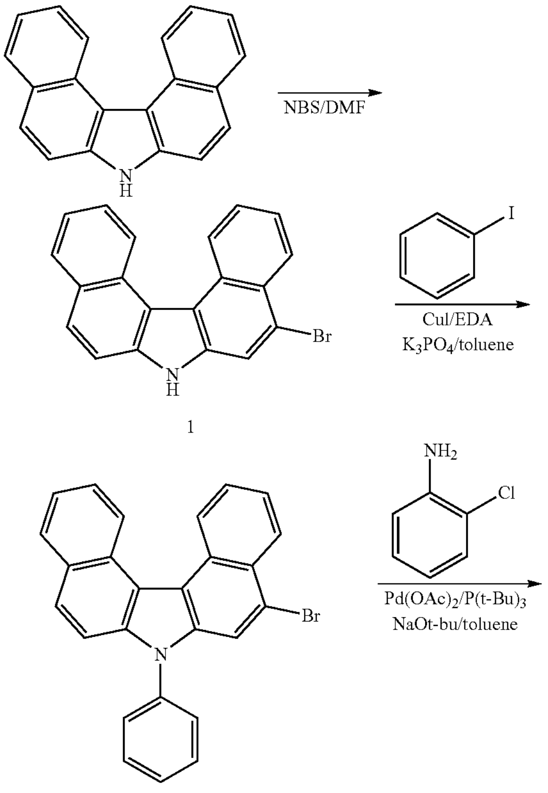

1

2

-continued

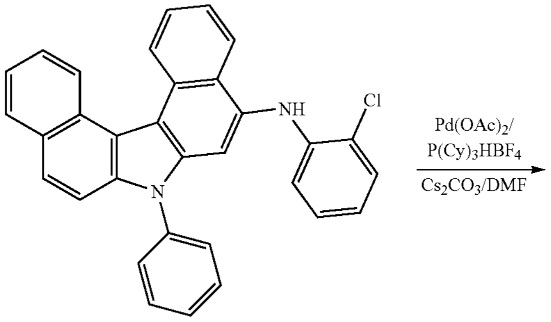

3

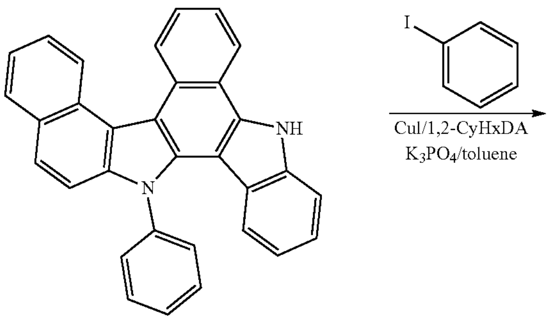

4

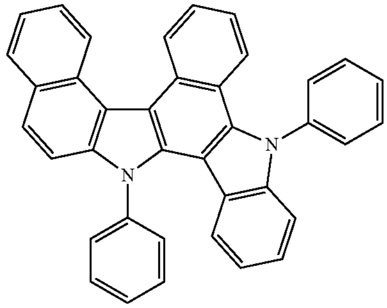

C1-128

1) Synthesis of Compound 1

7H-dibenzo[c,g]carbazole (60 g, 224 mmol) was dissolved in 900 mL of DMF into flask and then cooled at 0° C. with stirring. NBS (36 g, 202 mmol) was dissolved in 220 mL of DMF and added dropwise to the mixture for 2.5 hours. Thereafter the mixture was stirred for 2 hours at room temperature. After completion of the reaction, the reaction mixture was washed off with $Na_2S_2O_3$ (aq) and water. Thereafter the organic layer was extracted with ethyl acetate and the residual water was removed from the organic layer by using $MgSO_4$.

Thereafter, the remaining product was dried and filtrated with silica filter to obtain compound 1 (79 g, yield: 79%).

2) Synthesis of Compound 2

Compound 1 (76 g, 220 mmol), iodobenzene (90 g, 439 mmol), CuI (20.90 g, 110 mmol), ethylenediamine (EDA) (13 g, 110 mmol), and $K_3PO_4$ (139 g, 659 mmol) were added in 1.1 L of toluene and refluxed for 2.5 hours. Thereafter, MeOH was added and the resulting solid was filtered under reduced pressure. The remaining product was then purified by column chromatography to obtain compound 2 (55.1 g, yield: 60%).

3) Synthesis of Compound 3

Compound 2 (54.6 g, 129 mmol), 2-chloroaniline (20 g, 155 mmol), $Pd(OAc)_2$ (2.9 g, 13 mmol), $P(t-Bu)_3$ (5.2 g, 26 mmol), and NaOt-Bu (31 g, 323 mmol) were added in 650 mL of toluene and stirred for 4 hours. After cooling to room temperature, $NH_4Cl$ (aq) was added to the mixture. The organic layer was extracted with ethyl acetate and dried with magnesium sulfate followed by vacuum distillation. Thereafter, the remaining product was purified by column chromatography to obtain compound 3 (47.9 g, yield: 79%).

4) Synthesis of Compound 4

Compound 3 (48 g, 103 mmol), $Pd(OAc)_2$ (2.3 g, 10 mmol), ligand(tricyclohexylphosphonium tetrafluoroborate) (7.6 g, 21 mmol), $CS_2CO_3$ (100 g, 308 mmol) were added in 400 mL of DMA and stirred for 1 hours. After cooling to room temperature, $NH_4Cl$(aq) was added to the reaction mixture. The organic layer was then extracted with methylene chloride (MC) and the extracted organic layer was dried with magnesium sulfate followed by vacuum distillation. Thereafter the remaining product was purified by column chromatography to obtain compound 4 (44 g, yield: 79%).

5) Synthesis of Compound C1-128 Compound 4 (5 g, 12 mmol), iodobenzene (3.5 g, 17 mmol), CuI (1.1 g, 6 mmol), 1,2-diaminocyclohexane (2.6 g, 23 mmol), and $K_3PO_4$ (4.9 g, 23 mmol) were added in 60 mL of o-xylene and refluxed for 1 day. After completion of the reaction, the mixture was cooled to room temperature and filtrated with silica filter with methylene chloride (MC) followed by vacuum distillation. The resulting product was purified by column chromatography with MC/Hex to obtain compound C1-128 (1.3 g, yield: 22%).

$^1$H NMR (600 MHz, DMSO, δ) 9.16-9.15 (d, 1H), 8.99-8.98 (d, 1H), 8.14-8.13 (d, 1H), 7.94-7.93 (d, 1H), 7.94-7.68 (m, 9H), 7.65-7.61 (m, 3H), 7.60-7.54 (m, 3H), 7.25-7.21 (m, 2H), 7.08-7.07 (d, 1H), 6.78-6.76 (m, 1H) 5.95-5.94 (d, 1H)

| | MW | UV | PL | M.P. |
|---|---|---|---|---|
| C1-128 | 508.62 | 342 nm | 427 nm | 184° C. |

[Example 2] Preparation of Compound C1-129

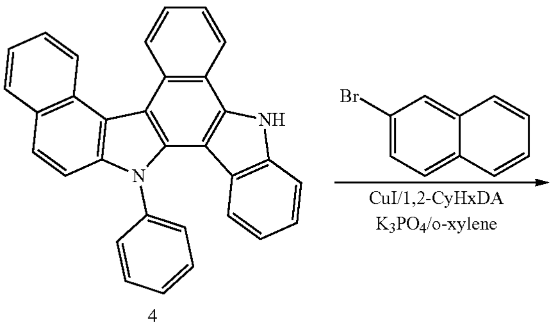

4

-continued

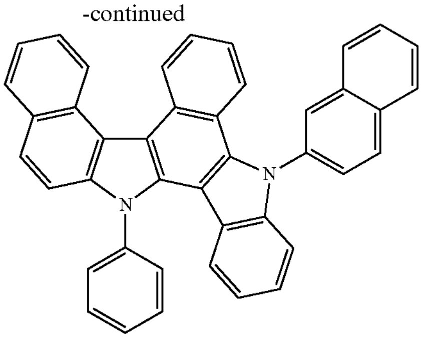

C1-129

Compound 4 (7 g, 16 mmol), 2-bromonaphthalene (6.7 g, 32 mmol), CuI (1.5 g, 8 mmol), 1,2-diaminocyclohexane (3.7 g, 32 mmol), and $K_3PO_4$ (10.3 g, 49 mmol) were added in 80 mL of o-xylene and refluxed for 1 day. After completion of the reaction, the mixture was cooled to room temperature, and then filtered through a celite filter with MC followed by vacuum distillation. The resulting product was purified by column chromatography with MC/Hex to obtain compound C1-129 (1.3 g, yield: 22%).

$^1H$ NMR (600 MHz, DMSO, δ) 9.17-9.15 (d, 1H), 9.00-8.99 (d, 1H), 8.31-8.30 (m, 2H), 8.20-8.18 (d, 1H), 8.15-8.14 (d, 1H), 8.11-8.10 (d, 1H), 7.95-7.94 (d, 1H), 7.83-7.79 (m, 5H), 7.73-7.69 (m, 4H), 7.60-7.57 (m, 4H), 7.21-7.18 (m, 2H), 7.14-7.13 (d, 1H), 6.78-8.77 (t, 1H) 5.98-5.96 (d, 1H)

| | MW | UV | PL | M.P. |
|---|---|---|---|---|
| C1-129 | 558.68 | 340 nm | 431 nm | 263° C. |

[Example 3] Preparation of Compound C1-131

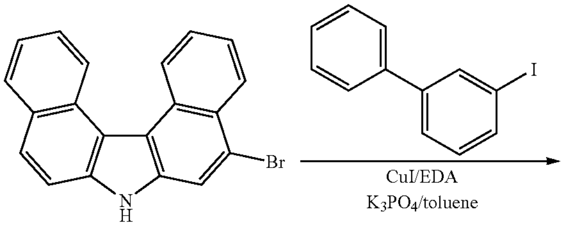

1

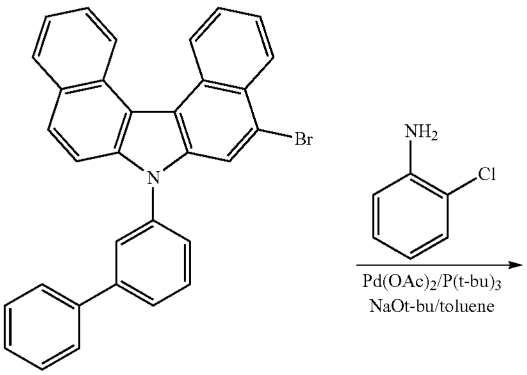

14

-continued

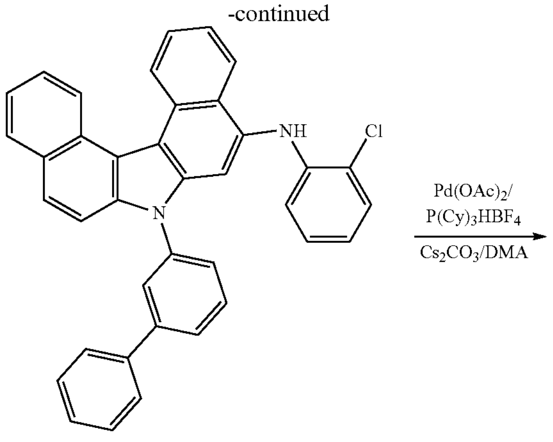

15

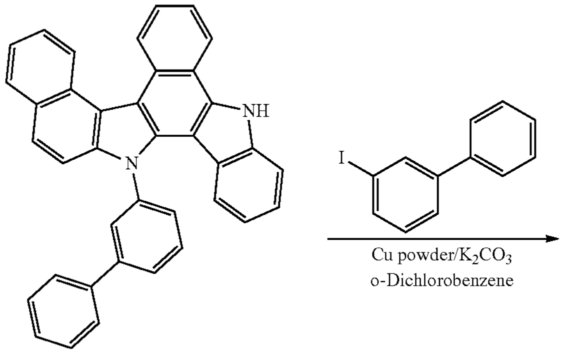

16

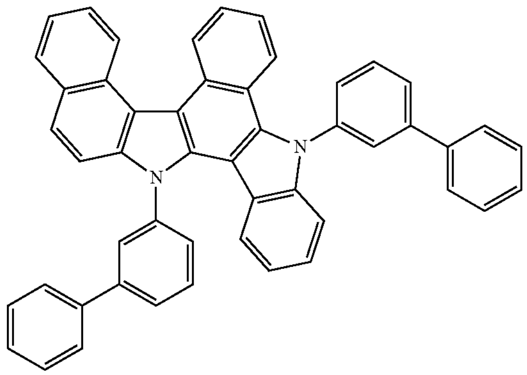

C1-131

1) Synthesis of Compound 14

Compound 1 (15 g, 220 mmol), 3-iodo-1,1-biphenyl (18 g, 65 mmol), CuI (4.1 g, 22 mmol), ethylenediamine (EDA) (2.6 g, 43 mmol), and $K_3PO_4$(23 g, 108 mmol) were added in 216 mL of toluene and refluxed for 4 hours. MeOH was added thereto, and the resulting solid was filtered under reduced pressure. The resulting product was purified by column chromatography to obtain compound 14 (16 g, yield: 74%).

2) Synthesis of Compound 15

Compound 14 (15 g, 30 mmol), 2-chloroaniline (7.7 g, 60 mmol), $Pd(OAc)_2$ (0.67 g, 3 mmol), $P(t-Bu)_3$ (1.2 g, 6 mmol), and NaOt-Bu (7.2 g, 75 mmol) were added in 150 mL of toluene and refluxed for 2 hours. After cooling to room temperature, $NH_4Cl$ (aq) was added thereto and then the organic layer was extracted with EA. The extracted organic layer was then dried with magnesium sulfate followed by vacuum distillation. The resulting product was purified by column chromatography to obtain compound 15 (10.1 g, yield: 62%).

3) Synthesis of Compound 16

Compound 15 (10 g, 18 mmol), $Pd(OAc)_2$ (0.41 g, 1.8 mmol), ligand(tricyclohexylphosphonium tetrafluoroborate) (1.35 g, 3.7 mmol), and $Cs_2CO_3$ (18 g, 55 mmol) were added in 92 mL of DMA and refluxed for 1 hour. After cooling to room temperature, $NH_4Cl$ (aq) was added thereto and then the organic layer was extracted with MC. The extracted organic layer was then dried with magnesium sulfate followed by vacuum distillation. The resulting product was purified by column chromatography to obtain compound 16 (7.1 g, yield: 76%).

4) Synthesis of Compound C1-131

Compound 16 (6.7 g, 13 mmol), 3-iodo-1,1'-biphenyl (7.4 g, 26 mmol), Cu powder (042 g, 7 mmol), and $K_2CO_3$ (3.6 g, 26 mmol) were added in 70 mL of o-dichlorobenzene and refluxed for 1 day. After completion of the reaction, the mixture was cooled to room temperature, and then filtrated through a celite filter with MC followed by vacuum distillation. The resulting product was purified by column chromatography with MC/Hex to obtain compound C1-131 (3.1 g, yield: 36%).

$^1H$ NMR (600 MHz, DMSO, δ) 9.18-9.17 (d, 1H), 9.01-9.00 (d, 1H), 8.16-8.15 (d, 1H), 811-8.09 (d, 1H), 8.06-8.05 (m, 2H), 8.00-7.79 (m, 7H), 7.73-7.57 (m, 8H), 7.48-7.38 (m, 6H), 7.30-7.28 (t, 1H), 7.22-7.18 (m, 2H), 6.80-6.78 (t, 1H), 6.07-6.06 (d, 1H)

| | MW | M.P. |
|---|---|---|
| C1-131 | 660.82 | 259° C. |

[Example 4] Preparation of Compound C1-130

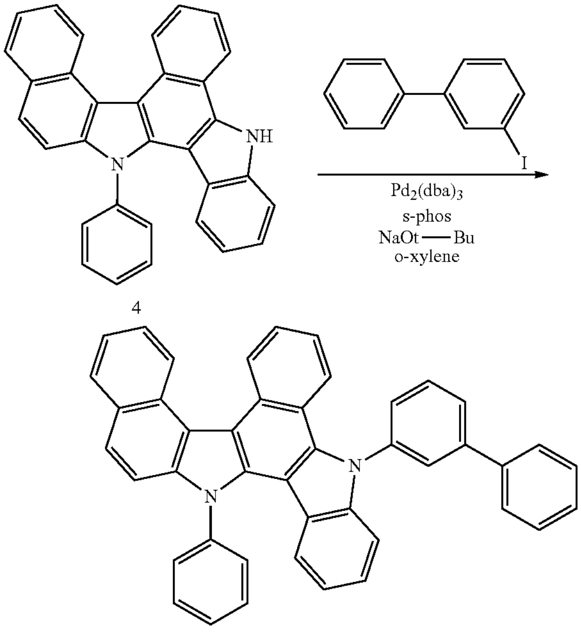

4

C1-130

Compound 4 (4 g, 9.25 mmol), 3-iodo-1,1'-biphenyl (3.1 g, 11.1 mmol), $Pd_2(dba)_3$ (0.42 g, 0.46 mmol), s-phos (0.38 g, 0.92 mmol), and NaOt-Bu (2.2 g, 23.13 mmol) were added in 46 mL of o-xylene and stirred for 1 day. The organic layer was extracted with MC followed by vacuum distillation. Thereafter, the resulting product was purified by column chromatography with MC/Hex to obtain compound C1-130 (1.2 g, yield: 23%).

$^1H$ NMR (600 MHz, DMSO, δ) 9.17-9.15 (d, 1H), 9.00-8.98 (d, 1H), 8.15-8.13 (d, 1H), 807-8.06 (d, 1H), 7.98 (m, 1H), 7.95-7.94 (d, 1H), 7.88-7.86 (t, 1H), 7.82-7.80 (m, 7H), 7.71-7.67 (m, 2H), 7.65-7.61 (m, 2H), 7.60-7.55 (m, 2H), 7.49-7.47 (t, 2H), 7.42-7.39 (t, 1H), 7.30-7.27 (t, 1H), 7.26-7.23 (t, 1H), 7.20-7.19 (d, 1H), 6.80-6.77 (t, 1H), 5.97-5.95 (d, 1H)

| | MW | M.P. |
|---|---|---|
| C1-130 | 584.7 | 249.6° C. |

[Example 5] Preparation of Compound C1-133

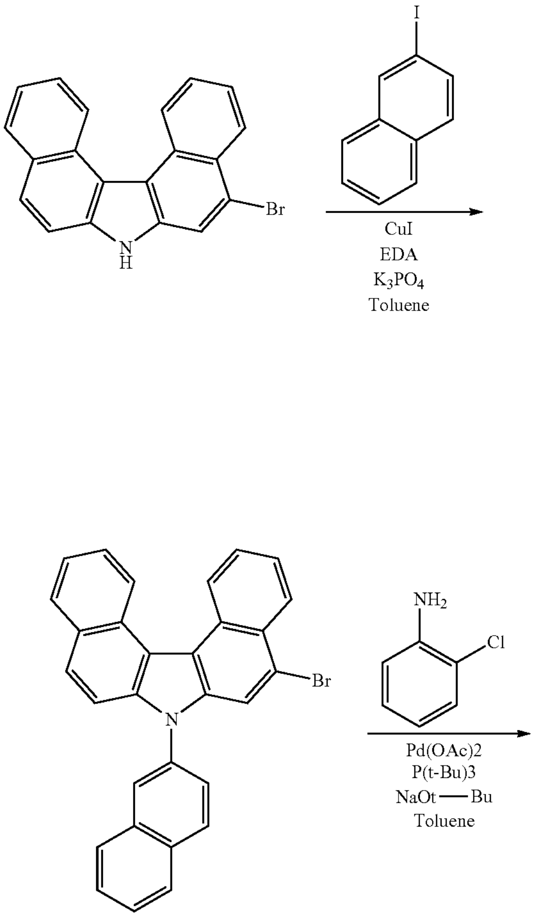

1

-continued

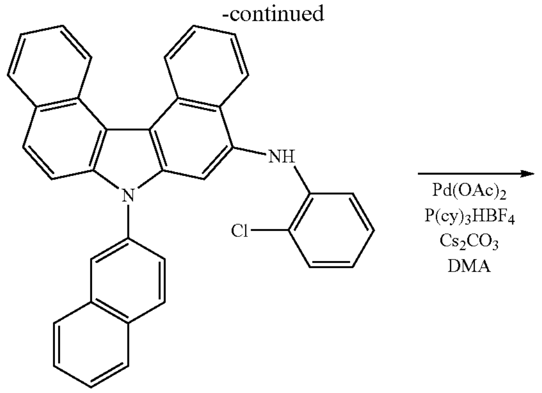

2

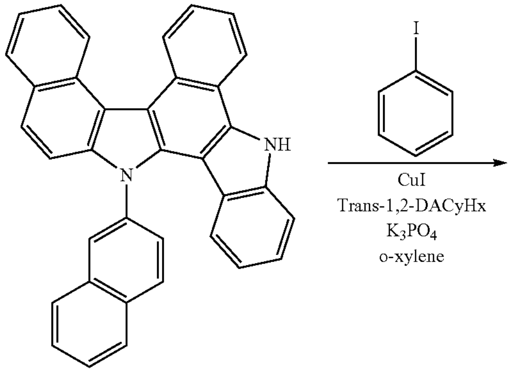

3

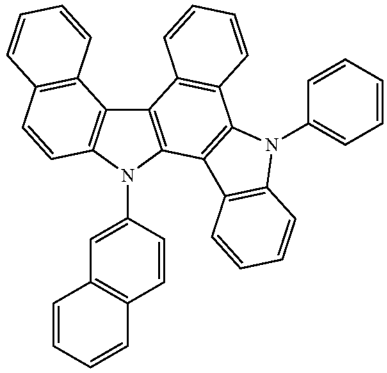

C1-133

1) Synthesis of Compound 1

5-bromo-7H-dibenzo[c,g]carbazole (8.5 g, 0.025 mol), 2-iodo-naphthalene (10.7 g, 0.042 mol), EDA (1.49 g, 0.025 mol), $K_3PO_4$ (13.1 g, 0.062 mol), and CuI (2.3 g, 0.012 mol) were added in 124 mL of toluene and stirred for 1 day. After completion of the reaction, the organic layer was extracted with MC followed by vacuum distillation. The resulting product was purified by column chromatography with MC/Hex to obtain compound 1 (7.6 g, yield: 58%).

2) Synthesis of Compound 2

Compound 1 (7.5 g, 0.016 mol), 2-chloro-benzenamine (2.4 g, 0.019 mol), $Pd(OAc)_2$ (0.36 g, 0.002 mol), $P(t\text{-}Bu)_3$ (0.15 g, 0.003 mol), and NaOt-Bu (3.8 g, 0.04 mol) were added in 80 mL of toluene and stirred at 100° C. for 1 day. After completion of the reaction, the mixture was cooled to room temperature, and the organic layer was extracted with distilled water and EA followed by vacuum distillation. The resulting product was purified by column chromatography to obtain compound 2 (3.6 g, yield: 43%).

3) Synthesis of Compound 3

Compound 2 (5.8 g, 0.011 mol), $P(Cy_3)HFB_4$ (0.82 g, 0.002 mol), $Pd(OAc)_2$ (0.25 g, 0.001 mol), and $Cs_2CO_3$ (10.9 g, 0.033 mol) were added in 44.4 mL of DMA and stirred for 1 day. After completion of the reaction, the mixture was cooled to room temperature, and the organic layer was extracted with distilled water and EA followed by vacuum distillation. The resulting product was purified by column chromatography with MC/Hex to obtain compound 3 (4.2 g, yield: 76%).

4) Synthesis of Compound C1-133

Compound 3 (4.2 g, 0.009 mol), iodobenzene (1.9 mL, 0.017 mol), CuI (0.8 g, 0.004 mol), 1,2-diaminocyclohexane (2 mL, 0.018 mol), and $K_3PO_4$ (3.7 g, 0.017 mol) were added in 44 mL of o-xylene and stirred for 1 day. After completion of the reaction, the organic layer was extracted with MC followed by vacuum distillation. The resulting product was purified by column chromatography with MC/Hex to obtain compound C1-133 (1.2 g, yield: 24%).

$^1H$ NMR (600 MHz, DMSO, δ) 9.19-9.07 (d, 1H), 9.01-9.00 (d, 1H), 8.37 (s, 1H), 8.35-8.34 (d, 1H), 8.23-8.22 (d, 1H), 8.15-8.14 (d, 1H), 806-8.05 (d, 1H), 7.94-7.92 (m, 2H), 7.78-7.56 (m, 12H), 7.30-7.27 (t, 1H), 7.11-7.09 (t, 1H), 7.05-7.04 (d, 1H), 6.41-6.39 (t, 1H), 5.88-5.86 (d, 1H)

| | MW | M.P. |
|---|---|---|
| C1-133 | 558.7 | 272.6° C. |

[Example 6] Preparation of Compound C1-132

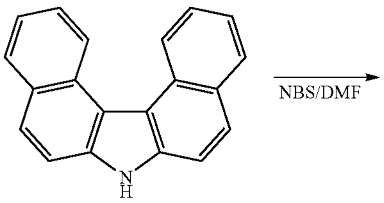

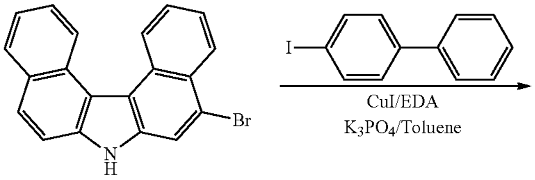

1

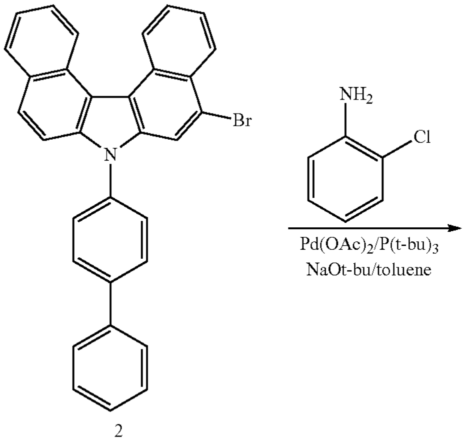

2

-continued

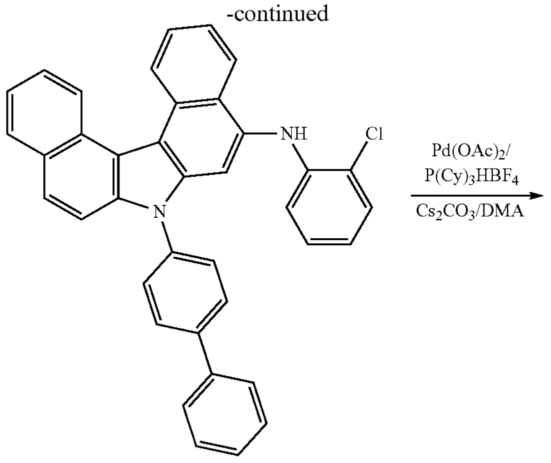

3

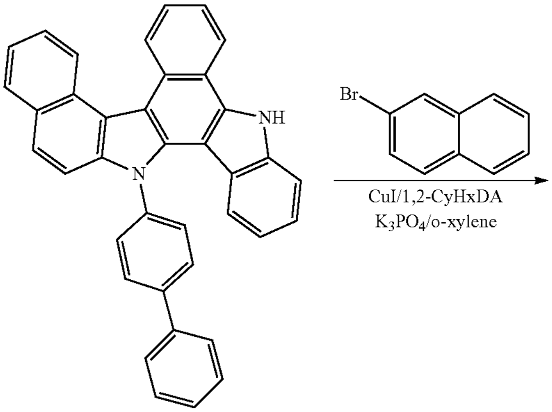

4

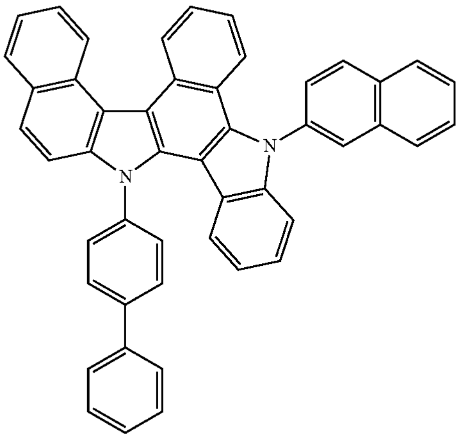

C1-132

1) Synthesis of Compound 1

7H-dibenzo[c,g]carbazole (50 g, 187 mmol) was dissolved in 750 mL of DMF into flask and then cooled to 0° C. with stirring. NBS (30 g, 168 mmol) was dissolved in 250 mL of DMF and added dropwise to the mixture for 1 hour. Thereafter, the mixture was stirred for 2 hours at room temperature. After completion of the reaction, the reaction mixture was washed off with $Na_2S_2O_3$ (aq) and water. Thereafter, the organic layer was extracted with ethyl acetate and the residual water was removed from the organic layer by using $MgSO_4$. Thereafter, the remaining product was dried and filtrated with silica filter to obtain compound 1 (40 g, yield: 62%).

2) Synthesis of Compound 2

Compound 1 (11 g, 32 mmol), 4-iodo-1,1'biphenyl (17.8 g, 64 mmol), CuI (3.0 g, 15.9 mmol), ethylenediamine (1.91 g, 31.8 mmol), and $K_3PO_4$ (20.3 g, 95 mmol) were added in 160 mL of toluene and refluxed for 4 hours. Thereafter, MeOH was added thereto and the resulting solid was filtered under reduced pressure. The remaining product was then purified by column chromatography to obtain compound 2 (13.0 g, yield: 82%).

3) Synthesis of Compound 3

Compound 2 (130 g, 26 mmol), 2-chloroaniline (6.7 g, 52 mmol), $Pd(OAc)_2$ (0.59 g, 2.6 mmol), $P(t\text{-}Bu)_3$ (1.1 g, 5.2 mmol), and NaOt-Bu (6.3 g, 65 mmol) were added in 130 mL of toluene and refluxed for 4 hours. After cooling to room temperature, $NH_4Cl$ (aq) was added to the mixture. The organic layer was then extracted with EA and the extracted organic layer was dried with magnesium sulfate. The resulting solid was distilled under reduced pressure and purified by column chromatography to obtain compound 3 (9.2 g, yield: 65%).

4) Synthesis of Compound 4

Compound 3 (9.2 g, 17 mmol), $Pd(OAc)_2$ (0.38 g, 2 mmol), ligand(tricyclohexylphosphonium tetrafluoroborate) (1.2 g, 3 mmol), and $Cs_2CO_3$ (138 g, 42 mmol) were added in 70 mL of DMA and refluxed for 1 hour. After cooling to room temperature, $NH_4Cl$ (aq) was added to the mixture followed by vacuum distillation. Thereafter the resulting product was purified by column chromatography to obtain compound 4 (6.0 g, yield: 70%).

5) Synthesis of Compound C1-132

Compound 4 (6 g, 12 mmol), 2-bromonaphthalene (4.9 g, 24 mmol), CuI (1.1 g, 6 mmol), 1,2-diaminocyclohexane (2.7 g, 24 mmol), and $K_3PO_4$ (7.5 g, 35 mmol) were added in 60 mL of o-xylene and stirred for 1 day. After cooling to room temperature, the organic layer was extracted with ethyl acetate and water, and the extracted organic layer was dried with magnesium sulfate. The mixture was filtered through a celite filter with MC followed by vacuum distillation. The resulting product was purified by column chromatography with MC/Hex to obtain compound C1-132 (2.1 g, yield: 28%).

$^1H$ NMR (600 MHz, DMSO, δ) 9.18-9.17 (d, 1H), 9.01-8.99 (d, 1H), 8.33-8.31 (m, 2H), 8.20-8.19 (d, 1H), 8.17-8.15 (d, 1H), 8.12-8.08 (m, 3H), 7.98-7.97 (d, 1H), 7.93-7.89 (m, 4H), 7.70-7.68 (m, 5H), 7.63-7.57 (m, 5H) 7.50-7.48 (t, 1H), 7.22-7.19 (t, 1H), 7.15-7.13 (d, 1H), 6.77-6.74 (td, 1H), 6.16-6.15 (d, 1H)

| | MW | M.P. |
|---|---|---|
| C1-132 | 508.62 | 294° C. |

[Example 7] Preparation of Compound C1-6

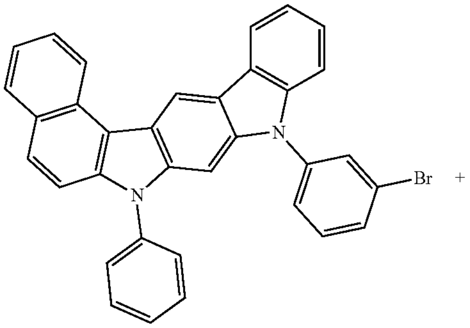

1-1

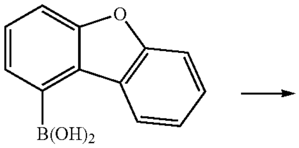

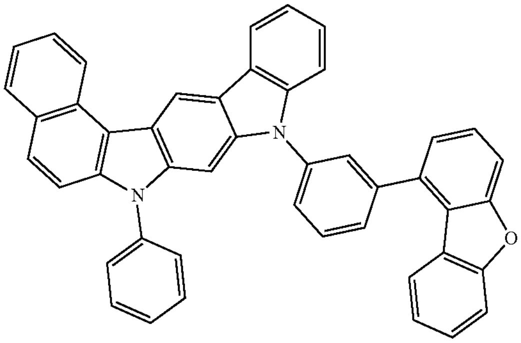

C1-6

Compound 1-1 (7 g, 13 mmol), dibenzo[b,d]furan-1-yl boronic acid (3 g, 14.3 mmol), $K_2CO_3$ (5.4 g, 39 mmol), and $Pd(PPh_3)_4$ (0.75 g, 0.65 mmol) were dissolved in 30 mL of $H_2O$, 60 mL of toluene, and 30 mL of EtOH into a flask and refluxed at 120° C. for 3 hours. After completion of the reaction, the organic layer was extracted with ethyl acetate and the residual water was removed from the organic layer by using magnesium sulfate. Thereafter, the remaining product was dried and purified by column chromatography to obtain compound C1-6 (5.7 g, yield: 70%).

$^1$H NMR (600 MHz, $CDCl_3$, 5) 9305 (s, 1H), 9.049-9.035 (d, J=8.4 Hz, 1H), 8.379-8.367 (d, J=7.2 Hz, 1H), 8.022-8.008 (d, J=8.4 Hz, 1H) 7.816-7.705 (m, 6H), 7.699-7.392 (m, 16H) 7.195-7.127 (m, 2H)

| | MW | M.P. |
|---|---|---|
| C1-6 | 642.73 | 154° C. |

[Example 8] Preparation of Compound C1-47

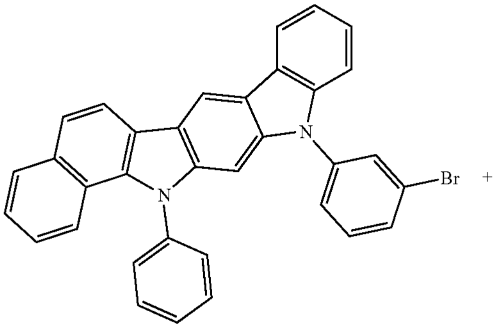

1-1

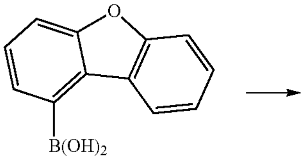

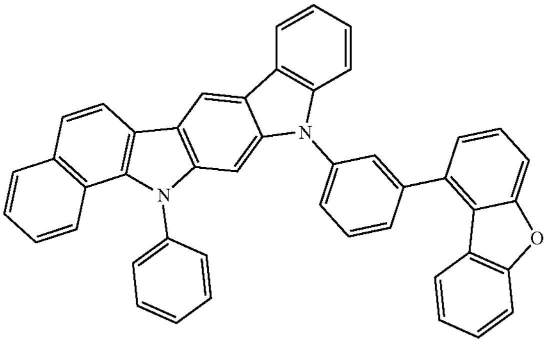

C1-47

Compound 1-1 (5.7 g, 10.6 mmol), dibenzo[b,d]furan-1-yl boronic acid (2.5 g, 11.7 mmol), $K_2CO_3$ (4.4 g, 31.8 mmol), and $Pd(PPh_3)_4$ (0.61 g, 0.653 mmol) were dissolved in 30 mL of $H_2O$, 60 mL of toluene, and 30 mL of EtOH in a flask and refluxed at 120° C. for 3 hours. After completion of the reaction, the organic layer was extracted with ethyl acetate and the residual water was removed from the organic layer by using magnesium sulfate. Thereafter, the remaining product was dried and purified by column chromatography to obtain compound C1-47 (1.2 g, yield: 18%).

$^1$H NMR (600 MHz, $CDCl_3$, 5) 8.880 (s, 1H), 8.378-8.364 (d, J=8.4 Hz, 1H), 8.297-8.284 (d, J=7.8 Hz, 1H), 8.000-7.987 (d, J=7.8 Hz, 1H) 7.777-7.702 (m, 5H), 7.615-7.332 (m, 15H), 7.189-7.127 (m, 4H)

| | MW | M.P. |
|---|---|---|
| C1-47 | 624.73 | 239° C. |

[Example 9] Preparation of Compound C1-46

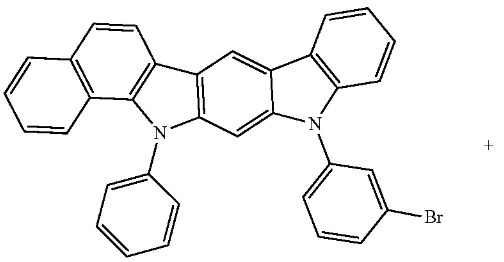

1-1

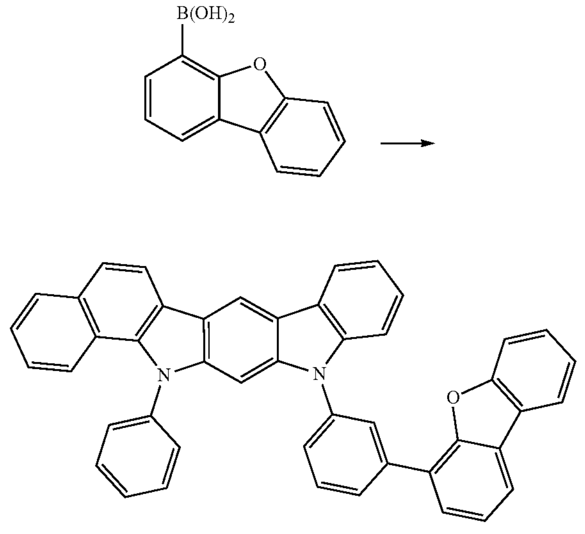

C1-46

Compound 1-1 (5.0 g, 9.3 mmol), dibenzo[b,d]furan-4-yl boronic acid (2.2 g, 10.2 mmol), $Pd(PPh_3)_4$ (0.54 g, 0.47 mmol), and $K_2CO_3$ (2.6 g, 18.6 mmol) were dissolved in 20 mL of toluene, 8 mL of EtOH, and 10 mL of $H_2O$ in a flask and refluxed at 120° C. for 3 hours. After completion of the reaction, the organic layer was extracted with ethyl acetate and the residual water was removed from the organic layer by using magnesium sulfate. Thereafter, the remaining product was dried and purified by column chromatography to obtain compound C1-46 (3.5 g, yield: 60%).

$^1$H NMR (600 MHz, $DMSO_3$, δ) 9.210 (s, 1H), 8.516-8.502 (d, 1H), 8.408-8.395 (d, 1H), 8.219-8.198 (m, 2H), 8.115-8.109 (t, 1H), 8.087-8.073 (d, 1H), 8.040-8.028 (d, 1H), 7.856-7.842 (d, 1H), 7.833-7.807 (t, 1H), 7.733-7.611 (m, 9H), 7.562-7.531 (m, 2H), 7.515-7.490 (t, 1H), 7.451-7.426 (t, 1H), 7.293-7.279 (d, 1H), 7.258-7.232 (t, 1H), 7.119 (s, 1H)

| | MW | M.P. |
|---|---|---|
| C1-46 | 624.7 | 161° C. |

[Example 10] Preparation of Compound C1-41

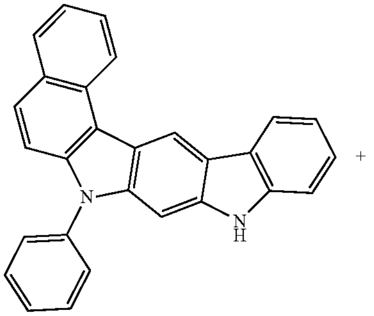

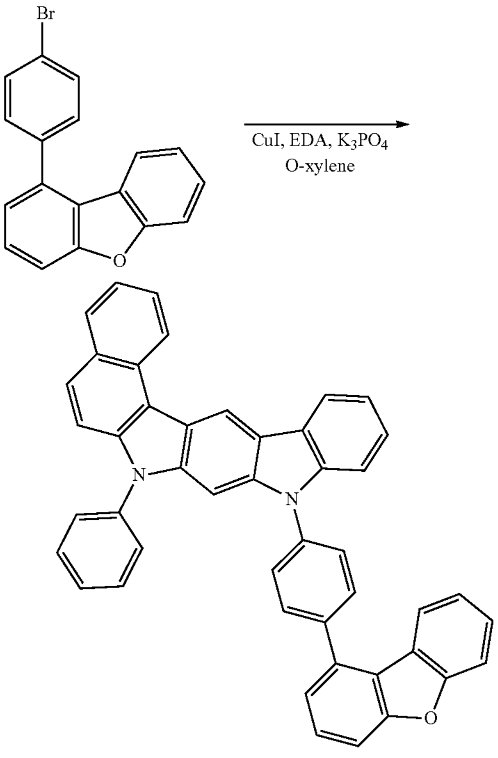

C1-41

7-phenyl-7,9-dihydrobenzo[g]indolo[2,3-b]carbazole (3.6 g, 9.285 mmol), 1-(4-bromophenyl)dibenzo[b,d]furan (3 g, 9.285 mmol), CuI (0.08 g, 0.464 mmol), EDA (0.5 g, 9.285 mmol), and $K_3PO_4$ (4.9 g, 23.21 mmol) were added in 50 mL of o-xylene and stirred for 1 day. After completion of the reaction, the mixture was cooled to room temperature, and then extracted with distilled water and MeOH. The resulting product was purified by column chromatography with MC/Hex to obtain compound C1-41 (2.7 g, yield: 47%).

$^1$H NMR (DMSO-$d_6$) δ: 9.69 (s, 1H), 9.26 (d, J=8.3 Hz, 1H), 8.69 (dd, J=7.7, 1.2 Hz, 1H), 8.14 (dd, J=8.0, 1.1 Hz, 1H), 7.97 (d, J=8.8 Hz, 1H), 7.92 (s, 4H), 7.88 (ddd, J=8.2, 6.9, 1.3 Hz, 1H), 7.82-7.76 (m, 4H), 7.73 (t, J=7.8 Hz, 2H), 7.70-7.48 (m, 8H), 7.48-7.44 (m, 2H), 7.42 (td, J=7.3, 1.0 Hz, 1H), 7.26-7.20 (m, 1H)

| | MW | M.P. |
|---|---|---|
| C1-41 | 624.7 | 309.7° C. |

[Example 11] Preparation of Compound C1-3

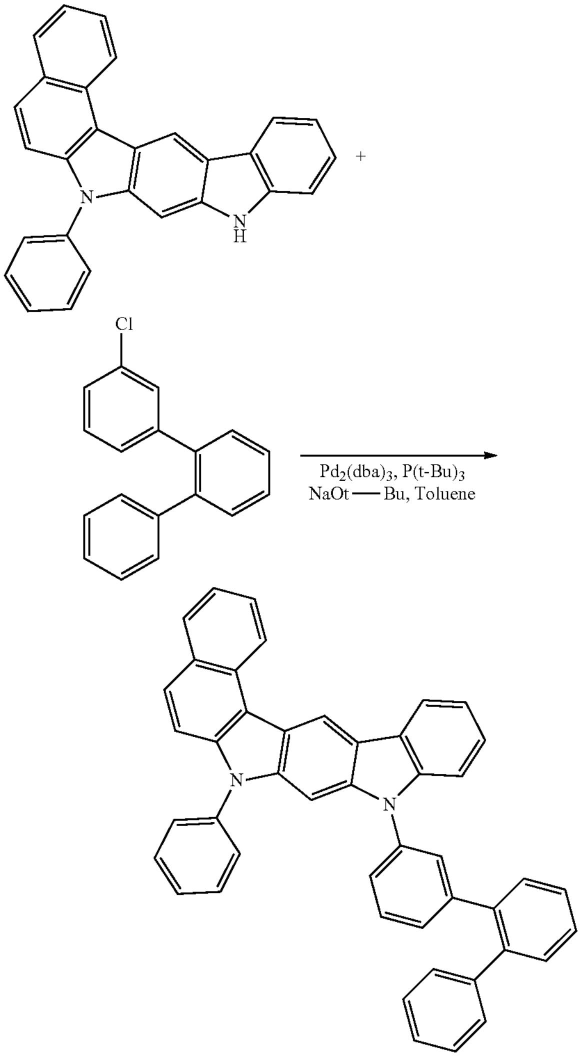

C1-3

7-phenyl-7,9-dihydrobenzo[g]indolo[2,3-b]carbazole (7.6 g, 18.88 mmol), 3-chloro-1,1':2',1"-terphenyl (5 g, 18.88 mmol), $Pd_2(dba)_3$ (0.86 g, 0.940 mmol), NaOt-Bu (4.5 g, 47.22 mmol), and $P(t-Bu)_3$ (0.38 g, 1.888 mmol) were added in 100 mL of toluene and stirred for 1 day. After completion of the reaction, the mixture was cooled to room temperature and then extracted with distilled water and MeOH. The resulting product was purified by column chromatography with MC/Hex to obtain compound C1-3 (0.7 g, yield: 6.2%).

$^1H$ NMR (DMSO-$d_6$) δ: 9.58 (s, 1H), 9.20 (d, J=8.4 Hz, 1H), 8.57 (d, J=7.8 Hz, 1H), 8.11 (d, J=8.3 Hz, 1H), 7.94 (d, J=8.9 Hz, 1H), 7.84 (ddd, J=8.3, 6.8, 1.3 Hz, 1H), 7.72 (d, J=6.2 Hz, 4H), 7.64-7.47 (m, 8H) 7.44 (dt, J=6.0, 1.9 Hz, 1H), 7.40-7.17 (m, 10H), 6.50 (d, J=7.9 Hz, 1H)

| | MW | M.P |
|---|---|---|
| C1-3 | 610.7 | 194.6° C. |

[Example 12] Preparation of Compound C1-11

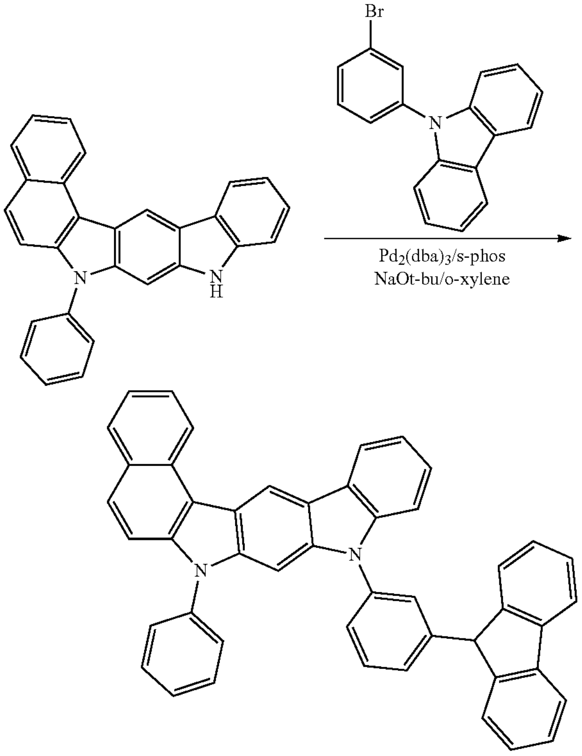

C1-11

7-phenyl-7,9-dihydrobenzo[g]indolo[2,3-b]carbazole (5.1 g, 13 mmol), 9-(3-bromophenyl)-9H-carbazole (4.7 g, 14.6 mmol), $Pd_2(dba)_3$ (0.604 g, 0.66 mmol), s-phos (0.546 g, 1.33 mmol), and NaOt-bu (3.20 g, 33.3 mmol) were added in 50 mL of o-xylene into a flask followed by refluxing at 190° C. for 2 hours. After completion of the reaction, the organic layer was extracted with EA and the extracted organic layer was dried with $MgSO_4$. After purifying by column chromatography, MeOH was added thereto and the resulting solid was filtered under reduced pressure to obtain compound C1-11 (4.4 g, yield: 53.0%).

$^1H$ NMR (600 MHz, DMSO-$d_6$, δ) 9.66 (s, 1H), 9.24 (d, J=8.4 Hz, 1H), 8.66 (d, J=7.7 Hz, 1H), 8.26 (d, J=7.8 Hz, 2H), 8.13 (d, J=8.1 Hz, 1H), 8.01-7.94 (m, 2H), 7.91-7.84 (m, 3H), 7.79 (dd, J=8.2, 1.8 Hz, 1H), 7.77-7.74 (m, 2H), 7.69 (t, J=7.6 Hz, 2H), 7.62-7.55 (m, 3H), 7.53 (d, J=8.1 Hz, 1H), 7.49-7.45 (m, 2H), 7.39 (dd, J=14.4, 6.9 Hz, 5H) 7.31 (t, J=7.5 Hz, 2H)

| | MW | M.P. |
|---|---|---|
| C1-11 | 623.76 | 240° C. |

[Example 13] Preparation of Compound C1-18

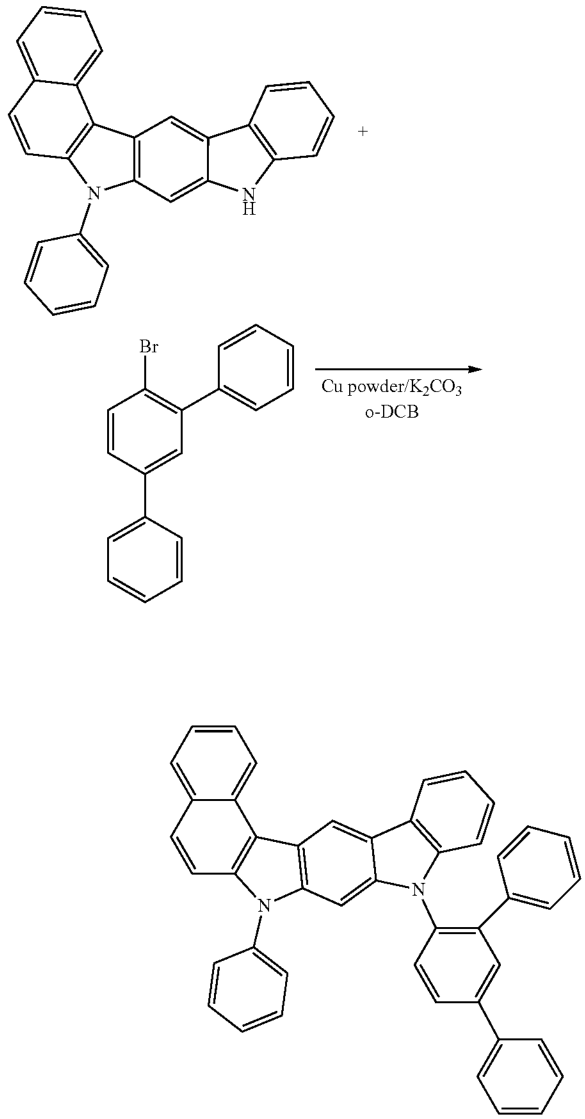

C1-18

7-phenyl-7,9-dihydrobenzo[g]indolo[2,3-b]carbazole (5.0 g, 13 mmol), 4'-bromo-1,1':3',1"-terphenyl (6.06 g, 20 mmol), Cu powder (1.307 g, 0.65 mmol), and $K_2CO_3$ (3.4 g, 26 mmol) were added in 60 mL of o-DCB into a flask followed by refluxing at 23° C. for 12 hours. After completion of the reaction, the organic layer was extracted with EA and the extracted organic layer was dried with $MgSO_4$. After purifying by column chromatography, MeOH was added thereto, and the resulting solid was filtered under reduced pressure to obtain compound C1-18 (1.3 g, yield: 16.3%).

$^1$H NMR (600 MHz, DMSO-$d_6$, δ) 9.51 (s, 1H), 9.16 (d, J=8.3 Hz, 1H), 8.57 (d, J=7.8 Hz, 1H), 8.10 (d, J=8.0 Hz, 1H), 7.98-7.85 (m, 6H), 7.83 (t, J=7.6 Hz, 1H), 7.76 (s, 1H), 7.70 (d, J=8.1 Hz, 1H), 7.61-7.51 (m, 5H), 7.51-7.42 (m, 3H), 7.38 (t, J=7.8 Hz, 1H), 7.31 (t, J=7.3 Hz, 1H), 7.25 (d, J=8.0 Hz, 1H), 7.13-7.06 (m, 4H), 7.03 (d, J=6.8 Hz, 1H), 6.79 (s, 1H)

| | MW | M.P. |
|---|---|---|
| C1-18 | 610.74 | 296° C. |

[Example 14] Preparation of Compound C1-20

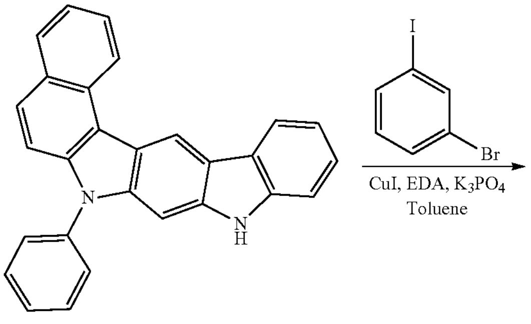

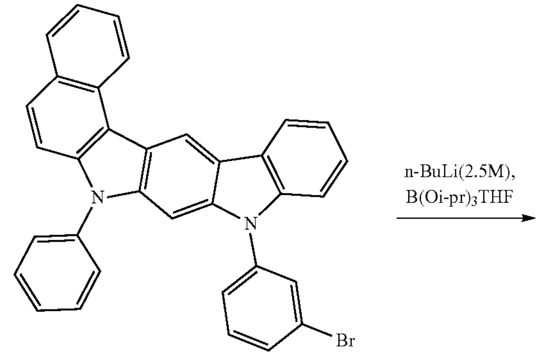

1

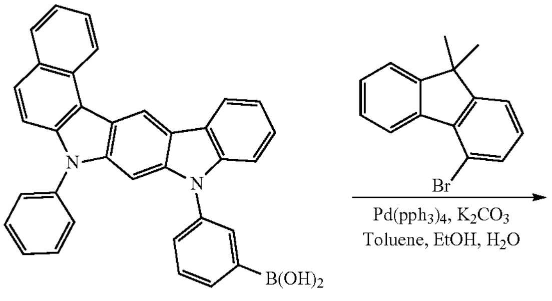

2

-continued

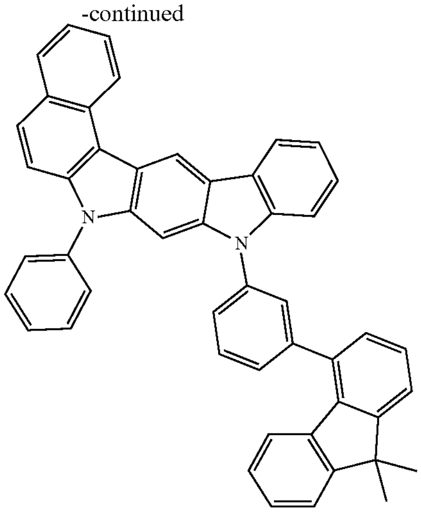

C1-20

1) Synthesis of Compound 1

7-phenyl-7,9-dihydrobenzo[g]indolo[2,3-b]carbazole (10 g, 26.14 mmol), 1-bromo-3-iodobenzene (14.8 g, 52.29 mmol), CuI (2.5 g, 13.07 mmol), EDA (1.57 g, 26.14 mmol), and $K_3PO_4$ (13.8 g, 65.36 mmol) were added in 130 mL of toluene and stirred for 1 day. After completion of the reaction, the mixture was cooled to room temperature, and then extracted with distilled water and MeOH. The resulting product was purified by column chromatography with MC/Hex to obtain compound 1 (9 g, yield: 64%).

2) Synthesis of Compound 2

Compound 1 (9 g, 16.74 mmol) was added in 85 mL of THF and n-BuLi (2.5M) (8.7 mL, 21.77 mmol) was added thereto with stirring for 1 hour at −78° C. $B(Oi\text{-}pr)_3$ (5.7 mL, 25.12 mmol) was then added to the mixture and stirred for 1 day. After completion of the reaction, $NH_4Cl$ and distilled water added to the mixture and stirred for 30 minutes. Thereafter, the organic layer was extracted with distilled water and EA, and then the extracted organic layer was concentrated to obtain compound 2 (6.8 g, yield: 80%).

3) Synthesis of Compound C1-20

Compound 2 (6.8 g, 13.53 mmol), 4-bromo-9,9-dimethyl-9H-fluorene (3.7 g, 13.53 mmol), $Pd(PPh_3)_4$ (0.8 g, 0.676 mmol), and $K_2CO_3$ (3.7 g, 27.07 mmol) were added in 60 mL of toluene, 15 mL of EtOH, and 15 mL of water and refluxed for 3 hours. After completion of the reaction, the mixture was cooled to room temperature, and then extracted with distilled water and EA followed by vacuum distillation. The resulting product was purified by column chromatography with MC/Hex to obtain compound C1-20 (1.5 g, yield: 17%).

$^1$H NMR (DMSO-$d_6$) δ: 9.64 (s, 1H), 9.22 (d, J=8.4 Hz, 1H), 8.64 (dt, J=7.6, 0.9 Hz, 1H), 8.14-8.10 (m, 1H), 7.94 (d, J=8.9 Hz, 1H), 7.90-7.77 (m, 3H), 7.68 (s, 3H), 7.65-7.53 (m, 7H), 7.53-7.33 (m, 6H), 7.27 (td, J=7.4, 1.1 Hz, 1H), 7.17 (d, J=7.6 Hz, 1H), 6.92 (d, J=47.9 Hz, 2H), 1.49 (d, J=17.3 Hz, 6H)

| | MW | M.P. |
|---|---|---|
| C1-20 | 650.8 | 166.3° C. |

[Example 15] Preparation of Compound C1-2

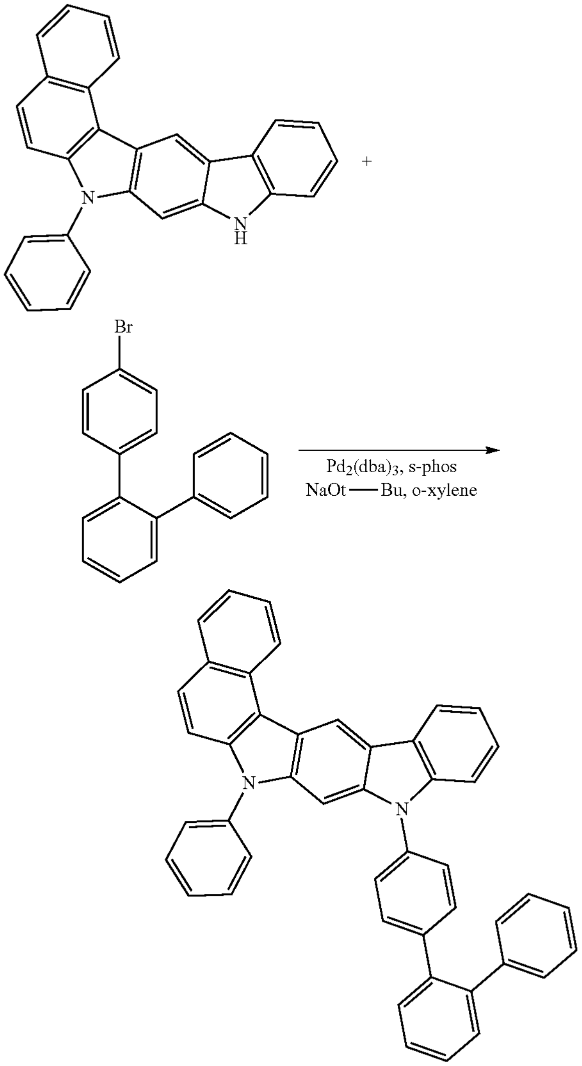

C1-2

7-phenyl-7,9-dihydrobenzo[g]indolo[2,3-b]carbazole (5 g, 13.07 mmol), 4-bromo-1,1':2',1"-terphenyl (4 g, 13.07 mmol), $Pd_2(dba)_3$ (0.6 g, 0.653 mmol), NaOt-Bu (3.8 g 39.21 mmol), and s-phos (0.5 g, 1.307 mmol) were added in 70 mL of o-xylene and stirred for 1 day. After completion of the reaction, the mixture was cooled to room temperature, and then extracted with distilled water and MeOH. The resulting product was purified by column chromatography with MC/Hex to obtain compound C1-2 (63 g, yield: 78%).

$^1$H NMR (DMSO-$d_6$) δ: 9.63 (s, 1H), 9.23 (d, J=8.3 Hz, 1H), 8.63 (dd, J=7.7, 1.1 Hz, 1H), 8.12 (d, J=8.2 Hz, 1H), 7.95 (d, J=8.9 Hz, 1H), 7.85 (ddd, J=8.2, 6.8, 1.4 Hz, 1H), 7.79-7.73 (m, 2H), 7.72-7.66 (m, 3H), 7.60-7.47 (m, 8H), 7.44 (ddd, J=8.2, 7.1, 1.3 Hz, 1H), 7.38-7.33 (m, 3H), 7.32-7.24 (m, 2H), 7.22-7.14 (m, 5H)

| | MW | M.P. |
|---|---|---|
| C1-2 | 610.7 | 288° C. |

[Example 16] Preparation of Compound C1-7

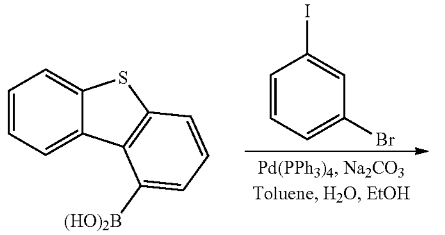

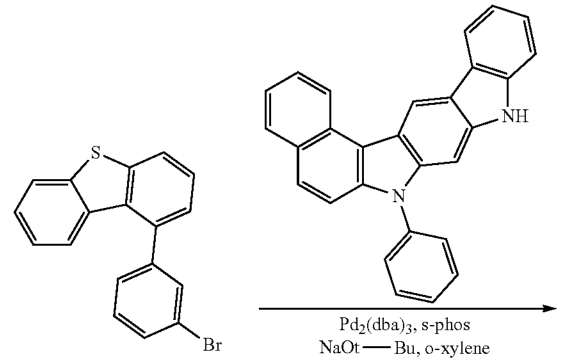

1

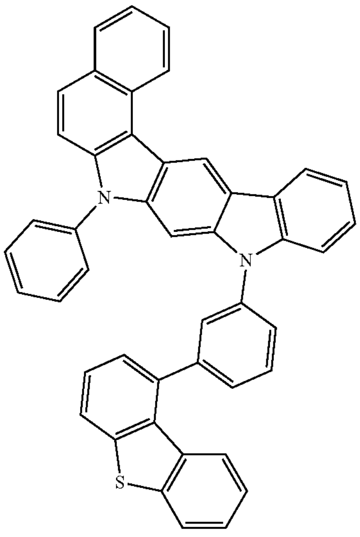

C1-7

1) Synthesis of Compound 1

Dibenzo[b,d]thiophene-1-yl boronic acid (20 g, 87.71 mmol), 1-bromo-3-iodobenzene (50 g, 175.4 mmol), $Pd(PPh_3)_4$ (5 g, 4.385 mmol), and $Na_2CO_3$ (18 g, 175.4 mmol) were added in 360 mL of toluene, 90 mL of water, and 90 mL of EtOH, and refluxed for 3 hours. After completion of the reaction, the mixture was cooled to room temperature, and then extracted with distilled water and EA followed by vacuum distillation. Thereafter, the resulting product was purified by column chromatography with Hex to obtain compound 1 (20 g, yield: 67%).

2) Synthesis of Compound C1-7 Compound 1 (4.4 g, 13.07 mmol), 7-phenyl-7,9-dihydrobenzo[g]indolo[2,3-b]carbazole (5 g, 13.07 mmol), $Pd_2(dba)_3$ (0.6 g, 0.653 mmol), s-phos (0.5 g, 1.307 mmol), and NaOt-Bu (3.7 g, 39.21 mmol) were added in 70 mL of o-xylene and refluxed for 2 hours. After completion of the reaction, the mixture was cooled to room temperature, and then extracted with MeOH. Thereafter, the resulting product was purified by column chromatography with MC/Hex to obtain compound C1-7 (5.1 g, yield: 60%).

$^1H$ NMR (DMSO-$d_6$) δ: 9.63 (s, 1H), 9.22 (d, J=8.4 Hz, 1H), 8.64 (dd, J=7.5, 1.2 Hz, 1H), 8.14-8.09 (m, 2H), 8.07 (dt, J=8.1, 0.9 Hz, 1H), 7.94 (d, J=8.9 Hz, 1H), 7.91-7.82 (m, 3H), 7.72 (d, J=2.0 Hz, 1H), 7.67 (d, J=7.6 Hz, 2H), 7.63-7.48 (m, 8H), 7.48-7.41 (m, 2H), 740 (d, J=6.1 Hz, 1H), 7.36 (td, J=7.4, 1.0 Hz, 1H), 7.33 (d, J=7.3 Hz, 1H), 7.09 (d, J=49.0 Hz, 2H)

| | MW | M.P. |
|---|---|---|
| C1-7 | 640.7 | 226.7° C. |

[Example 17] Preparation of Compound C2-18

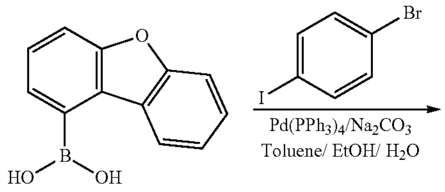

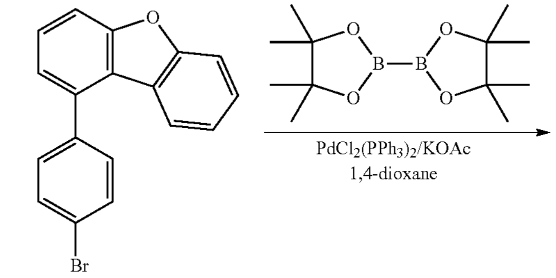

1

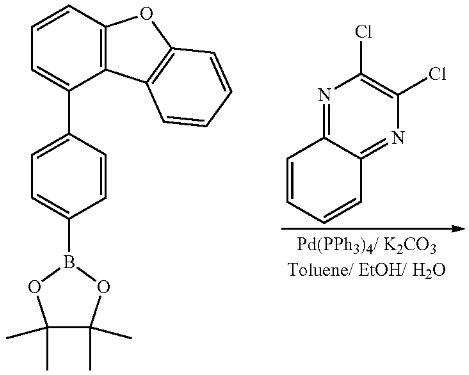

2

-continued

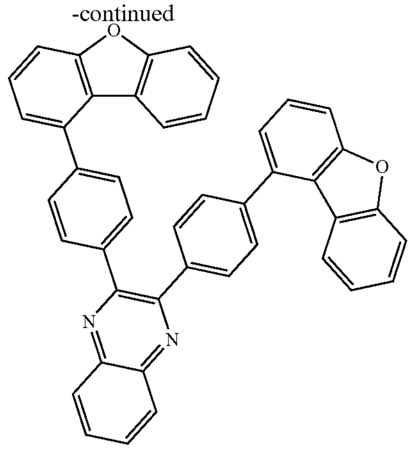

C2-18

1) Synthesis of Compound 1

Dibenzo[b,d]furan-1-yl boronic acid (40.0 g, 189 mmol), 1-bromo-4-iodobenzene (80.06 g, 283 mmol), $Pd(PPh_3)_4$ (10.90 g, 9 mmol), and $Na_2CO_3$ (49.99 g, 472 mmol) were added dropwise in 550 mL of toluene, 200 mL of EtOH, and 200 mL of $H_2O$ into a flask, followed by refluxing at 150° C. for 2 hours. After completion of the reaction, the organic layer was extracted with EA and dried with $MgSO_4$. After purifying by column chromatography, MeOH was added thereto, and the resulting solid was filtered under reduced pressure to obtain compound 1 (30.1 g. yield: 49.3%).

2) Synthesis of Compound 2

Compound 1 (90 g, 28 mmol), 4,4,4',4',5,5,5',5'-octamethyl-2,2'-bi-1,3,2-dioxaborolane (10.61 g, 42 mmol), $PdCl_2(PPh_3)_2$ (0.977 g, 1 mmol), and KOAc (6.832 g, 70 mmol) were added dropwise in 150 mL of 1,4-dioxane followed by refluxing at 140° C. for 1 hour. After completion of the reaction, the organic layer was extracted with EA and dried with $MgSO_4$. After purifying by column chromatography, MeOH was added thereto, and the resulting solid was filtered under reduced pressure to obtain compound 2 (10.2 g, yield: 98.93%).

3) Synthesis of Compound C2-18

2,3-dichloroquinoxaline (2.50 g, 13 mmol), compound 2 (10.23 g, 28 mmol), $Pd(PPh_3)_4$ (1.451 g, 1 mmol), and $K_2CO_3$ (8.680 g, 63 mmol) were added dropwise in 10 mL of toluene, 3 mL of EtOH, and 3 mL of $H_2O$ into a flask followed by refluxing at 150° C. for 2 hours. After completion of the reaction, the organic layer was extracted with EA and dried with $MgSO_4$. After purifying by column chromatography, MeOH was added thereto, and the resulting solid was filtered under reduced pressure to obtain compound C2-18 (1.6 g, yield: 20.0%).

$^1$H NMR (600 MHz, DMSO-ds, 5) 8.28 (dd, J=63, 3.4 Hz, 2H), 7.98 (dd, J=6.3, 3.4 Hz, 2H), 7.85-7.80 (m, 4H), 7.77 (dd, J=8.3, 0.9 Hz, 2H), 7.73-7.68 (m, 4H), 7.66 (d, J=8.1 Hz, 2H), 7.63 (dd, J=8, 2, 7.4 Hz, 2H), 7.42 (dt, J=7.9, 0.9 Hz, 2H), 7.37 (dd, J=7.4, 0.9 Hz, 2H), 7.30 (ddd, J=8.4, 7.2, 1.3 Hz, 2H), 6.91 (td, J=7.6, 1.0 Hz, 2H)

| | MW | M.P. |
|---|---|---|
| C2-18 | 614.70 | 231° C. |

[Example 18] Preparation of Compound C2-3

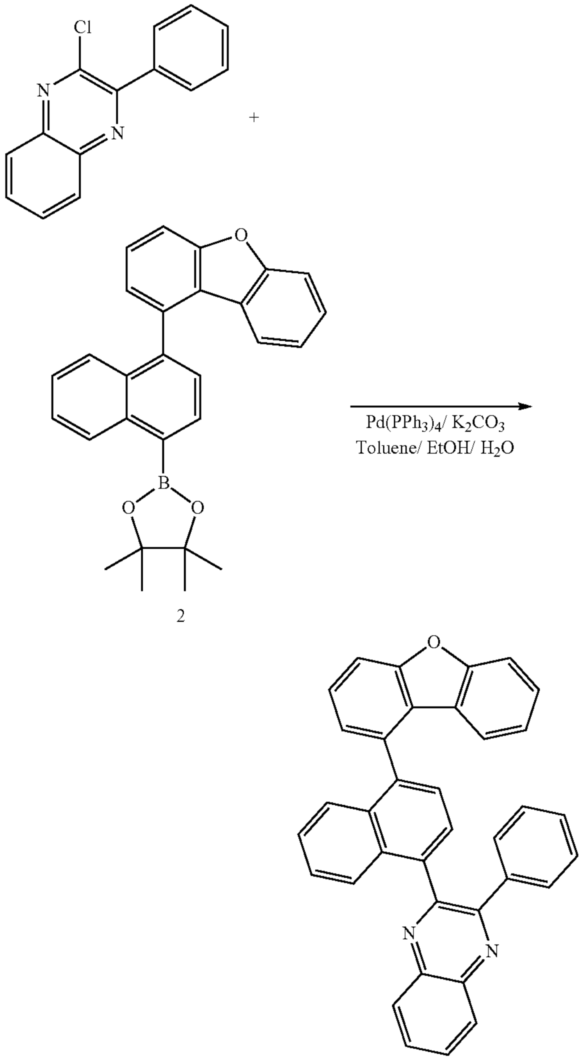

2

C2-3

2-chloro-3-phenylquinoxaline (4.0 g, 17 mmol), compound 2 (8.38 g, 20 mmol), $Pd(PPh_3)_4$ (0.960 g, 0.83 mmol), and $K_2CO_3$ (6.89 g, 50 mmol) were added dropwise in 50 mL of toluene, 20 mL of EtOH, and 20 mL of $H_2O$ followed by refluxing at 140° C. for 2 hours. After completion of the reaction, the organic layer was extracted with EA and dried with $MgSO_4$. After purifying by column chromatography, MeOH was added thereto, and the resulting solid was filtered under reduced pressure to obtain compound C2-3 (32 g, yield: 38.6%).

$^1$H NMR (600 MHz, DMSO-$d_6$, δ) 8.34-8.29 (m, 1H), 8.25 (d, J=7.8 Hz, 1H), 8.04-7.95 (m, 2H), 7.87 (dd, J=8.3, 0.9 Hz, 1H), 7.76-7.69 (m, 4H), 7.62 (d, J=7.2 Hz, 1H), 7.54 (d, J=7.5 Hz, 2H), 7.48-7.39 (m, 4H), 7.37 (s, 1H), 7.30 (dt, J=26.1, 7.6 Hz, 3H), 7.19 (s, 1H), 7.03 (t, J=7.5 Hz, 1H)

| | MW | M.P. |
|---|---|---|
| C2-3 | 498.59 | 245° C. |

[Example 19] Preparation of Compound C2-29

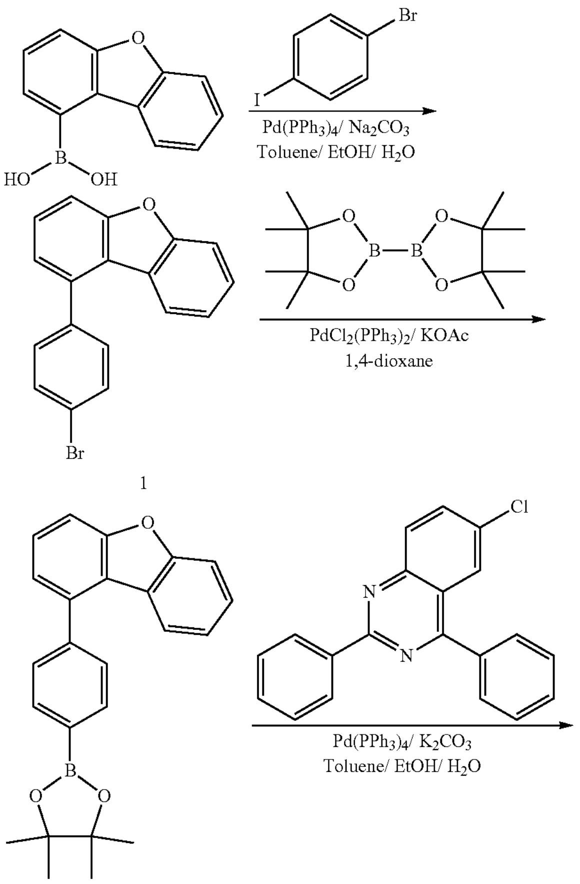

1

2

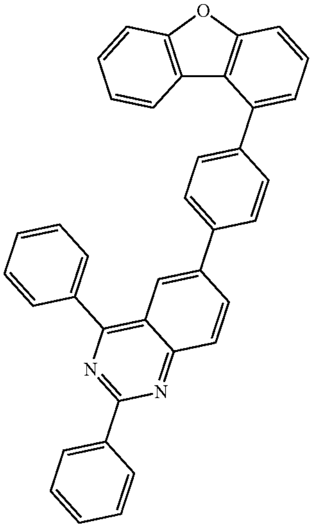

C2-29

1) Synthesis of Compound 1

Dibenzo[b,d]furan-1-yl boronic acid (80.0 g, 377 mmol), 1-bromo-4-iodobenzene (160.13 g, 566 mmol), $Pd(PPh_3)_4$ (21.80 g, 19 mmol), and $Na_2CO_3$ (99.99 g, 943 mmol) were added dropwise in 550 mL of toluene, 200 mL of EtOH, and 200 mL of $H_2O$ into a flask followed by refluxing at 150° C. for 2.5 hours. After completion of the reaction, the organic layer was extracted with EA and dried with $MgSO_4$. After purifying by column chromatography, MeOH was added thereto, and the resulting solid was filtered under reduced pressure to obtain compound 1 (51.8 g, yield: 42.5%).

2) Synthesis of Compound 2

Compound 1 (30.0 g, 93 mmol), 4,4,4',4',5,5,5',5'-octamethyl-2,2'-bi-1,3,2-dioxaborolane (35.4 g, 139 mmol), $PdCl_2(PPh_3)_2$ (3.26 g, 5 mmol), and KOAc (22.77 g, 232 mmol) were added dropwise in 150 mL of 1,4-dioxane followed by refluxing at 140° C. for 1 hour. After completion of the reaction, the organic layer was extracted with EA and dried with $MgSO_4$. After purifying by column chromatography, MeOH was added thereto, and the resulting solid was filtered under reduced pressure to obtain compound 2 (23.3 g, yield: 67.8%).

3) Synthesis of Compound C2-29

6-chloro-2,4-diphenylquinazoline (4.28 g, 14 mmol), compound 2 (6.00 g, 16 mmol), $Pd(PPh_3)_4$ (0.780 g, 0.675 mmol), and $K_2CO_3$ (4.67 g, 34 mmol) were added dropwise in 40 mL of toluene, 15 mL of EtOH, and 15 mL of $H_2O$ into a flask followed by refluxing at 150° C. for 2 hours. After completion of the reaction, the organic layer was extracted with EA and dried with $MgSO_4$. After purifying by column chromatography, MeOH was added thereto, and the resulting solid was filtered under reduced pressure to obtain compound C2-29 (4.3 g, yield: 60.7%).

$^1$H NMR (600 MHz, DMSO-d, δ) 8.69-8.64 (m, 2H), 8.54 (dd, J=8.7, 2.0 Hz, 1H), 8.42 (d, J=2.0 Hz, 1H), 8.31 (d, J=8.7 Hz, 1H), 8.03 (dd, J=21.1, 7.3 Hz, 4H), 7.83-7.69 (m, 7H), 7.66-7.56 (m, 5H), 7.51 (t, J=7.7 Hz, 1H), 7.37 (d, J=7.4 Hz, 1H), 7.25 (t, J=7.6 Hz, 1H)

| | MW | M.P. |
|---|---|---|
| C2-29 | 524.62 | 242° C. |

[Example 20] Preparation of Compound C2-27

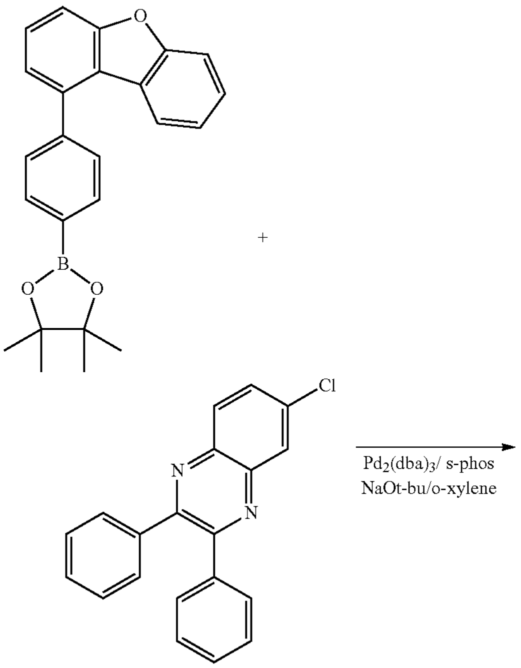

-continued

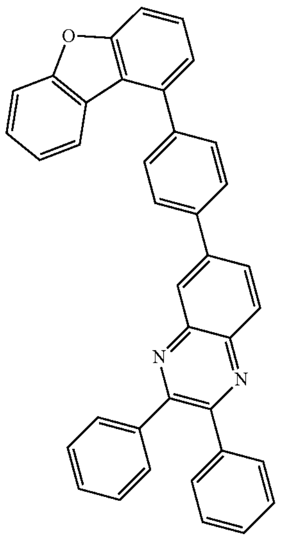

C2-27

6-chloro-2,3-diphenylquinoxaline (4.28 g, 14 mmol), 2-(4-(dibenzo[b,d]furan-1-yl)phenyl)-4,4,5,5-tetramethyl-1,3,2-dioxaborolane (600 g, 16 mmol), $Pd_2(dba)_3$ (0.618 g, 0.675 mmol), s-phos (0.554 g, 1 mmol), and NaOt-Bu (3.24 g, 34 mmol) were added dropwise in 70 mL of o-xylene into a flask followed by refluxing at 140° C. for 2 hours. After completion of the reaction, the organic layer was extracted with EA and dried with $MgSO_4$. After purifying by column chromatography, MeOH was added thereto, and the resulting solid was filtered under reduced pressure to obtain compound C2-27 (4.6 g, yield: 64.9%).

$^1H$ NMR (600 MHz, DMSO-do, 6) 8.59 (d, J=2.1 Hz, 1H), 8.41 (dd, J=8.7, 2.1 Hz, 1H), 8.30 (d, J=8.7 Hz, 1H), 8.21 (d, J=8.2 Hz, 2H), 7.87-7.83 (m, 2H), 7.81-7.74 (m, 2H), 7.68-7.62 (m, 2H), 7.57-7.50 (m, 5H), 7.45-7.36 (m, 7H), 7.27 (t, J=7.6 Hz, 1H)

| | MW | M.P. |
|---|---|---|
| C2-27 | 524.62 | 225° C. |

[Example 21] Preparation of Compound C2-91

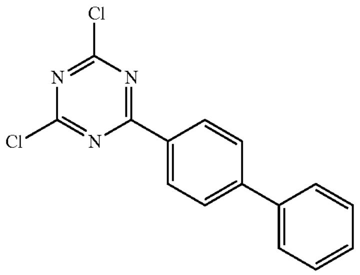

1

+

-continued

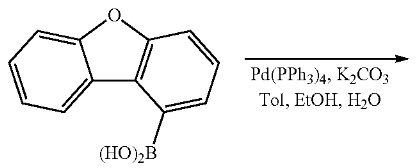

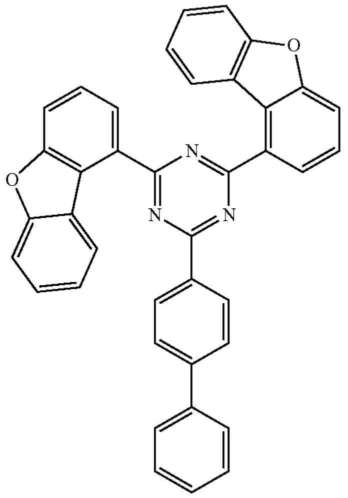

C2-91

Compound 1 (4 g, 13.3 mmol), dibenzo[b,d]furan-1-yl boronic acid (5.9 g, 28 mmol), tetrakis(triphenylphosphin) palladium(O) ($Pd(PPh_3)_4$) (768 mg, 0.66 mmol), 13 mL of $K_2CO_3$ (2M), 52 mL of toluene, and 13 mL of ethanol were added into a flask and dissolved. The mixture was then refluxed at 120° C. for 4 hours. After completion of the reaction, the organic layer was extracted with EA and the residual water was removed from the organic layer by using magnesium sulfate. Thereafter, the remaining product was dried and purified by column chromatography to obtain compound C2-91 (2.5 g, yield: 33%).

| | MW | M.P. |
|---|---|---|
| C2-91 | 565.63 | 294° C. |

[Example 22] Preparation of Compound C2-121

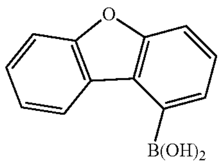

+

-continued

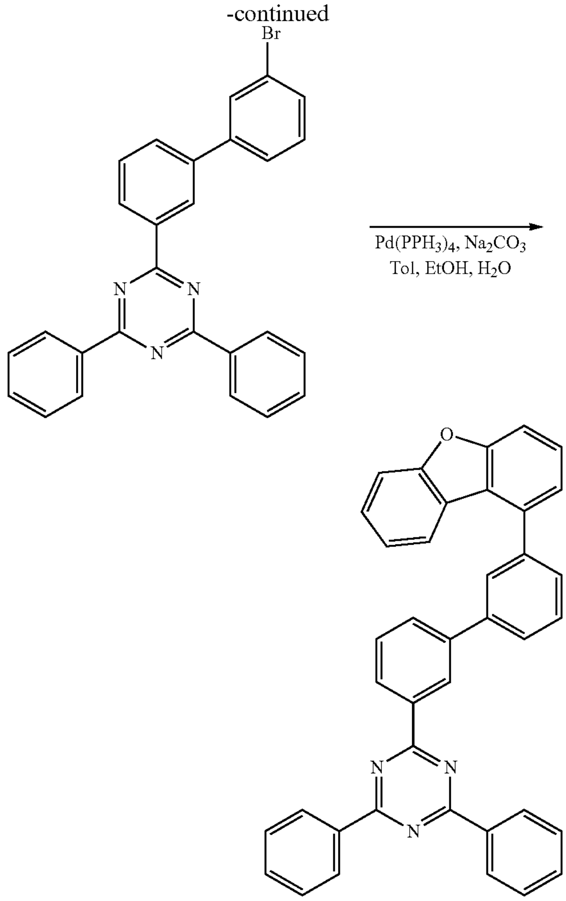

C2-121

1) Synthesis of Compound C2-121

Dibenzo[b,d]furan-1-ylboronic acid (3.0 g, 14.2 mmol), 2-(3'-bromo-[1,1-biphenyl]-3-yl)-4,6-diphenyl-1,3,5-triazine (7.3 g, 15.6 mmol), tetrakis(triphenylphosphin)palladium(0) (0.8 g, 0.71 mmol), $Na_2CO_3$ (3.9 g, 28.4 mmol), 30 mL of toluene, 8 mL of EtOH, and 15 mL of $H_2O$ were added into flask and dissolved. The mixture was then refluxed for 2 hours. After completion of the reaction, the organic layer was extracted with ethyl acetate and the residual water was removed from the organic layer by using magnesium sulfate. Thereafter, the remaining product was dried and purified by column chromatography to obtain compound C2-121 (2.7 g, yield: 35%).

| | MW | M.P |
|---|---|---|
| C2-121 | 551.6 | 233° C. |

[Example 23] Preparation of Compound C2-107

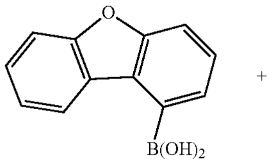

-continued

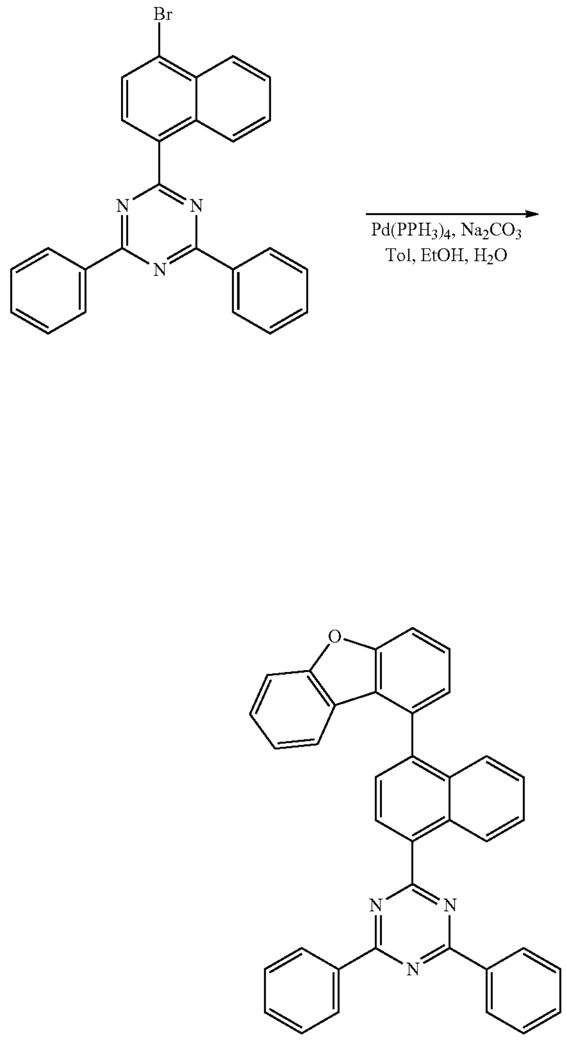

C2-107

1) Synthesis of Compound C2-107

Dibenzo[b,d]furan-1-ylboronic acid (3.0 g, 14.2 mmol), 2-(4-bromonaphthalen-1-yl)-4,6-diphenyl-1,3,5-triazine (6.3 g, 14.2 mmol), tetrakis(triphenylphosphin)palladium(0) (0.82 g, 0.71 mmol), $Na_2CO_3$ (3.9 g, 28.4 mmol), 30 mL of toluene, 8 mL of EtOH, and 15 mL of $H_2O$ were added into flask and dissolved. The mixture was then refluxed for 2 hours. After completion of the reaction, the organic layer was extracted with ethyl acetate and the residual water was removed from the organic layer by using magnesium sulfate. Thereafter, the remaining product was dried and purified by column chromatography to obtain compound C2-107 (1.9 g, yield: 26%).

| | MW | M.P |
|---|---|---|
| C2-107 | 525.6 | 203° C. |

[Example 24] Preparation of Compound C2-95

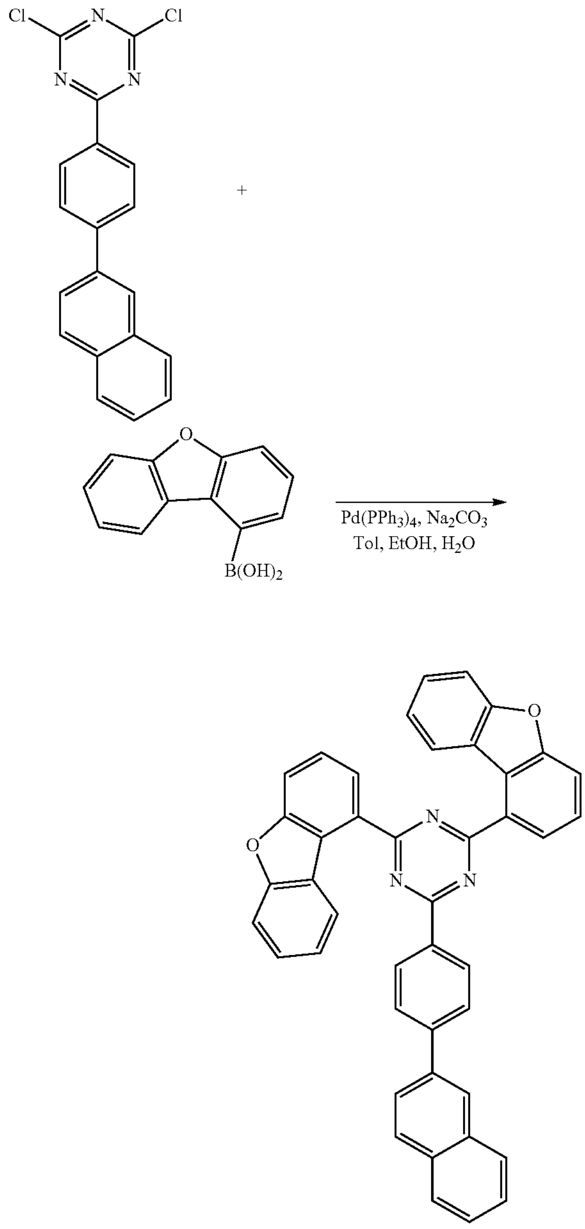

C2-95

1) Synthesis of Compound C2-95

2,4-dichloro-6-(4-(naphthalen-2-yl)phenyl)-1,3,5-triazine (1.6 g, 4.54 mmol), dibenzo[b,d]furan-1-ylboronic acid (2.12 g, 10 mmol), tetrakis(triphenylphosphin)palladium(0) (0.26 g, 0.23 mmol), $Na_2CO_3$ (1.3 g, 9.0 mmol), 16 mL of toluene, 1 mL of EtOH, and 4 mL of $H_2O$ were added into flask and dissolved. The mixture was then refluxed for 3 hours. After completion of the reaction, the organic layer was extracted with ethyl acetate and the residual water was removed from the organic layer by using magnesium sulfate. Thereafter, the remaining product was dried and purified by column chromatography to obtain compound C2-95 (1.0 g. yield: 36%).

| | MW | M.P |
|---|---|---|
| C2-95 | 615.7 | 304° C. |

[Example 25] Preparation of Compound C2-113

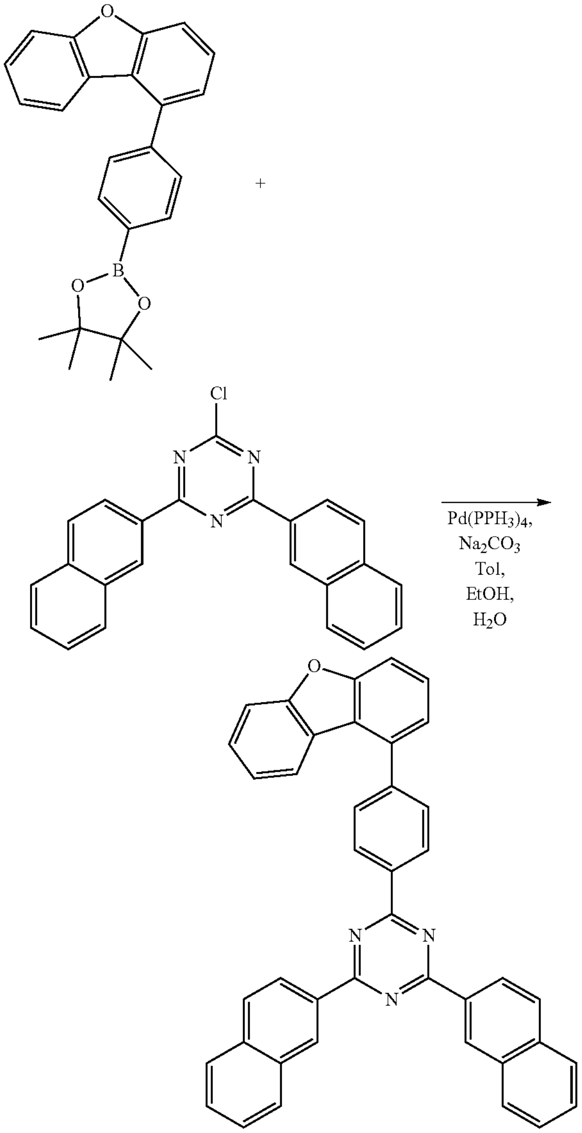

C2-113

1) Synthesis of Compound C2-113

2-(4-(dibenzo[b,d]furan-1-yl)phenyl)-4,4,5,5-tetramethyl-1,3,2-dioxaborolane (4.0 g, 10.8 mmol), 2-chloro-4,6-di(naphthalen-2-yl)-1,3,5-triazine (4.4 g, 11.9 mmol), tetrakis(triphenylphosphin)palladium(0) (0.6 g, 0.54 mmol), $Na_2CO_3$ (3.0 g, 21.6 mmol), 30 mL of toluene, 7 mL of EtOH, and 10 mL of $H_2O$ were added into flask and dissolved. The mixture was then refluxed for 7 hours. After completion of the reaction, the organic layer was extracted with ethyl acetate and the residual water was removed from the organic layer by using magnesium sulfate. Thereafter, the remaining product was dried and purified by column chromatography to obtain compound C2-113 (4.0 g, yield: 65%).

| | MW | M.P |
|---|---|---|
| C2-113 | 575.2 | 261° C. |

[Example 26] Preparation of Compound C2-115

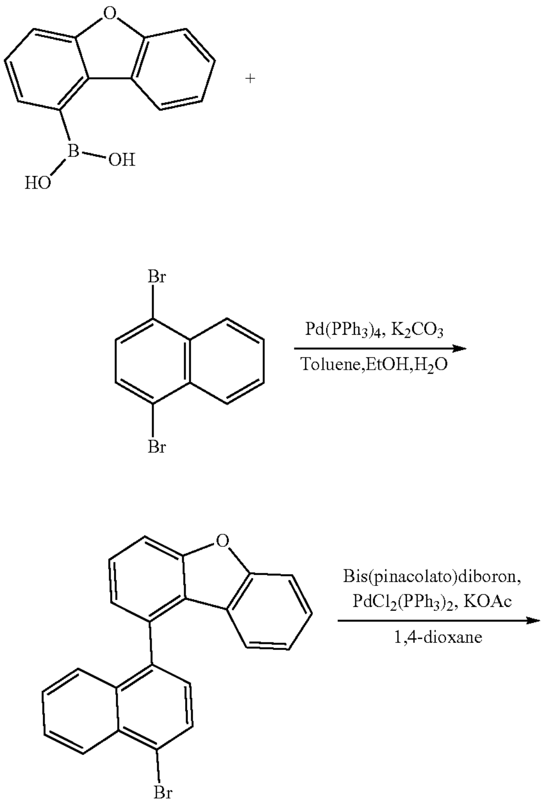

1-1

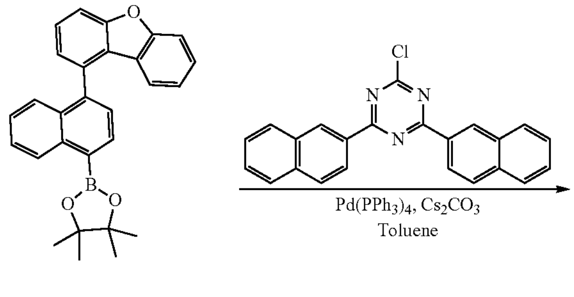

1-2

-continued

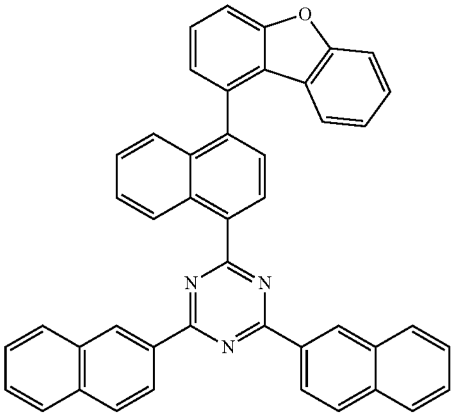

C2-115

1) Synthesis of Compound 1-1

Dibenzo[b,d]furan-1-ylboronic acid (20 g; 94.3 mmol), 1,4-dibromonaphthalene (53.9 g, 188.67 mmol), $K_2CO_3$ (32.6 g, 235.75 mmol), $Pd(PPh_3)_4$ (5.4 g, 4.7 mmol), 470 mL of toluene, 235 mL of EtOH, and 235 mL of $H_2O$ were added into flask and dissolved. The mixture was then refluxed at 140° C. for 4 hours. After completion of the reaction, the organic layer was extracted with ethyl acetate and the residual water was removed from the organic layer by using magnesium sulfate. Thereafter, the remaining product was dried and purified by column chromatography to obtain compound 1-1 (20 g, yield: 56.8%).

2) Synthesis of Compound 1-2

Compound 1-1 (20 g, 53.6 mmol), bis(pinacolato)diboron (16.3 g, 64.3 mmol), $PdCl_2(PPh_3)_2$ (3.76 g, 5.36 mmol), KOAc (10.5 g, 107.2 mmol), and 270 mL of 1,4-dioxane were added into flask and dissolved. The mixture was then refluxed at 150° C. for 4 hours. After completion of the reaction, the organic layer was extracted with ethyl acetate and the residual water was removed from the organic layer by using magnesium sulfate. Thereafter, the remaining product was dried and purified by column chromatography to obtain compound 1-2 (23 g, yield: 100%).

3) Synthesis of Compound C2-115

Compound 1-2 (7 g, 16.6 mmol), 2-chloro-4,6-di(naphthalen-2-yl)-1,3,5-triazine (7.35 g, 19.9 mmol), $Cs_2CO_3$ (13.5 g, 41.5 mmol), $Pd(PPh_3)_4$ (0.959 mg, 0.83 mmol), and 83 mL of toluene were added into flask and dissolved. The mixture was then refluxed at 130° C. for 18 hours. After completion of the reaction, the organic layer was extracted with ethyl acetate and the residual water was removed from the organic layer by using magnesium sulfate. Thereafter, the remaining product was dried and purified by column chromatography to obtain compound C2-115 (2 g, yield: 19.2%).

| | MW | M.P |
|---|---|---|
| C2-115 | 625.73 | 150° C. |

[Example 27] Preparation of Compound C2-124

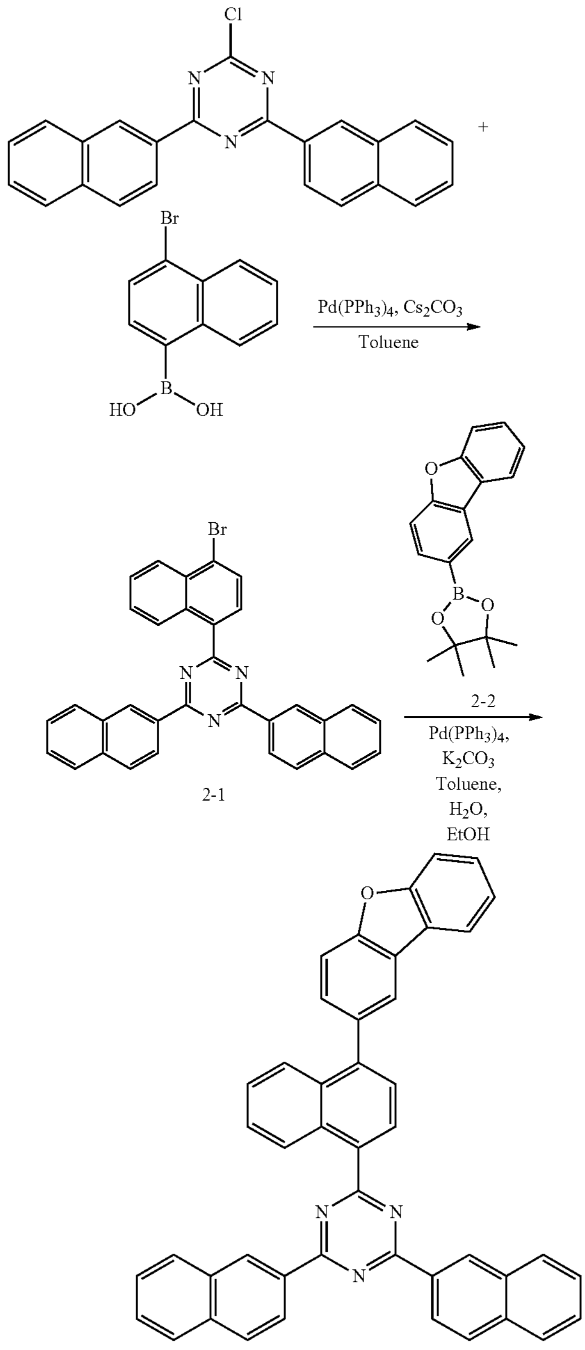

2-1

C2-124

1) Synthesis of Compound 2-1

2-chloro-4,6-di(naphthalen-2-yl)-1,3,5-triazine (32.2 g, 87.7 mmol), (4-bromonaphthalen-1-yl)boronic acid (20 g, 79.7 mmol), $Cs_2CO_3$ (65 g, 199.25 mmol), $Pd(PPh_3)_4$ (4.6 g, 3.985 mmol), and 400 mL of toluene were added into flask and dissolved. The mixture was then refluxed at 140° C. for 4 hours. After completion of the reaction, the organic layer was extracted with ethyl acetate and the residual water was removed from the organic layer by using magnesium sulfate.

Thereafter, the remaining product was dried and purified by column chromatography to obtain compound 2-1 (20 g, yield: 46.6%).

2) Synthesis of Compound C2-124

Compound 2-1 (7 g, 13 mmol), compound 2-2 (4.6 g, 15.6 mmol), $K_2CO_3$ (4.5 g, 32.5 mmol), and $Pd(PPh_3)_4$ (0.75 g, 0.65 mmol) were added in 65 mL of toluene, 32.5 mL of EtOH, and 32.5 mL of $H_2O$ into flask and dissolved. The mixture was then refluxed at 130° C. for 3 hours. After completion of the reaction, the organic layer was extracted with ethyl acetate and the residual water was removed from the organic layer by using magnesium sulfate. Thereafter, the remaining product was dried and purified by column chromatography to obtain compound C2-124 (3.4 g, yield: 41%).

| | MW | M.P |
|---|---|---|
| C2-124 | 625.73 | 250° C. |

[Example 28] Preparation of Compound C2-114

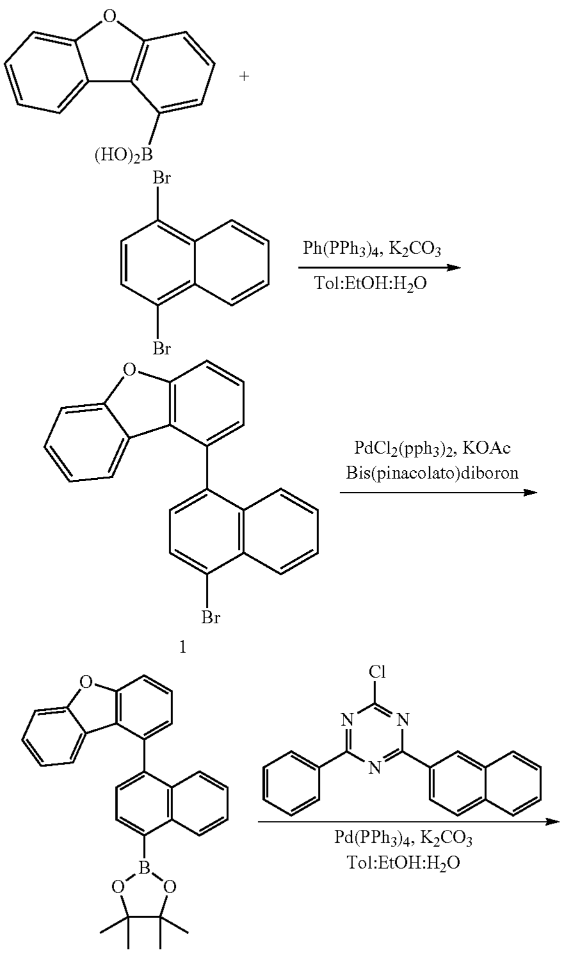

1

2

-continued

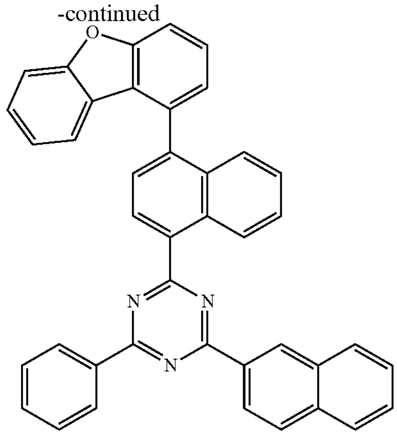

C2-114

1) Synthesis of Compound 1

Dibenzo[b,d]furan-1-ylboronic acid (20 g, 94.33 mmol), 1,4-dibromonaphthalene (54 g, 188.6 mmol), $Pd(PPh_3)_4$ (54 g, 4.716 mmol), and $K_2CO_3$ (26 g, 188.6 mmol) were added in 380 mL of toluene, 95 mL of EtOH, and 95 mL of water and refluxed for 3 hours. After completion of the reaction, the mixture was cooled to room temperature, and then and the organic layer was extracted with distilled water and EA followed by vacuum distillation. The resulting product was purified by column chromatography with MC/Hex to obtain compound 1 (20 g, yield: 55%).

2) Synthesis of Compound 2

Compound 1 (20 g, 53.59 mmol) was added in $PdCl_2(PPh_3)_2$ (3.7 g, 53.59 mmol), KOAc (10.5 g, 107.1 mmol), bis(pinacolato)diboron (17.7 g, 69.66 mmol), 270 mL of 1,4-dioxane and refluxed for 2 hours. After completion of the reaction, the mixture was extracted with MC after Celite filter, and then the organic layer was concentrated. The resulting product was purified by column chromatography with MC/Hex to obtain compound 2 (20 g, yield: 88%).

3) Synthesis of Compound C2-114

Compound 2 (6 g, 14.16 mmol), 2-chloro-4-(naphthalen-2-yl)-6-phenyl-1,3,5-triazine (5 g, 15.73 mmol), $Pd(PPh_3)_4$ (0.9 g, 0.786 mmol), and $K_2CO_3$ (4.3 g, 31.47 mmol) were added in 64 mL of toluene, 16 mL of EtOH, and 16 mL of water, and refluxed for 2 hours. After completion of the reaction, the mixture was cooled to room temperature, and then filtered with distilled water and EA followed by vacuum distillation. The resulting product was purified by column chromatography with MC/Hex to obtain compound C2-114 (4 g, yield: 44%).

| | MW | M.P |
|---|---|---|
| C2-114 | 575.6 | 131.3° C. |

[Example 29] Preparation of Compound C2-90

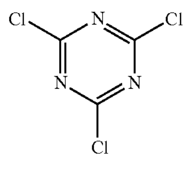

+

-continued

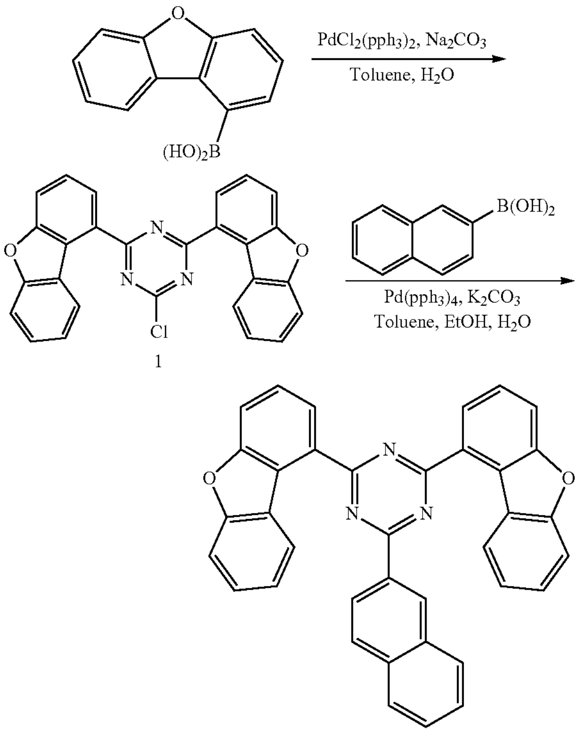

C2-90

1) Synthesis of Compound 1

2,4,6-trichloro-1,3,5-triazine (10 g, 54.22 mmol), dibenzo[b,d]furan-1-ylboronic acid (20.7 g, 97.60 mmol), $PdCl_2(PPh_3)_2$ (0.76 g, 1.084 mmol), and $Na_2CO_3$ (5.7 g, 54.22 mmol) were added in 150 mL of toluene and 30 mL water, and then stirred for 2 days. After completion of the reaction, the mixture was cooled to room temperature, and then extracted with distilled water and MeOH to obtain compound 1 (3.4 g, yield: 14%).

2) Synthesis of Compound C2-90

Compound 1 (3.4 g, 7.592 mmol), naphthalen-2-ylboronic acid (1.5 g, 9.111 mmol), $Pd_2(PPh_3)_4$ (0.4 g, 0.379 mmol), and $K_2CO_3$ (2 g, 15.18 mmol) were added in 32 mL of toluene, 8 mL of EtOH, and 8 mL of water, and refluxed at 140° C. for 1 hour. After completion of the reaction, the mixture was extracted with MC after vacuum evaporation, and then the organic layer was concentrated. The resulting product was purified by column chromatography with MC/Hex to obtain compound C2-90 (0.88 g, yield: 21%).

[Example 30] Preparation of Compound C2-123

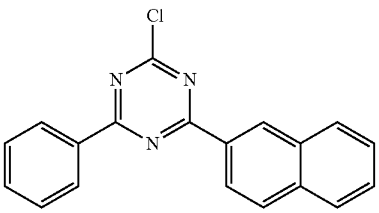

+

-continued

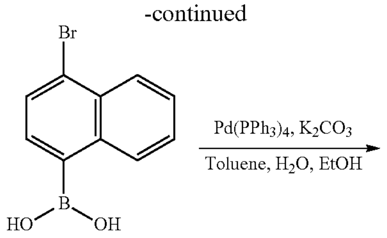

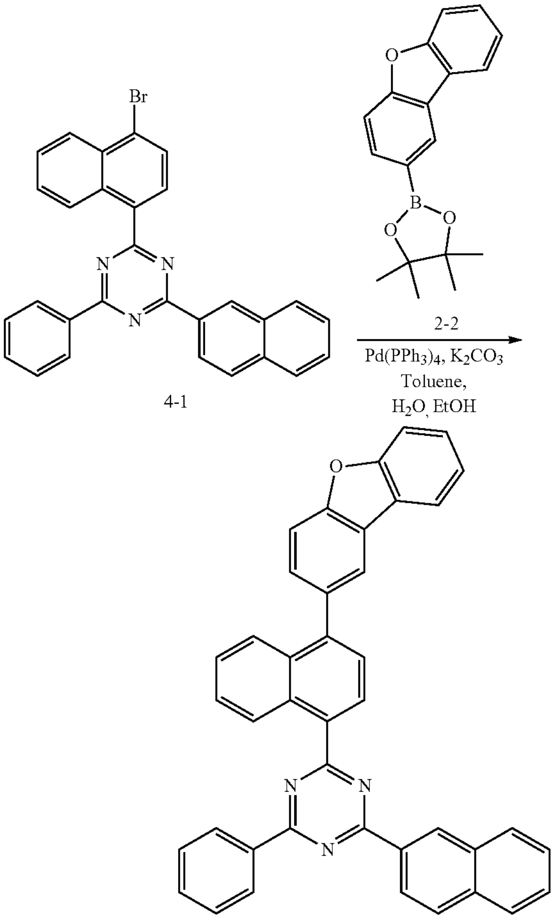

4-1

2-2

C2-123

1) Synthesis of Compound 4-1

2-chloro-4-(naphthalen-2-yl)-6-phenyl-1,3,5-triazine (24.7 g, 77.7 mmol), (4-bromonaphthalen-1-yl)boronic acid (15.0 g, 59.8 mmol), $K_2CO_3$ (20.7 g, 149.5 mmol), and $Pd(PPh_3)_4$ (3.4 g, 3.0 mmol) were dissolved in 200 mL of toluene, 50 mL of EtOH, and 50 mL of $H_2C$ into flask, and refluxed at 130° C. for 2 hours. After completion of the reaction, the organic layer was extracted with ethyl acetate and the residual water was removed from the organic layer by using magnesium sulfate. Thereafter, the remaining product was dried and purified by column chromatography to obtain compound 4-1 (15 g, yield: 51.3%).

2) Synthesis of Compound C2-123

Compound 4-1 (7.5 g, 15.4 mmol), Compound 2-2 (5.0 g, 16.9 mmol), $K_2CO_3$ (5.3 g, 38.4 mmol), and $Pd(PPh_3)_4$ (888 mg, 0.768 mmol) were dissolved in 45 mL of toluene, 15 mL of EtOH, and 15 mL of $H_2O$, and refluxed at 130° C. for 6 hours. After completion of the reaction, the organic layer was extracted with ethyl acetate and the residual water was removed from the organic layer by using magnesium sulfate. Thereafter, the remaining product was dried and purified by column chromatography to obtain compound C2-123 (4.5 g, yield: 51%).

| | MW | M.P |
| --- | --- | --- |
| C2-123 | 575.66 | 213° C. |

[Example 31] Preparation of Compound C-5

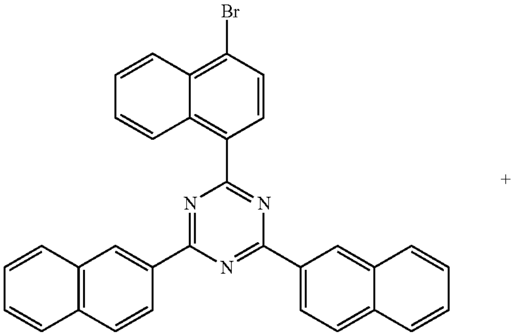

2-1

-continued

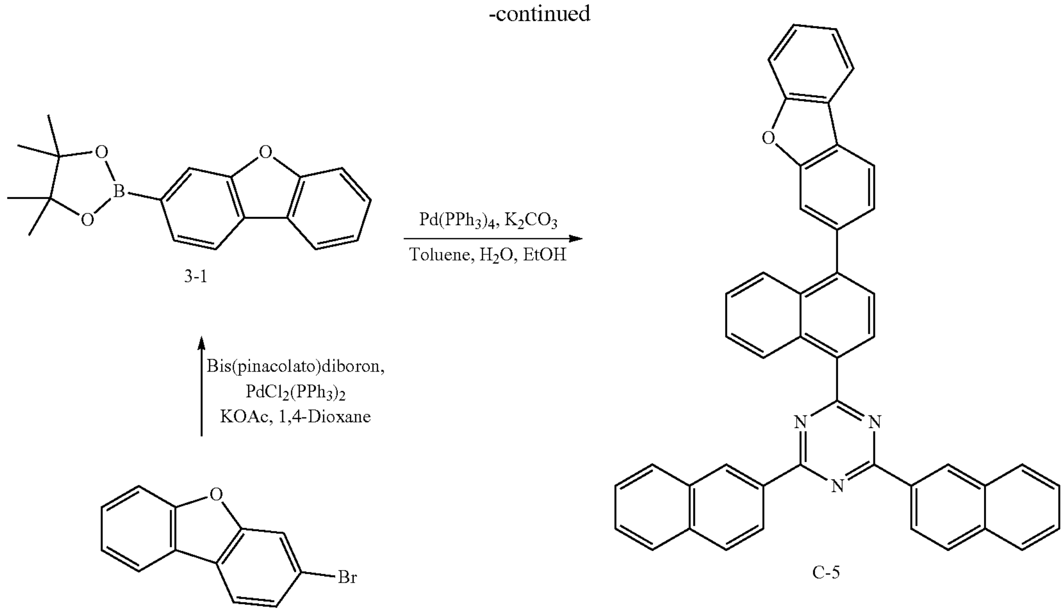

3-1

C-5

1) Synthesis of Compound 3-1

3-bromodibenzofuran (5 g, 20 mmol), bis(pinacolato) diboron (7.6 g, 30 mmol), $PdCl_2(PPh_3)_2$ (1.4 g, 2 mmol), KOAc (3.9 g, 50 mmol), and 100 mL of 1,4-dioxane were added into flask and dissolved. The mixture was then refluxed at 150° C. for 4 hours. After completion of the reaction, the organic layer was extracted with ethyl acetate and the residual water was removed from the organic layer by using magnesium sulfate. Thereafter, the remaining product was dried and purified by column chromatography to obtain compound 3-1 (5 g, yield: 85%).

2) Synthesis of Compound C-5

Compound 2-1 (4.4 g, 12.3 mmol), Compound 3-1 (5 g, 13.5 mmol), $K_2CO_3$ (4.5 g, 32.5 mmol), $Pd(PPh_3)_4$ (0.75 g, 0.65 mmol), 60 mL of toluene, 30 mL of EtOH, and 30 mL of $H_2O$ were added into flask and dissolved. The mixture was refluxed at 130° C. for 3 hours. After completion of the reaction, the organic layer was extracted with ethyl acetate and the residual water was removed from the organic layer by using magnesium sulfate. Thereafter, the remaining product was dried and purified by column chromatography to obtain compound C-5 (4 g, yield: 49%).

| | MW | M.P |
|---|---|---|
| C-5 | 625.73 | 272° C. |

[Device Examples 1-1 to 3-2] Producing OLEDs in which the First Host Compound and the Second Compound According to the Present Disclosure are Co-Deposited as a Host OLEDs according to the present disclosure were produced. First, a transparent electrode indium tin oxide (ITO) thin film (10 Ω/sq) on a glass substrate for an OLED (GEOMATEC CO., LTD., Japan) was subjected to an ultrasonic washing with acetone and isopropylalcohol, sequentially, and then was stored in isopropanol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-7}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus, and was evaporated by applying an electric current to the cell, thereby forming a second hole injection layer having a thickness of 5 nm on the first hole injection layer. Compound HT-1 was then introduced into another cell of the vacuum vapor deposition apparatus, and was evaporated by applying an electric current to the cell, thereby forming a first hole transport layer having a thickness of 10 nm on the second hole injection layer. Compound HT-2 was then introduced into another cell of the vacuum vapor deposition apparatus, and was evaporated by applying an electric current to the cell, thereby forming a second hole transport layer having a thickness of 60 nm on the first hole transport layer. After forming the hole injection layers and the hole transport layers, a light-emitting layer was formed thereon as follows: The first host compound and the second host compound of the following Table 1 were introduced into one cell of the vacuum vapor depositing apparatus as a host, and compound D-39 was introduced into another cell as a dopant. The two host materials were evaporated at a rate of 1:1 and at the same time the dopant was evaporated at a different rate, thereby the dopant was doped in a doping amount of 3 wt % with respect to the total amount of the host and the dopant, to form a light-emitting layer having a thickness of 40 nm on the hole transport layer. Next, compounds ET-1 and EI-1 as electron transport materials were evaporated at a weight ratio of 50:50, and were deposited to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, OLEDs were produced. Each compound was purified by vacuum sublimation under $10^{-6}$ torr and then used.

[Comparative Examples 1 to 3] Producing OLEDs Comprising the Conventional Compounds as a Host OLEDs were produced in the same manner as in the Device Example, except that only one host compound was used, respectively.

The results of the driving voltage, voltage reduction rate, and the luminous efficiency at a luminance of 1,000 nits, and the roll-off value indicating the difference in the efficiency value at 5,000 nits and at 1,000 nits, and the time taken to reduce from 100% to 97% of light intensity at a luminance of 1,000 nits (T97), of the OLEDs of the Device Examples and the Comparative Examples produced as described above, are shown in the following Table 1.

TABLE 1

| | First Host Compound | Second Host Compound | Driving Voltage (V) | Voltage Reduction Rate (%) | Luminous Efficiency (cd/A) | Roll-off (Cd/A) | T97 (hr) |
|---|---|---|---|---|---|---|---|
| Comparative Example 1 | — | C2-114 | 4.6 | — | 18.8 | 6.2 | 7 |
| Device Example 1-1 | C1-113 | C2-114 | 4.2 | 8.7 | 23.8 | 3.7 | 116 |
| Device Example 1-2 | C1-6 | C2-114 | 4.0 | 13.0 | 27.1 | 2.7 | 171 |
| Comparative Example 2 | — | C2-90 | 4.0 | — | 21.6 | 4.9 | 24 |
| Device Example 2 | C1-128 | C2-90 | 3.9 | 2.5 | 21.0 | 0.4 | 134 |
| Comparative Example 3 | — | C2-91 | 4.1 | — | 21.1 | 5.5 | 28 |
| Device Example 3-1 | C1-44 | C2-91 | 3.8 | 7.3 | 20.5 | 2.5 | 26 |
| Device Example 3-2 | C1-15 | C2-91 | 3.7 | 9.8 | 24.1 | 1.9 | 155 |

From Table 1 above, it was confirmed that the organic electroluminescent device comprising a specific combination of compounds according to the present disclosure as a host material can remarkably lower the driving voltage and improve the roll-off characteristics, thereby showing high efficiency even at high luminance, compared with the organic electroluminescent device comprising only one conventional host compound. Further, it was confirmed that the organic electroluminescent device according to the present disclosure can show equal or higher efficiency and/or improved lifespan characteristics than that of the conventional organic electroluminescent device.

[Device Examples 4 and 5] Producing OLEDs in which the First Host Compound and the Second Compound According to the Present Disclosure are Co-Deposited as a Host OLEDs were produced in the same manner as in Device Example 3-2, except that compound D-78 was used as a dopant, instead of compound D-39 and the compound of the following Table 2 was used as a host.

The results of the driving voltage, the luminous efficiency, and the CIE color coordinates at a luminance of 1,000 nits, of the organic electroluminescent device of Device Examples 4 and 5 produced as described above, are shown in the following Table 2.

TABLE 2

| | First Host Compound | Second Host Compound | Driving Voltage (V) | Luminous Efficiency (cd/A) | Color Coordinates (x) | (y) |
|---|---|---|---|---|---|---|
| Device Example 4 | C1-134 | C2-91 | 2.9 | 31.3 | 0.670 | 0.330 |
| Device Example 5 | C1-138 | C2-91 | 2.9 | 29.8 | 0.673 | 0.327 |

From Table 2 above, it was confirmed that the organic electroluminescent device comprising a specific combination of compounds according to the present disclosure as a host material and specific compounds according to the present disclosure as a dopant material can show low driving voltage, high luminance efficiency, and/or excellent color purity compared with the conventional organic electroluminescent device.

The compounds used in Device Examples 1-1 to 3-2, 4, and 5, and Comparative Examples 1 to 3 are shown in Table 3 below.

TABLE 3
| | |
|---|---|
| Hole Injection Layer/Hole Transport Layer | 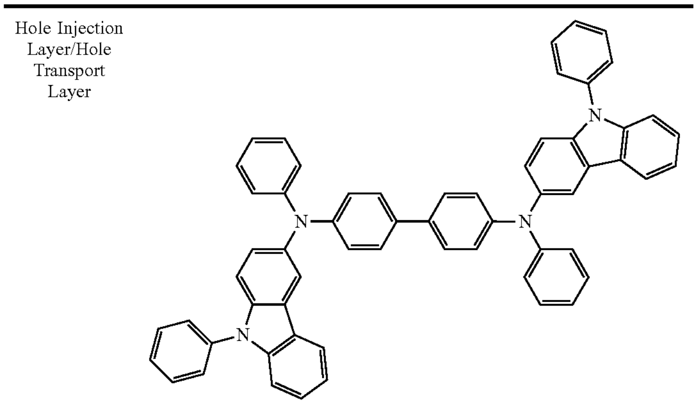 HI-1 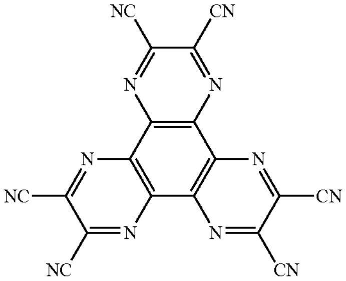 HI-2 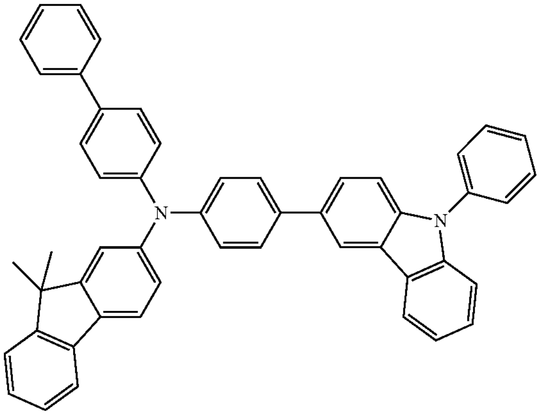 HT-1 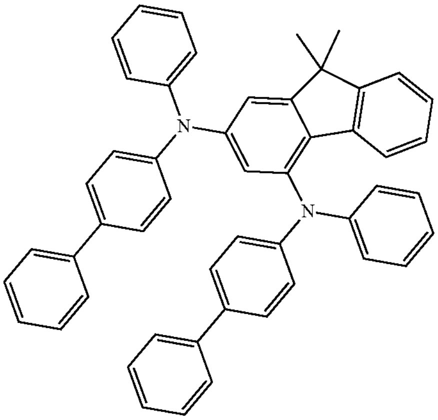 HT-2 |

TABLE 3-continued
| | |
|---|---|
| Light-Emitting Layer | 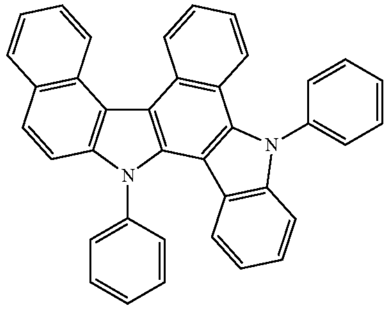 C1-128 |
| | 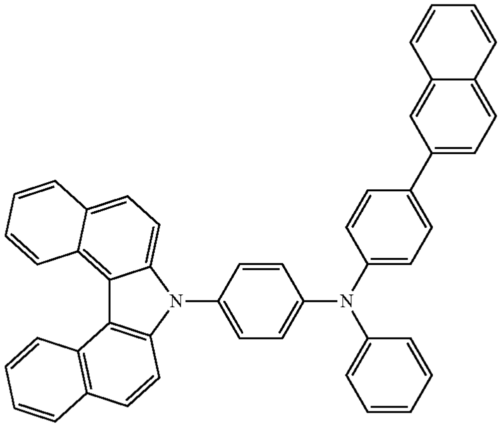 C1-113 |
| | 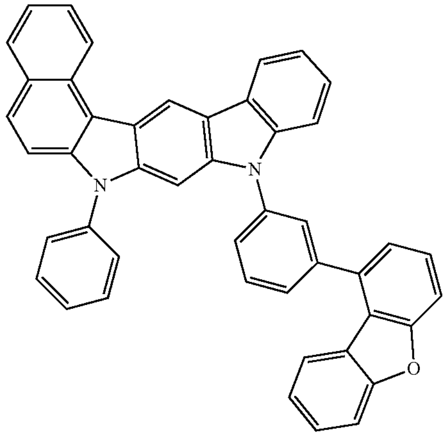 C1-6 |

TABLE 3-continued
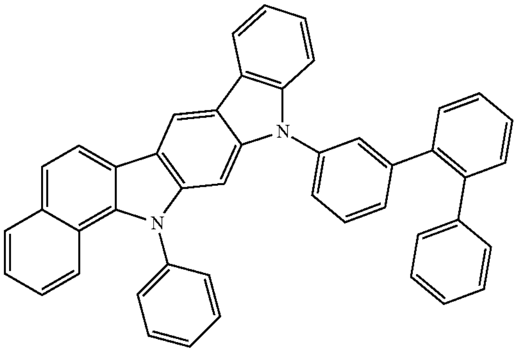
C1-44
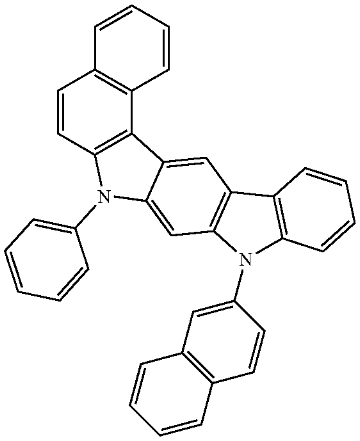
C1-15
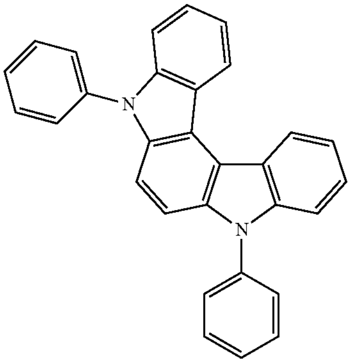
C1-134
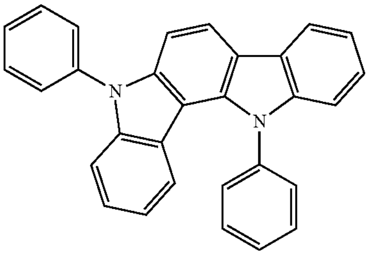
C1-138

TABLE 3-continued
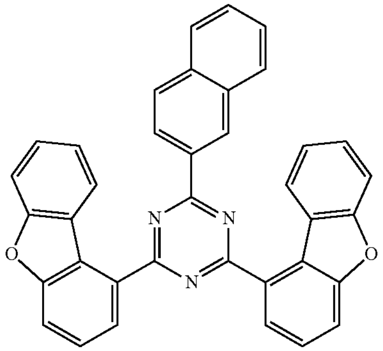
C2-90
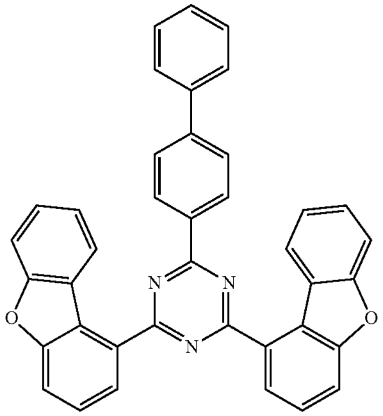
C2-91
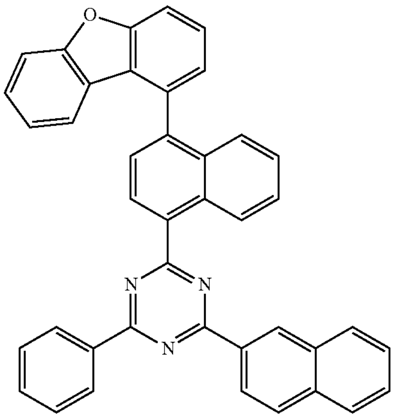
C2-114

TABLE 3-continued
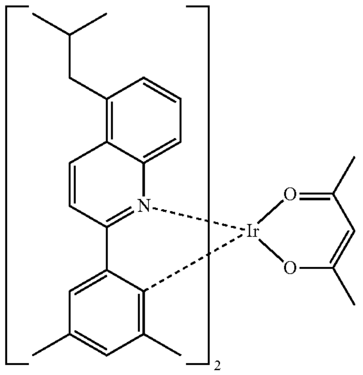
D-39
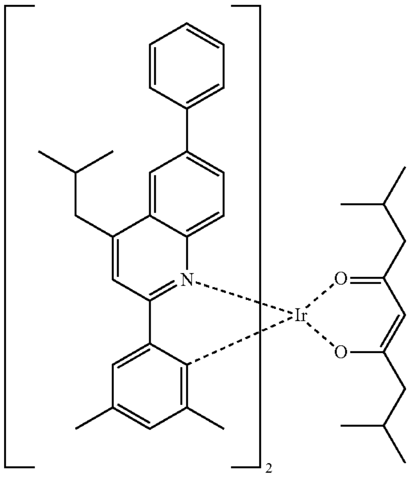
D-78
Electron Transport Layer/ Electron Injection Layer
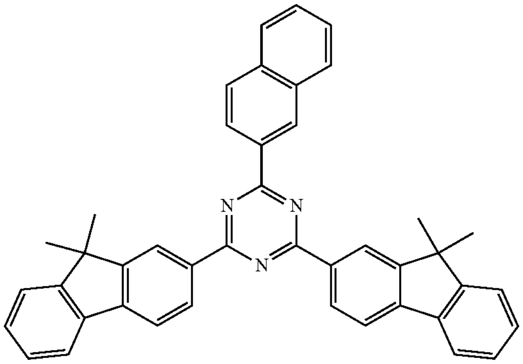
ET-1
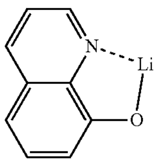
EI-1

[Device Examples 6 and 7] Producing OLEDs Comprising the Compound According to the Present Disclosure OLEDs comprising the organic electroluminescent compound according to the present disclosure were produced. First, a transparent electrode indium tin oxide (ITO) thin film (10 Ω/sq) on a glass substrate for an OLED (GEOMATEC CO., LTD., Japan) was subjected to an ultrasonic washing with trichloroethylene, acetone, ethanol and distilled water, sequentially, and then was stored in isopropanol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus, and was evaporated by applying an electric current to the cell, thereby forming a second hole injection layer having a thickness of 5 nm on the first hole injection layer. Compound HT-1 was then introduced into another cell of the vacuum vapor deposition apparatus, and was evaporated by applying an electric current to the cell, thereby forming a first hole transport layer having a thickness of 10 nm on the second hole injection layer. Compound HT-2 was then introduced into another cell of the vacuum vapor deposition apparatus, and was evaporated by applying an electric current to the cell, thereby forming a second hole transport layer having a thickness of 60 nm on the first hole transport layer. After forming the hole injection layers and the hole transport layers, a light-emitting layer was formed thereon as follows: The compound of the following Table 4 as a host was introduced into one cell of the vacuum vapor deposition apparatus and compound D-39 was introduced into another cell as a dopant. The host and dopant materials were evaporated at a different rate, thereby the dopant was doped in a doping amount of 3 wt % with respect to the total amount of the host and the dopant, to form a light-emitting layer having a thickness of 40 nm on the hole transport layer. Next, compounds ET-1 and EI-1 were introduced into another cell, were evaporated at a rate of 1:1, and were deposited to form an electron transport layer having a thickness of 35 nm on the light-emitting layer. Next, compound EI-1 as an electron injection layer having a thickness of 2 nm was deposited on the electron transport layer, and an Al cathode having a thickness of 80 nm was deposited on the electron injection layer by another vacuum vapor deposition apparatus. Thus, OLEDs were produced.

[Comparative Examples 4 to 6] Producing OLEDs Comprising the Conventional Compounds as a Host OLEDs were produced in the same manner as in the Device Examples, except that the compound of the following Table 4 was used as a host, respectively.

The results of the time taken to reduce from 100% to 97% of light intensity and from 100% to 80% of light intensity at a luminance of 5,000 nits (lifespan; T97 and T80), of the OLEDs of Device Examples 6 and 7 and Comparative Examples 4 to 6 produced as described above, are shown in the following Table 4.

TABLE 4

| | Host | T97 (hr) | T80 (hr) |
|---|---|---|---|
| Device Example 6 | C2-115 | 28 | 296 |
| Device Example 7 | C2-114 | 7 | 243 |
| Comparative Example 4 | C2-121 | 5.5 | 56 |
| Comparative Example 5 | C2-113 | 5.5 | 142 |
| Comparative Example 6 | C2-120 | 5.9 | 108 |

From Table 4 above, by comprising the compound according to the present disclosure as a host material, it is possible to provide an organic electroluminescent device having a remarkably improved lifespan.

The compounds used in Device Examples 6 and 7 and Comparative Examples 4 to 6 are shown in Table 5 below.

TABLE 5

| | |
|---|---|
| Hole Injection Layer/ Hole Transport Layer | 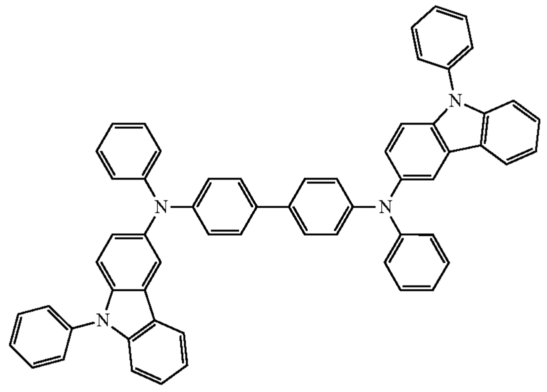 HI-1 |

TABLE 5-continued
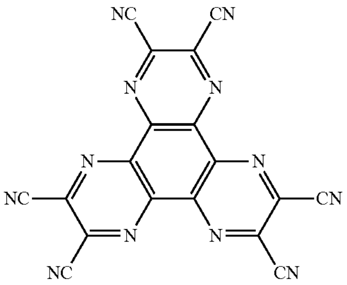
HI-2
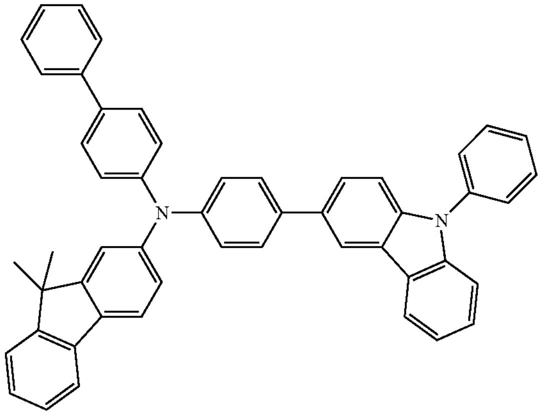
HT-1
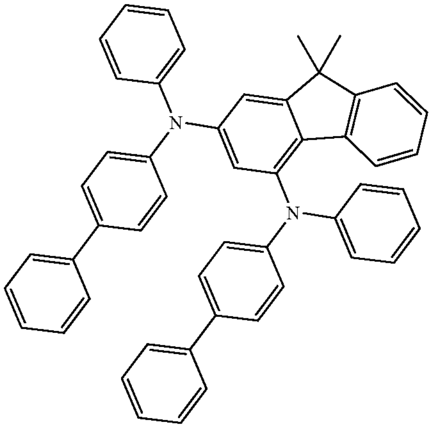
HT-2

TABLE 5-continued
Light-Emitting Layer
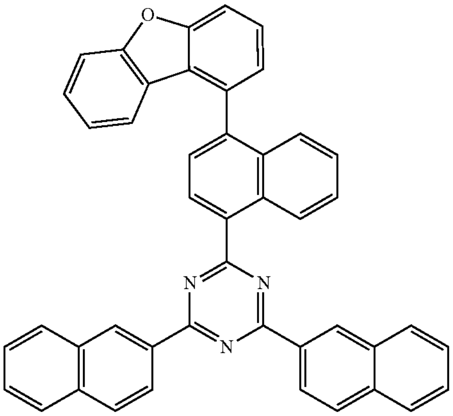
C2-115
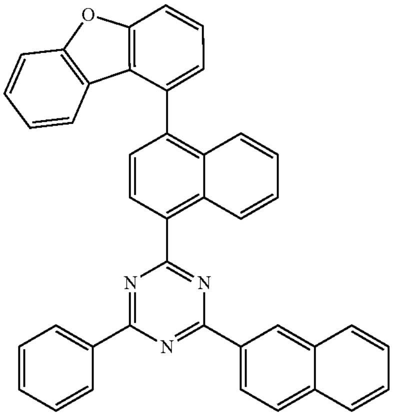
C2-114
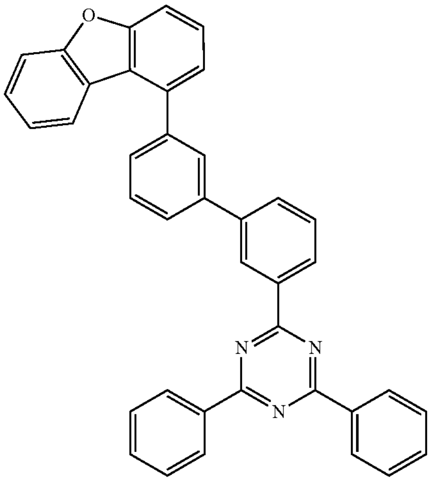
C2-121

TABLE 5-continued
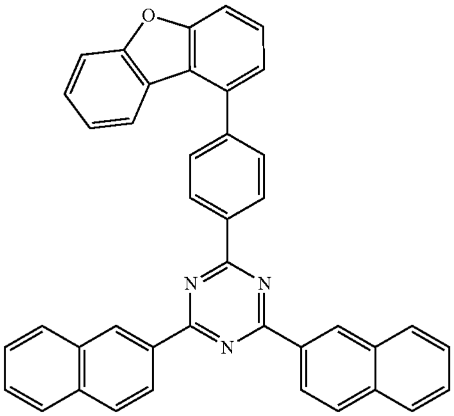
C2-113
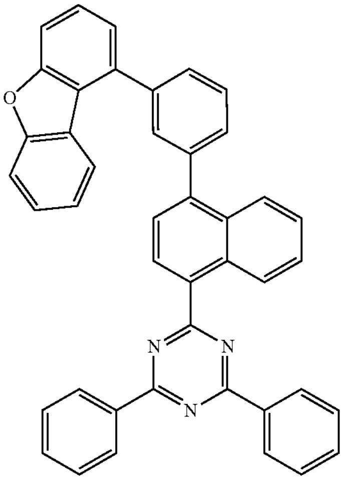
C2-120
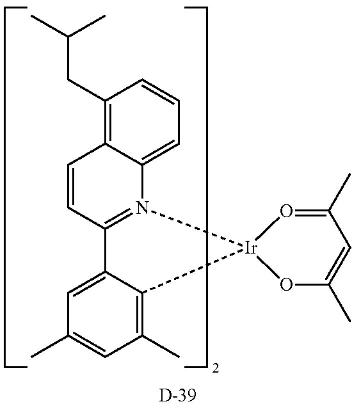
D-39

TABLE 5-continued

| | |
|---|---|
| Electron Transport Layer/ Electron Injection Layer | 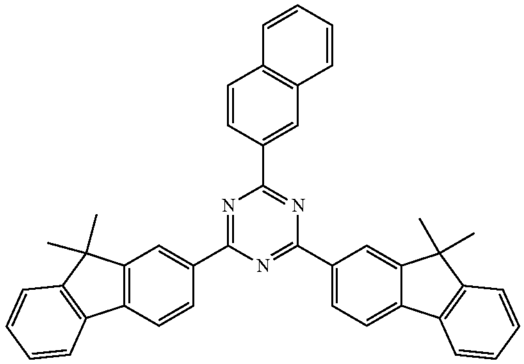 ET-1 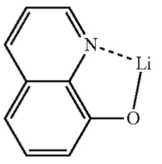 EI-1 |

The invention claimed is:

1. A plurality of host materials comprising a first host material comprising the compound represented by the following formula 1-1 or 1-4 and a second host material comprising the compound represented by the following formula 2:

(1-1)

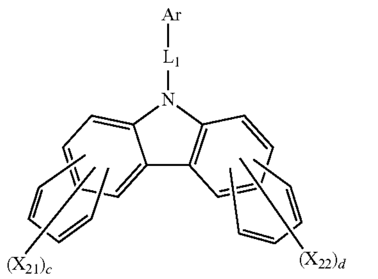

(1-4)

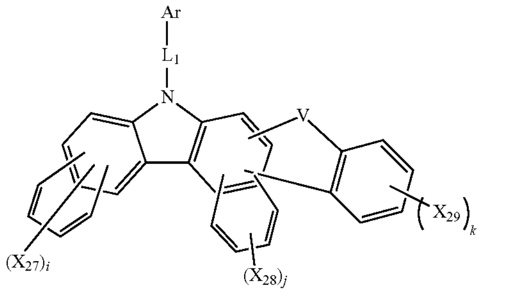

wherein,

Ar represents a substituted or unsubstituted (C6-C30)aryl, or a substituted or unsubstituted (3- to 30-membered) heteroaryl containing at least one of N, O, and S, or —$NX_9X_{10}$;

$L_1$ represents a single bond, a substituted or unsubstituted (C6-C30)arylene, or a substituted or unsubstituted (3- to 30-membered) heteroarylene;

$X_9$ and $X_{10}$ each independently represent a substituted or unsubstituted (C1-C30)alkyl, a substituted or unsubstituted (C3-C30)cycloalkyl, a substituted or unsubstituted (C6-C30)aryl, or a substituted or unsubstituted (3- to 30-membered) heteroaryl; and V each independently represents $CX_{18}X_{19}$, $NX_{20}$, O, or S;

$X_{20}$ represents a deuterium-substituted or unsubstituted (C6-C30)aryl, or a substituted or unsubstituted (3- to 30-membered) heteroaryl;

$X_{18}$, $X_{19}$, $X_{21}$, $X_{22}$, and $X_{27}$ to $X_{29}$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; and c, d and i each independently represent an integer of 1 to 6, j and k each independently represent an integer of 1 to 4, when c, d, i, j and k are 2 or more, each of $X_{21}$, each of $X_{22}$, each of $X_{27}$, each of $X_{28}$, and each of $X_{29}$ may be the same or different:

(2)

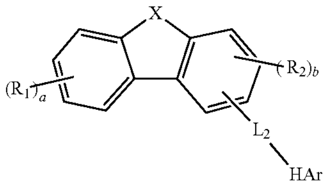

wherein,

X represents —O—;

HAr represents a substituted or unsubstituted (3- to 30-membered) heteroaryl containing at least one nitrogen atom;

$L_2$ represents a single bond, a substituted or unsubstituted (C6-C30)arylene, or a substituted or unsubstituted (3- to 30-membered)heteroarylene;

$R_1$ and $R_2$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to adjacent substituents to form a ring; and a represents an integer of 1 to 4, b represents an integer of 1 to 3, when a and b are 2 or more, each of $R_1$ and each of $R_2$ may be the same or different.

2. The plurality of host materials according to claim 1, wherein the substituents of the substituted alkyl, the substituted cycloalkyl, the substituted aryl, the substituted arylene, the substituted heteroaryl, the substituted heteroarylene, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, or the substituted alkylarylamino, each independently are at least one selected from the group consisting of deuterium; halogen; cyano; carboxyl; nitro; hydroxyl; (C1-C30)alkyl; halo(C1-C30)alkyl; (C2-C30)alkenyl; (C2-C30)alkynyl; (C1-C30) alkoxy; (C1-C30)alkylthio; (C3-C30)cycloalkyl; (C3-C30) cycloalkenyl; (3- to 7-membered) heterocycloalkyl; (C6-C30)aryloxy; (C6-C30)arylthio; at least one of (C1-C30) alkyl-, (C6-C30)aryl- and di(C6-C30)arylamino-substituted or unsubstituted (3- to 50-membered) heteroaryl; at least one of cyano-, (C1-C30)alkyl-, (3- to 50-membered) heteroaryl-, di(C6-C30)arylamino- and tri(C6-C30)arylsilyl-substituted or unsubstituted (C6-C30)aryl; tri(C1-C30)alkylsilyl; tri (C6-C30)arylsilyl; di(C1-C30)alkyl(C6-C30)arylsilyl; (C1-C30)alkyldi(C6-C30)arylsilyl; amino; mono- or di-(C1-C30)alkylamino; mono- or di-(C6-C30)arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl (C6-C30)arylboronyl; (C6-C30)ar(C1-C30)alkyl; and (C1-C30)alkyl(C6-C30)aryl.

3. The plurality of host materials according to claim 1, wherein Ar is a substituted or unsubstituted phenyl, a substituted or unsubstituted naphthyl, a substituted or unsubstituted biphenyl, a substituted or unsubstituted terphenyl, a substituted or unsubstituted spirobifluorenyl, a substituted or unsubstituted pyridyl, a substituted or unsubstituted triazinyl, a substituted or unsubstituted pyrimidinyl, a substituted or unsubstituted quinolyl, a substituted or unsubstituted quinazolinyl, a substituted or unsubstituted quinoxalinyl, a substituted or unsubstituted benzoquinazolinyl, a substituted or unsubstituted benzoquinoxalinyl, a substituted or unsubstituted benzofuropyrimidinyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted fluorenyl, a substituted or unsubstituted benzofluorenyl, a substituted or unsubstituted triphenylenyl, a substituted or unsubstituted benzonaphthofuranyl, or a substituted or unsubstituted benzonaphthothiophenyl.

4. The plurality of host materials according to claim 1, wherein the formula 2 is represented by at least one of the following formulae 2-1 and 2-2:

(2-1)

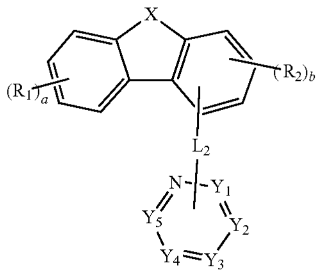

(2-2)

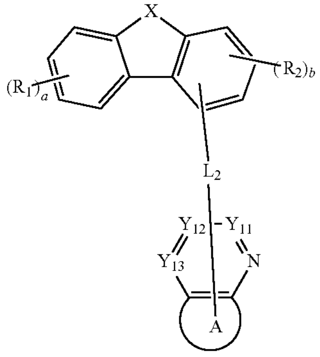

wherein,

X, $R_1$, $R_2$, $L_2$, a, and b are as defined in claim 1;

A ring represents a substituted or unsubstituted (6- to 10-membered) ring;

$Y_1$ to $Y_5$, and $Y_{11}$ to $Y_{13}$ each independently represent N or $CR_3$; and $R_3$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30)alkylsilyl, a substituted or unsubstituted di(C1-C30)alkyl (C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or adjacent $R_3$s may be linked to each other to form a ring.

5. The plurality of host materials according to claim 1, wherein HAr is a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzothienopyrimidinyl, a substituted or unsubstituted carbazolyl, or a substituted or unsubstituted pyridopyrazinyl.

6. The plurality of host materials according to claim 1, wherein the compound represented by formula 1-1 or 1-4 is at least one selected from the group consisting of:

C1-100

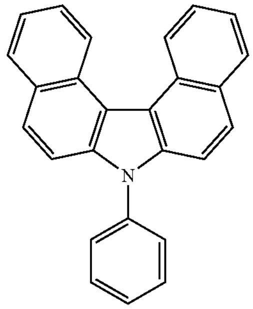

C1-101

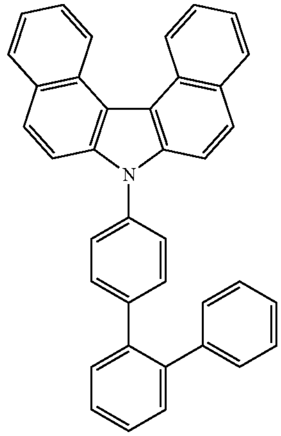

C1-102

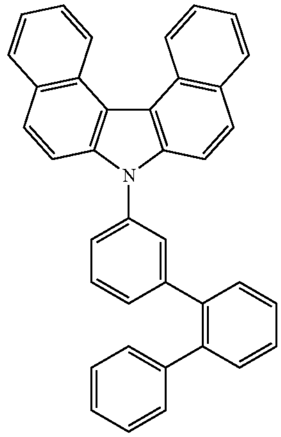

-continued

C1-103

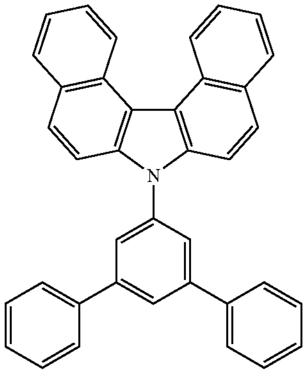

C1-104

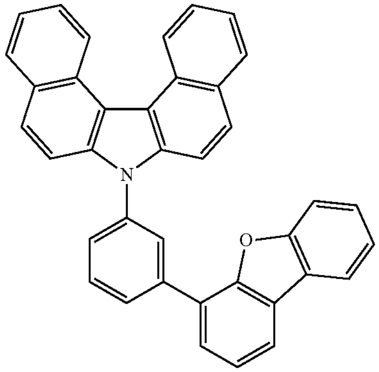

C1-105

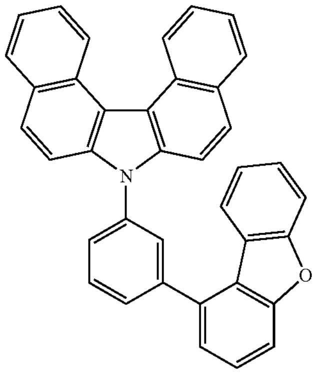

C1-106

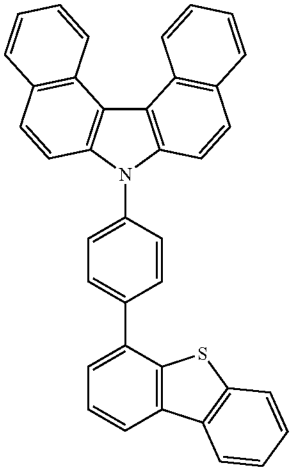

-continued
C1-107
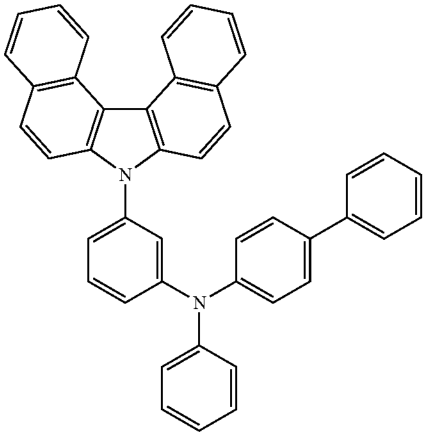
C1-108
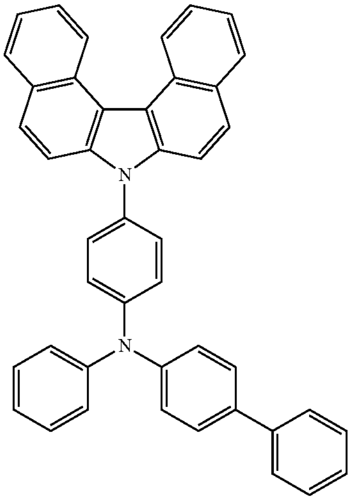
C1-109
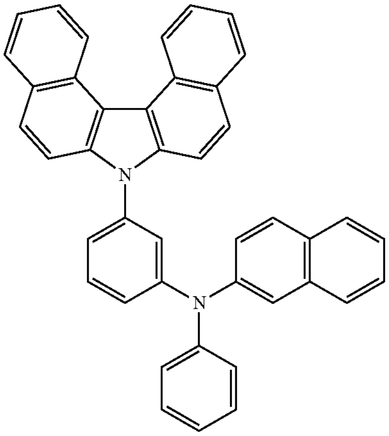
-continued
C1-110
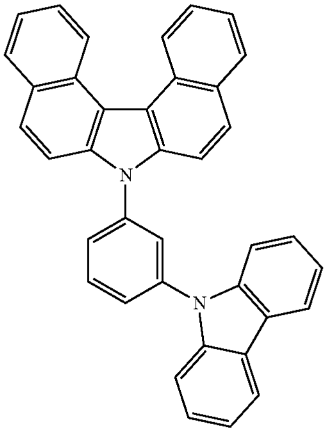
C1-111
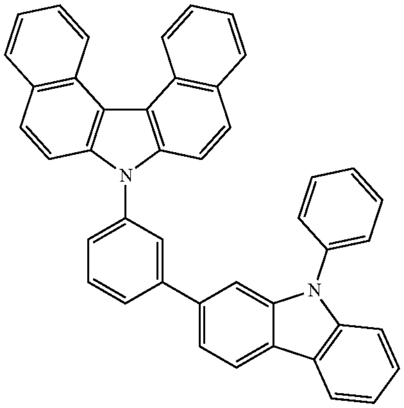
C1-112
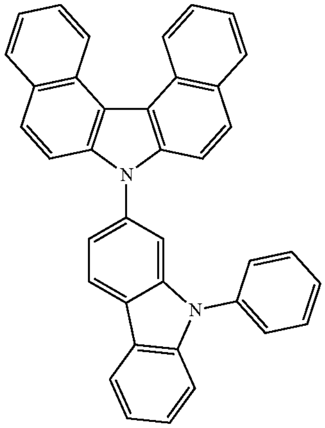

-continued
C1-113
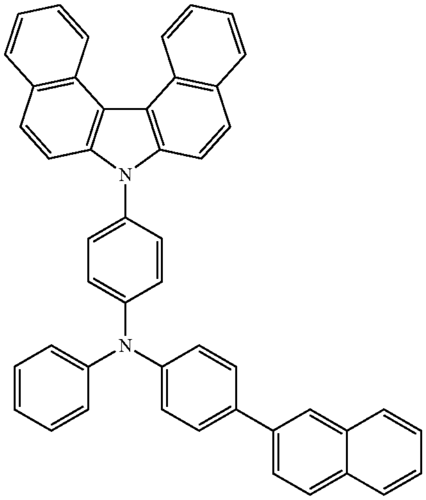
C1-114
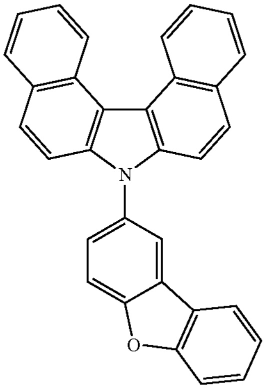
C1-115
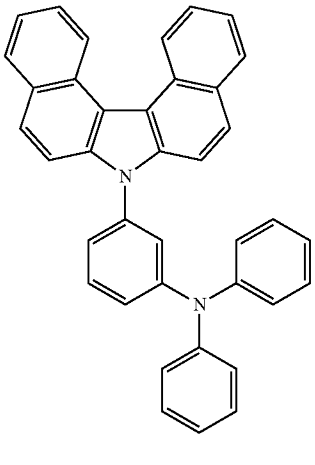
-continued
C1-116
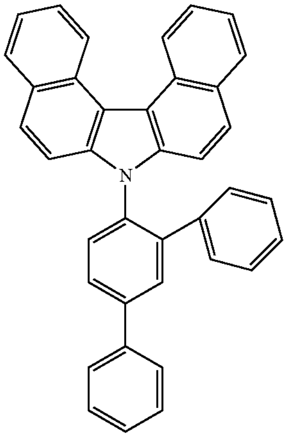
C1-117
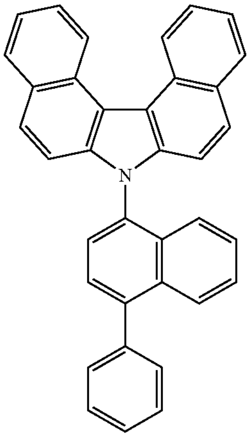
C1-118
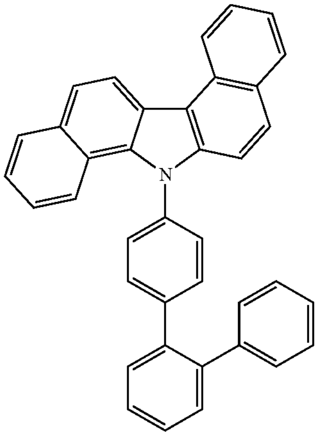
C1-119
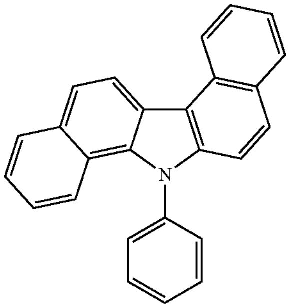

-continued
C1-120
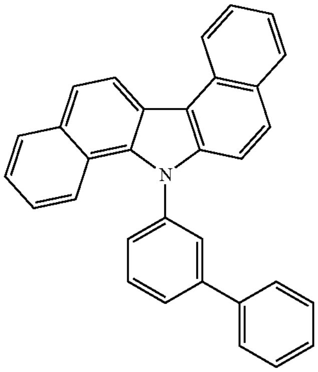
C1-121
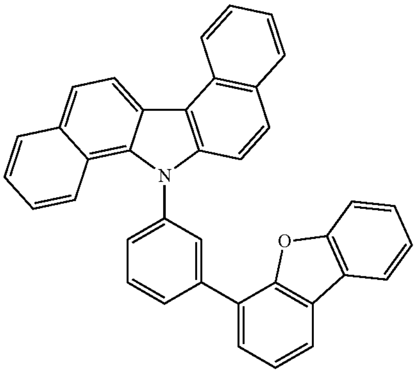
C1-122
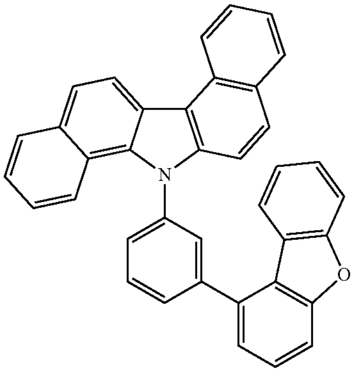
C1-123
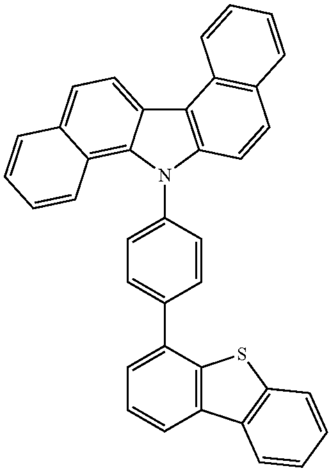
-continued
C1-124
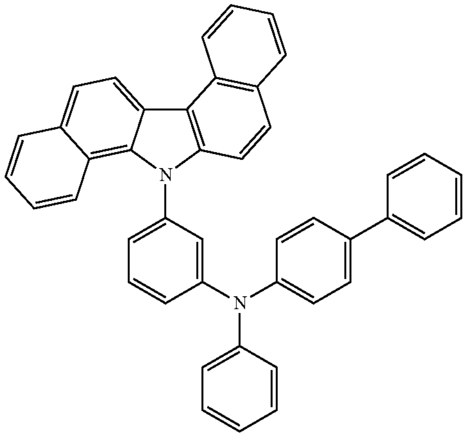
C1-125
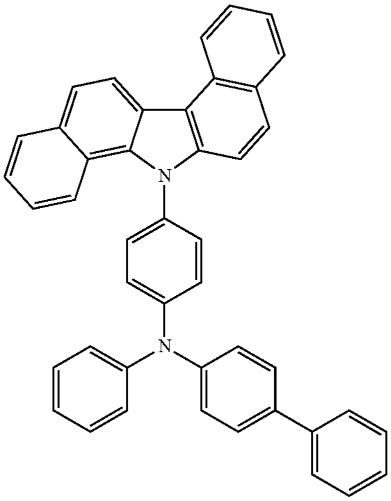
C1-126
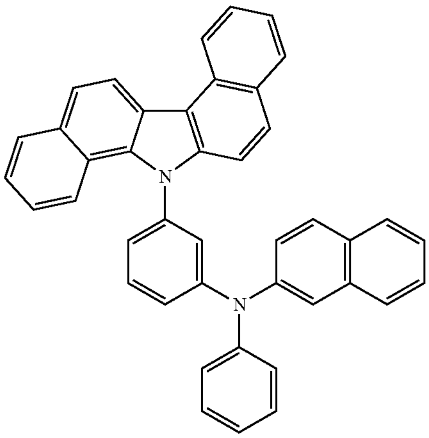

-continued
C1-127
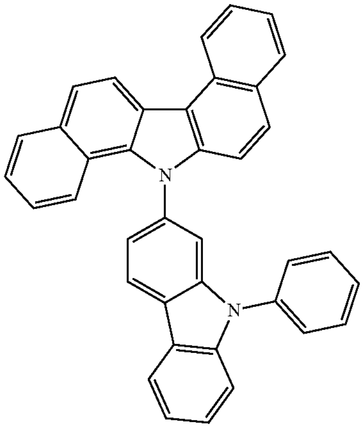
C1-128
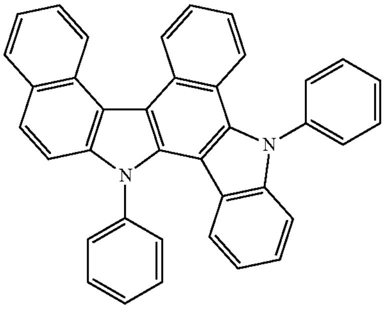
C1-129
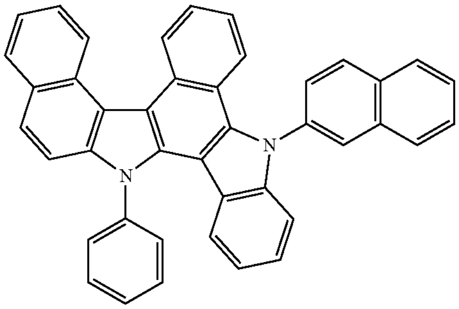
C1-130
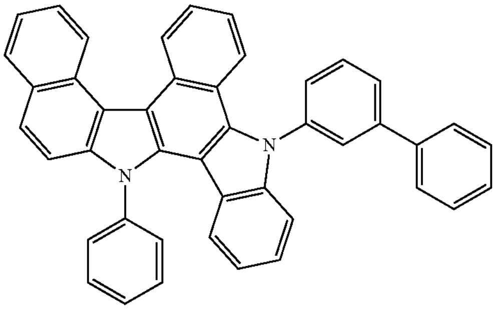
-continued
C1-131
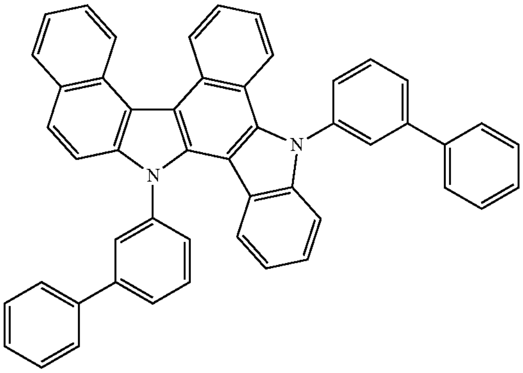
C1-132
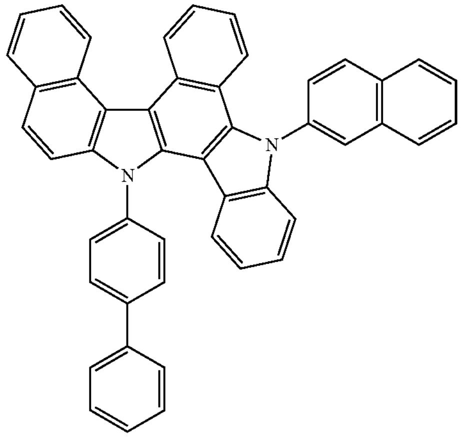
and
C1-133
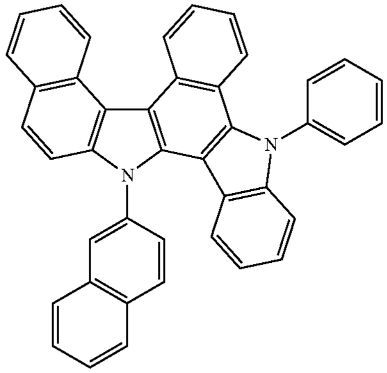
.
7. The plurality of host materials according to claim 1, wherein the compound represented by formula 2 is at least one selected from the group consisting of:

-continued
C2-1
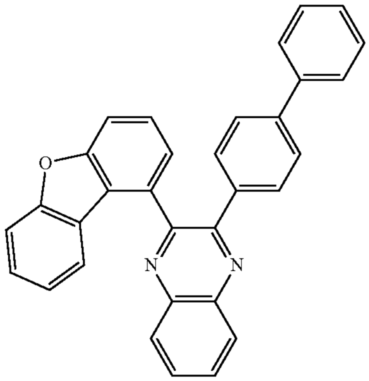
C2-2
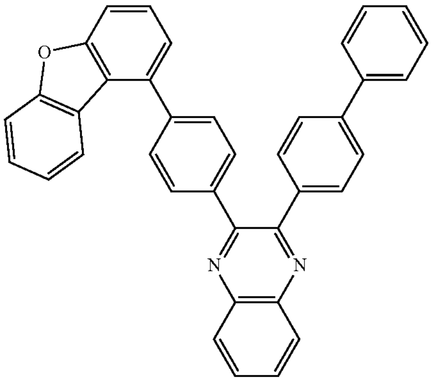
C2-3
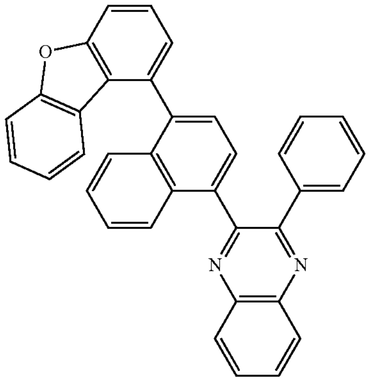
C2-4
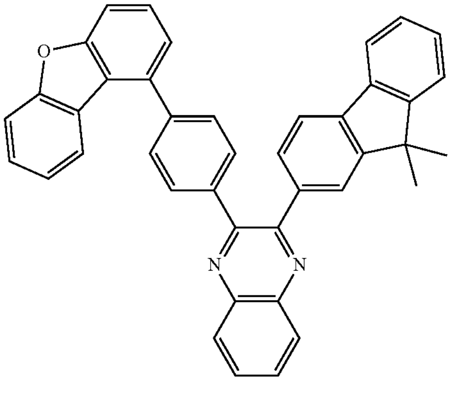
C2-5
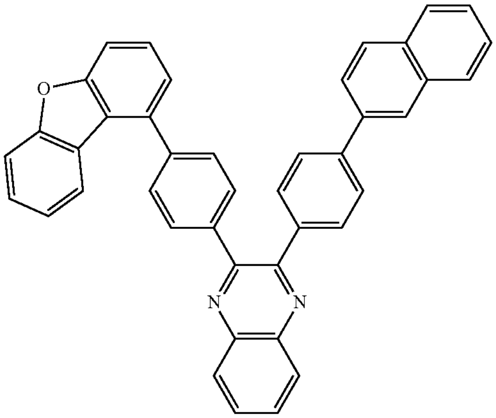
C2-6
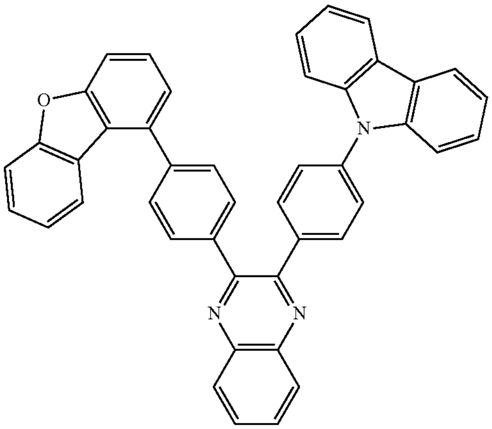
C2-7
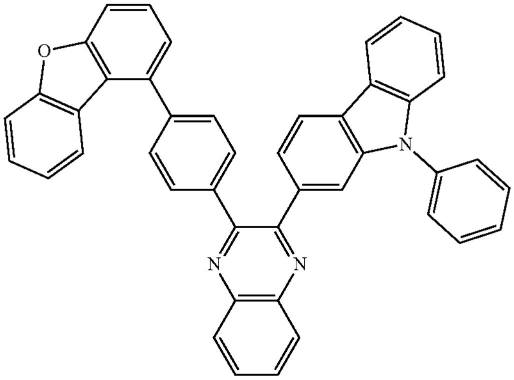

-continued
C2-8
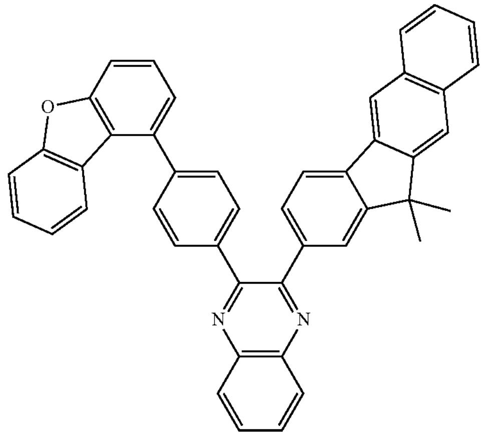
C2-9
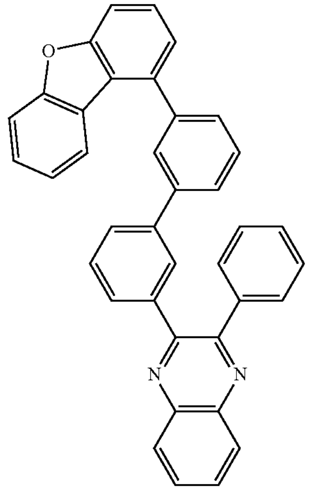
C2-10
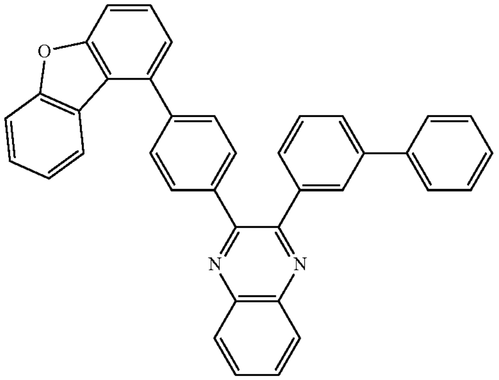
-continued
C2-11
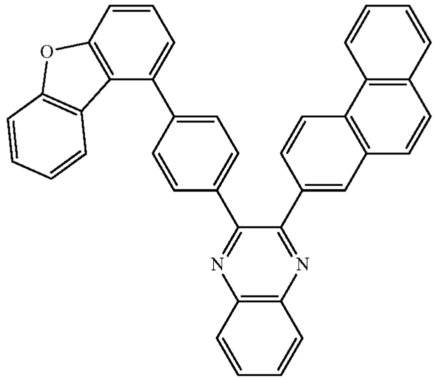
C2-12
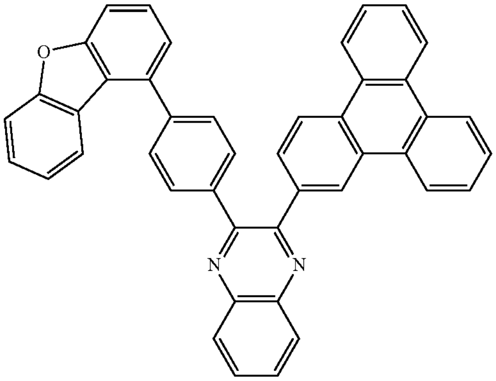
C2-13
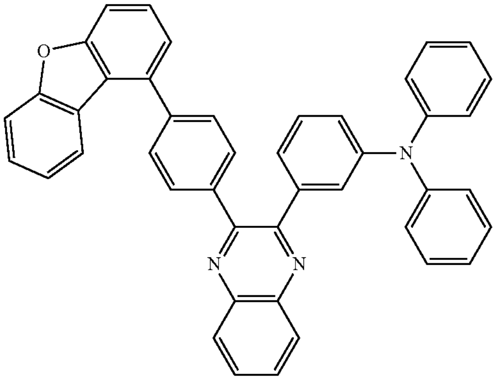
C2-14
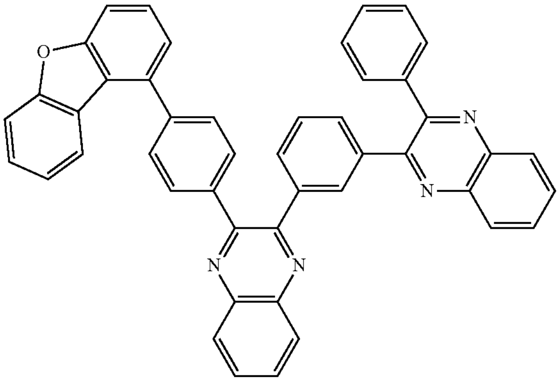

-continued
C2-15
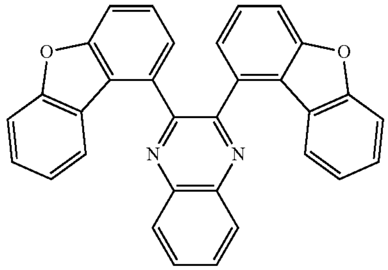
C2-16
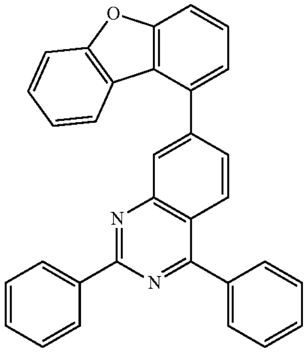
C2-17
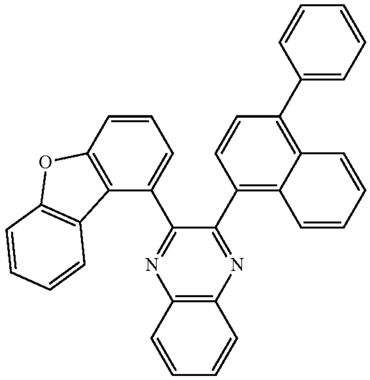
C2-18
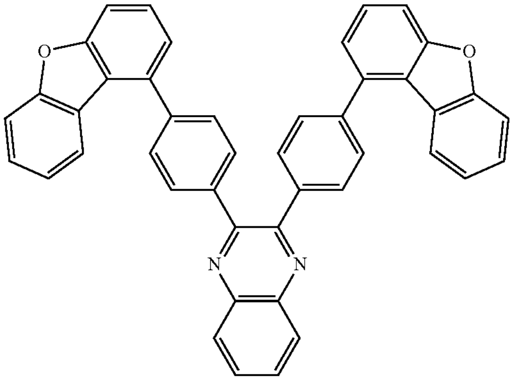
-continued
C2-19
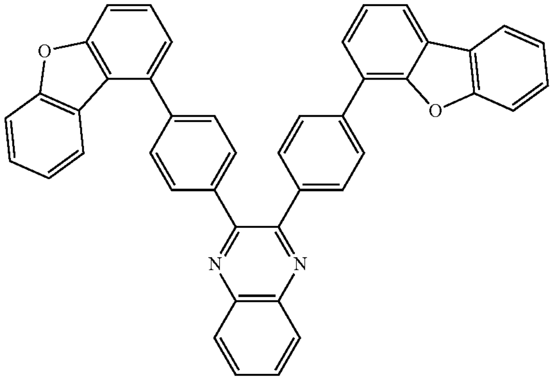
C2-20
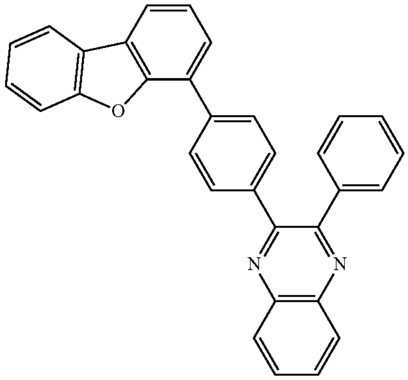
C2-21
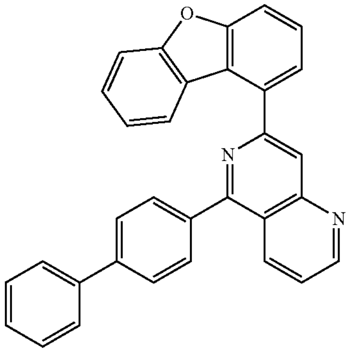
C2-22
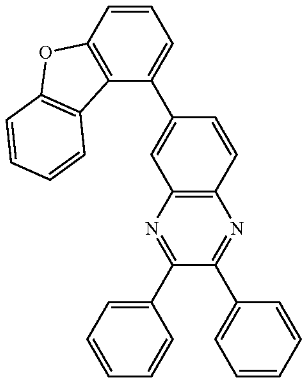

-continued
C2-23
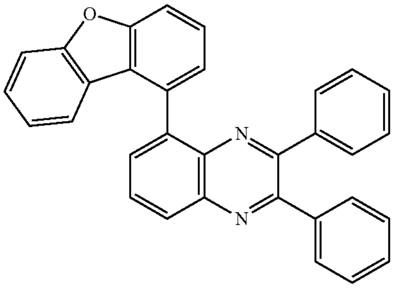
C2-24
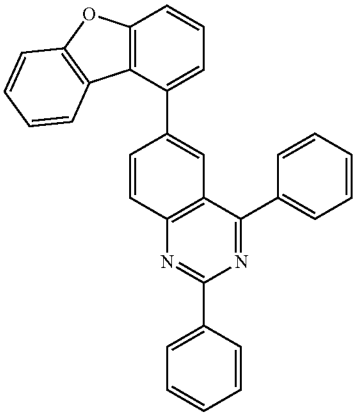
C2-25
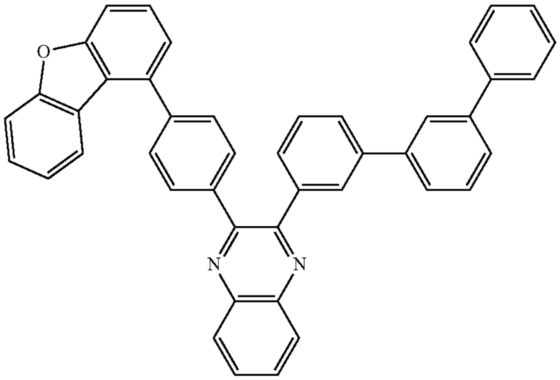
C2-26
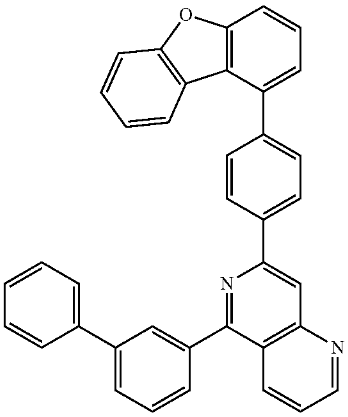
-continued
C2-27
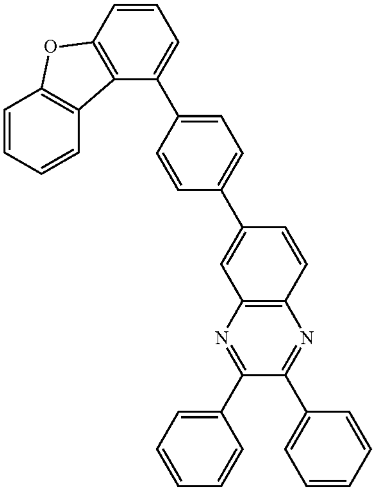
C2-28
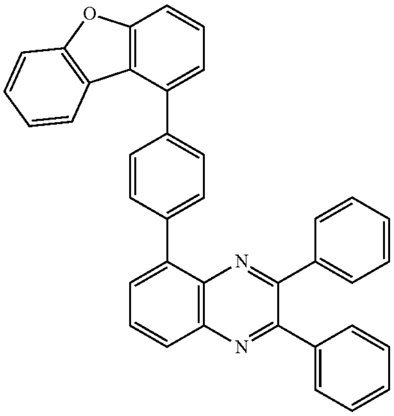
C2-29
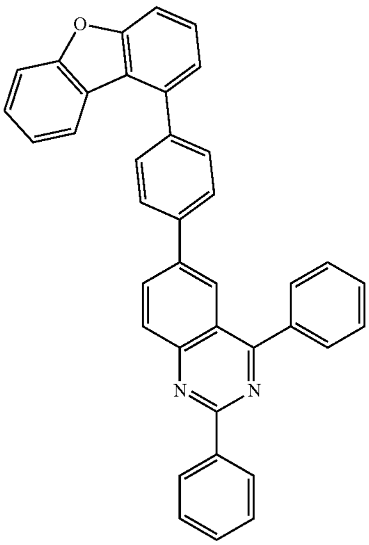

-continued
C2-30
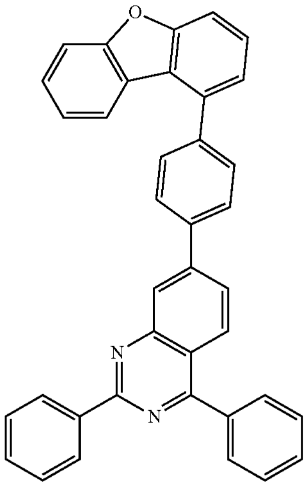
C2-31
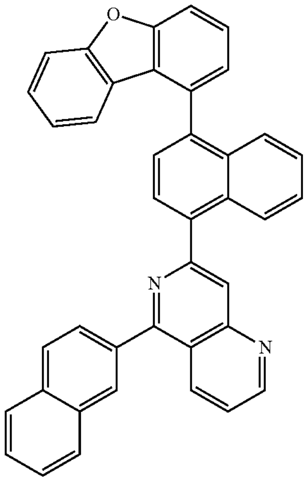
C2-32
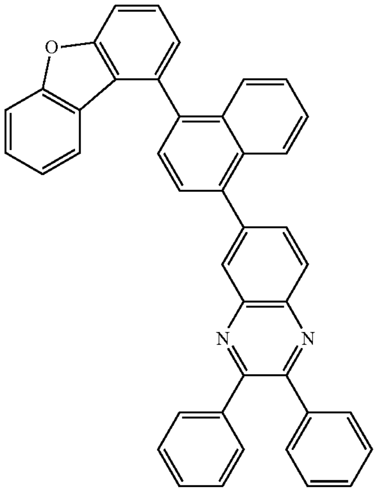
-continued
C2-33
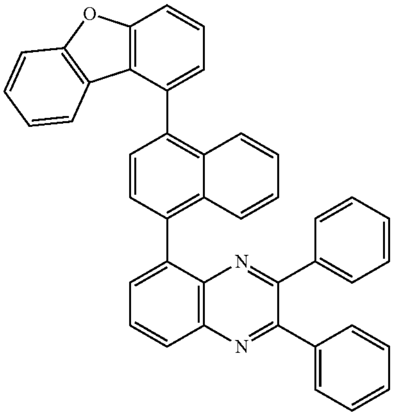
C2-34
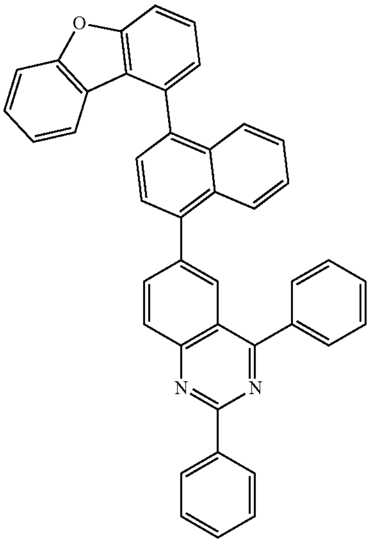
C2-35
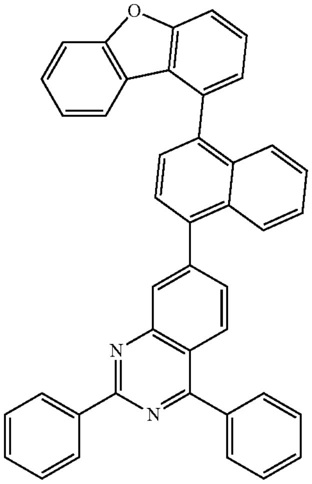

-continued
C2-36
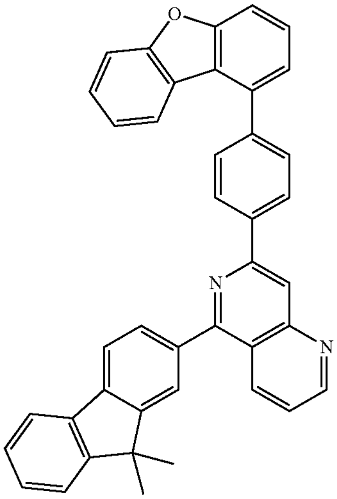
C2-37
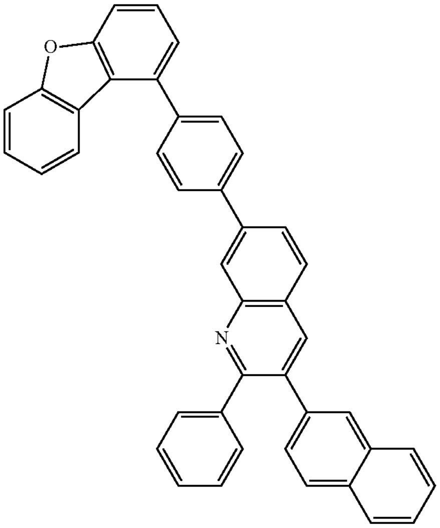
C2-38
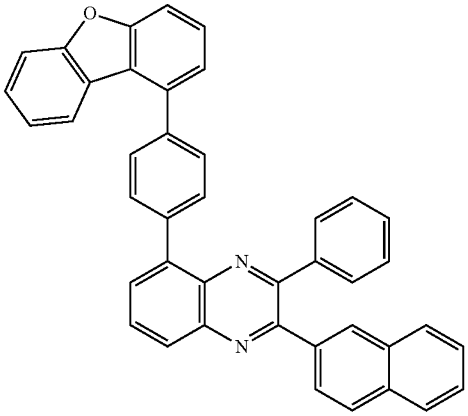
-continued
C2-39
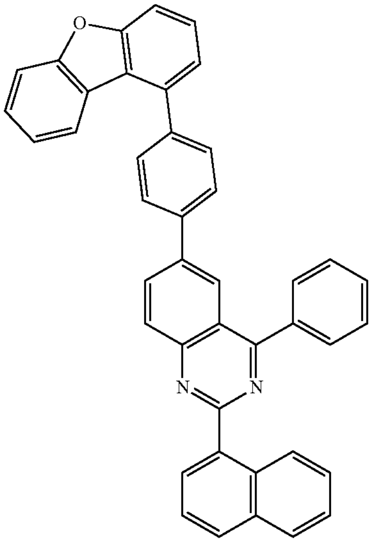
C2-40
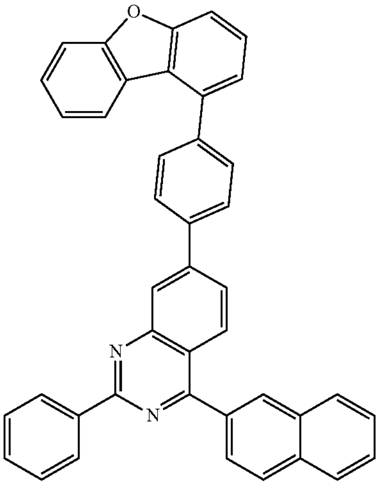
C2-41
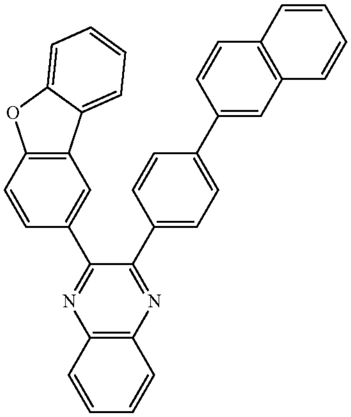

-continued
C2-42
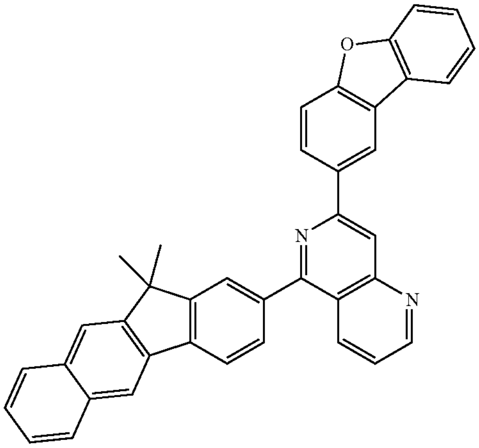
C2-43
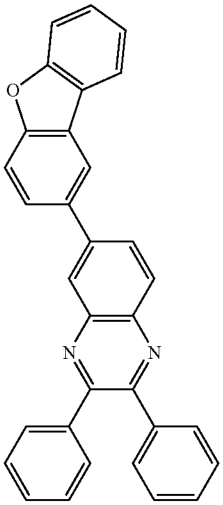
C2-44
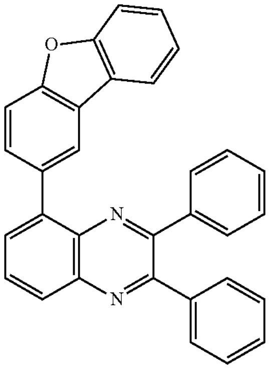
-continued
C2-45
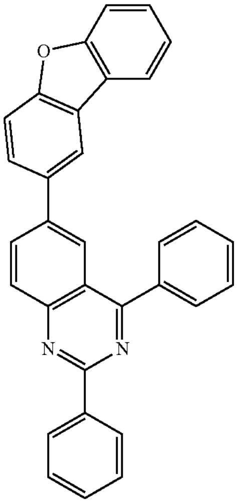
C2-46
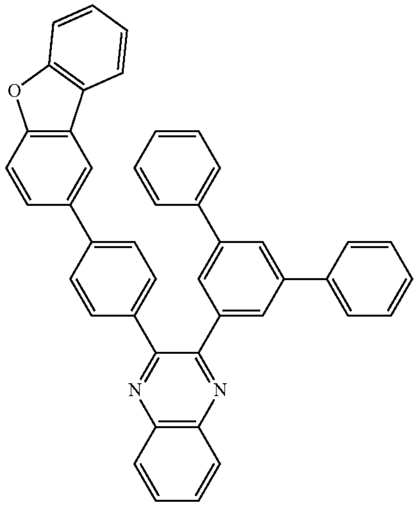
C2-47
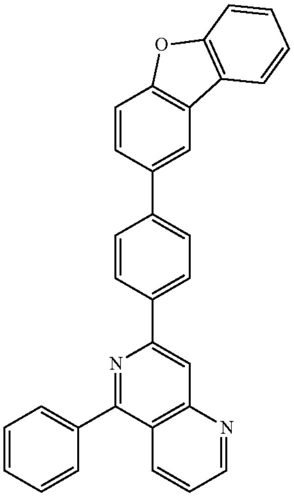

-continued
C2-48
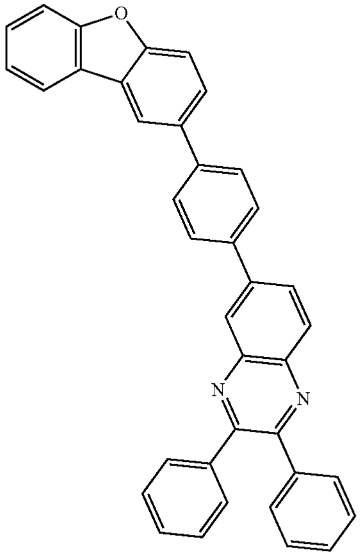
C2-49
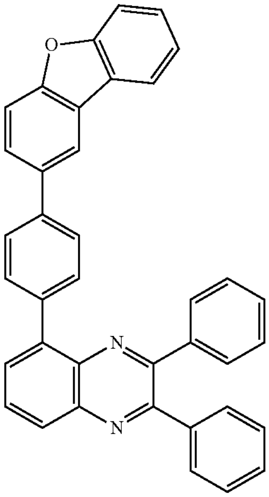
-continued
C2-50
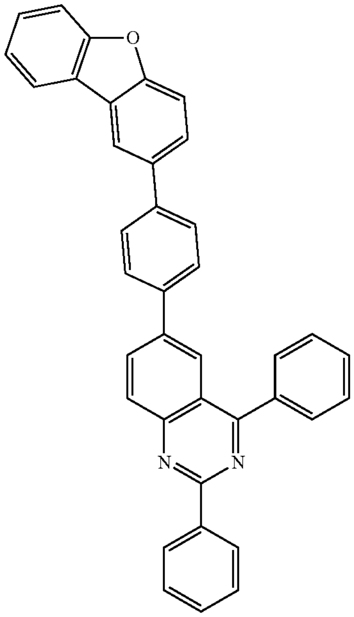
C2-51
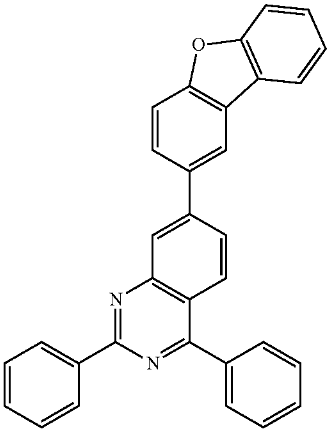
C2-52
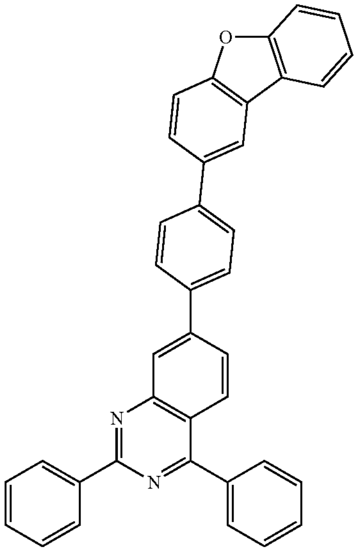

-continued
C2-53
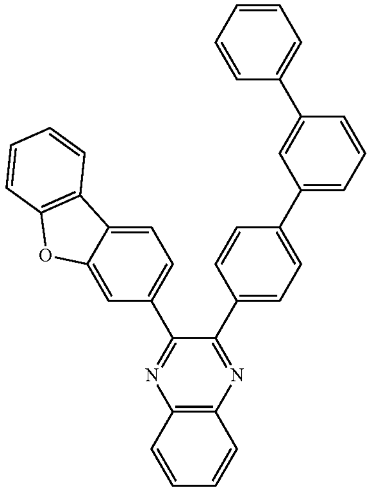
C2-54
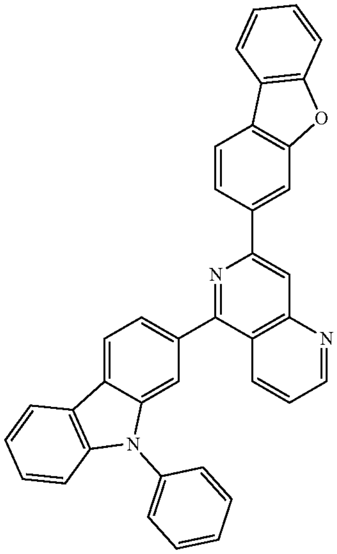
C2-55
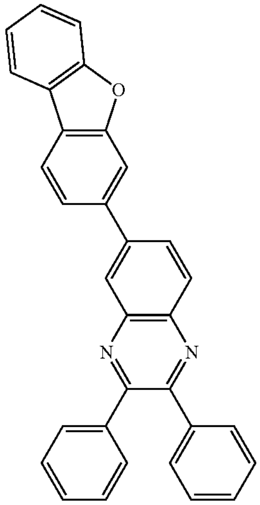
-continued
C2-56
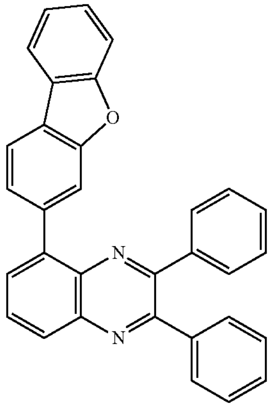
C2-57
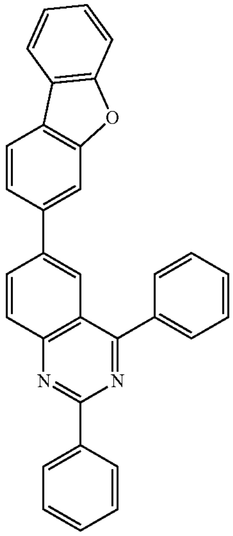
C2-58
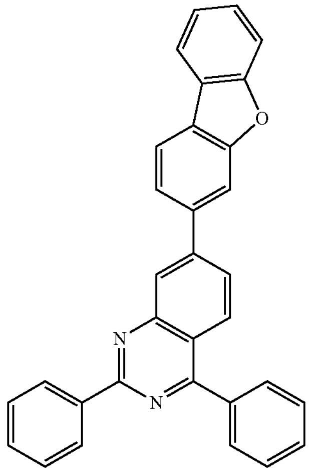

-continued
C2-59
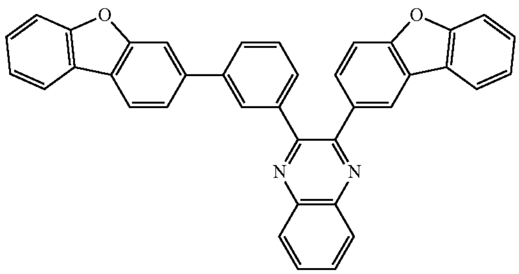
C2-60
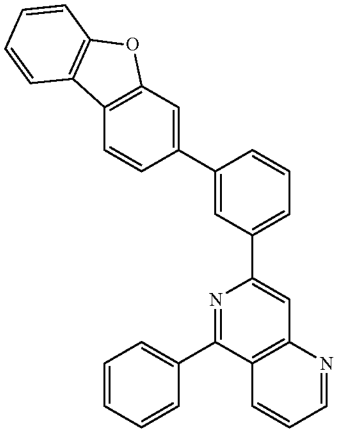
C2-61
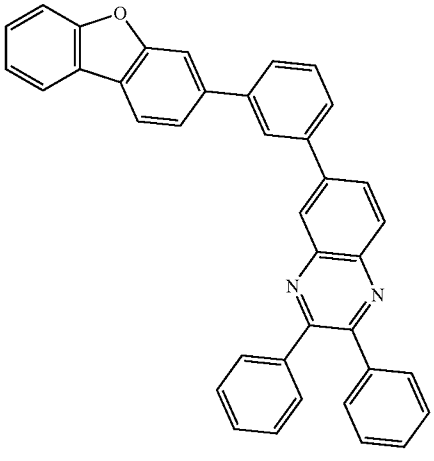
C2-62
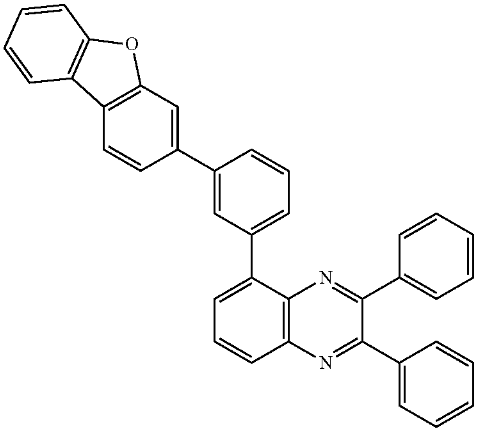
-continued
C2-63
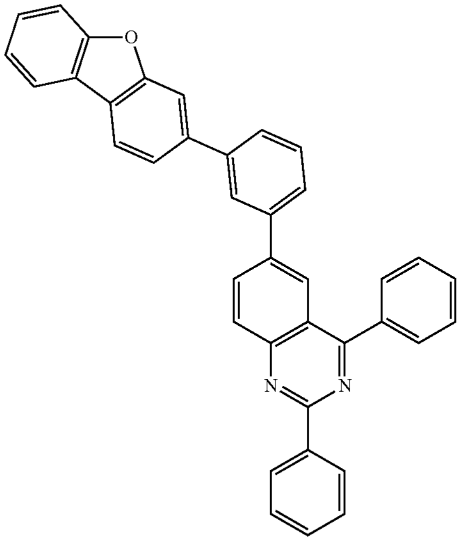
C2-64
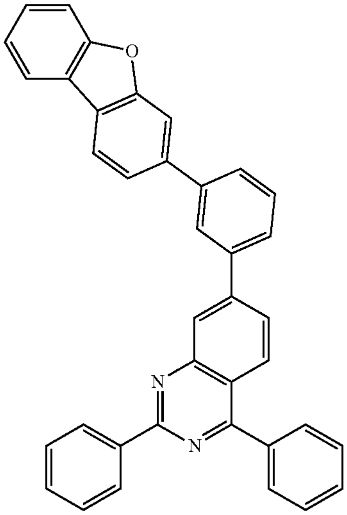
C2-65
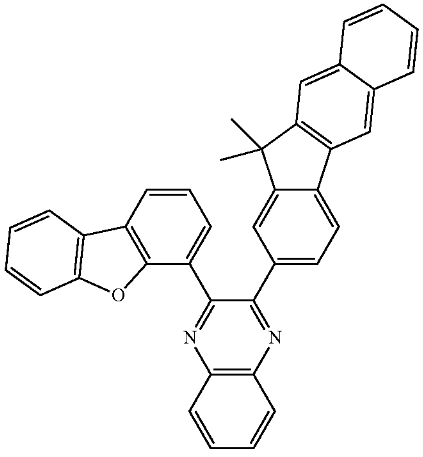

-continued
C2-66
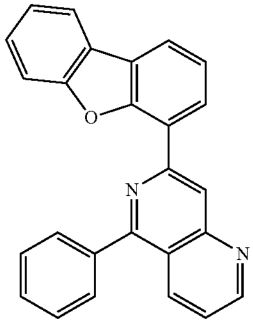
C2-67
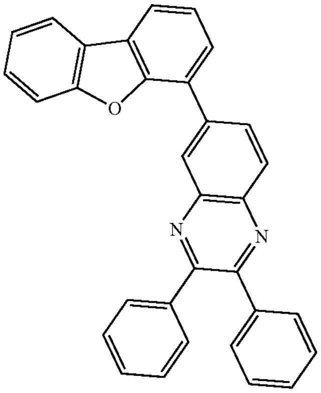
C2-68
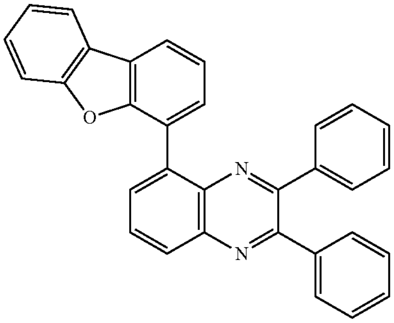
C2-69
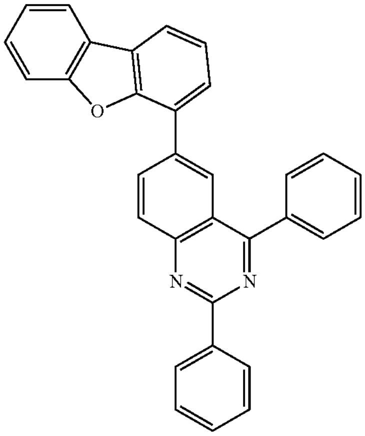
-continued
C2-70
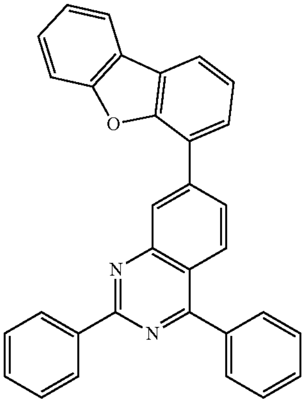
C2-71
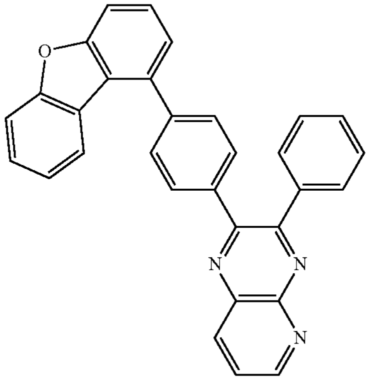
C2-72
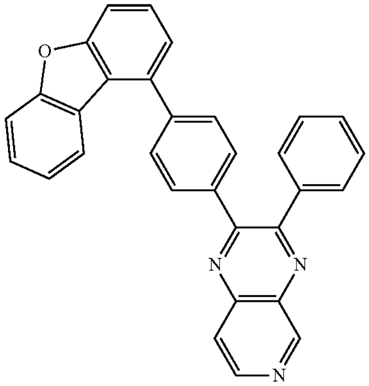
C2-73
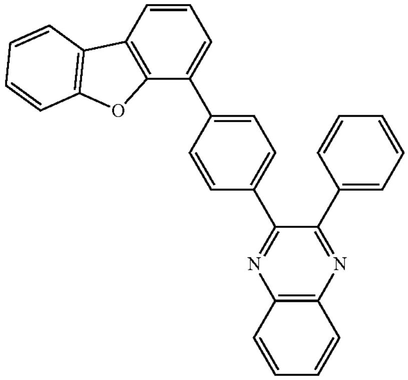

-continued
C2-74
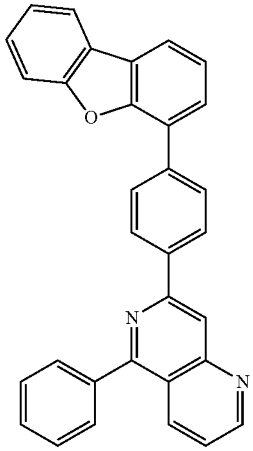
C2-75
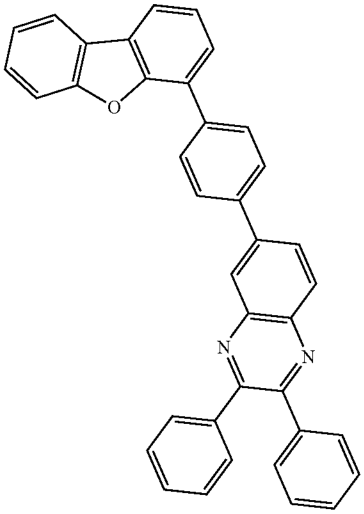
C2-76
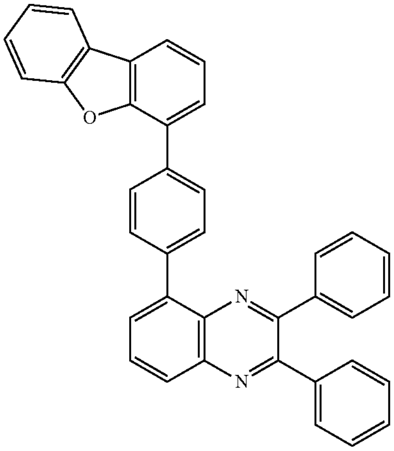
-continued
C2-77
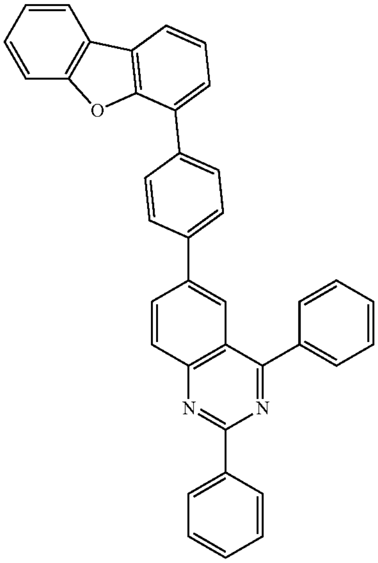
C2-78
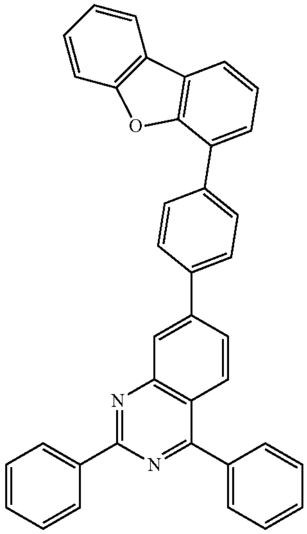
C2-79
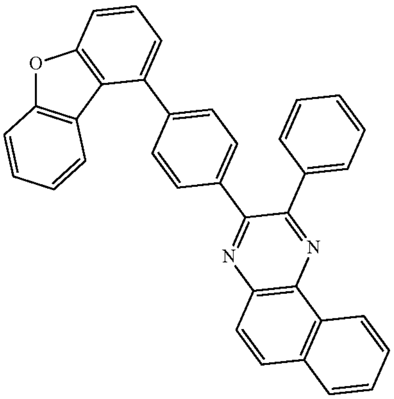

-continued
C2-80
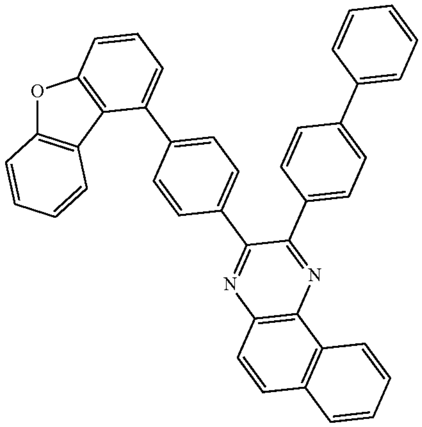
C2-81
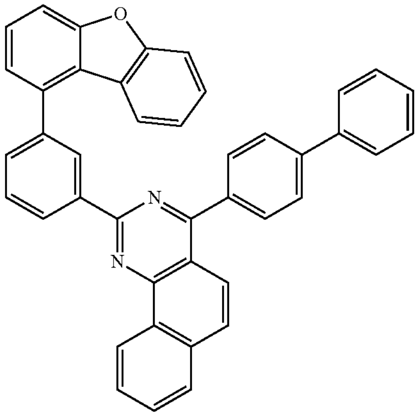
C2-82
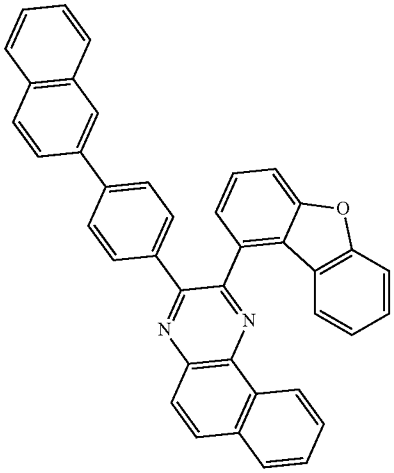
-continued
C2-83
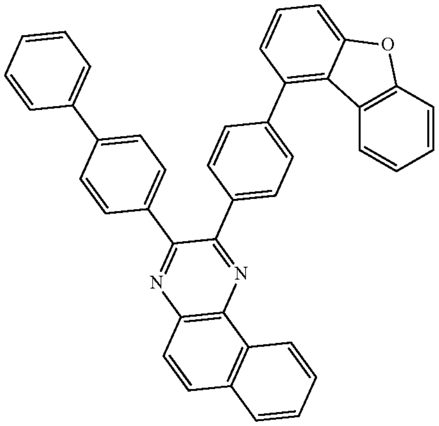
C2-84
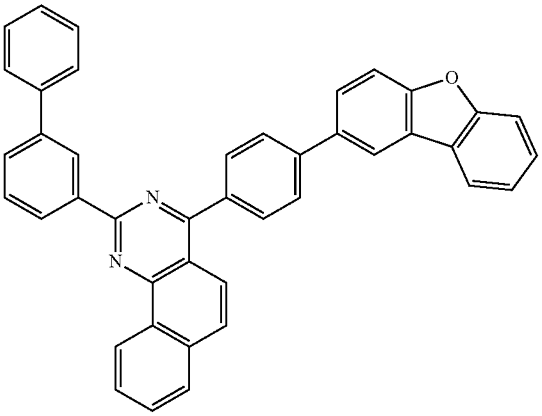
C2-85
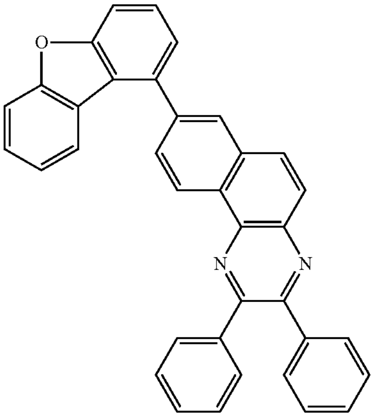

-continued
C2-86
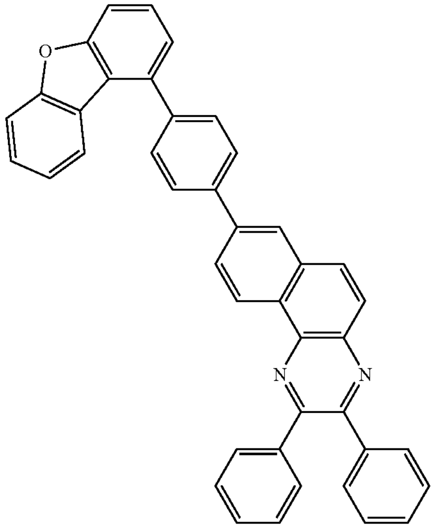
C2-87
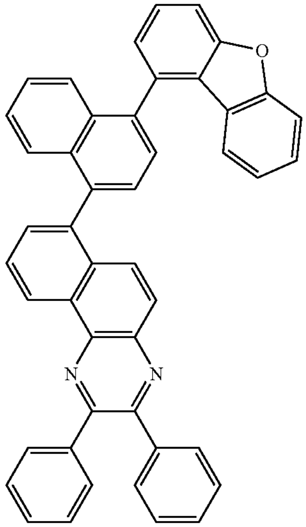
C2-88
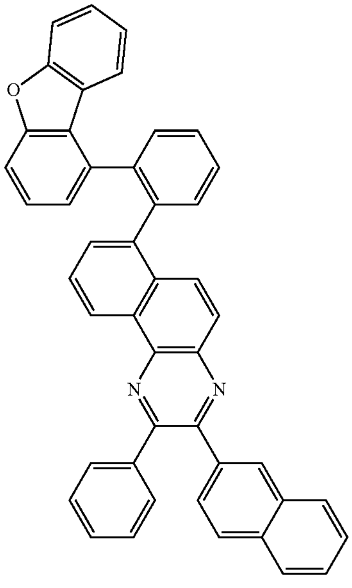
-continued
C2-89
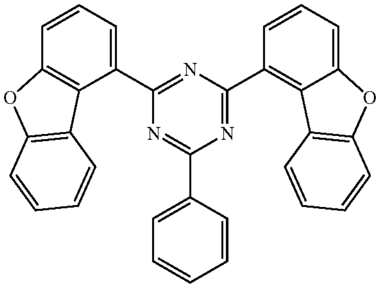
C2-90
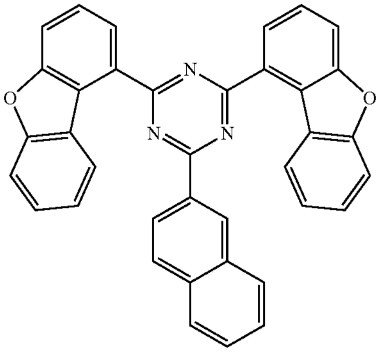
C2-91
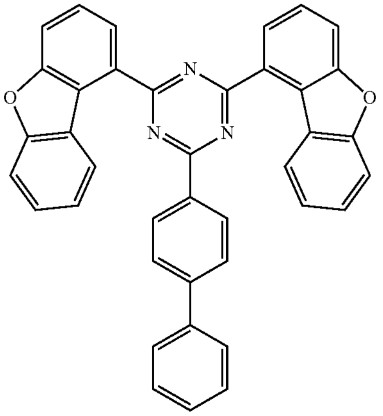
C2-92
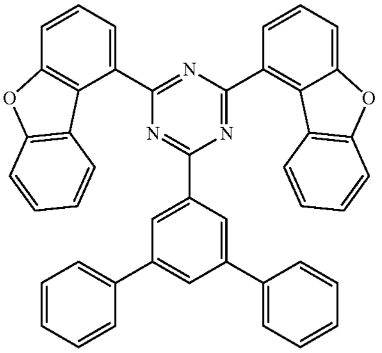

-continued
C2-93
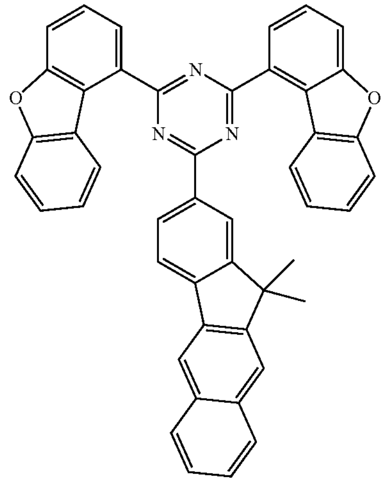
C2-94
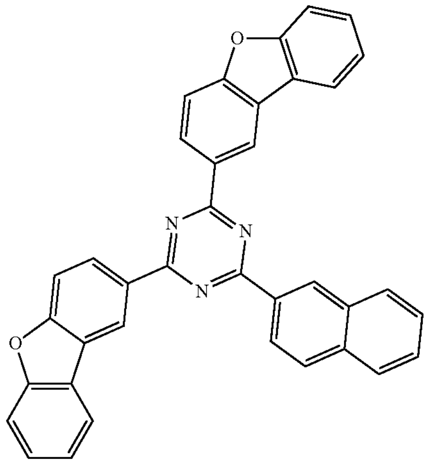
C2-95
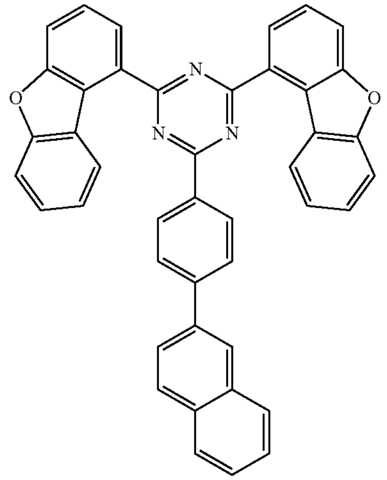
-continued
C2-96
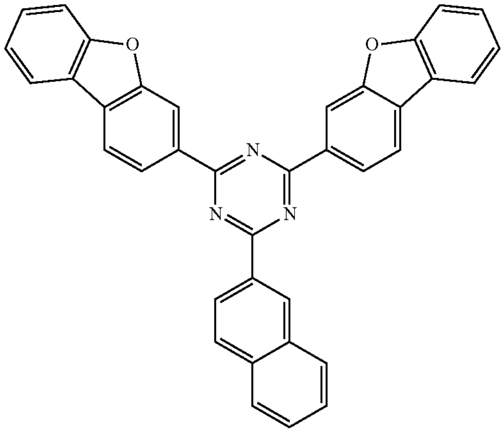
C2-97
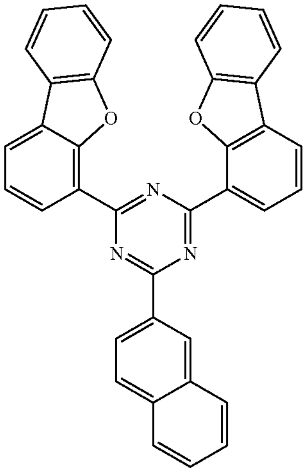
C2-98
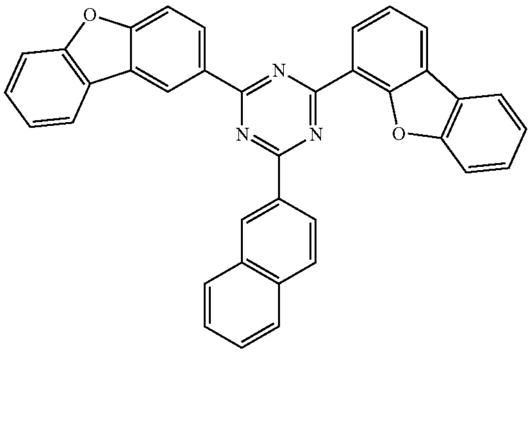

-continued
C2-99
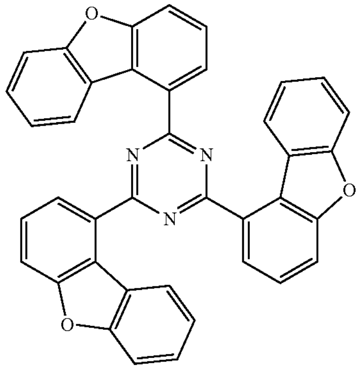
C2-100
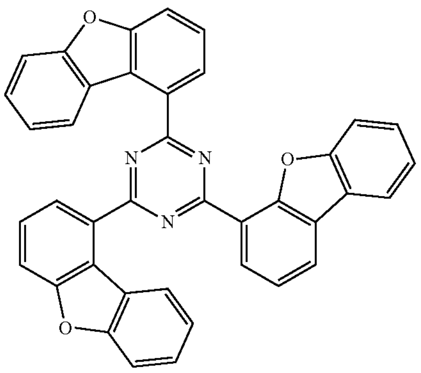
C2-101
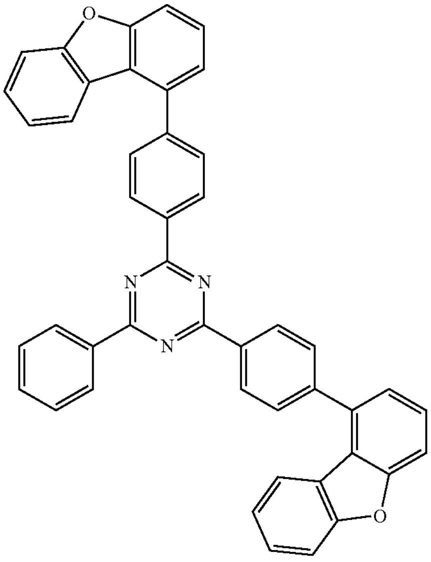
-continued
C2-102
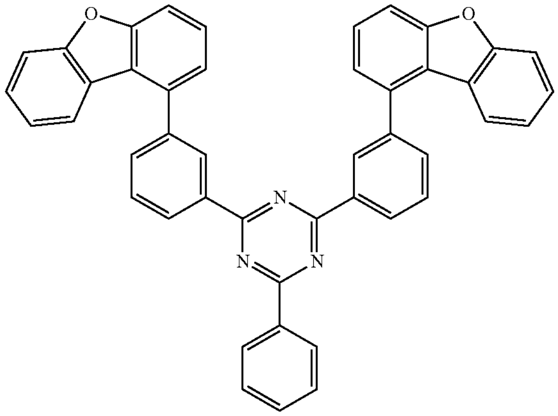
C2-103
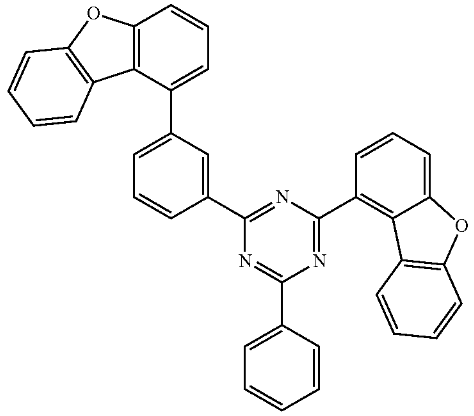
C2-104
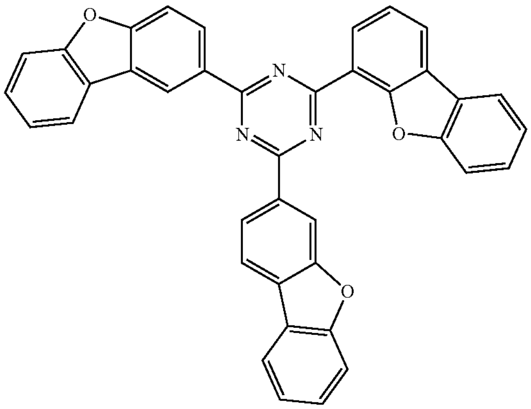

-continued
C2-105
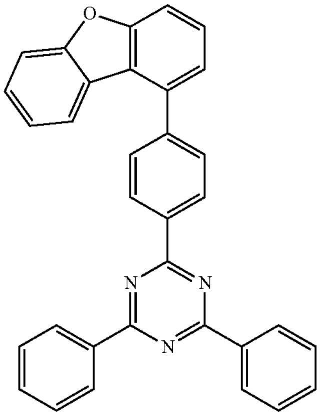
C2-106
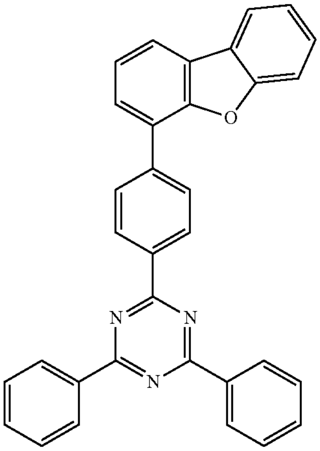
C2-107
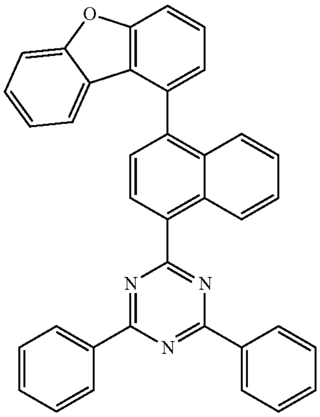
-continued
C2-108
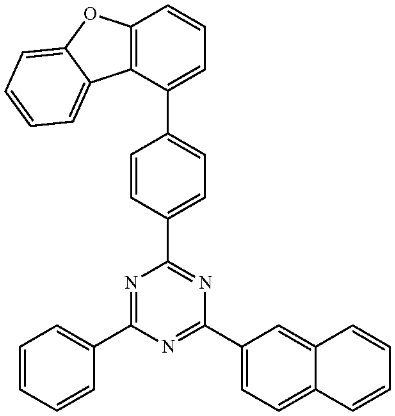
C2-109
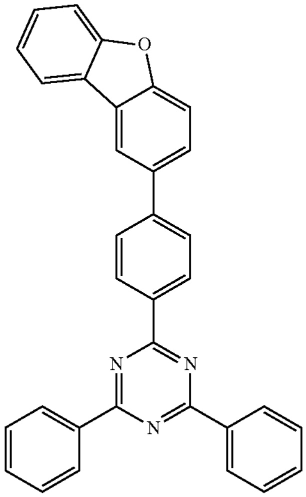
C2-110
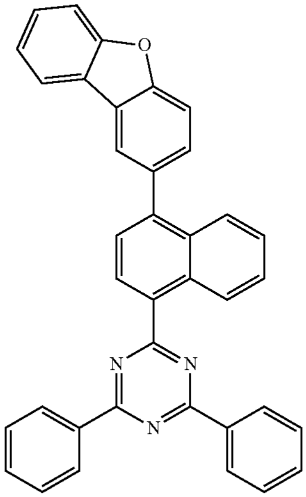

-continued
C2-111
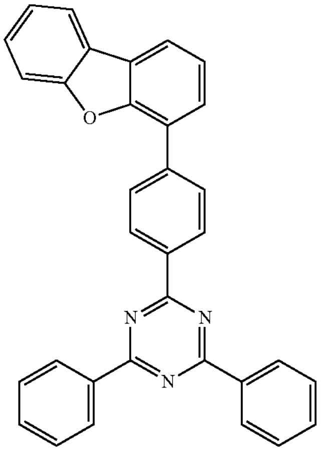
C2-112
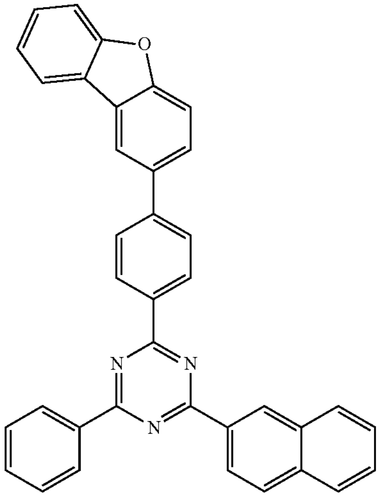
C2-113
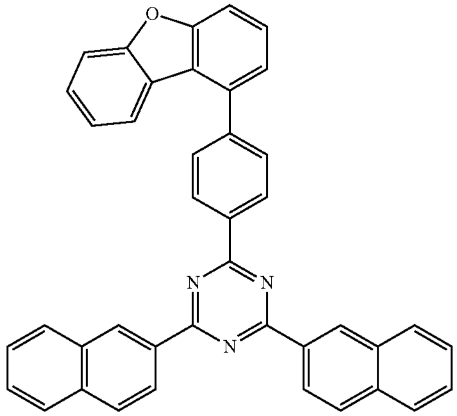
-continued
C2-114
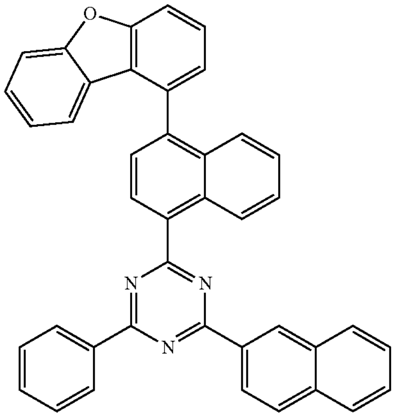
C2-115
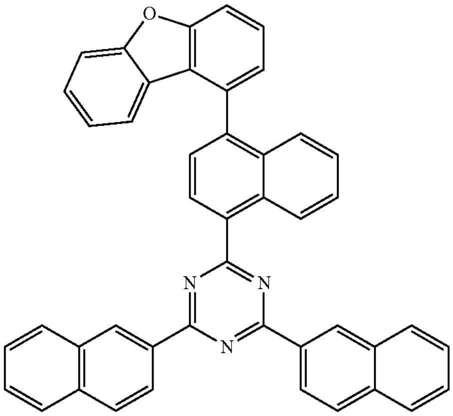
C2-116
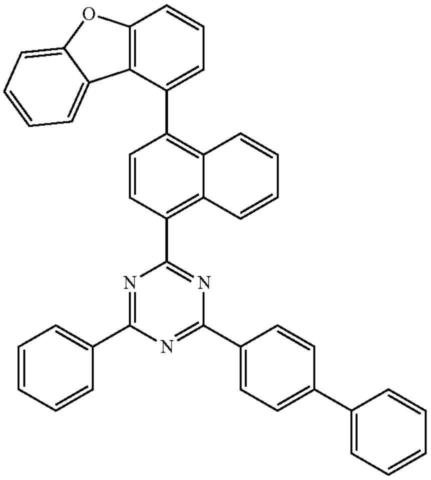

-continued
C2-117
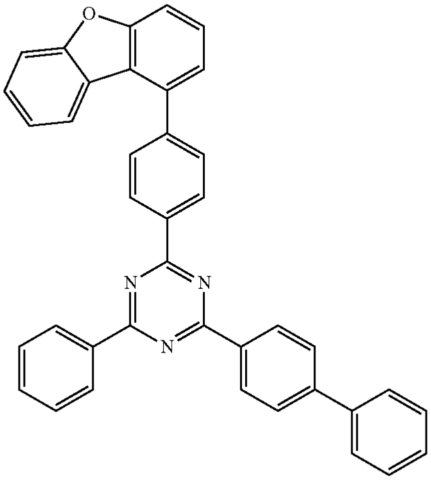
C2-118
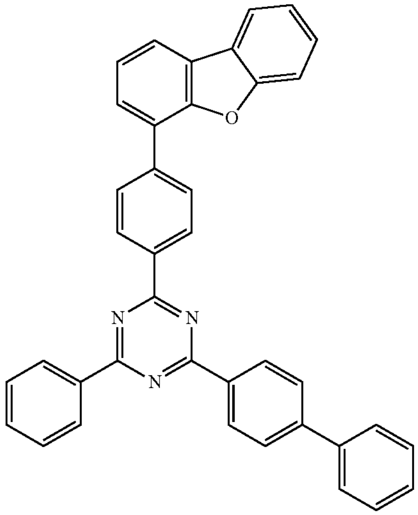
C2-119
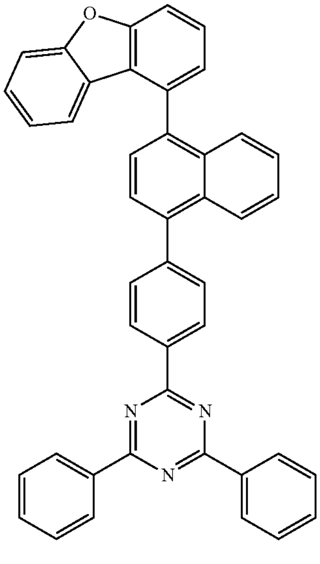
-continued
C2-120
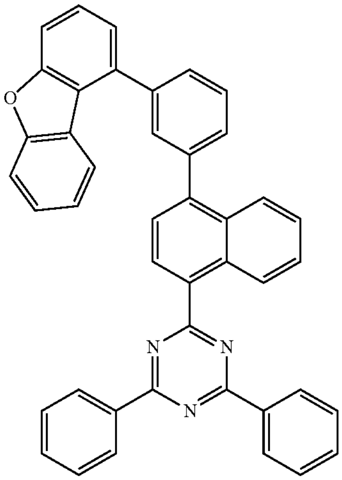
C2-121
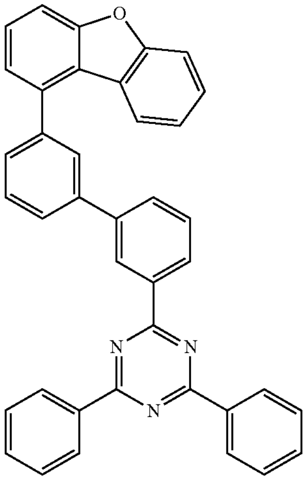
C2-122
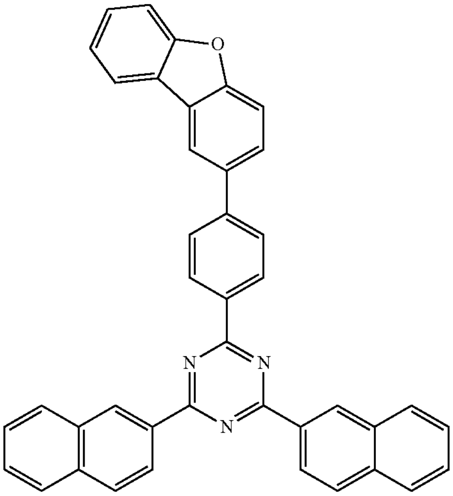

-continued
C2-123
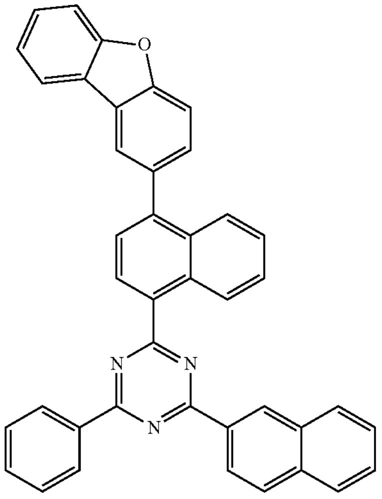
C2-124
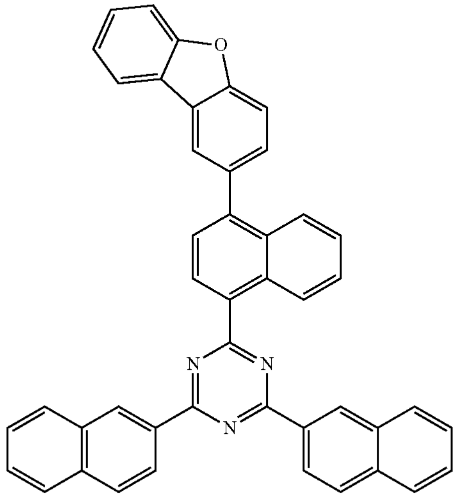
C2-125
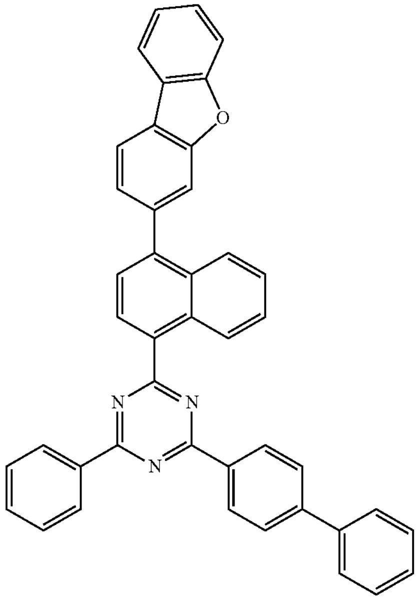
-continued
C2-126
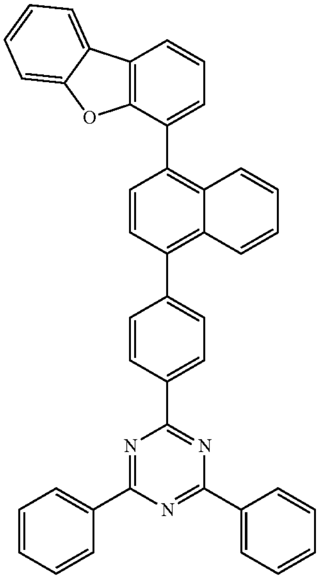
C2-127
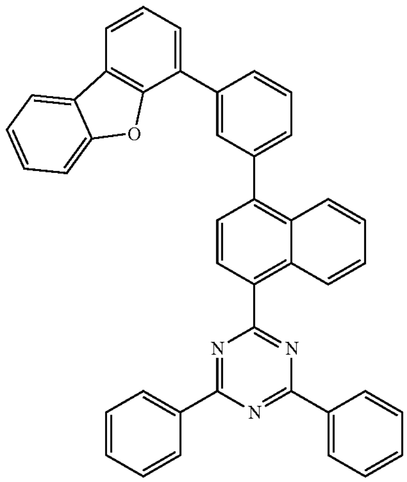
C2-128
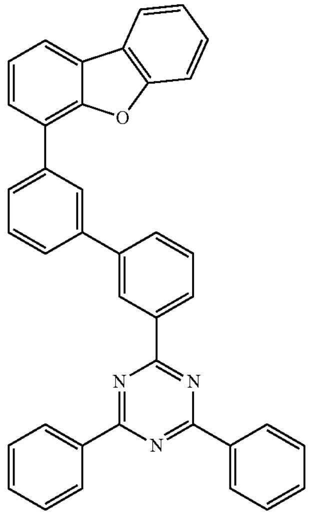

-continued
C2-129
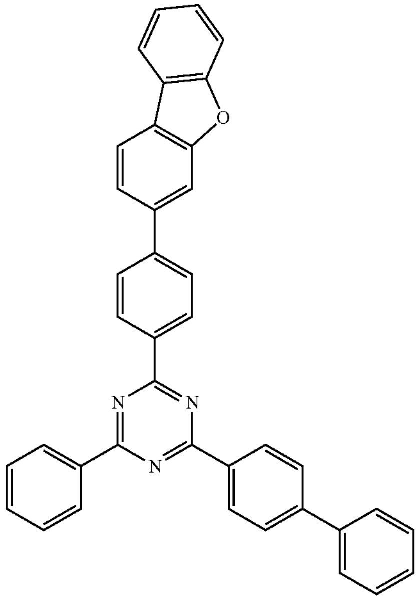
C2-266
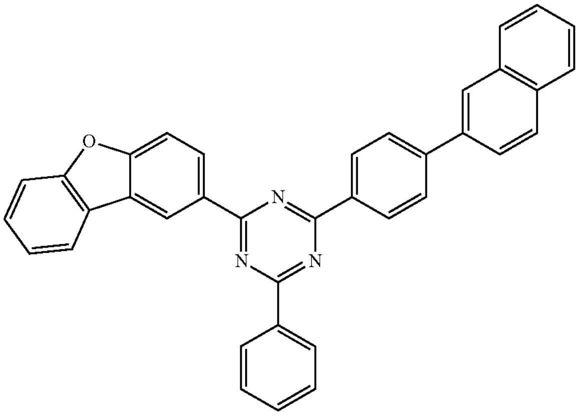
C2-267
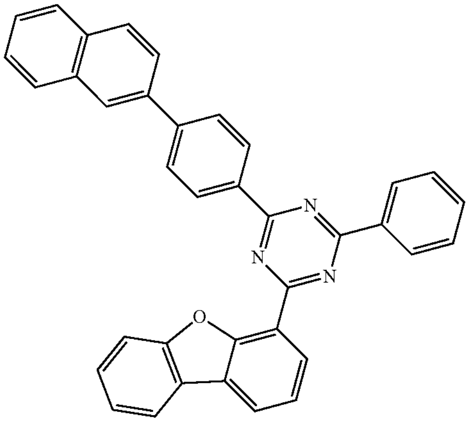
C2-130
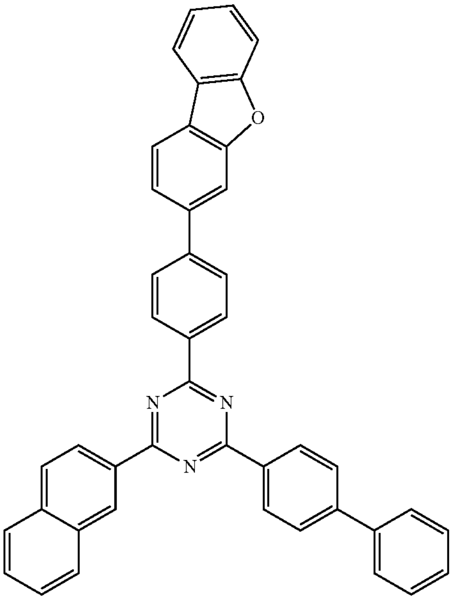
C2-268
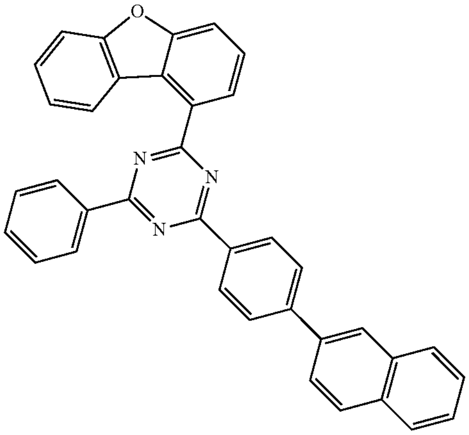

-continued
C2-270
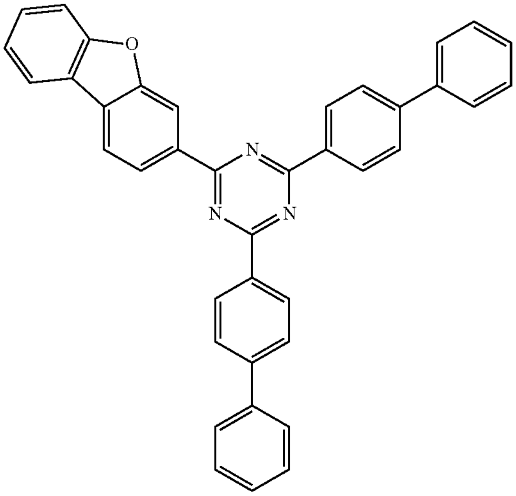
C2-271
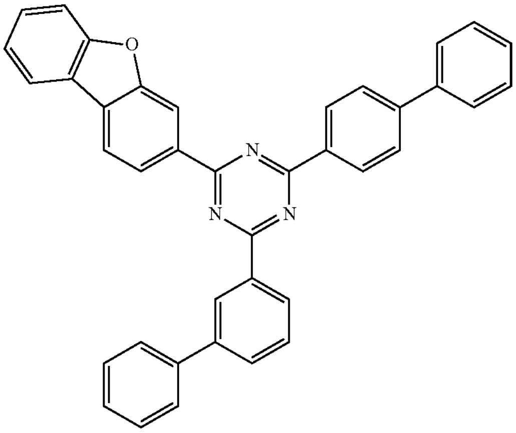
C2-272
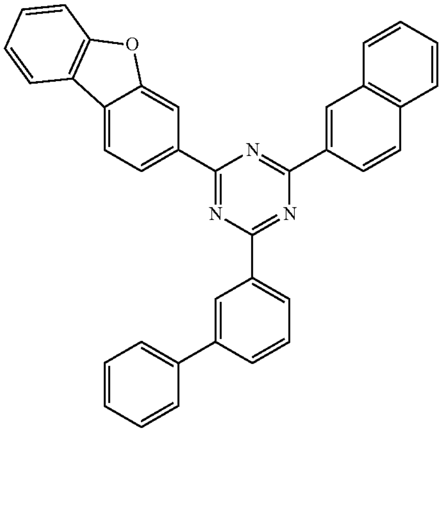
-continued
C2-273
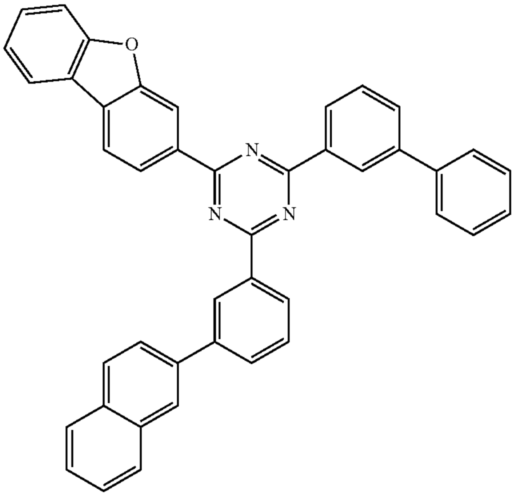
C2-274
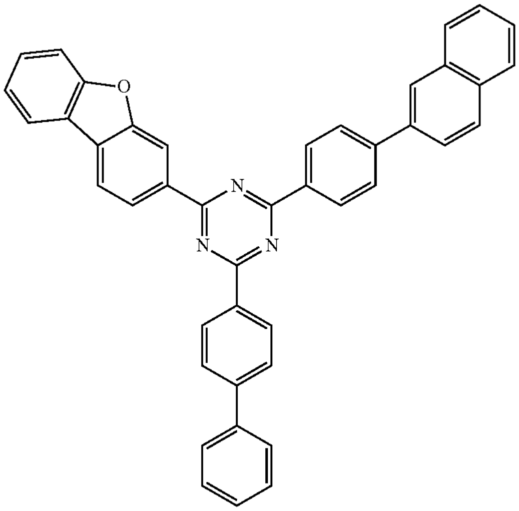
and
C2-275
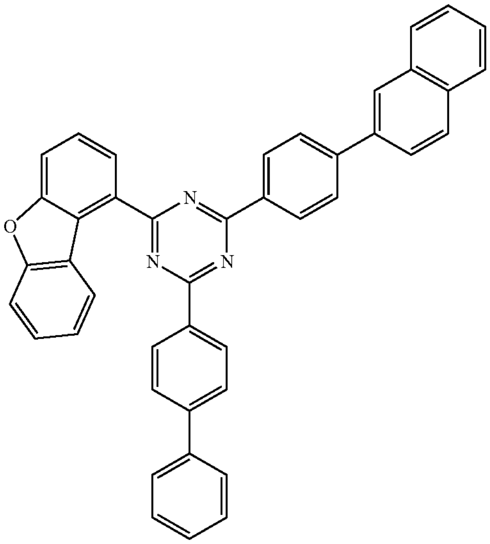
.

8. An organic electroluminescent device comprising an anode, a cathode, and at least one light-emitting layer between the anode and the cathode, wherein the at least one light-emitting layer comprises the plurality of host materials according to claim 1.

9. An organic electroluminescent compound represented by the following formula 2-1-1:

(2-1-1)

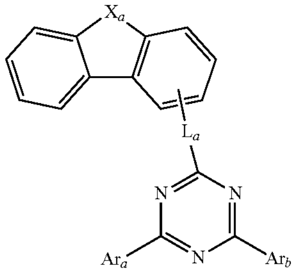

wherein, $X_a$ represents O or S;

$L_a$ represents an unsubstituted naphthylene except 1,2-naphthylene structure; and $Ar_a$ represents an unsubstituted phenyl, an unsubstituted naphthyl, an unsubstituted biphenyl, or an unsubstituted terphenyl; and $Ar_b$ represents an unsubstituted naphthyl, an unsubstituted biphenyl, or an unsubstituted terphenyl.

10. The organic electroluminescent compound according to claim 9, wherein the compound represented by formula 2-1-1 is selected from the group consisting of:

C2-114

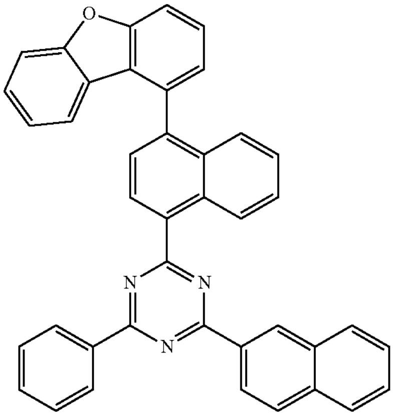

-continued

C2-115

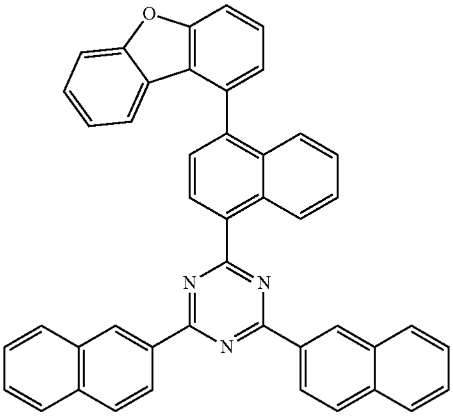

C2-116

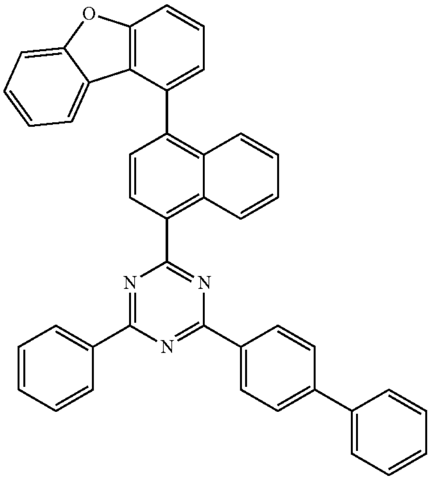

C2-123

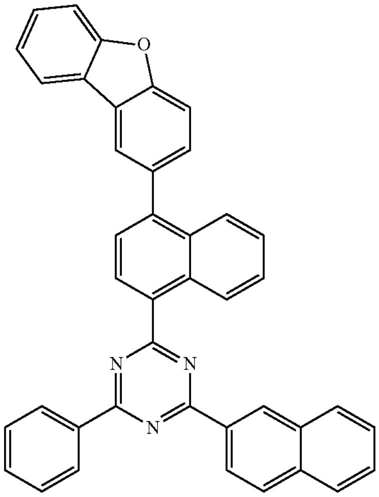

-continued
C2-124
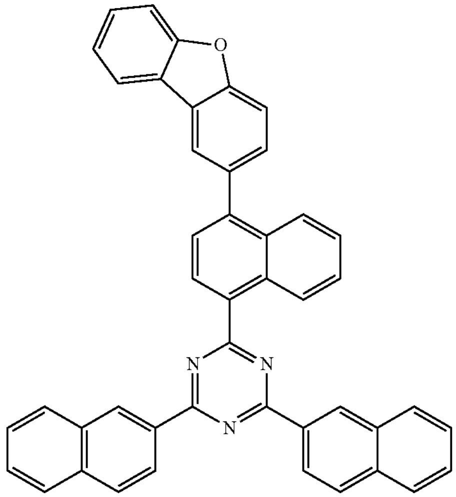
C2-125
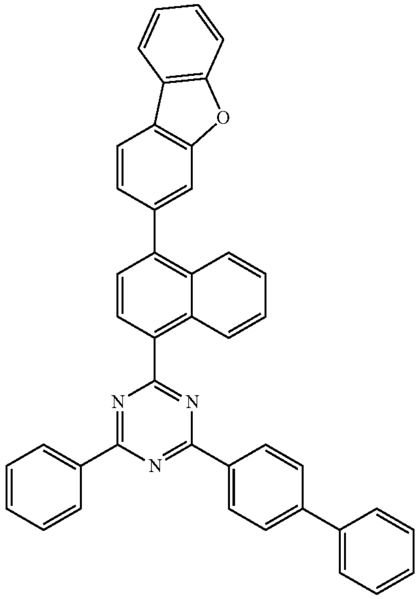
C2-244
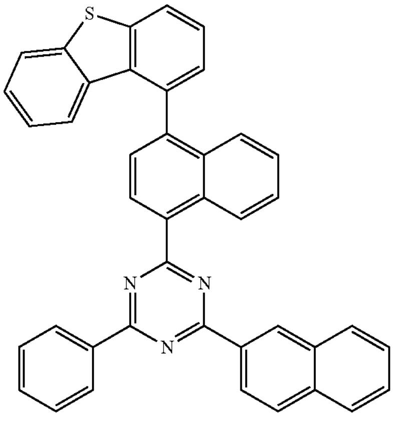
-continued
C2-245
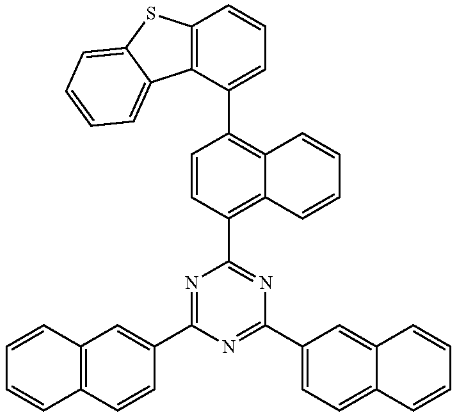
C2-246
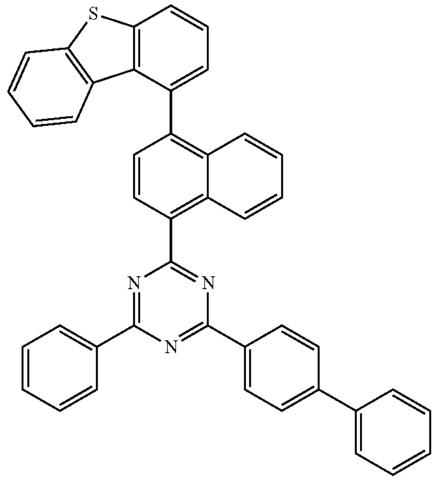
C2-253
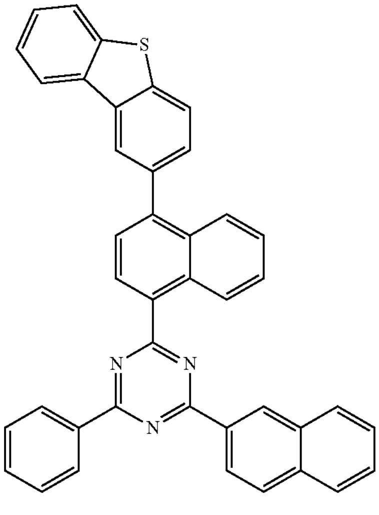

-continued
C2-254
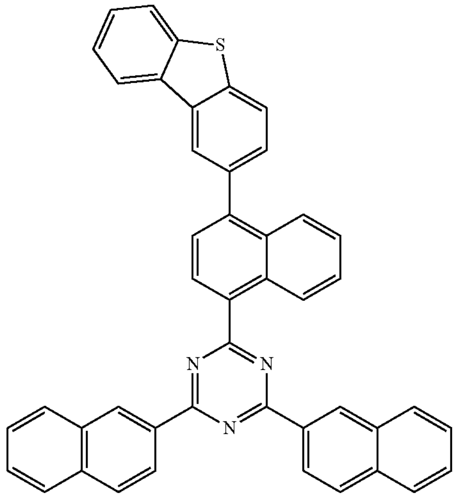
C2-255
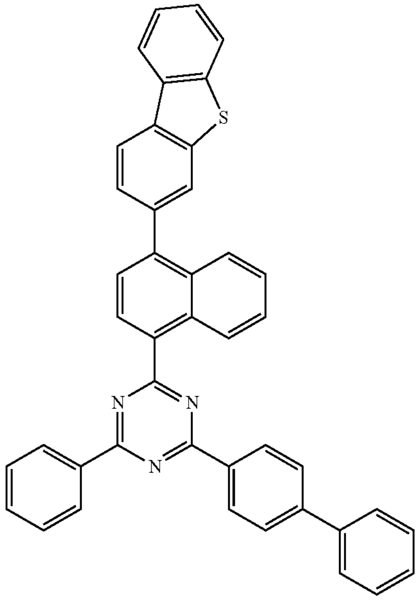
-continued
C-2
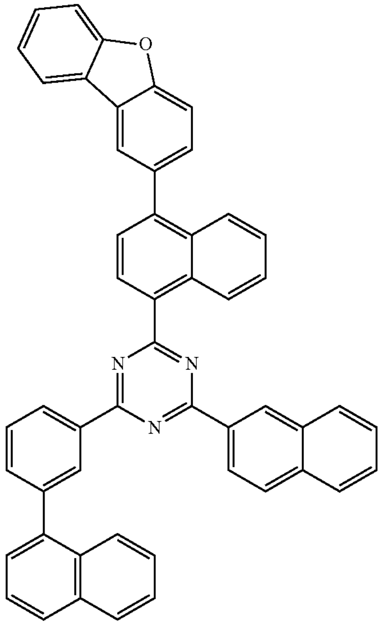
C-4
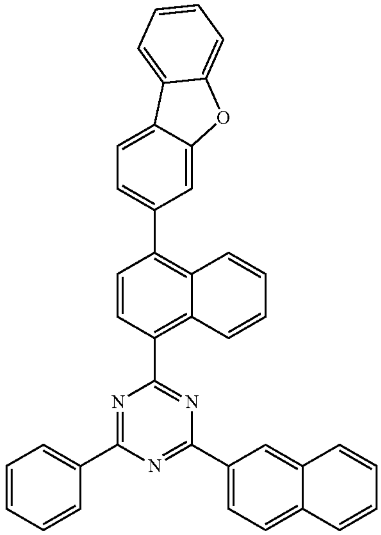

C-5
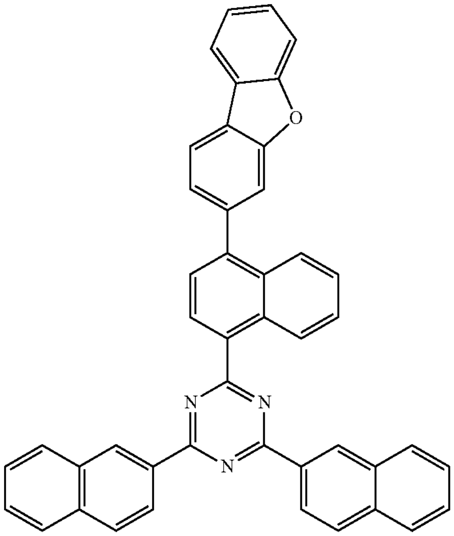
C-6
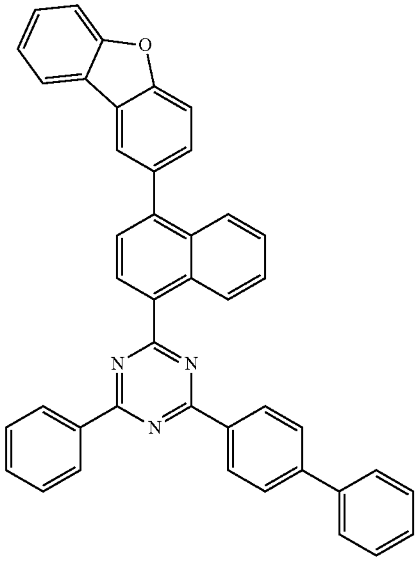
C-7
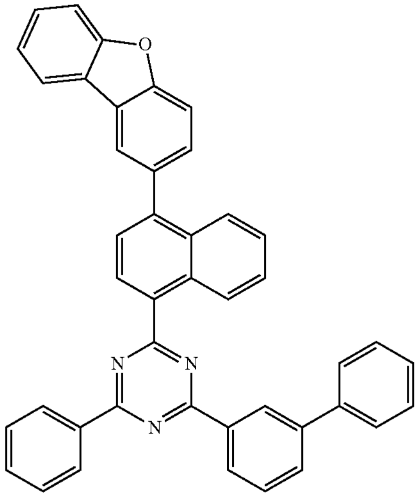
C-8
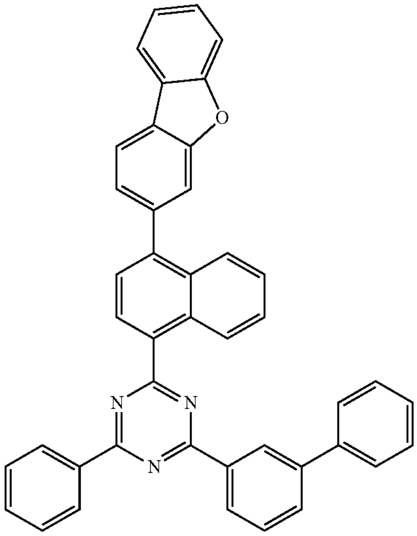
C-9
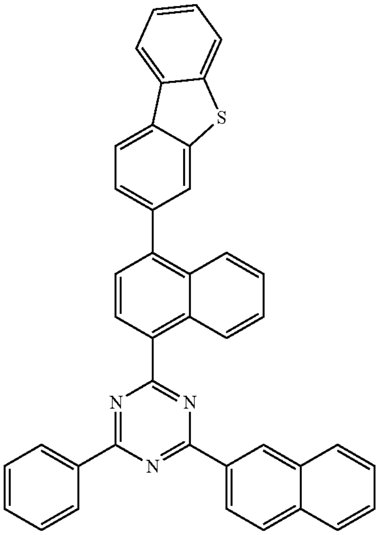
C-10
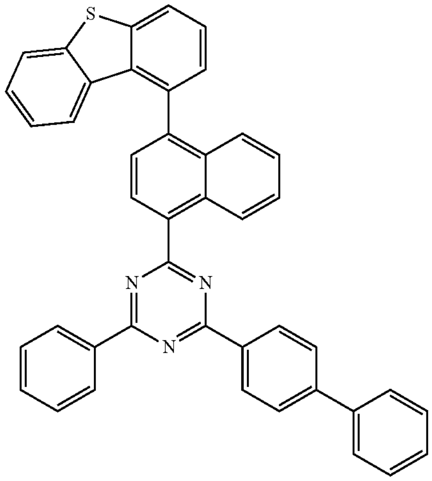

-continued
C-11
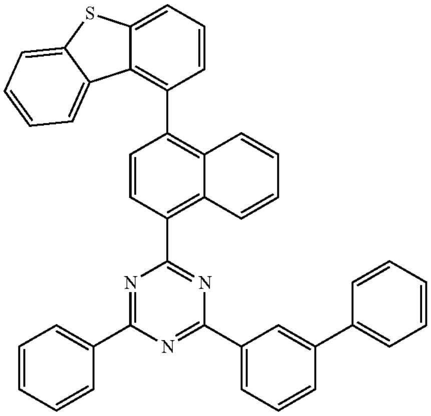
C-12
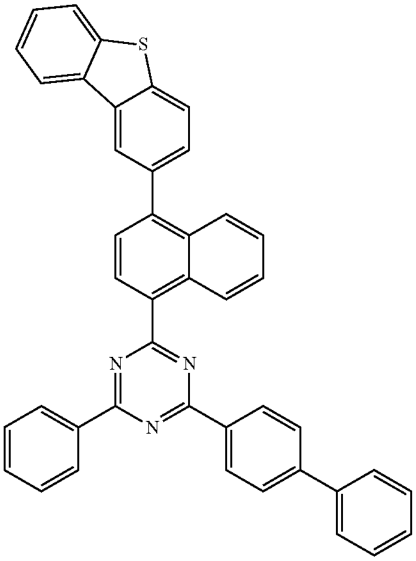
C-13
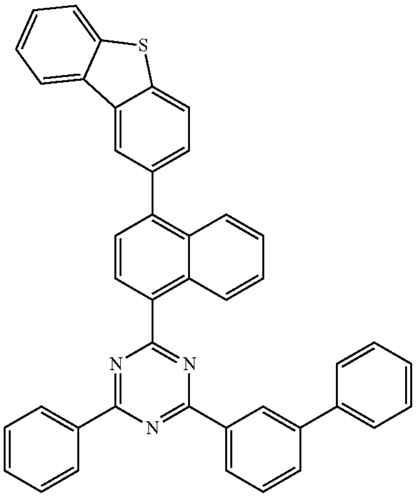
-continued
C-14
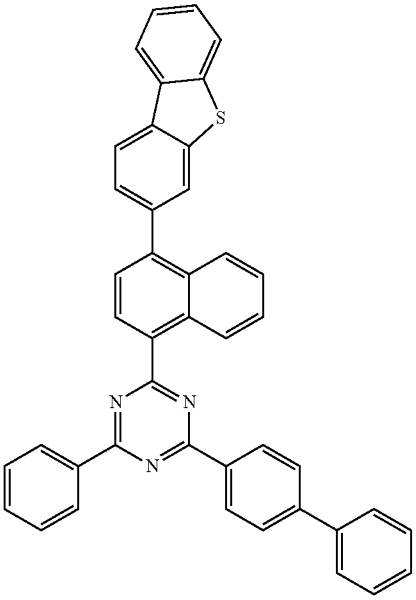
C-15
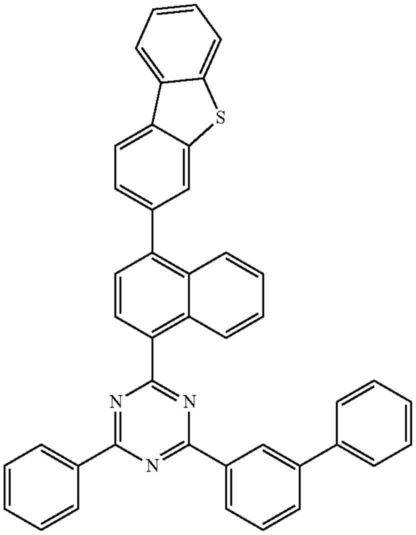

-continued
C-16
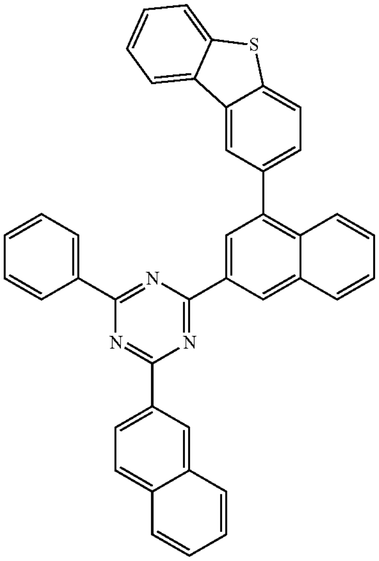
C-17
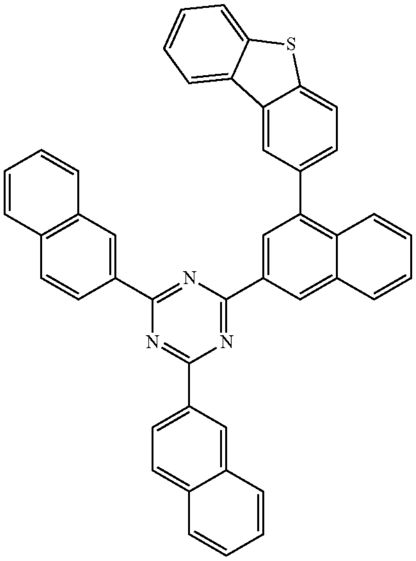
-continued
C-18
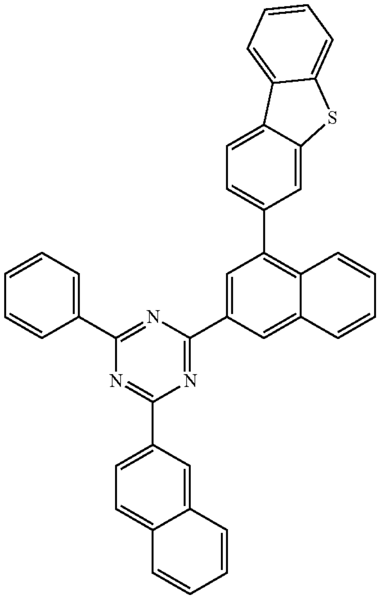
C-19
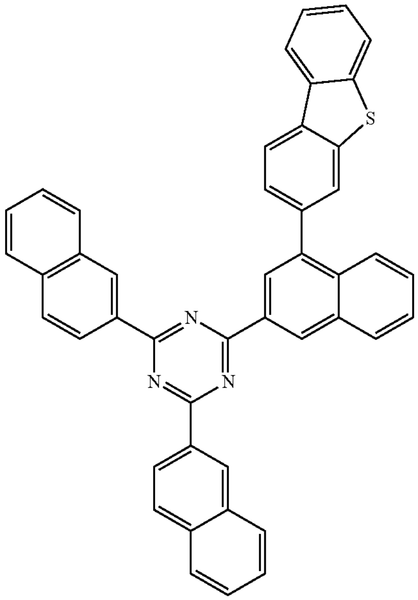

-continued
C-20
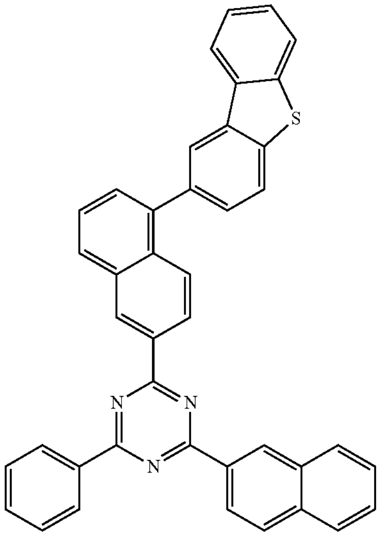
C-21
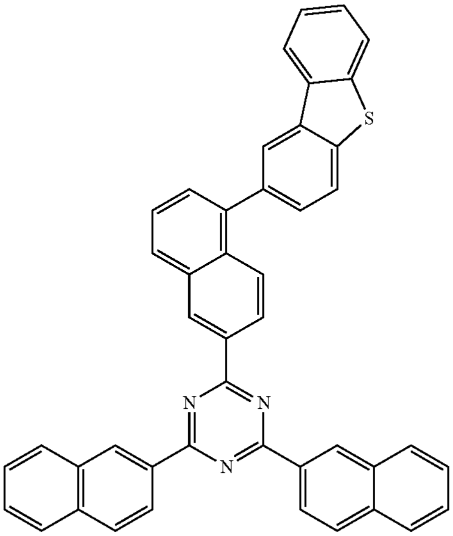
C-22
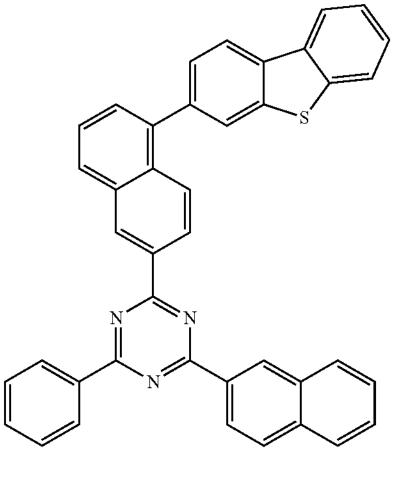
-continued
C-23
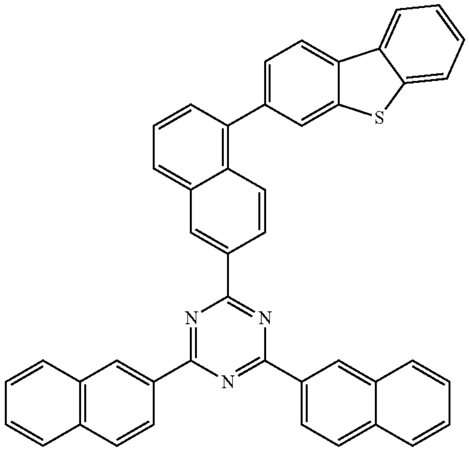
C-24
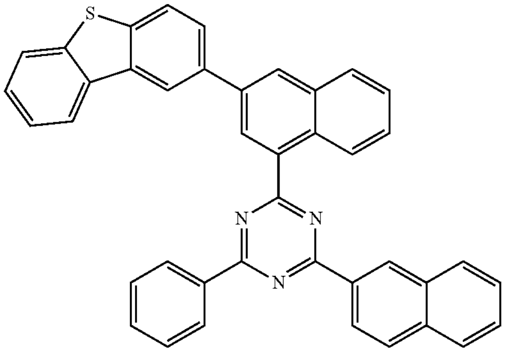
C-25
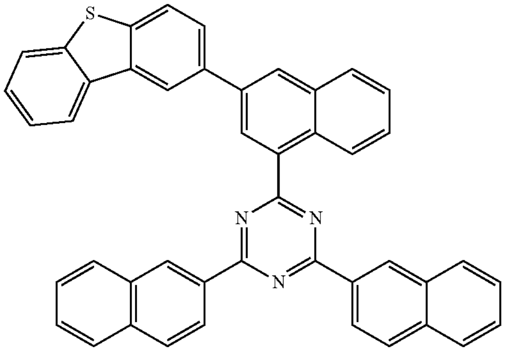
C-26
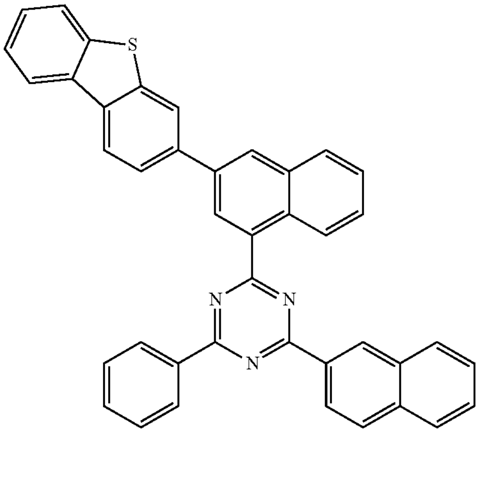

-continued
C-27
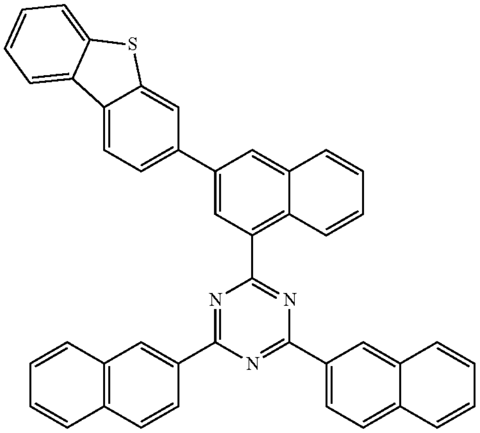
C-28
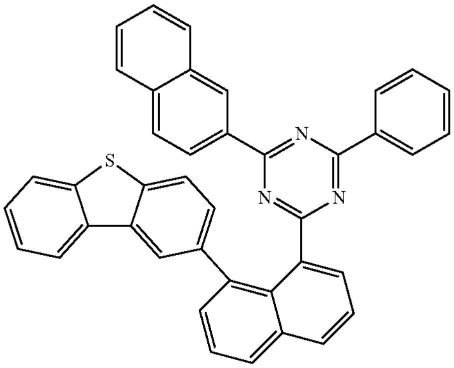
C-29
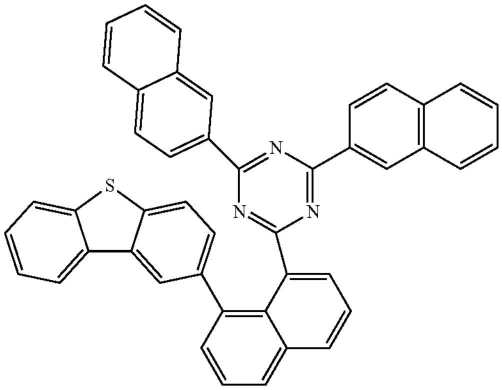
C-30
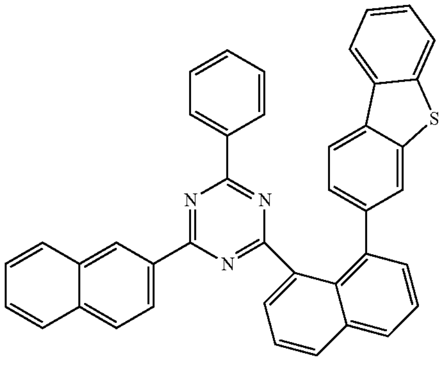
-continued
C-32
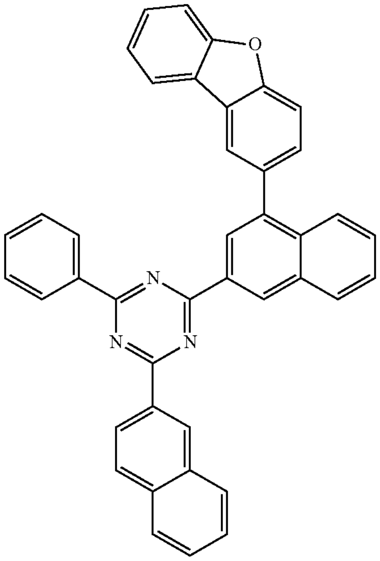
C-33
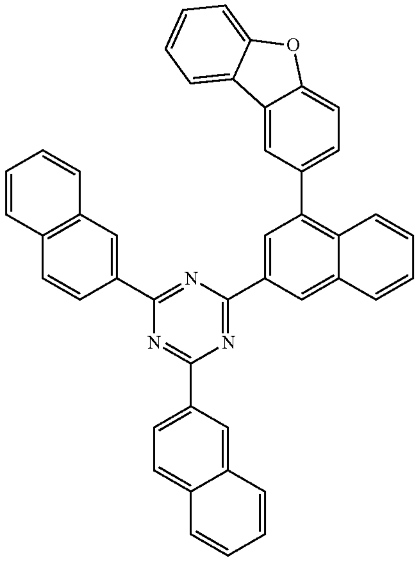

-continued
C-35
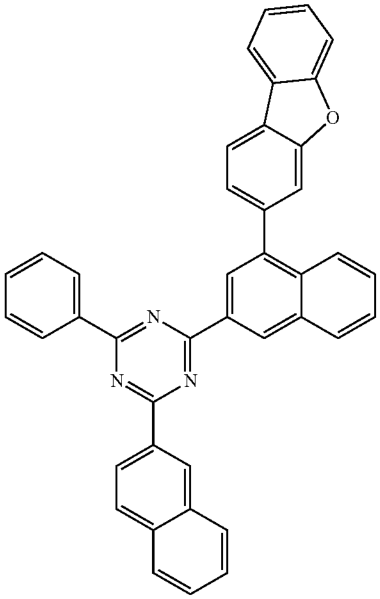
C-36
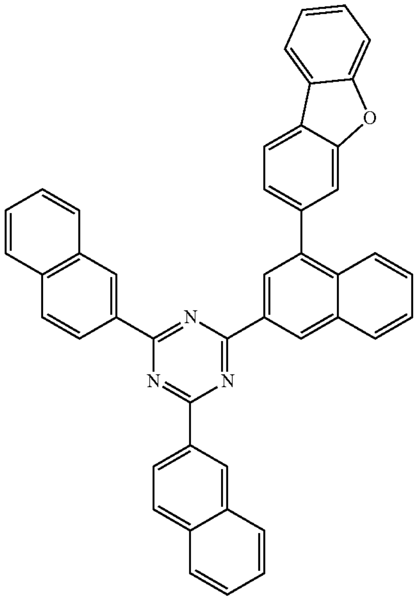
-continued
C-38
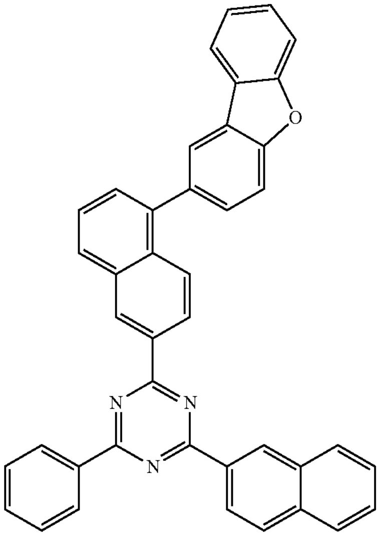
C-39
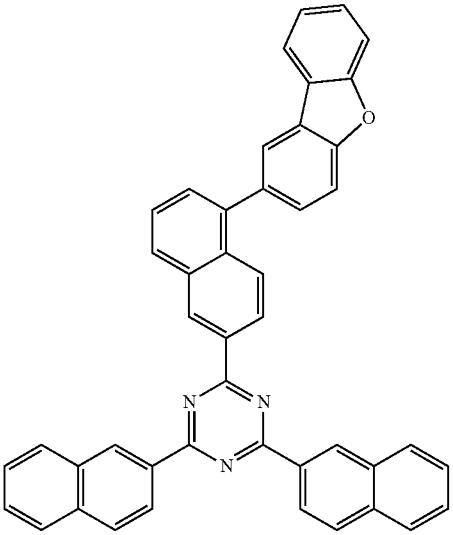
C-41
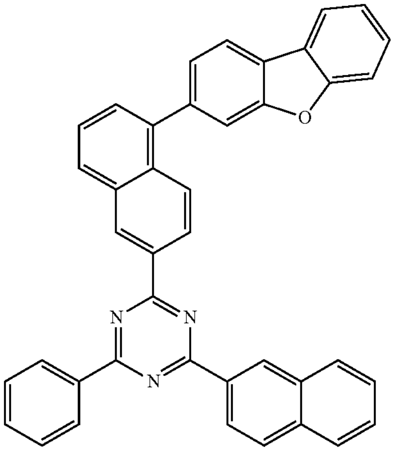

-continued
C-42
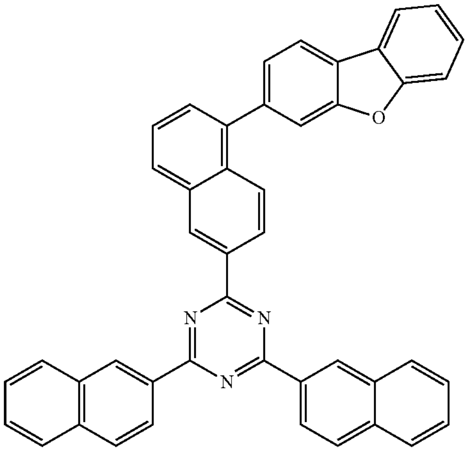
C-44
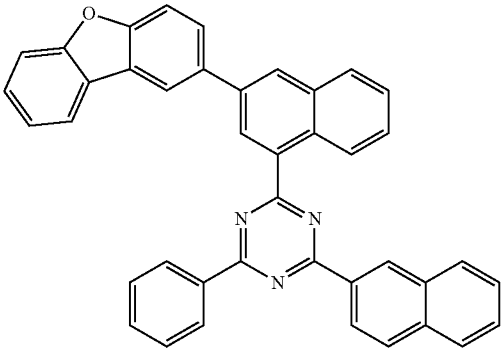
C-45
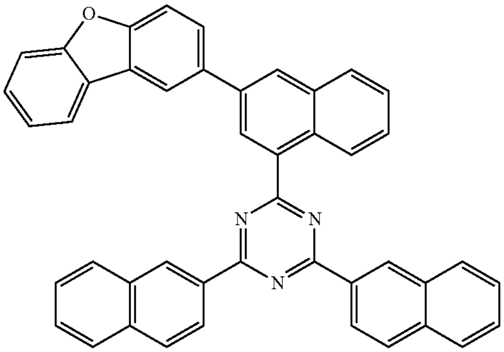
C-47
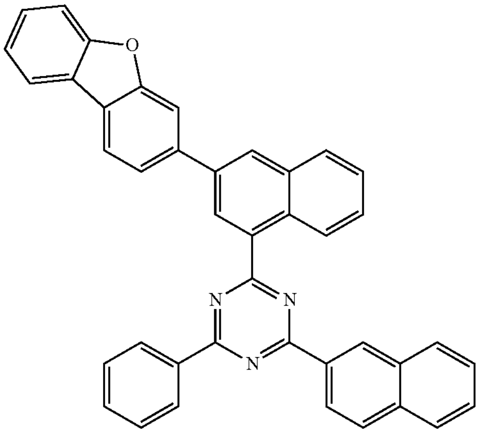
-continued
C-48
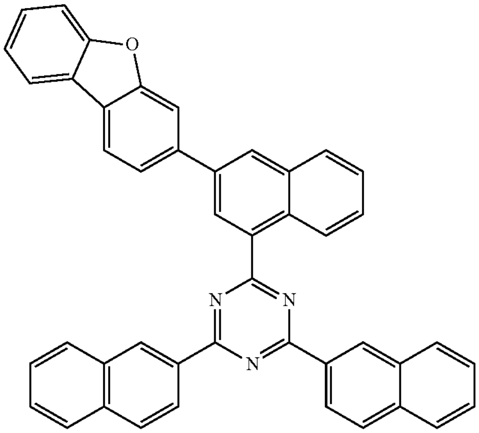
C-49
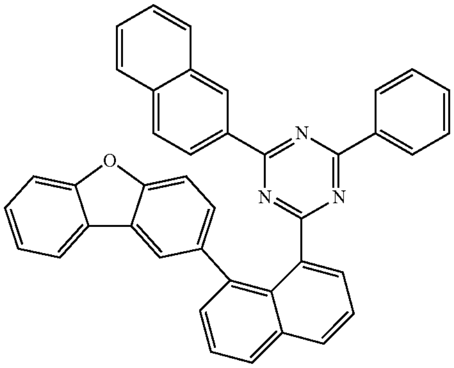
C-50
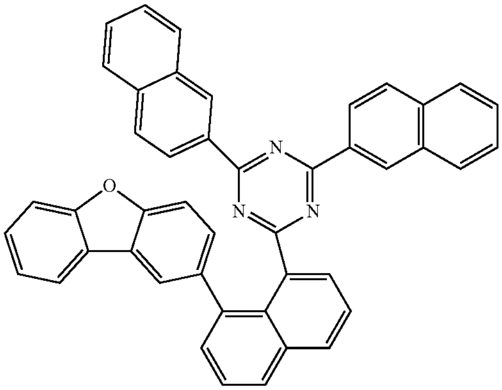
C-51
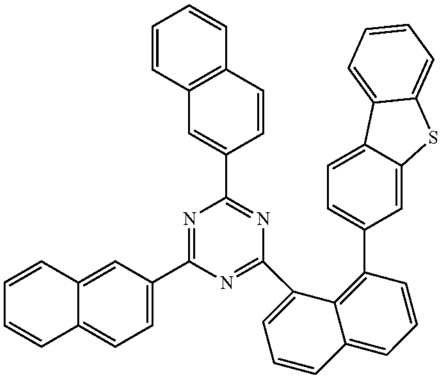

-continued
C-52
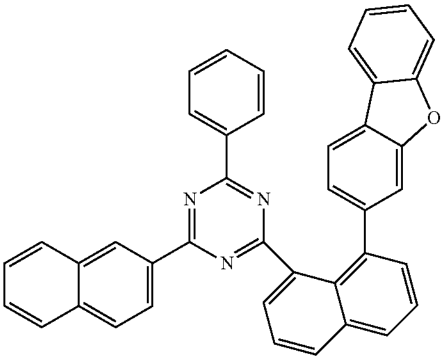
C-53
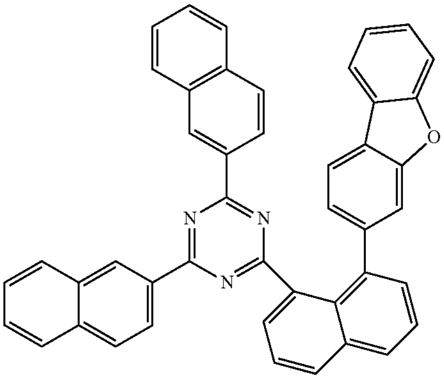
C-55
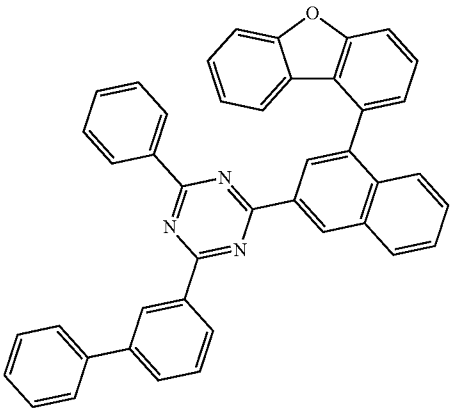
-continued
C-56
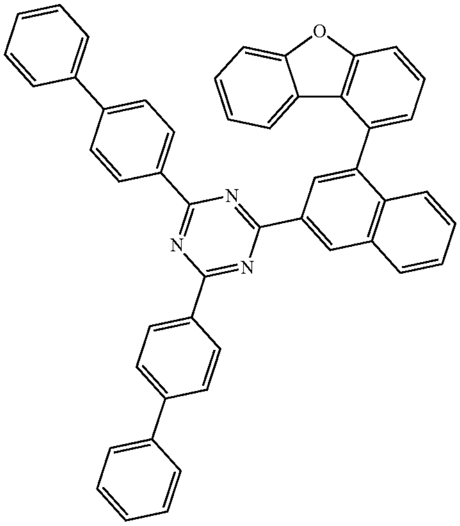
C-57
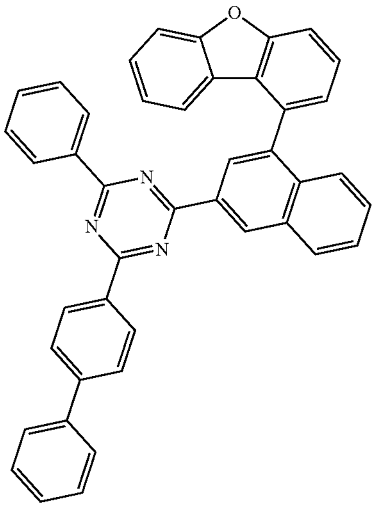
C-58
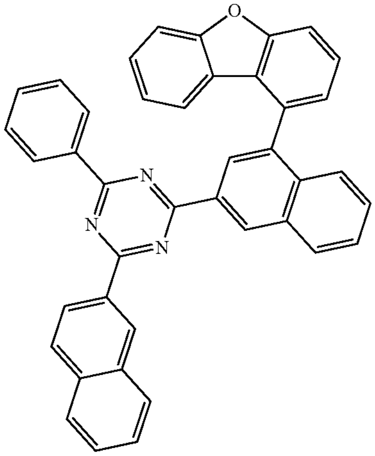

-continued
C-59
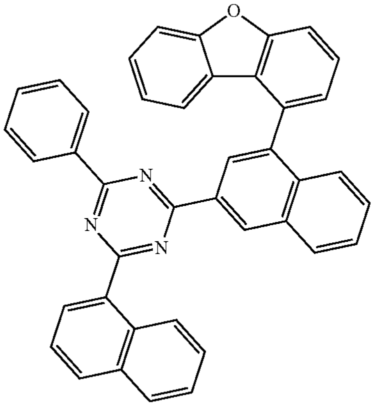
C-60
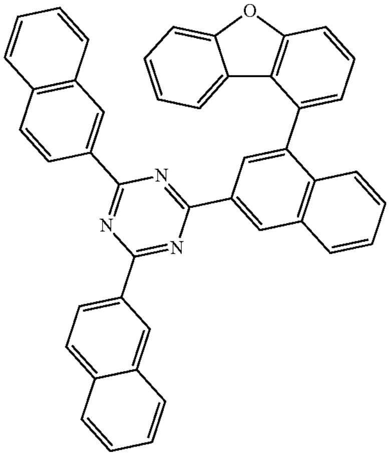
C-61
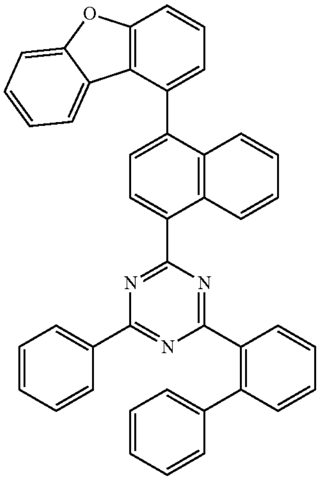
-continued
C-62
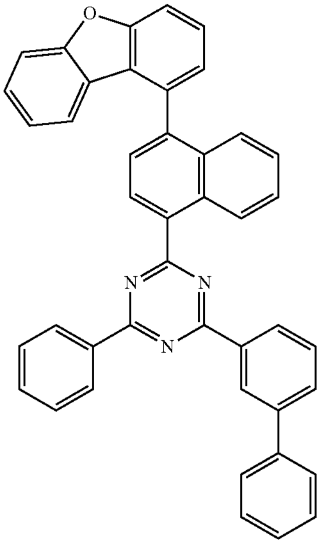
C-63
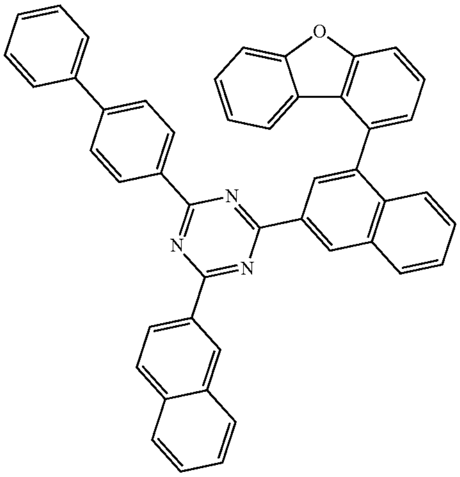
C-64
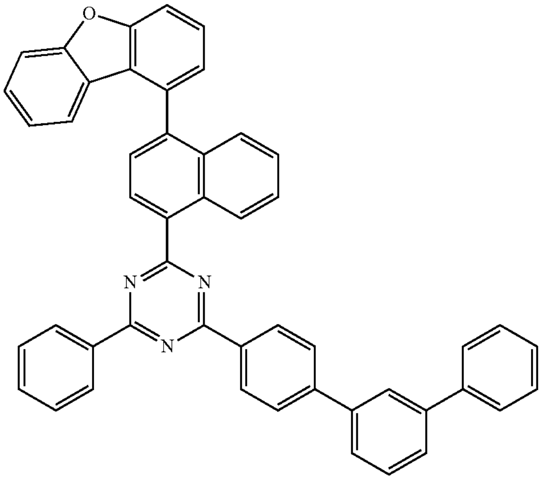

-continued
C-65
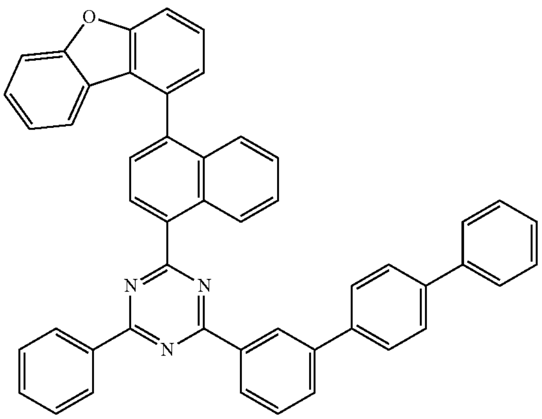
C-66
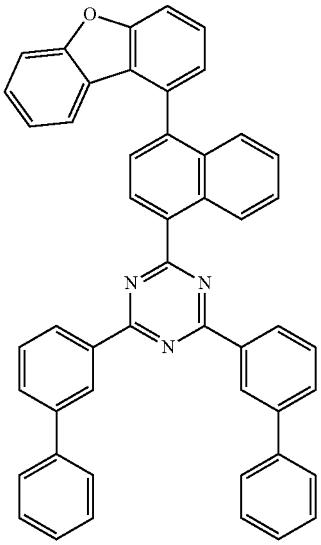
C-67
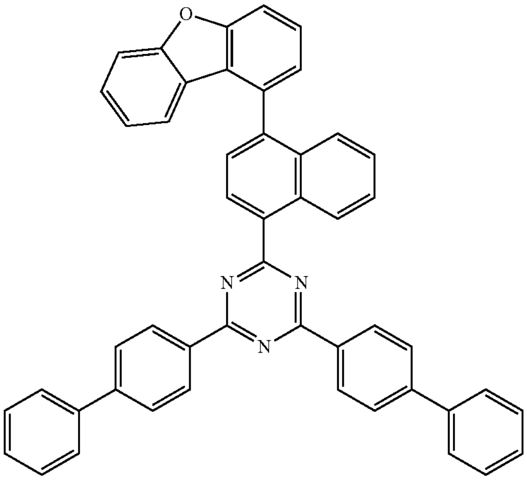
-continued
C-68
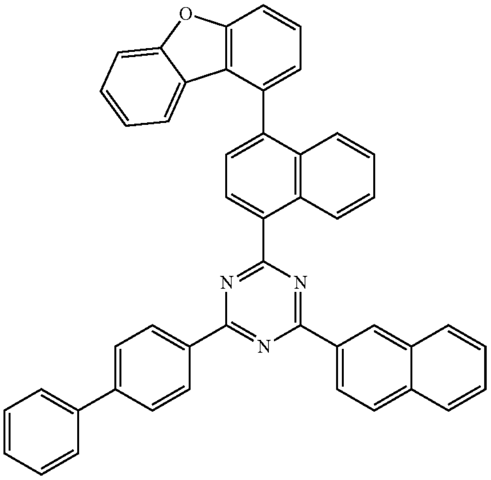
C-69
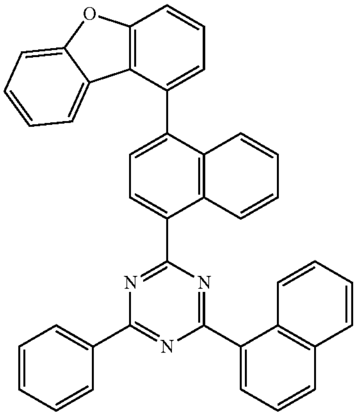
C-71
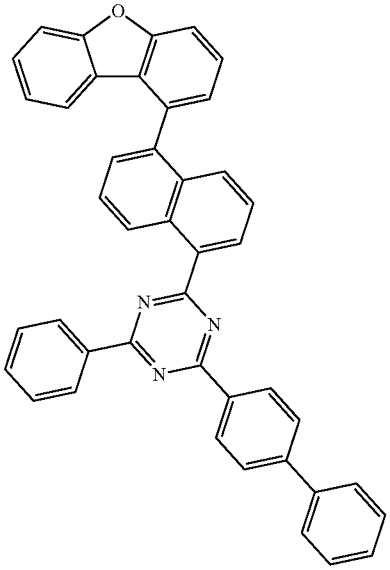

-continued
C-72
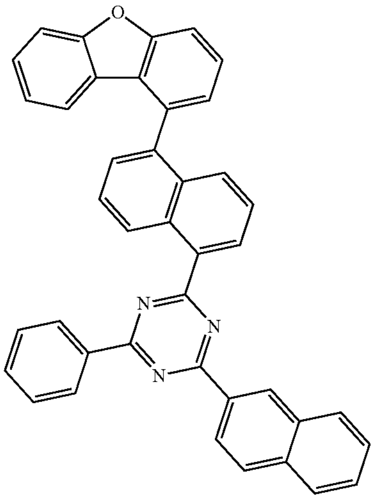
C-73
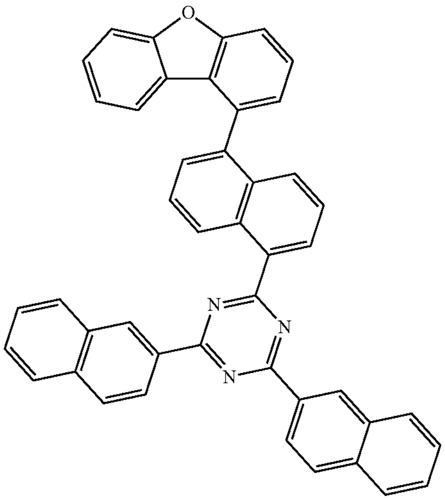
C-74
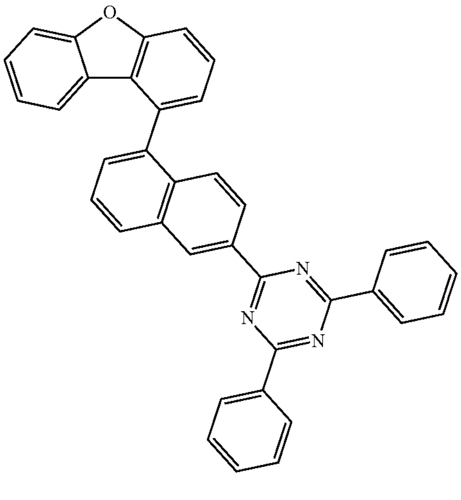
-continued
C-75
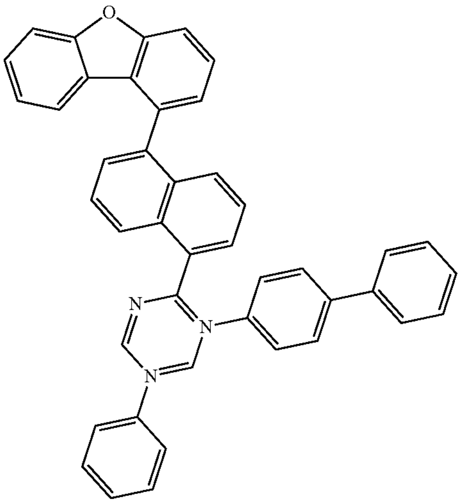
C-77
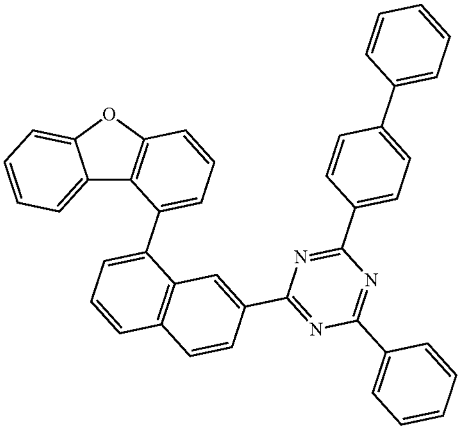
C-78
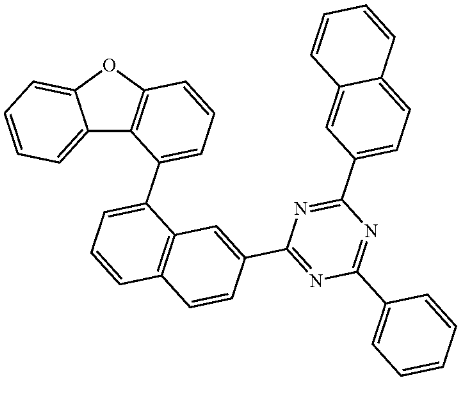

-continued
C-79
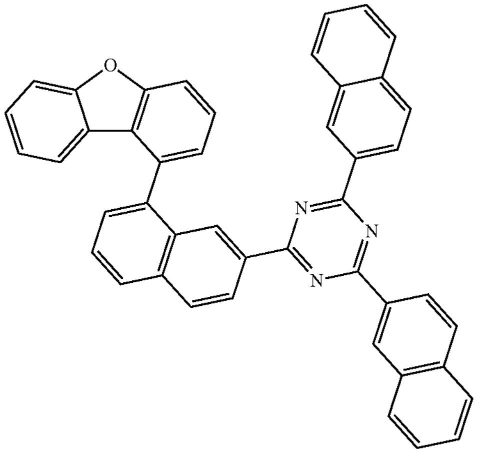
C-80
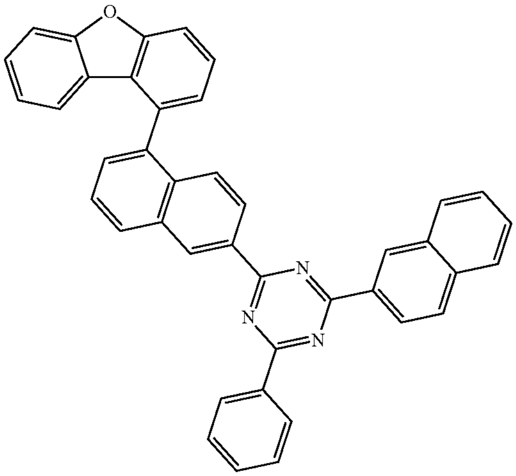
C-81
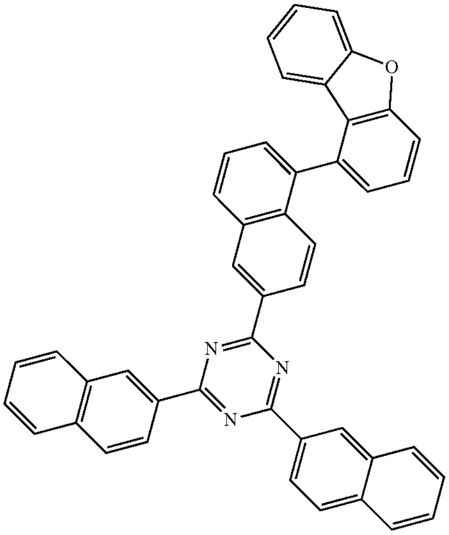
-continued
C-82
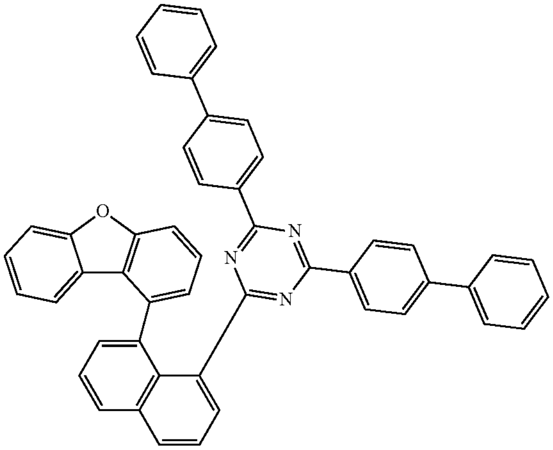
C-83
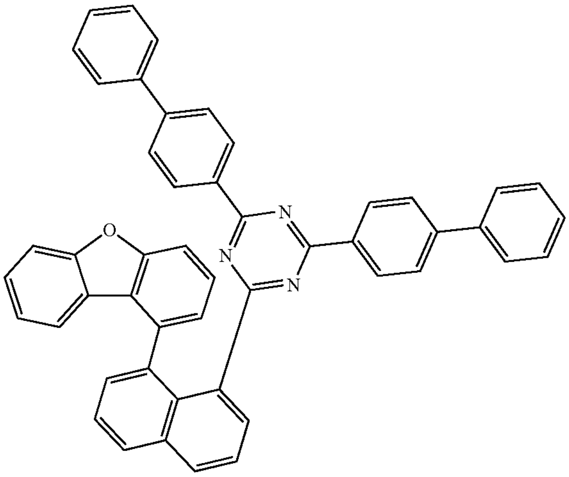
C-84
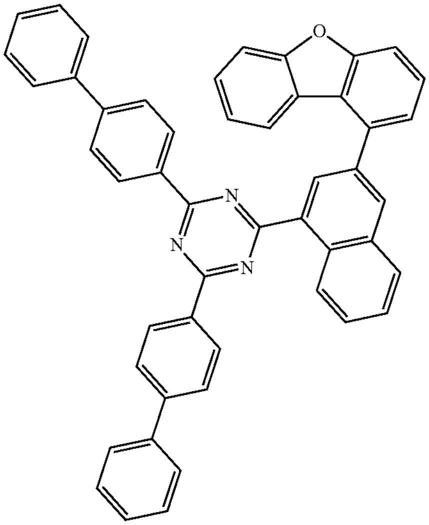

-continued
C-85
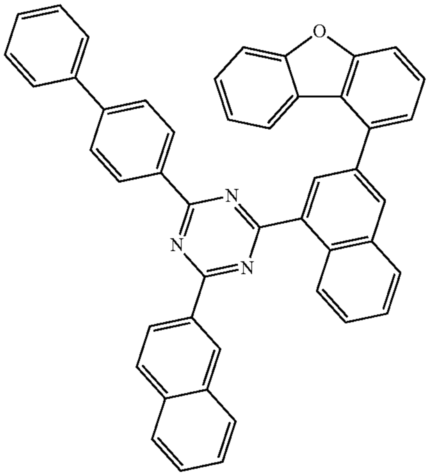
C-87
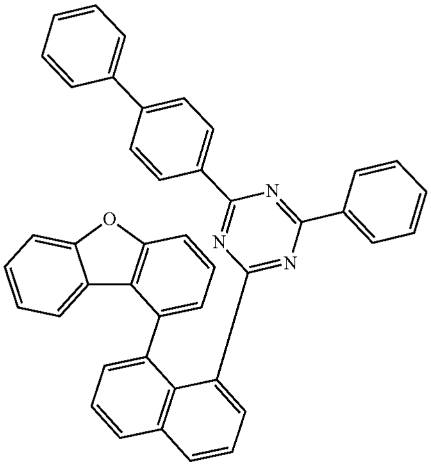
C-88
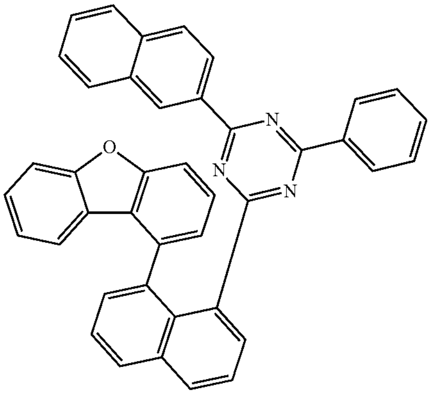
-continued
C-89
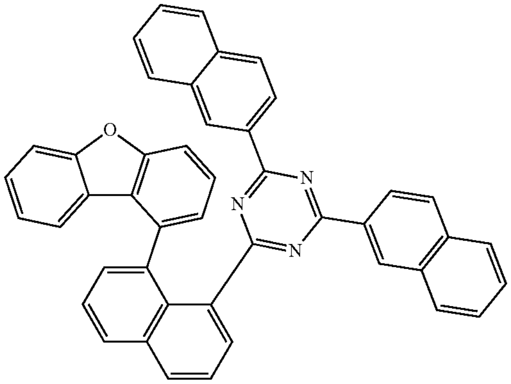
C-91
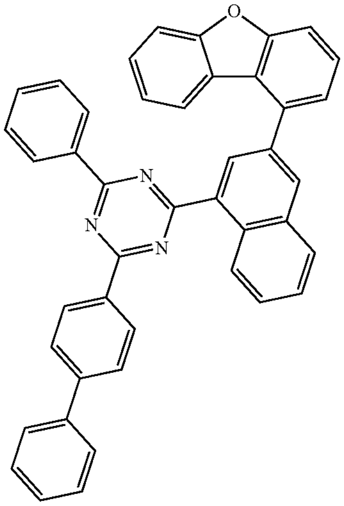
C-92
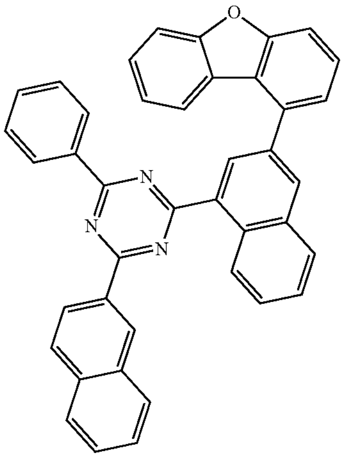

-continued
C-93
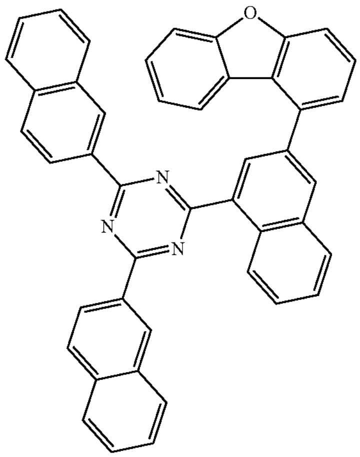
C-95
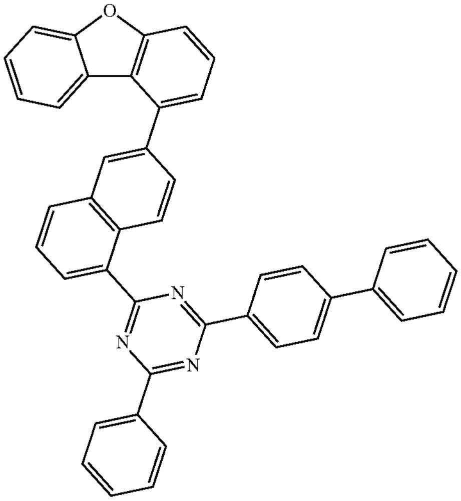
C-97
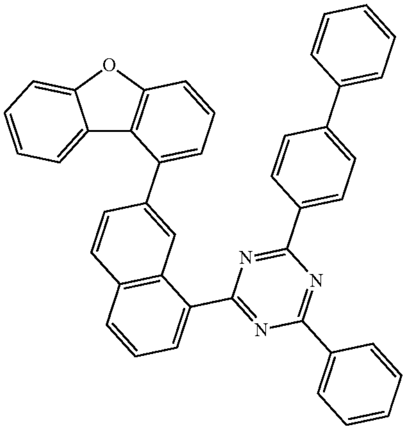
-continued
C-98
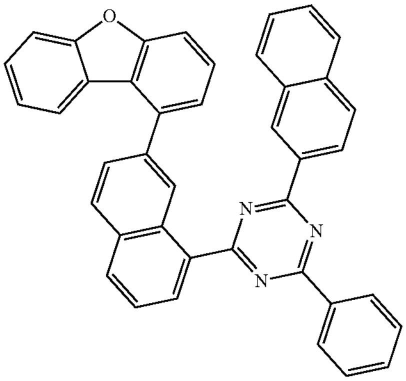
C-99
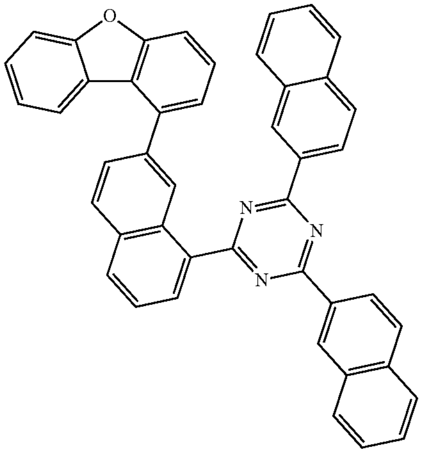
C-100
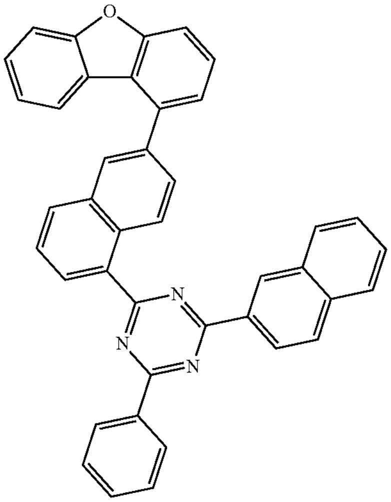

-continued
C-102
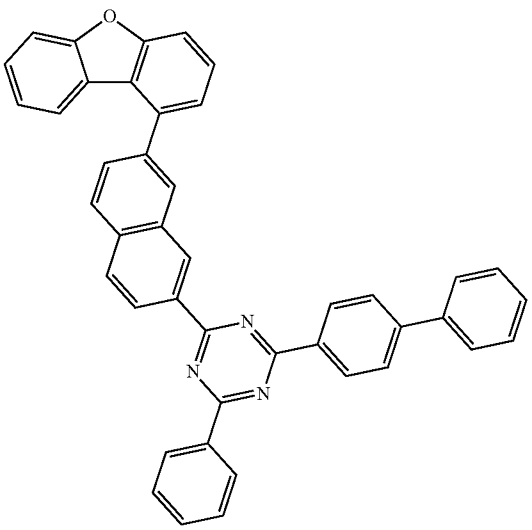
C-103
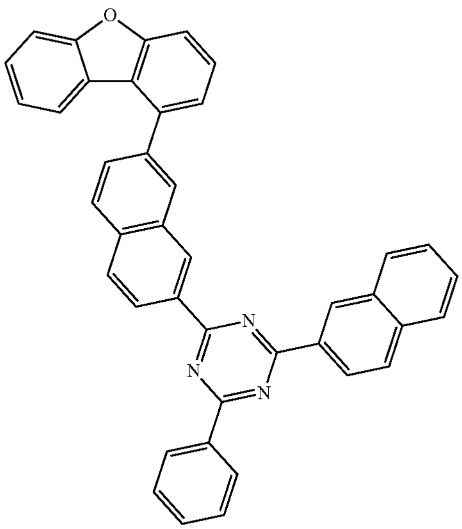
C-104
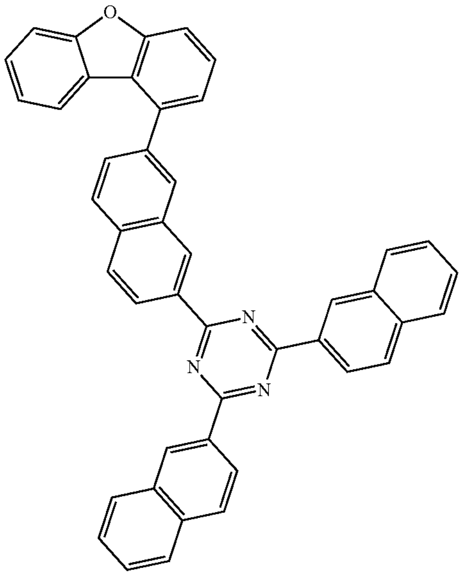
-continued
C-105
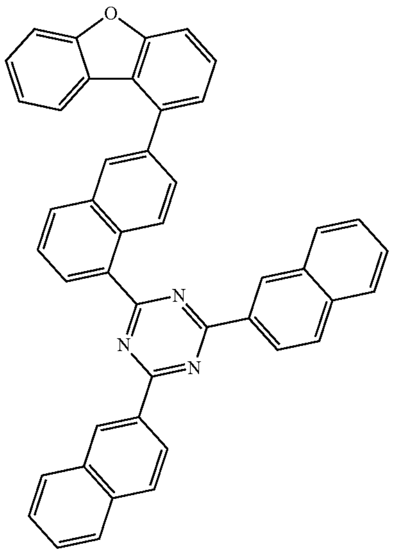
C-107
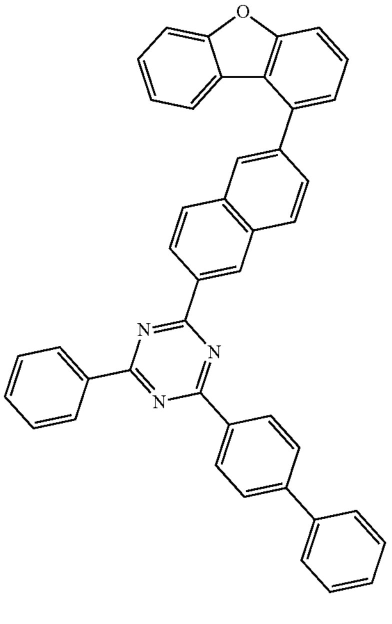

-continued
C-108
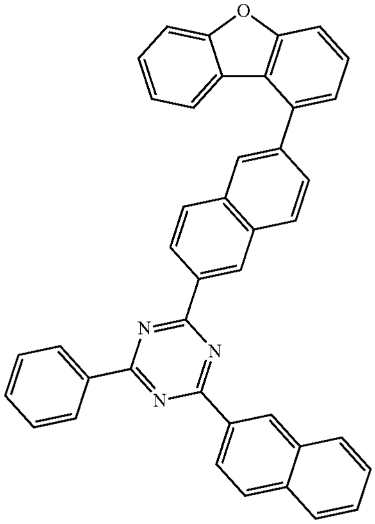
and
-continued
C-109
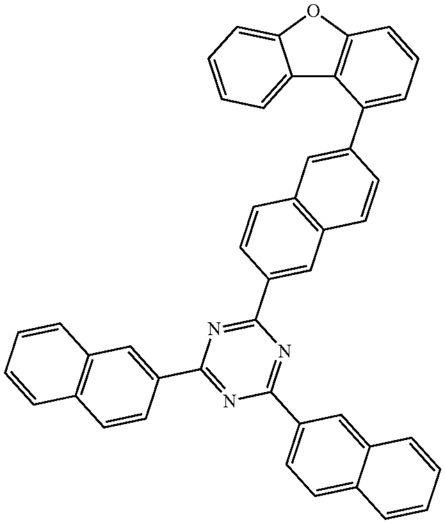
.
11. An organic electroluminescent device comprising the organic electroluminescent compound according to claim 9.
12. The organic electroluminescent device according to claim 11, wherein the organic electroluminescent compound is contained in a light-emitting layer.
* * * * *